US007381541B2

(12) United States Patent
Flachmann et al.

(10) Patent No.: US 7,381,541 B2
(45) Date of Patent: Jun. 3, 2008

(54) **METHODS FOR PRODUCING ANIMAL FEED PREPARATIONS WITH ASTAXANTHIN-CONTAINING PLANTS OR PARTS OF PLANTS OF THE GENUS *TAGETES***

(75) Inventors: Ralf Flachmann, Quedlinburg (DE); Matt Sauer, Quedlinburg (DE); Christel Renate Schopfer, Quedlinburg (DE); Martin Klebsattel, Quedlinburg (DE); Angelika-Maria Pfeiffer, Birkenheide (DE); Thomas Luck, Neustadt (DE); Dirk Voeste, Schifferstadt (DE)

(73) Assignees: SunGene GmbH & Co. KGaA (DE); BASF Aktiengesellschaft (DE); BASF Plant Science GmbH (DE)

( * ) Notice: Subject to any disclaimer, the term of this patent is extended or adjusted under 35 U.S.C. 154(b) by 173 days.

(21) Appl. No.: 10/524,647

(22) PCT Filed: Aug. 18, 2003

(86) PCT No.: PCT/EP03/09109

§ 371 (c)(1),
(2), (4) Date: Feb. 17, 2005

(87) PCT Pub. No.: WO2004/017749

PCT Pub. Date: Mar. 4, 2004

(65) Prior Publication Data

US 2005/0281909 A1    Dec. 22, 2005

(30) Foreign Application Priority Data

Aug. 20, 2002 (DE) ............................... 102 38 978
Aug. 20, 2002 (DE) ............................... 102 38 979
Aug. 20, 2002 (DE) ............................... 102 38 980
Nov. 13, 2002 (DE) ............................... 102 53 112
Dec. 16, 2002 (DE) ............................... 102 58 971

(51) Int. Cl.
*C12P 23/00* (2006.01)

(52) U.S. Cl. ............................ 435/67; 424/764; 426/2; 800/282

(58) Field of Classification Search ................ 435/67; 424/764; 426/2; 800/282
See application file for complete search history.

(56) References Cited

U.S. PATENT DOCUMENTS

| 5,876,782 | A  | * | 3/1999 | Sas et al. ................. 426/635 |
| 6,221,417 | B1 | * | 4/2001 | Sas et al. ................. 426/540 |
| 6,372,946 | B1 | * | 4/2002 | Schloemer et al. ......... 568/347 |
| 7,033,622 | B2 | * | 4/2006 | Hauptmann et al. ........ 424/764 |
| 2004/0010826 | A1 | * | 1/2004 | Hauptmann et al. ........ 800/323 |
| 2005/0003474 | A1 | * | 1/2005 | Desouza et al. ............. 435/67 |
| 2006/0053513 | A1 | * | 3/2006 | Steiger et al. .............. 800/282 |
| 2006/0162020 | A1 | * | 7/2006 | Sauer et al. ................ 800/282 |

FOREIGN PATENT DOCUMENTS

| WO | WO 92/01754 A1   | 2/1992  |
| WO | WO 99/07867 A1   | 2/1999  |
| WO | WO 00/32788 A2   | 6/2000  |
| WO | WO 03/077950 A1 *| 9/2003  |
| WO | WO 03/077950 A1  | 9/2003  |
| WO | WO 03/080849 A2  | 10/2003 |

OTHER PUBLICATIONS

U.S. Appl. No. 10/524,648, Christal R. Schopfer et al.
U.S. Appl. No. 10/524,652, Christel R. Schopfer et al.
U.S. Appl. No. 10/524,972, Christel R. Schopfer et al.
U.S. Appl. No. 10/524,971, Martin Klebsattel et al.

* cited by examiner

*Primary Examiner*—Ralph Gitomer
(74) *Attorney, Agent, or Firm*—Connolly Bove Lodge & Hutz LLP

(57) ABSTRACT

The present invention relates to the use of astaxanthin-containing plants or parts of plants of the genus *Tagetes* or astaxanthin-containing extracts of astaxanthin-containing plants or parts of plants of the genus *Tagetes* for oral administration to animals, methods for producing animal feed preparations, the animal feed preparations themselves, a method for pigmenting animals or animal products, and also a method for producing pigmented animals and animal products.

4 Claims, 15 Drawing Sheets

Figure 1: Nucleotide sequence comparison

```
KETO2.seq  ATGCAGCTAGCAGCGACAGTAATGTTGGAGCAGCTTACCGGAAGCGCTGAGGCACTCAAGGAGAAGGAGAAGGAGGTTGCAGGCAGCTCTGACGTGTTGC  100
X86782.seq ATGCAGCTAGCAGCGACAGTAATGTTGGAGCAGCTTACCGGAAGCGCTGAGGCACTCAAGGAGAAGGAGAAGGAGGTTGCAGGCAGCTCTGACGTGTTGC  100

KETO2.seq  GTACATGGGCGACCCAGTACTCGCTTCCGTCAGAGGAGTCAGACGCGGCCCGCCCGGGACTGAAGAATGCCTACAAGCCACCCACCTTCCGACACAAAGGG  200
X86782.seq GTACATGGGCGACCCAGTACTCGCTTCCGTCAGAAGAGTCAGACGCGGCCCGCCCGGGACTGAAGAATGCCTACAAGCCACCCACCTTCCGACACAAAGGG  200

KETO2.seq  CATCACAATGGCGCTAGCTGTCATCGGCTCCTGGGCCGCAGTGTTCCTCCACGCCATTTTTCAAATCAAGCTTCCGACCTCCTTGGACCAGCTGCACTGG  300
X86782.seq CATCACAATGGCGCTACGTGTCATCGGCTCCTGGGCCGCAGTGTTCCTCCACGCCATTTTTCAAATCAAGCTTCCGACCTCCTTGGACCAGCTGCACTGG  300

KETO2.seq  CTGCCCGTGTCAGATGCCACAGCTCAGCTGGTTAGCGGCAGCAGCAGCCTGCTGCACATCGTCGTAGTATTCTTTGTCCTGGAGTTCCTGTACACAGGCC  400
X86782.seq CTGCCCGTGTCAGATGCCACAGCTCAGCTGGTTAGCGGCACGAGCAGCCTGCTCGACATCGTCGTAGTATTCTTTGTCCTGGAGTTCCTGTACACAGGCC  400

KETO2.seq  TTTTTATCACCACGCATGATGCTATGCATGGCACCATCGCCATGAGAAACAGGCAGCTTAATGACTTCTTGGGCAGAGTATGCATCTCCTTGTACGCCTG  500
X86782.seq TTTTTATCACCACGCATGATGCTATGCATGGCACCATCGCCATGAGAAACAGGCAGCTTAATGACTTCTTGGGCAGAGTATGCATCTCCTTGTACGCCTG  500

KETO2.seq  GTTTGATTACAACATGCTGCACCGCAAGCATTGGGAGCACCACAACCACACTGGCGAGGTGGGCAAGGACCCTGACTTCCACAGGGGAAACCCTGGCATT  600
X86782.seq GTTTGATTACAACATGCTGCACCGCAAGCATTGGGAGCACCACAACCACACTGGCGAGGTGGGCAAGGACCCTGACTTCCACAGGGGAAACCCTGGCATT  600

KETO2.seq  GTGCCCTGGTTTGCCAGCTTCATGTCCAGCTACATGTCGATGTGGCAGTTTGCGCGCCTCGCATGGTGGACGGTGGTCATGCAGCTGCTGGGTGCGCCAA  700
X86782.seq GTGCCCTGGTTTGCCAGCTTCATGTCCAGCTACATGTCGATGTGGCAGTTTGCGCGCCTCGCATGGTGGACGGTGGTCATGCAGCTGCTGGGTGCGCCAA  700

KETO2.seq  TGGCGAACCTGCTGGTGTTCATGGCGGCCGCGCCCATCCTGTCCGCCTTCCGCTTGTTCTACTTTGGCACGTACATGCCCCACAAGCCTGAGCCTGGCGC  800
X86782.seq TGGCGAACCTGCTGGTGTTCATGGCGGCCGCGCCCATCCTGTCCGCCTTCCGCTTGTTCTACTTTGGCACGTACATGCCCCACAAGCCTGAGCCTGGCGC  800

KETO2.seq  CGCGTCAGGCTCTTCACCAGCCGTCATGAACTGGTGGAAGTCGCGCACTAGCCAGGCGTCCGACCTGGTCAGCTTTCTGACCTGCTACCACTTCGACCTG  900
X86782.seq CGCGTCAGGCTCTTCACCAGCCGTCATGAACTGGTGGAAGTCGCGCACTAGCCAGGCGTCCGACCTGGTCAGCTTTCTGACCTGCTACCACTTCGACCTG  900

KETO2.seq  CACTGGGAGCACCACCGCTGGCCCTTTGCCCCCTGGTGGGAGCTGCCCAACTGCCGCCGCCTGTCTGGCCGAGGTCTGGTTCCTGCCTAG             990
X86782.seq CACTGGGAGCACCACCGCTGGCCCTTCGCCCCCTGGTGGGAGCTGCCCAACTGCCGCCGCCTGTCTGGCCGAGGTCTGGTTCCTGCCTAG             990
```

Figure 2: Protein sequence comparison

```
KETO2.pro   M Q L A A T V M L E Q L T G S A E A L K E K E K E V A G S S D V L R T W A T Q Y S L P S E E S D A A   50
X86782.pro  M Q L A A T V M L E Q L T G S A E A L K E K E K E V A G S S D V L R T W A T Q Y S L P S E E S D A A   50

KETO2.pro   R P G L K N A Y K P P P S D T K G I T M A L A V I G S W A A V F L H A I F Q I K L P T S L D Q L H W   100
X86782.pro  R P G L K N A Y K P P P S D T K G I T M A L R V I G S W A A V F L H A I F Q I K L P T S L D Q L H W   100

KETO2.pro   L P V S D A T A Q L V S G S S S L L H I V V V F F V L E F L Y T G L F I T T H D A M H G T I A M R N   150
X86782.pro  L P V S D A T A Q L V S G T S S L L D I V V V F F V L E F L Y T G L F I T T H D A M H G T I A M R N   150

KETO2.pro   R Q L N D F L G R V C I S L Y A W F D Y N M L H R K H W E H H N H T G E V G K D P D F H R G N P G I   200
X86782.pro  R Q L N D F L G R V C I S L Y A W F D Y N M L H R K H W E H H N H T G E V G K D P D F H R G N P G I   200

KETO2.pro   V P W F A S F M S S Y M S M W Q F A R L A W W T V V M Q L L G A P M A N L L V F M A A A P I L S A F   250
X86782.pro  V P W F A S F M S S Y M S M W Q F A R L A W W T V V M Q L L G A P M A N L L V F M A A A P I L S A F   250

KETO2.pro   R L F Y F G T Y M P H K P E P G A A S G S S P A V M N W W K S R T S Q A S D L V S F L T C Y H F D L   300
X86782.pro  R L F Y F G T Y M P H K P E P G A A S G S S P A V M N W W K S R T S Q A S D L V S F L T C Y H F D L   300

KETO2.pro   H W E H H R W P F A P W W E L P N C R R L S G R G L V P A                                           329
X86782.pro  H W E H H R W P F A P W W E L P N C R R L S G R G L V P A                                           329
```

Figure 3: Construct for the overexpression of the ketolase (β-C-4-oxygenase) protein from *H. pluvialis* using rbcS transit peptide from pea under the control of the d35S promoter (Tagetes transformation construct)
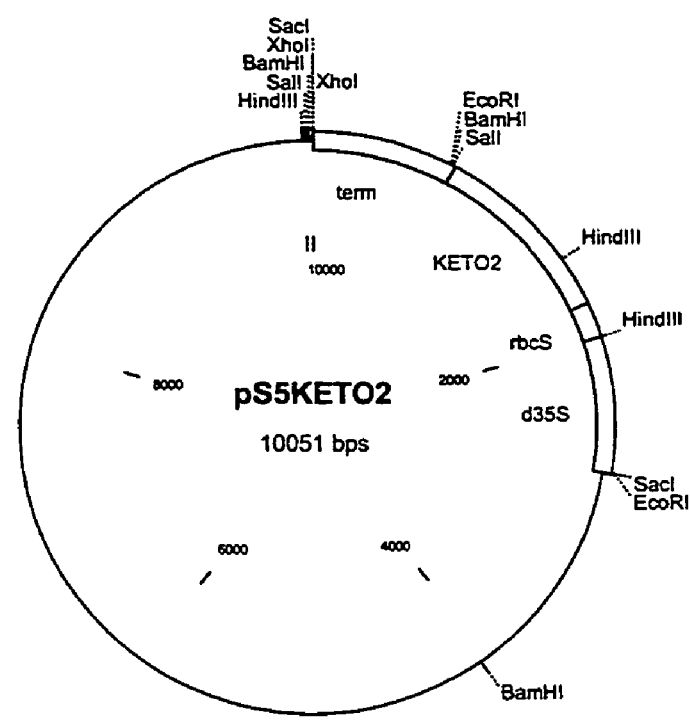

Figure 4: Construct pS5AP3PKETO2 for the overexpression of the ketolase (β-C-4-oxygenase) proteins from H. pluvialis using rbcS transit peptide from pea under the control of the AP3P promoter (Tagetes transformation construct)
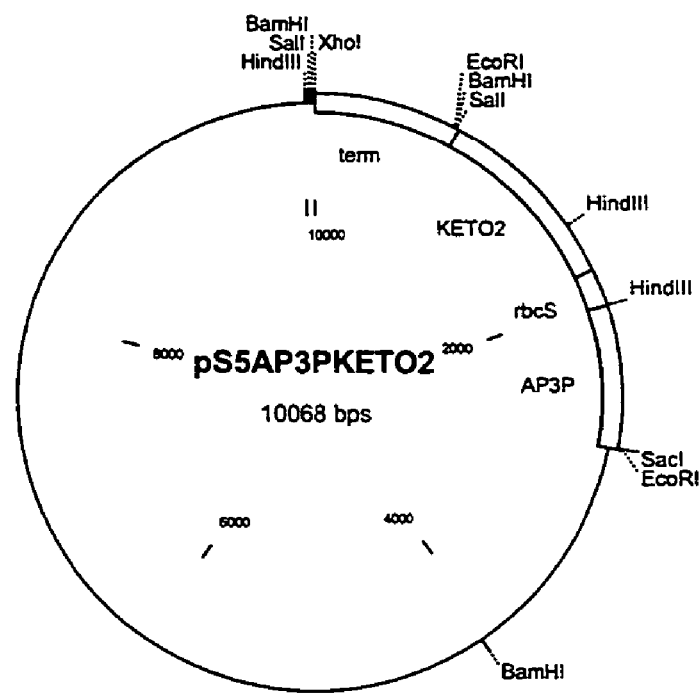

Figure 7: Cloning cassette for producing inverted-repeat expression cassettes for the flower-specific expression of epsilon-cyclase dsRNAs in Tagetes erecta
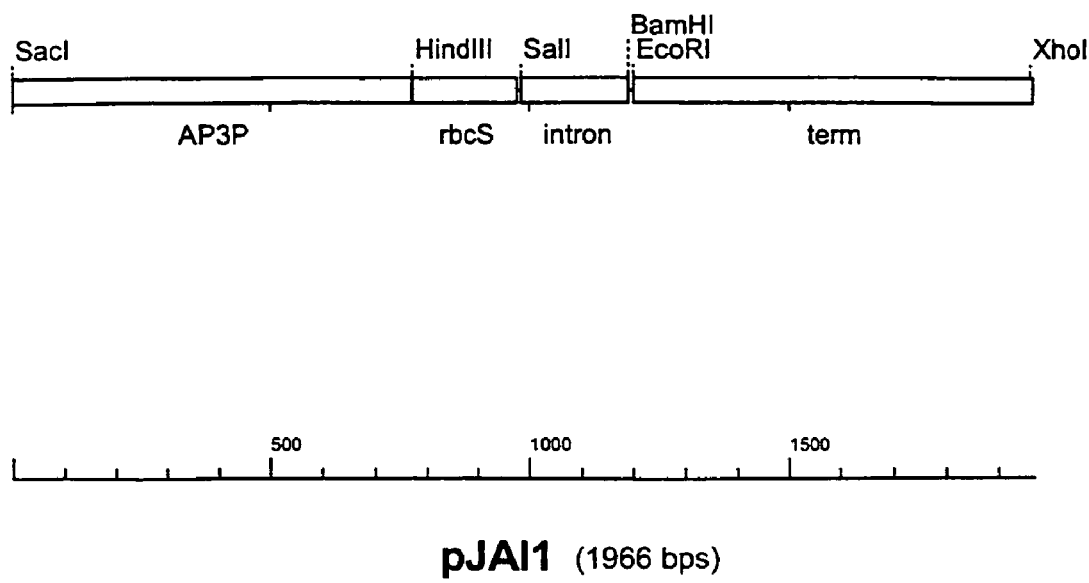
pJAI1 (1966 bps)

Figure 8: Expression vector for the flower-specific production of dsRNA transcripts comprising 5'-terminal fragments of the epsilon-cyclase cDNA (AF251016) under the control of the AP3P promoter
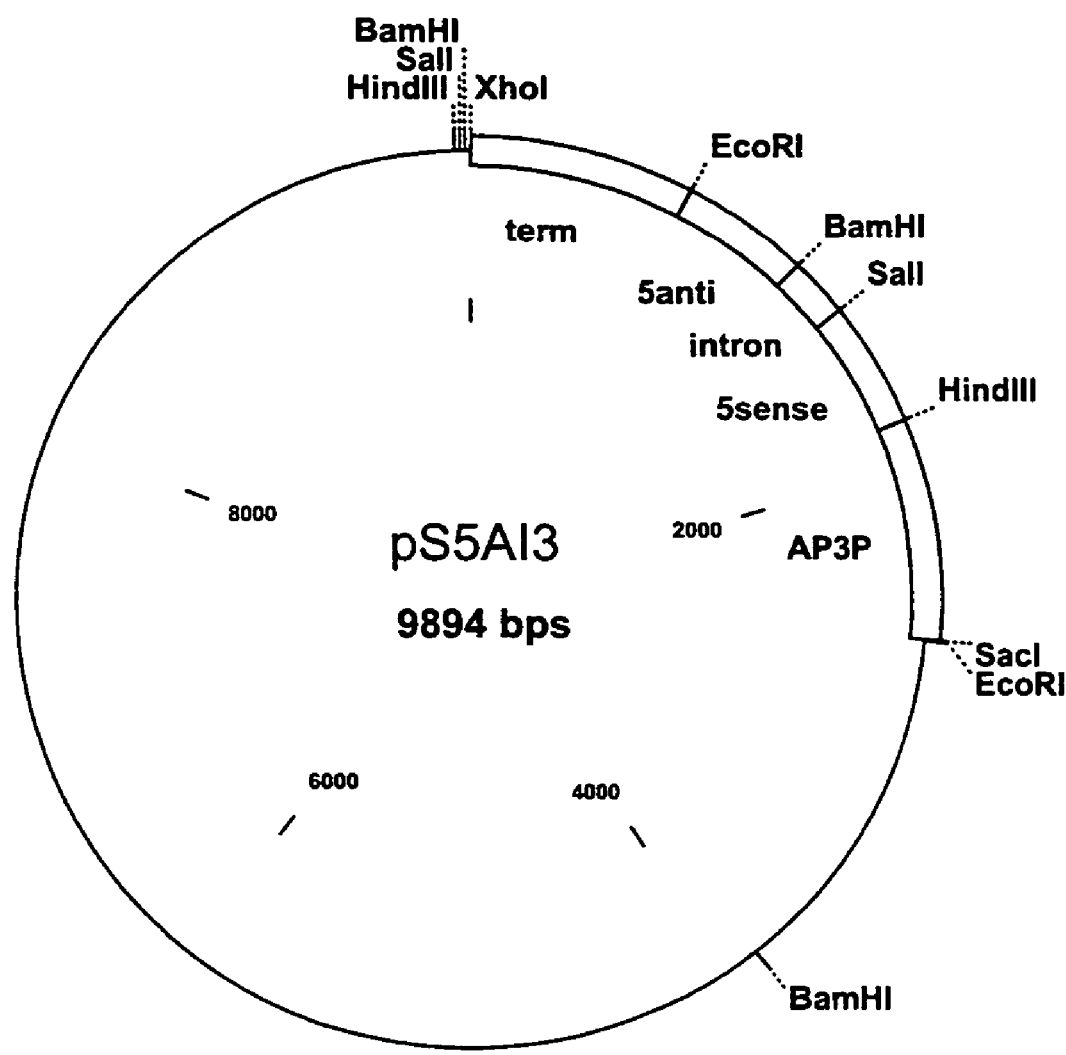

Figure 9: Expression vector for the flower-specific production of dsRNA transcripts comprising 5'-terminal fragments of the epsilon-cyclase cDNA (AF251016) under the control of the CHRC promoter
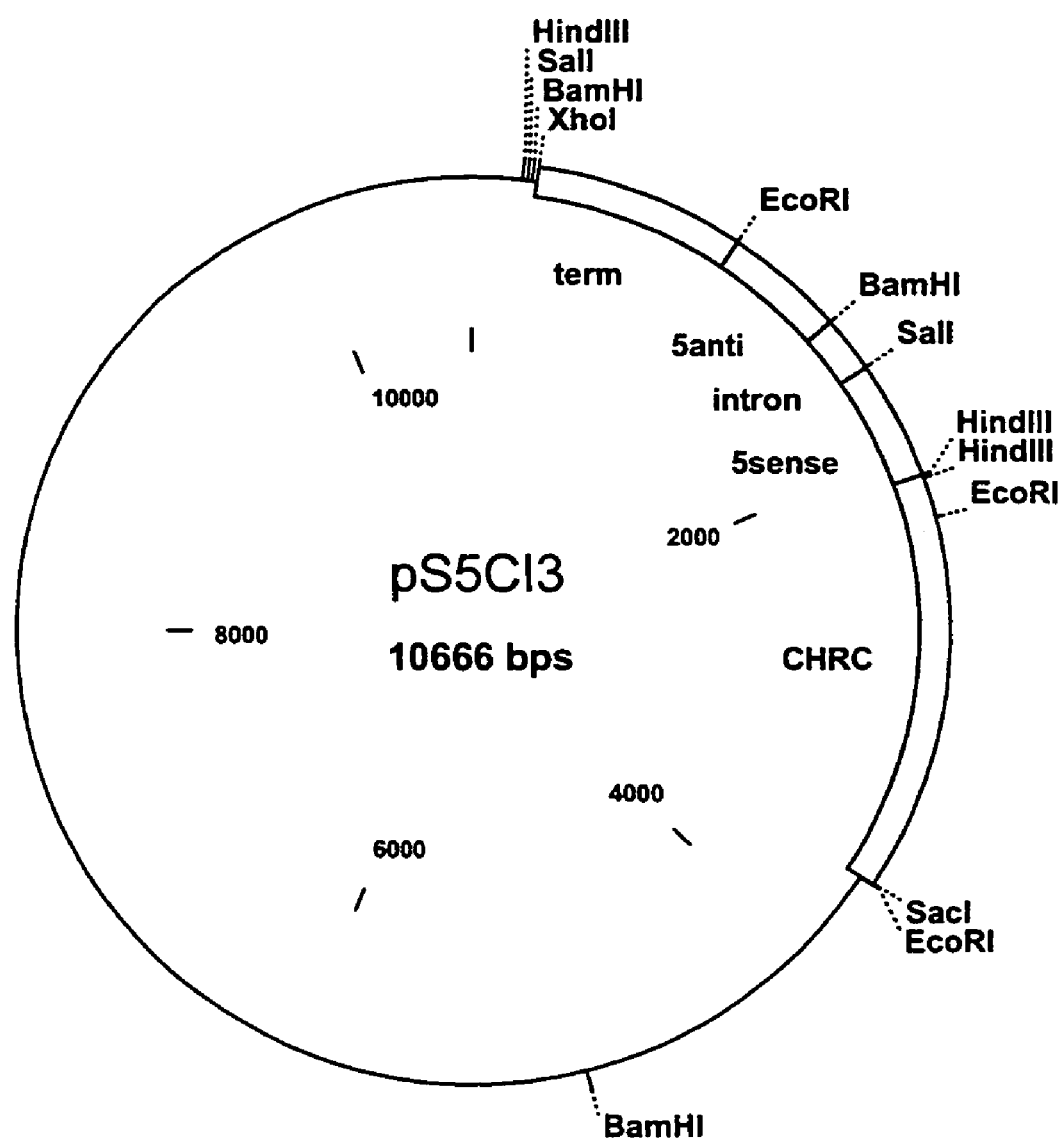

Figure 10: Expression vector for the flower-specific production of dsRNA transcripts comprising 3'-terminal fragments of the epsilon-cyclase cDNA (AF251016) under the control of the AP3P promoter
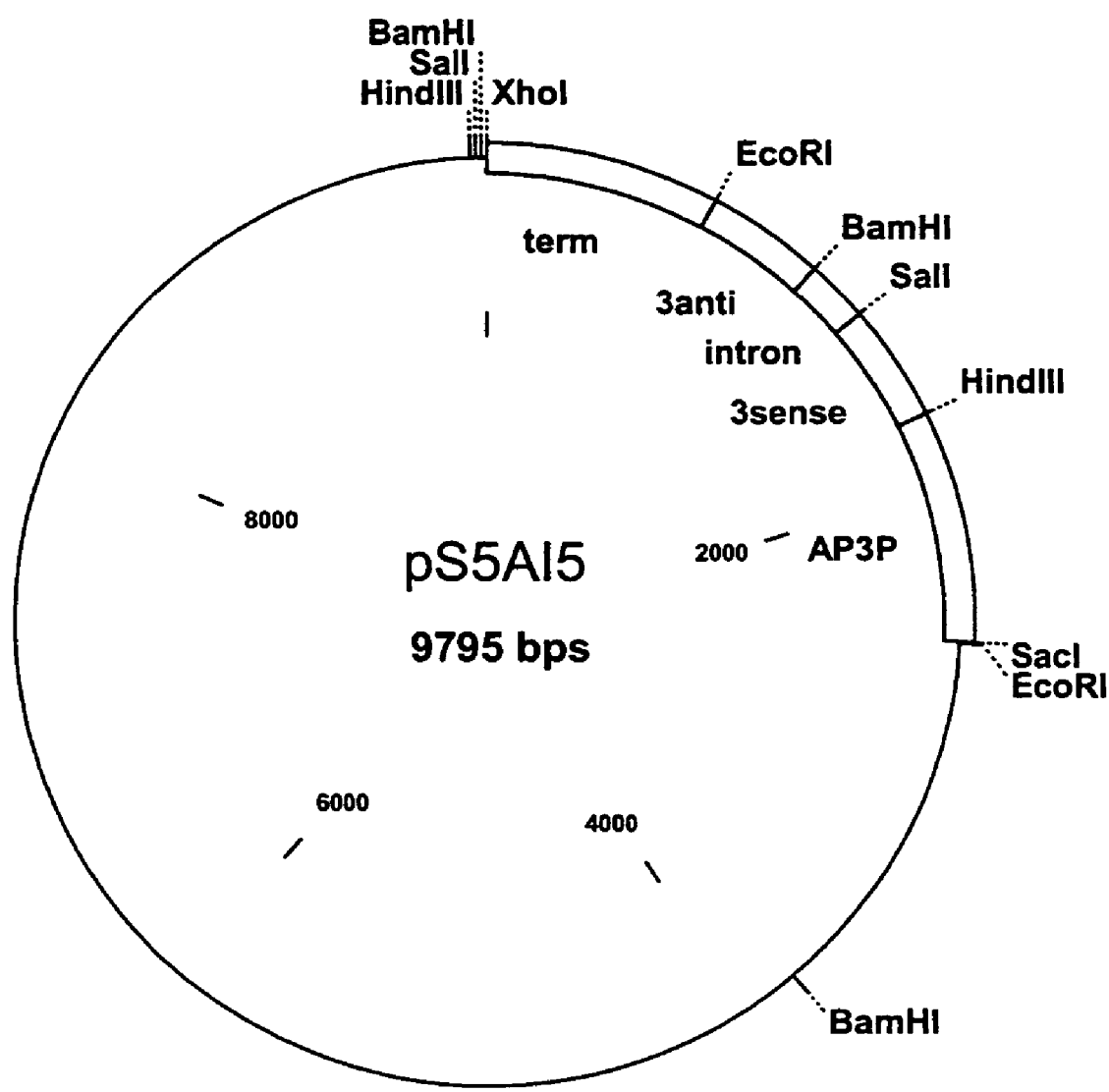

Figure 11: Inverse PCR amplicon which comprises the 312 bp fragment of the epsilon-cyclase promoter
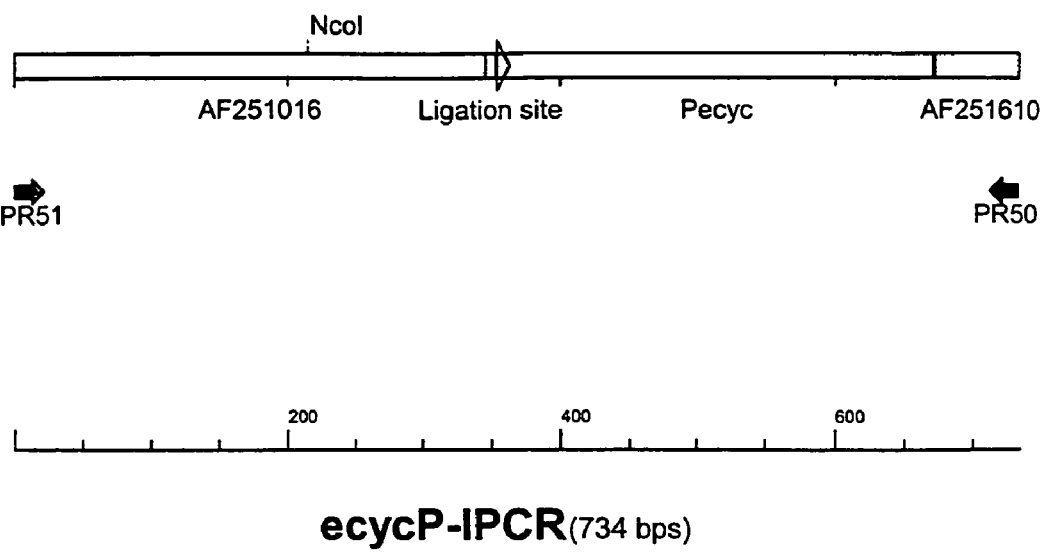

Figure 12: TAIL PCR amplicon which comprises the 199 bp fragment of the epsilon-cyclase promoter
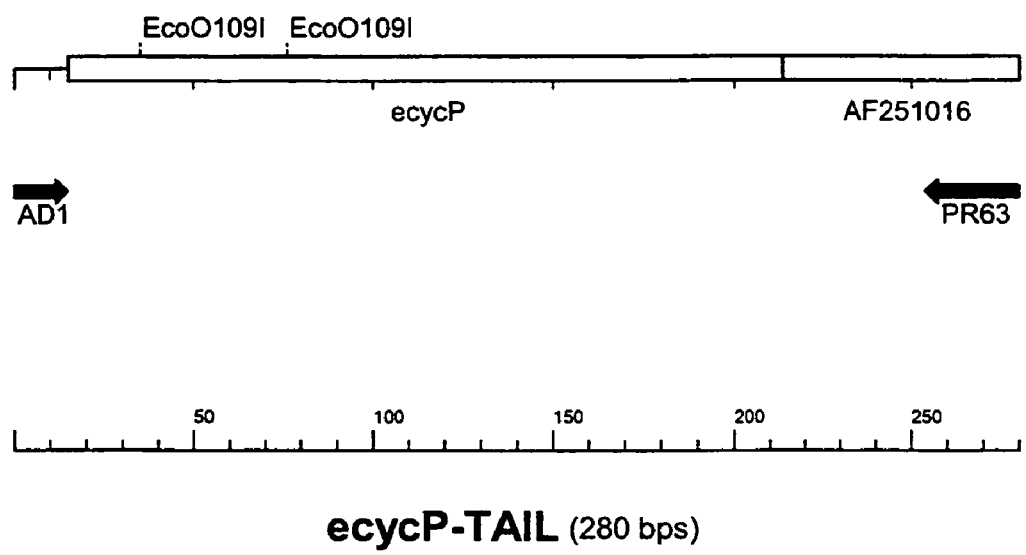

Figure 13: Expression vector for the flower-specific production of dsRNA transcripts comprising the 312 bp promoter fragment of epsilon-cyclase under the control of the AP3P promoter
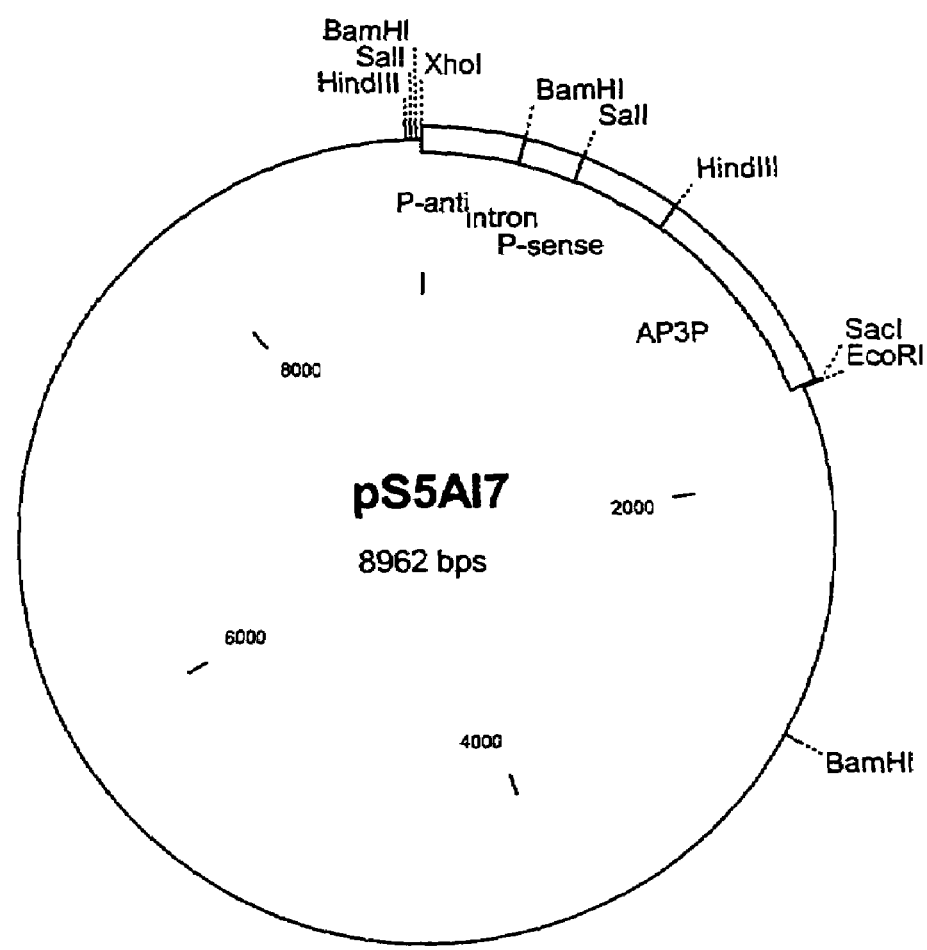

Figure 14: Expression vector for the flower-specific production of dsRNA transcripts comprising the 312 bp promoter fragment of epsilon-cyclase under the control of the CHRC promoter
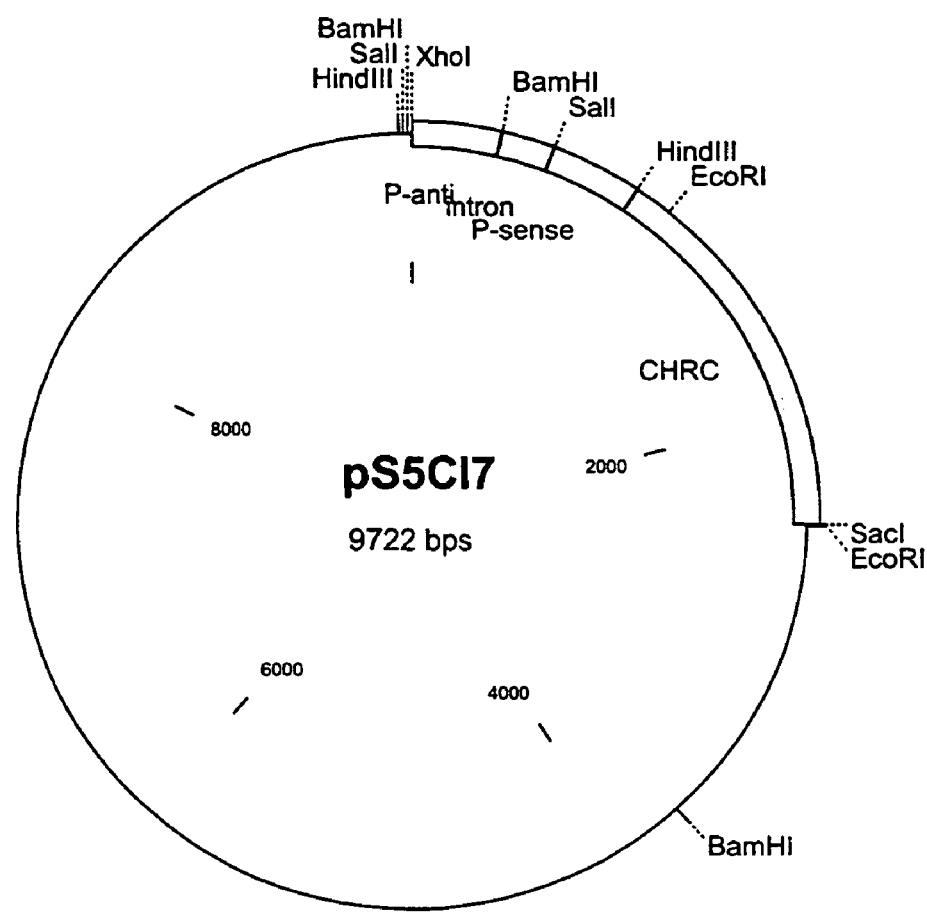

Figure 15: Expression vector for the flower-specific production of dsRNA transcripts comprising the 312 bp promoter fragment of epsilon-cyclase under the control not only of the AP3P promoter, but also the CHRC promoter
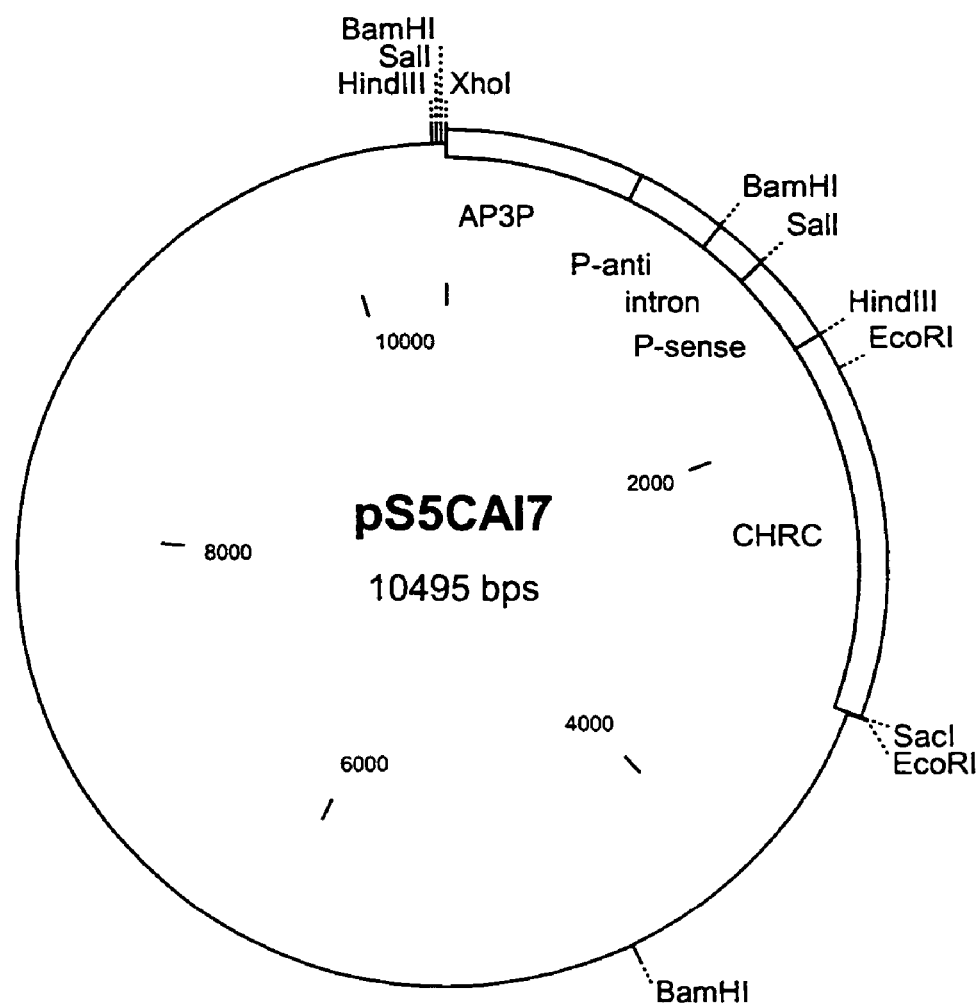

SEQUENCE LISTING

<160> NUMBER OF SEQ ID NOS: 142

<210> SEQ ID NO 1
<211> LENGTH: 1771
<212> TYPE: DNA
<213> ORGANISM: Haematococcus pluvialis
<220> FEATURE:
<221> NAME/KEY: CDS
<222> LOCATION: (166)..(1155)

<400> SEQUENCE: 1

```
ggcacgagct tgcacgcaag tcagcgcgcg caagtcaaca cctgccggtc cacagcctca      60
aataataaag agctcaagcg tttgtgcgcc tcgacgtggc cagtctgcac tgccttgaac     120
ccgcgagtct cccgccgcac tgactgccat agcacagcta gacga atg cag cta gca    177
                                              Met Gln Leu Ala
                                                1 gcg aca gta atg ttg gag cag ctt acc gga agc gct gag gca ctc aag      225
Ala Thr Val Met Leu Glu Gln Leu Thr Gly Ser Ala Glu Ala Leu Lys
5                   10                  15                  20 gag aag gag aag gag gtt gca ggc agc tct gac gtg ttg cgt aca tgg      273
Glu Lys Glu Lys Glu Val Ala Gly Ser Ser Asp Val Leu Arg Thr Trp
                25                  30                  35 gcg acc cag tac tcg ctt ccg tca gaa gag tca gac gcg gcc cgc ccg      321
Ala Thr Gln Tyr Ser Leu Pro Ser Glu Glu Ser Asp Ala Ala Arg Pro
            40                  45                  50
```

```
                                                              -continued gga ctg aag aat gcc tac aag cca cca cct tcc gac aca aag ggc atc         369
Gly Leu Lys Asn Ala Tyr Lys Pro Pro Pro Ser Asp Thr Lys Gly Ile
         55                   60                  65 aca atg gcg cta cgt gtc atc ggc tcc tgg gcc gca gtg ttc ctc cac         417
Thr Met Ala Leu Arg Val Ile Gly Ser Trp Ala Ala Val Phe Leu His
     70                   75                  80 gcc att ttt caa atc aag ctt ccg acc tcc ttg gac cag ctg cac tgg         465
Ala Ile Phe Gln Ile Lys Leu Pro Thr Ser Leu Asp Gln Leu His Trp
 85                   90                  95                 100 ctg ccc gtg tca gat gcc aca gct cag ctg gtt agc ggc acg agc agc         513
Leu Pro Val Ser Asp Ala Thr Ala Gln Leu Val Ser Gly Thr Ser Ser
                 105                 110                 115 ctg ctc gac atc gtc gta gta ttc ttt gtc ctg gag ttc ctg tac aca         561
Leu Leu Asp Ile Val Val Val Phe Phe Val Leu Glu Phe Leu Tyr Thr
                 120                 125                 130 ggc ctt ttt atc acc acg cat gat gct atg cat ggc acc atc gcc atg         609
Gly Leu Phe Ile Thr Thr His Asp Ala Met His Gly Thr Ile Ala Met
         135                 140                 145 aga aac agg cag ctt aat gac ttc ttg ggc aga gta tgc atc tcc ttg         657
Arg Asn Arg Gln Leu Asn Asp Phe Leu Gly Arg Val Cys Ile Ser Leu
 150                 155                 160 tac gcc tgg ttt gat tac aac atg ctg cac cgc aag cat tgg gag cac         705
Tyr Ala Trp Phe Asp Tyr Asn Met Leu His Arg Lys His Trp Glu His
165                 170                 175                 180 cac aac cac act ggc gag gtg ggc aag gac cct gac ttc cac agg gga         753
His Asn His Thr Gly Glu Val Gly Lys Asp Pro Asp Phe His Arg Gly
                 185                 190                 195 aac cct ggc att gtg ccc tgg ttt gcc agc ttc atg tcc agc tac atg         801
Asn Pro Gly Ile Val Pro Trp Phe Ala Ser Phe Met Ser Ser Tyr Met
         200                 205                 210 tcg atg tgg cag ttt gcg cgc ctc gca tgg tgg acg gtg gtc atg cag         849
Ser Met Trp Gln Phe Ala Arg Leu Ala Trp Trp Thr Val Val Met Gln
         215                 220                 225 ctg ctg ggt gcg cca atg gcg aac ctg ctg gtg ttc atg gcg gcc gcg         897
Leu Leu Gly Ala Pro Met Ala Asn Leu Leu Val Phe Met Ala Ala Ala
 230                 235                 240 ccc atc ctg tcc gcc ttc cgc ttg ttc tac ttt ggc acg tac atg ccc         945
Pro Ile Leu Ser Ala Phe Arg Leu Phe Tyr Phe Gly Thr Tyr Met Pro
245                 250                 255                 260 cac aag cct gag cct ggc gcc gcg tca ggc tct tca cca gcc gtc atg         993
His Lys Pro Glu Pro Gly Ala Ala Ser Gly Ser Ser Pro Ala Val Met
                 265                 270                 275 aac tgg tgg aag tcg cgc act agc cag gcg tcc gac ctg gtc agc ttt        1041
Asn Trp Trp Lys Ser Arg Thr Ser Gln Ala Ser Asp Leu Val Ser Phe
         280                 285                 290 ctg acc tgc tac cac ttc gac ctg cac tgg gag cac cac cgc tgg ccc        1089
Leu Thr Cys Tyr His Phe Asp Leu His Trp Glu His His Arg Trp Pro
         295                 300                 305 ttc gcc ccc tgg tgg gag ctg ccc aac tgc cgc cgc ctg tct ggc cga        1137
Phe Ala Pro Trp Trp Glu Leu Pro Asn Cys Arg Arg Leu Ser Gly Arg
         310                 315                 320 ggt ctg gtt cct gcc tag ctggacacac tgcagtgggc cctgctgcca               1185
Gly Leu Val Pro Ala
325 gctgggcatg caggttgtgg caggactggg tgaggtgaaa agctgcaggc gctgctgccg      1245 gacacgctgc atgggctacc ctgtgtagct gccgccacta ggggaggggg tttgtagctg      1305 tcgagcttgc cccatggatg aagctgtgta gtggtcagg gagtacaccc acaggccaac       1365 acccttgcag gagatgtctt gcgtcgggag gagtgttggg cagtgtagat gctatgattg      1425
```

```
tatcttaatg ctgaagcctt taggggagcg acacttagtg ctgggcaggc aacgccctgc    1485
aaggtgcagg cacaagctag gctggacgag gactcggtgg caggcaggtg aagaggtgcg    1545
ggagggtggt gccacaccca ctgggcaaga ccatgctgca atgctggcgg tgtggcagtg    1605
agagctgcgt gattaactgg gctatggatt gtttgagcag tctcacttat tctttgatat    1665
agatactggt caggcaggtc aggagagtga gtatgaacaa gttgagaggt ggtgcgctgc    1725
ccctgcgctt atgaagctgt aacaataaag tggttcaaaa aaaaaa                    1771
```

<210> SEQ ID NO 2
<211> LENGTH: 329
<212> TYPE: PRT
<213> ORGANISM: Haematococcus pluvialis

<400> SEQUENCE: 2

```
Met Gln Leu Ala Ala Thr Val Met Leu Glu Gln Leu Thr Gly Ser Ala
1               5                   10                  15

Glu Ala Leu Lys Glu Lys Glu Lys Val Ala Gly Ser Ser Asp Val
            20                  25                  30

Leu Arg Thr Trp Ala Thr Gln Tyr Ser Leu Pro Ser Glu Glu Ser Asp
        35                  40                  45

Ala Ala Arg Pro Gly Leu Lys Asn Ala Tyr Lys Pro Pro Ser Asp
    50                  55                  60

Thr Lys Gly Ile Thr Met Ala Leu Arg Val Ile Gly Ser Trp Ala Ala
65                  70                  75                  80

Val Phe Leu His Ala Ile Phe Gln Ile Lys Leu Pro Thr Ser Leu Asp
                85                  90                  95

Gln Leu His Trp Leu Pro Val Ser Asp Ala Thr Ala Gln Leu Val Ser
            100                 105                 110

Gly Thr Ser Ser Leu Leu Asp Ile Val Val Val Phe Val Leu Glu
        115                 120                 125

Phe Leu Tyr Thr Gly Leu Phe Ile Thr Thr His Asp Ala Met His Gly
130                 135                 140

Thr Ile Ala Met Arg Asn Arg Gln Leu Asn Asp Phe Leu Gly Arg Val
145                 150                 155                 160

Cys Ile Ser Leu Tyr Ala Trp Phe Asp Tyr Asn Met Leu His Arg Lys
                165                 170                 175

His Trp Glu His His Asn His Thr Gly Glu Val Gly Lys Asp Pro Asp
            180                 185                 190

Phe His Arg Gly Asn Pro Gly Ile Val Pro Trp Phe Ala Ser Phe Met
        195                 200                 205

Ser Ser Tyr Met Ser Met Trp Gln Phe Ala Arg Leu Ala Trp Trp Thr
    210                 215                 220

Val Val Met Gln Leu Leu Gly Ala Pro Met Ala Asn Leu Leu Val Phe
225                 230                 235                 240

Met Ala Ala Pro Ile Leu Ser Ala Phe Arg Leu Phe Tyr Phe Gly
                245                 250                 255

Thr Tyr Met Pro His Lys Pro Gly Ala Ala Ser Gly Ser
            260                 265                 270

Pro Ala Val Met Asn Trp Trp Lys Ser Arg Thr Ser Gln Ala Ser Asp
        275                 280                 285

Leu Val Ser Phe Leu Thr Cys Tyr His Phe Asp Leu His Trp Glu His
    290                 295                 300
```

-continued

```
            His Arg Trp Pro Phe Ala Pro Trp Trp Glu Leu Pro Asn Cys Arg Arg
            305                 310                 315                 320

Leu Ser Gly Arg Gly Leu Val Pro Ala
                        325

<210> SEQ ID NO 3
<211> LENGTH: 1662
<212> TYPE: DNA
<213> ORGANISM: Haematococcus pluvialis
<220> FEATURE:
<221> NAME/KEY: CDS
<222> LOCATION: (168)..(1130)

<400> SEQUENCE: 3
cggggcaact caagaaattc aacagctgca agcgcgcccc agcctcacag cgccaagtga      60
gctatcgacg tggttgtgag cgctcgacgt ggtccactga cgggcctgtg agcctctgcg     120
ctccgtcctc tgccaaatct cgcgtcgggg cctgcctaag tcgaaga atg cac gtc       176
                                                  Met His Val
                                                    1 gca tcg gca cta atg gtc gag cag aaa ggc agt gag gca gct gct tcc       224
Ala Ser Ala Leu Met Val Glu Gln Lys Gly Ser Glu Ala Ala Ala Ser
        5                  10                  15 agc cca gac gtc ttg aga gcg tgg gcg aca cag tat cac atg cca tcc       272
Ser Pro Asp Val Leu Arg Ala Trp Ala Thr Gln Tyr His Met Pro Ser
 20                  25                  30                  35 gag tcg tca gac gca gct cgt cct gcg cta aag cac gcc tac aaa cct       320
Glu Ser Ser Asp Ala Ala Arg Pro Ala Leu Lys His Ala Tyr Lys Pro
                 40                  45                  50 cca gca tct gac gcc aag ggc atc acg atg gcg ctg acc atc att ggc       368
Pro Ala Ser Asp Ala Lys Gly Ile Thr Met Ala Leu Thr Ile Ile Gly
             55                  60                  65 acc tgg acc gca gtg ttt tta cac gca ata ttt caa atc agg cta ccg       416
Thr Trp Thr Ala Val Phe Leu His Ala Ile Phe Gln Ile Arg Leu Pro
         70                  75                  80 aca tcc atg gac cag ctt cac tgg ttg cct gtg tcc gaa gcc aca gcc       464
Thr Ser Met Asp Gln Leu His Trp Leu Pro Val Ser Glu Ala Thr Ala
     85                  90                  95 cag ctt ttg ggc gga agc agc agc cta ctg cac atc gct gca gtc ttc       512
Gln Leu Leu Gly Gly Ser Ser Ser Leu Leu His Ile Ala Ala Val Phe
100                 105                 110                 115 att gta ctt gag ttc ctg tac act ggt cta ttc atc acc aca cat gac       560
Ile Val Leu Glu Phe Leu Tyr Thr Gly Leu Phe Ile Thr Thr His Asp
                120                 125                 130 gca atg cat ggc acc ata gct ttg agg cac agg cag ctc aat gat ctc       608
Ala Met His Gly Thr Ile Ala Leu Arg His Arg Gln Leu Asn Asp Leu
            135                 140                 145 ctt ggc aac atc tgc ata tca ctg tac gcc tgg ttt gac tac agc atg       656
Leu Gly Asn Ile Cys Ile Ser Leu Tyr Ala Trp Phe Asp Tyr Ser Met
        150                 155                 160 ctg cat cgc aag cac tgg gag cac cac aac cat act ggc gaa gtg ggg       704
Leu His Arg Lys His Trp Glu His His Asn His Thr Gly Glu Val Gly
    165                 170                 175 aaa gac cct gac ttc cac aag gga aat ccc ggc ctt gtc ccc tgg ttc       752
Lys Asp Pro Asp Phe His Lys Gly Asn Pro Gly Leu Val Pro Trp Phe
180                 185                 190                 195 gcc agc ttc atg tcc agc tac atg tcc ctg tgg cag ttt gcc cgg ctg       800
Ala Ser Phe Met Ser Ser Tyr Met Ser Leu Trp Gln Phe Ala Arg Leu
                200                 205                 210
```

```
gca tgg tgg gca gtg gtg atg caa atg ctg ggg gcg ccc atg gca aat         848
Ala Trp Trp Ala Val Val Met Gln Met Leu Gly Ala Pro Met Ala Asn
            215                 220                 225 ctc cta gtc ttc atg gct gca gcc cca atc ttg tca gca ttc cgc ctc         896
Leu Leu Val Phe Met Ala Ala Ala Pro Ile Leu Ser Ala Phe Arg Leu
            230                 235                 240 ttc tac ttc ggc act tac ctg cca cac aag cct gag cca ggc cct gca         944
Phe Tyr Phe Gly Thr Tyr Leu Pro His Lys Pro Glu Pro Gly Pro Ala
        245                 250                 255 gca ggc tct cag gtg atg gcc tgg ttc agg gcc aag aca agt gag gca         992
Ala Gly Ser Gln Val Met Ala Trp Phe Arg Ala Lys Thr Ser Glu Ala
    260                 265                 270                 275 tct gat gtg atg agt ttc ctg aca tgc tac cac ttt gac ctg cac tgg        1040
Ser Asp Val Met Ser Phe Leu Thr Cys Tyr His Phe Asp Leu His Trp
                280                 285                 290 gag cac cac agg tgg ccc ttt gcc ccc tgg tgg cag ctg ccc cac tgc        1088
Glu His His Arg Trp Pro Phe Ala Pro Trp Trp Gln Leu Pro His Cys
            295                 300                 305 cgc cgc ctg tcc ggg cgt ggc ctg gtg cct gcc ttg gca tga                1130
Arg Arg Leu Ser Gly Arg Gly Leu Val Pro Ala Leu Ala
            310                 315                 320 cctggtccct ccgctggtga cccagcgtct gcacaagagt gtcatgctac agggtgctgc      1190
ggccagtggc agcgcagtgc actctcagcc tgtatgggc taccgctgtg ccactgagca      1250
ctgggcatgc cactgagcac tgggcgtgct actgagcaat gggcgtgcta ctgagcaatg     1310
ggcgtgctac tgacaatggg cgtgctactg ggtctggca gtggctagga tggagtttga     1370
tgcattcagt agcggtggcc aacgtcatgt ggatggtgga agtgctgagg ggtttaggca     1430
gccggcattt gagagggcta agttataaat cgcatgctgc tcatgcgcac atatctgcac     1490
acagccaggg aaatcccttc gagagtgatt atgggacact tgtattggtt tcgtgctatt     1550
gttttattca gcagcagtac ttagtgaggg tgagagcagg gtggtgagag tggagtgagt     1610
gagtatgaac ctggtcagcg aggtgaacag cctgtaatga atgactctgt ct            1662

<210> SEQ ID NO 4
<211> LENGTH: 320
<212> TYPE: PRT
<213> ORGANISM: Haematococcus pluvialis

<400> SEQUENCE: 4

Met His Val Ala Ser Ala Leu Met Val Glu Gln Lys Gly Ser Glu Ala
1               5                   10                  15

Ala Ala Ser Ser Pro Asp Val Leu Arg Ala Trp Ala Thr Gln Tyr His
            20                  25                  30

Met Pro Ser Glu Ser Ser Asp Ala Ala Arg Pro Ala Leu Lys His Ala
        35                  40                  45

Tyr Lys Pro Pro Ala Ser Asp Ala Lys Gly Ile Thr Met Ala Leu Thr
    50                  55                  60

Ile Ile Gly Thr Trp Thr Ala Val Phe Leu His Ala Ile Phe Gln Ile
65                  70                  75                  80

Arg Leu Pro Thr Ser Met Asp Gln Leu His Trp Leu Pro Val Ser Glu
                85                  90                  95

Ala Thr Ala Gln Leu Leu Gly Gly Ser Ser Leu Leu His Ile Ala
            100                 105                 110

Ala Val Phe Ile Val Leu Glu Phe Leu Tyr Thr Gly Leu Phe Ile Thr
        115                 120                 125
```

-continued

Thr His Asp Ala Met His Gly Thr Ile Ala Leu Arg His Arg Gln Leu
        130                 135                 140

Asn Asp Leu Leu Gly Asn Ile Cys Ile Ser Leu Tyr Ala Trp Phe Asp
145                 150                 155                 160

Tyr Ser Met Leu His Arg Lys His Trp Glu His His Asn His Thr Gly
                165                 170                 175

Glu Val Gly Lys Asp Pro Asp Phe His Lys Gly Asn Pro Gly Leu Val
            180                 185                 190

Pro Trp Phe Ala Ser Phe Met Ser Ser Tyr Met Ser Leu Trp Gln Phe
        195                 200                 205

Ala Arg Leu Ala Trp Trp Ala Val Val Met Gln Met Leu Gly Ala Pro
    210                 215                 220

Met Ala Asn Leu Leu Val Phe Met Ala Ala Pro Ile Leu Ser Ala
225                 230                 235                 240

Phe Arg Leu Phe Tyr Phe Gly Thr Tyr Leu Pro His Lys Pro Glu Pro
                245                 250                 255

Gly Pro Ala Ala Gly Ser Gln Val Met Ala Trp Phe Arg Ala Lys Thr
            260                 265                 270

Ser Glu Ala Ser Asp Val Met Ser Phe Leu Thr Cys Tyr His Phe Asp
        275                 280                 285

Leu His Trp Glu His His Arg Trp Pro Phe Ala Pro Trp Trp Gln Leu
    290                 295                 300

Pro His Cys Arg Arg Leu Ser Gly Arg Gly Leu Val Pro Ala Leu Ala
305                 310                 315                 320

<210> SEQ ID NO 5
<211> LENGTH: 729
<212> TYPE: DNA
<213> ORGANISM: Agrobacterium aurantiacum
<220> FEATURE:
<221> NAME/KEY: CDS
<222> LOCATION: (1)..(729)

<400> SEQUENCE: 5

```
atg agc gca cat gcc ctg ccc aag gca gat ctg acc gcc acc agc ctg      48
Met Ser Ala His Ala Leu Pro Lys Ala Asp Leu Thr Ala Thr Ser Leu
1               5                   10                  15 atc gtc tcg ggc ggc atc atc gcc gct tgg ctg gcc ctg cat gtg cat      96
Ile Val Ser Gly Gly Ile Ile Ala Ala Trp Leu Ala Leu His Val His
                20                  25                  30 gcg ctg tgg ttt ctg gac gca gcg gcg cat ccc atc ctg gcg atc gca     144
Ala Leu Trp Phe Leu Asp Ala Ala Ala His Pro Ile Leu Ala Ile Ala
            35                  40                  45 aat ttc ctg ggg ctg acc tgg ctg tcg gtc gga ttg ttc atc atc gcg     192
Asn Phe Leu Gly Leu Thr Trp Leu Ser Val Gly Leu Phe Ile Ile Ala
        50                  55                  60 cat gac gcg atg cac ggg tcg gtg gtg ccg ggg cgt ccg cgc gcc aat     240
His Asp Ala Met His Gly Ser Val Val Pro Gly Arg Pro Arg Ala Asn
65                  70                  75                  80 gcg gcg atg ggc cag ctt gtc ctg tgg ctg tat gcc gga ttt tcg tgg     288
Ala Ala Met Gly Gln Leu Val Leu Trp Leu Tyr Ala Gly Phe Ser Trp
                85                  90                  95 cgc aag atg atc gtc aag cac atg gcc cat cac cgc cat gcc gga acc     336
Arg Lys Met Ile Val Lys His Met Ala His His Arg His Ala Gly Thr
                100                 105                 110 gac gac gac ccc gat ttc gac cat ggc ggc ccg gtc cgc tgg tac gcc     384
Asp Asp Asp Pro Asp Phe Asp His Gly Gly Pro Val Arg Trp Tyr Ala
            115                 120                 125
```

```
cgc ttc atc ggc acc tat ttc ggc tgg cgc gag ggg ctg ctg ctg ccc         432
Arg Phe Ile Gly Thr Tyr Phe Gly Trp Arg Glu Gly Leu Leu Leu Pro
    130                 135                 140 gtc atc gtg acg gtc tat gcg ctg atc ctt ggg gat cgc tgg atg tac         480
Val Ile Val Thr Val Tyr Ala Leu Ile Leu Gly Asp Arg Trp Met Tyr
145                 150                 155                 160 gtg gtc ttc tgg ccg ctg ccg tcg atc ctg gcg tcg atc cag ctg ttc         528
Val Val Phe Trp Pro Leu Pro Ser Ile Leu Ala Ser Ile Gln Leu Phe
                165                 170                 175 gtg ttc ggc acc tgg ctg ccg cac cgc ccc ggc cac gac gcg ttc ccg         576
Val Phe Gly Thr Trp Leu Pro His Arg Pro Gly His Asp Ala Phe Pro
            180                 185                 190 gac cgc cac aat gcg cgg tcg tcg cgg atc agc gac ccc gtg tcg ctg         624
Asp Arg His Asn Ala Arg Ser Ser Arg Ile Ser Asp Pro Val Ser Leu
        195                 200                 205 ctg acc tgc ttt cac ttt ggc ggt tat cat cac gaa cac cac ctg cac         672
Leu Thr Cys Phe His Phe Gly Gly Tyr His His Glu His His Leu His
    210                 215                 220 ccg acg gtg ccg tgg tgg cgc ctg ccc agc acc cgc acc aag ggg gac         720
Pro Thr Val Pro Trp Trp Arg Leu Pro Ser Thr Arg Thr Lys Gly Asp
225                 230                 235                 240 acc gca tga                                                             729
Thr Ala <210> SEQ ID NO 6
<211> LENGTH: 242
<212> TYPE: PRT
<213> ORGANISM: Agrobacterium aurantiacum

<400> SEQUENCE: 6

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
                20                  25                  30

Ala Leu Trp Phe Leu Asp Ala Ala Ala His Pro Ile Leu Ala Ile Ala
            35                  40                  45

Asn Phe Leu Gly Leu Thr Trp Leu Ser Val Gly Leu Phe Ile Ile Ala
        50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg Ala Gly Thr
                100                 105                 110

Asp Asp Asp Pro Asp Phe Asp His Gly Gly Pro Val Arg Trp Tyr Ala
            115                 120                 125

Arg Phe Ile Gly Thr Tyr Phe Gly Trp Arg Glu Gly Leu Leu Leu Pro
        130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
```

-continued

```
                210                 215                 220
Pro Thr Val Pro Trp Trp Arg Leu Pro Ser Thr Arg Thr Lys Gly Asp
225                 230                 235                 240

Thr Ala

<210> SEQ ID NO 7
<211> LENGTH: 1631
<212> TYPE: DNA
<213> ORGANISM: Alcaligenes sp.
<220> FEATURE:
<221> NAME/KEY: CDS
<222> LOCATION: (99)..(827)

<400> SEQUENCE: 7
ctgcaggccg ggcccggtgg ccaatggtcg caaccggcag gactggaaca ggacggcggg      60
ccggtctagg ctgtcgccct acgcagcagg agtttcgg atg tcc gga cgg aag cct    116
                                         Met Ser Gly Arg Lys Pro
                                           1               5 ggc aca act ggc gac acg atc gtc aat ctc ggt ctg acc gcc gcg atc      164
Gly Thr Thr Gly Asp Thr Ile Val Asn Leu Gly Leu Thr Ala Ala Ile
            10                  15                  20 ctg ctg tgc tgg ctg gtc ctg cac gcc ttt acg cta tgg ttg cta gat      212
Leu Leu Cys Trp Leu Val Leu His Ala Phe Thr Leu Trp Leu Leu Asp
        25                  30                  35 gcg gcc gcg cat ccg ctg ctt gcc gtg ctg tgc ctg gct ggg ctg acc      260
Ala Ala Ala His Pro Leu Leu Ala Val Leu Cys Leu Ala Gly Leu Thr
    40                  45                  50 tgg ctg tcg gtc ggg ctg ttc atc atc gcg cat gac gca atg cac ggg      308
Trp Leu Ser Val Gly Leu Phe Ile Ile Ala His Asp Ala Met His Gly
55                  60                  65                  70 tcc gtg gtg ccg ggg cgg ccg cgc gcc aat gcg gcg atc ggg caa ctg      356
Ser Val Val Pro Gly Arg Pro Arg Ala Asn Ala Ala Ile Gly Gln Leu
                75                  80                  85 gcg ctg tgg ctc tat gcg ggg ttc tcg tgg ccc aag ctg atc gcc aag      404
Ala Leu Trp Leu Tyr Ala Gly Phe Ser Trp Pro Lys Leu Ile Ala Lys
            90                  95                 100 cac atg acg cat cac cgg cac gcc ggc acc gac aac gat ccc gat ttc      452
His Met Thr His His Arg His Ala Gly Thr Asp Asn Asp Pro Asp Phe
        105                 110                 115 ggt cac gga ggg ccc gtg cgc tgg tac ggc agc ttc gtc tcc acc tat      500
Gly His Gly Gly Pro Val Arg Trp Tyr Gly Ser Phe Val Ser Thr Tyr
    120                 125                 130 ttc ggc tgg cga gag gga ctg ctg cta ccg gtg atc gtc acc acc tat      548
Phe Gly Trp Arg Glu Gly Leu Leu Leu Pro Val Ile Val Thr Thr Tyr
135                 140                 145                 150 gcg ctg atc ctg ggc gat cgc tgg atg tat gtc atc ttc tgg ccg gtc      596
Ala Leu Ile Leu Gly Asp Arg Trp Met Tyr Val Ile Phe Trp Pro Val
                155                 160                 165 ccg gcc gtt ctg gcg tcg atc cag att ttc gtc ttc gga act tgg ctg      644
Pro Ala Val Leu Ala Ser Ile Gln Ile Phe Val Phe Gly Thr Trp Leu
            170                 175                 180 ccc cac cgc ccg gga cat gac gat ttt ccc gac cgg cac aac gcg agg      692
Pro His Arg Pro Gly His Asp Asp Phe Pro Asp Arg His Asn Ala Arg
        185                 190                 195 tcg acc ggc atc ggc gac ccg ttg tca cta ctg acc tgc ttc cat ttc      740
Ser Thr Gly Ile Gly Asp Pro Leu Ser Leu Leu Thr Cys Phe His Phe
    200                 205                 210 ggc ggc tat cac cac gaa cat cac ctg cat ccg cat gtg ccg tgg tgg      788
Gly Gly Tyr His His Glu His His Leu His Pro His Val Pro Trp Trp
215                 220                 225                 230
```

-continued

```
cgc ctg cct cgt aca cgc aag acc gga ggc cgc gca tga cgcaattcct    837
Arg Leu Pro Arg Thr Arg Lys Thr Gly Gly Arg Ala
            235                 240 cattgtcgtg gcgacagtcc tcgtgatgga gctgaccgcc tattccgtcc accgctggat    897
tatgcacggc cccctaggct ggggctggca caagtcccat cacgaagagc acgaccacgc    957
gttggagaag aacgacctct acggcgtcgt cttcgcggtg ctggcgacga tcctcttcac   1017
cgtgggcgcc tattggtggc cggtgctgtg gtggatcgcc ctgggcatga cggtctatgg   1077
gttgatctat ttcatcctgc acgacgggct tgtgcatcaa cgctggccgt ttcggtatat   1137
tccgcggcgg ggctatttcc gcaggctcta ccaagctcat cgcctgcacc acgcggtcga   1197
ggggcgggac cactgcgtca gcttcggctt catctatgcc ccacccgtgg acaagctgaa   1257
gcaggatctg aagcggtcgg gtgtcctgcg cccccaggac gagcgtccgt cgtgatctct   1317
gatcccggcg tggccgcatg aaatccgacg tgctgctggc aggggccggc cttgccaacg   1377
gactgatcgc gctggcgatc cgcaaggcgc ggcccgacct cgcgtgctg ctgctggacc    1437
gtgcggcggg cgcctcggac gggcatactt ggtcctgcca cgacaccgat ttggcgccgc   1497
actggctgga ccgcctgaag ccgatcaggc gtggcgactg gcccgatcag gaggtgcggt   1557
tcccagacca ttcgcgaagg ctccgggccg gatatggctc gatcgacggg cgggggctga   1617
tgcgtgcggt gacc                                                    1631
```

<210> SEQ ID NO 8
<211> LENGTH: 242
<212> TYPE: PRT
<213> ORGANISM: Alcaligenes sp.

<400> SEQUENCE: 8

```
Met Ser Gly Arg Lys Pro Gly Thr Thr Gly Asp Thr Ile Val Asn Leu
1               5                   10                  15

Gly Leu Thr Ala Ala Ile Leu Leu Cys Trp Leu Val Leu His Ala Phe
            20                  25                  30

Thr Leu Trp Leu Leu Asp Ala Ala Ala His Pro Leu Leu Ala Val Leu
        35                  40                  45

Cys Leu Ala Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Ile Gly Gln Leu Ala Leu Trp Leu Tyr Ala Gly Phe Ser Trp
                85                  90                  95

Pro Lys Leu Ile Ala Lys His Met Thr His His Arg His Ala Gly Thr
            100                 105                 110

Asp Asn Asp Pro Asp Phe Gly His Gly Gly Pro Val Arg Trp Tyr Gly
        115                 120                 125

Ser Phe Val Ser Thr Tyr Phe Gly Trp Arg Glu Gly Leu Leu Leu Pro
    130                 135                 140

Val Ile Val Thr Thr Tyr Ala Leu Ile Leu Gly Asp Arg Trp Met Tyr
145                 150                 155                 160

Val Ile Phe Trp Pro Val Pro Ala Val Leu Ala Ser Ile Gln Ile Phe
                165                 170                 175

Val Phe Gly Thr Trp Leu Pro His Arg Pro Gly His Asp Asp Phe Pro
            180                 185                 190

Asp Arg His Asn Ala Arg Ser Thr Gly Ile Gly Asp Pro Leu Ser Leu
        195                 200                 205
```

```
Leu Thr Cys Phe His Phe Gly Gly Tyr His His Glu His His Leu His
        210                 215                 220

Pro His Val Pro Trp Trp Arg Leu Pro Arg Thr Arg Lys Thr Gly Gly
225                 230                 235                 240

Arg Ala

<210> SEQ ID NO 9
<211> LENGTH: 729
<212> TYPE: DNA
<213> ORGANISM: Paracoccus marcusii
<220> FEATURE:
<221> NAME/KEY: CDS

<400> SEQUENCE: 9 atg agc gca cat gcc ctg ccc aag gca gat ctg acc gcc aca agc ctg        48
Met Ser Ala His Ala Leu Pro Lys Ala Asp Leu Thr Ala Thr Ser Leu
1               5                   10                  15 atc gtc tcg ggc ggc atc atc gcc gca tgg ctg gcc ctg cat gtg cat        96
Ile Val Ser Gly Gly Ile Ile Ala Ala Trp Leu Ala Leu His Val His
                20                  25                  30 gcg ctg tgg ttt ctg gac gcg gcg gcc cat ccc atc ctg gcg gtc gcg       144
Ala Leu Trp Phe Leu Asp Ala Ala Ala His Pro Ile Leu Ala Val Ala
            35                  40                  45 aat ttc ctg ggg ctg acc tgg ctg tcg gtc gga ttg ttc atc atc gcg       192
Asn Phe Leu Gly Leu Thr Trp Leu Ser Val Gly Leu Phe Ile Ile Ala
        50                  55                  60 cat gac gcg atg cac ggg tcg gtc gtg ccg ggg cgt ccg cgc gcc aat       240
His Asp Ala Met His Gly Ser Val Val Pro Gly Arg Pro Arg Ala Asn
65                  70                  75                  80 gcg gcg atg ggc cag ctt gtc ctg tgg ctg tat gcc gga ttt tcg tgg       288
Ala Ala Met Gly Gln Leu Val Leu Trp Leu Tyr Ala Gly Phe Ser Trp
                85                  90                  95 cgc aag atg atc gtc aag cac atg gcc cat cac cgc cat gcc gga acc       336
Arg Lys Met Ile Val Lys His Met Ala His His Arg His Ala Gly Thr
                100                 105                 110 gac gac gac cca gat ttc gac cat ggc ggc ccg gtc cgc tgg tac gcc       384
Asp Asp Asp Pro Asp Phe Asp His Gly Gly Pro Val Arg Trp Tyr Ala
            115                 120                 125 cgc ttc atc ggc acc tat ttc ggc tgg cgc gag ggg ctg ctg ctg ccc       432
Arg Phe Ile Gly Thr Tyr Phe Gly Trp Arg Glu Gly Leu Leu Leu Pro
        130                 135                 140 gtc atc gtg acg gtc tat gcg ctg atc ctg ggg gat cgc tgg atg tac       480
Val Ile Val Thr Val Tyr Ala Leu Ile Leu Gly Asp Arg Trp Met Tyr
145                 150                 155                 160 gtg gtc ttc tgg ccg ttg ccg tcg atc ctg gcg tcg atc cag ctg ttc       528
Val Val Phe Trp Pro Leu Pro Ser Ile Leu Ala Ser Ile Gln Leu Phe
                165                 170                 175 gtg ttc ggc act tgg ctg ccg cac cgc ccc ggc cac gac gcg ttc ccg       576
Val Phe Gly Thr Trp Leu Pro His Arg Pro Gly His Asp Ala Phe Pro
            180                 185                 190 gac cgc cat aat gcg cgg tcg tcg cgg atc agc gac cct gtg tcg ctg       624
Asp Arg His Asn Ala Arg Ser Ser Arg Ile Ser Asp Pro Val Ser Leu
        195                 200                 205 ctg acc tgc ttt cat ttt ggc ggt tat cat cac gaa cac cac ctg cac       672
Leu Thr Cys Phe His Phe Gly Gly Tyr His His Glu His His Leu His
    210                 215                 220 ccg acg gtg ccg tgg tgg cgc ctg ccc agc acc cgc acc aag ggg gac       720
Pro Thr Val Pro Trp Trp Arg Leu Pro Ser Thr Arg Thr Lys Gly Asp
225                 230                 235                 240
```

```
acc gca tga                                                          729
Thr Ala <210> SEQ ID NO 10
<211> LENGTH: 242
<212> TYPE: PRT
<213> ORGANISM: Paracoccus marcusii

<400> SEQUENCE: 10

Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala Ala His Pro Ile Leu Ala Val Ala
        35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
        115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
        195                 200                 205

Leu Thr Cys Phe His Phe Gly Gly Tyr His His Glu His His Leu His
    210                 215                 220

Pro Thr Val Pro Trp Trp Arg Leu Pro Ser Thr Arg Thr Lys Gly Asp
225                 230                 235                 240

Thr Ala

<210> SEQ ID NO 11
<211> LENGTH: 1629
<212> TYPE: DNA
<213> ORGANISM: Synechococcus sp.
<220> FEATURE:
<221> NAME/KEY: CDS

<400> SEQUENCE: 11 atg atc acc acc gat gtt gtc att att ggg gcg ggg cac aat ggc tta    48
Met Ile Thr Thr Asp Val Val Ile Ile Gly Ala Gly His Asn Gly Leu
1               5                   10                  15 gtc tgt gca gcc tat ttg ctc caa cgg ggc ttg ggg gtg acg tta cta    96
Val Cys Ala Ala Tyr Leu Leu Gln Arg Gly Leu Gly Val Thr Leu Leu
            20                  25                  30 gaa aag cgg gaa gta cca ggg ggg gcg gcc acc aca gaa gct ctc atg   144
Glu Lys Arg Glu Val Pro Gly Gly Ala Ala Thr Thr Glu Ala Leu Met
        35                  40                  45
```

-continued

| | | |
|---|---|---|
| ccg gag cta tcc ccc cag ttt cgc ttt aac cgc tgt gcc att gac cac<br>Pro Glu Leu Ser Pro Gln Phe Arg Phe Asn Arg Cys Ala Ile Asp His<br>50                            55                      60 | | 192 |
| gaa ttt atc ttt ctg ggg ccg gtg ttg cag gag cta aat tta gcc cag<br>Glu Phe Ile Phe Leu Gly Pro Val Leu Gln Glu Leu Asn Leu Ala Gln<br>65                            70                      75                      80 | | 240 |
| tat ggt ttg gaa tat tta ttt tgt gac ccc agt gtt ttt tgt ccg ggg<br>Tyr Gly Leu Glu Tyr Leu Phe Cys Asp Pro Ser Val Phe Cys Pro Gly<br>                            85                      90                      95 | | 288 |
| ctg gat ggc caa gct ttt atg agc tac cgt tcc cta gaa aaa acc tgt<br>Leu Asp Gly Gln Ala Phe Met Ser Tyr Arg Ser Leu Glu Lys Thr Cys<br>                    100                      105                      110 | | 336 |
| gcc cac att gcc acc tat agc ccc cga gat gcg gaa aaa tat cgg caa<br>Ala His Ile Ala Thr Tyr Ser Pro Arg Asp Ala Glu Lys Tyr Arg Gln<br>115                        120                      125 | | 384 |
| ttt gtc aat tat tgg acg gat ttg ctc aac gct gtc cag cct gct ttt<br>Phe Val Asn Tyr Trp Thr Asp Leu Leu Asn Ala Val Gln Pro Ala Phe<br>                    130                      135                      140 | | 432 |
| aat gct ccg ccc cag gct tta cta gat tta gcc ctg aac tat ggt tgg<br>Asn Ala Pro Pro Gln Ala Leu Leu Asp Leu Ala Leu Asn Tyr Gly Trp<br>145                        150                      155                      160 | | 480 |
| gaa aac tta aaa tcc gtg ctg gcg atc gcc ggg tcg aaa acc aag gcg<br>Glu Asn Leu Lys Ser Val Leu Ala Ile Ala Gly Ser Lys Thr Lys Ala<br>                    165                      170                      175 | | 528 |
| ttg gat ttt atc cgc act atg atc ggc tcc ccg gaa gat gtg ctc aat<br>Leu Asp Phe Ile Arg Thr Met Ile Gly Ser Pro Glu Asp Val Leu Asn<br>                    180                      185                      190 | | 576 |
| gaa tgg ttc gac agc gaa cgg gtt aaa gct cct tta gct aga cta tgt<br>Glu Trp Phe Asp Ser Glu Arg Val Lys Ala Pro Leu Ala Arg Leu Cys<br>                    195                      200                      205 | | 624 |
| tcg gaa att ggc gct ccc cca tcc caa aag ggt agt agc tcc ggc atg<br>Ser Glu Ile Gly Ala Pro Pro Ser Gln Lys Gly Ser Ser Ser Gly Met<br>210                        215                      220 | | 672 |
| atg atg gtg gcc atg cgg cat ttg gag gga att gcc aga cca aaa gga<br>Met Met Val Ala Met Arg His Leu Glu Gly Ile Ala Arg Pro Lys Gly<br>225                        230                      235                      240 | | 720 |
| ggc act gga gcc ctc aca gaa gcc ttg gtg aag tta gtg caa gcc caa<br>Gly Thr Gly Ala Leu Thr Glu Ala Leu Val Lys Leu Val Gln Ala Gln<br>                    245                      250                      255 | | 768 |
| ggg gga aaa atc ctc act gac caa acc gtc aaa cgg gta ttg gtg gaa<br>Gly Gly Lys Ile Leu Thr Asp Gln Thr Val Lys Arg Val Leu Val Glu<br>                      260                      265                      270 | | 816 |
| aac aac cag gcg atc ggg gtg gag gta gct aac gga gaa cag tac cgg<br>Asn Asn Gln Ala Ile Gly Val Glu Val Ala Asn Gly Glu Gln Tyr Arg<br>                    275                      280                      285 | | 864 |
| gcc aaa aaa ggc gtg att tct aac atc gat gcc cgc cgt tta ttt ttg<br>Ala Lys Lys Gly Val Ile Ser Asn Ile Asp Ala Arg Arg Leu Phe Leu<br>                    290                      295                      300 | | 912 |
| caa ttg gtg gaa ccg ggg gcc cta gcc aag gtg aat caa aac cta ggg<br>Gln Leu Val Glu Pro Gly Ala Leu Ala Lys Val Asn Gln Asn Leu Gly<br>305                        310                      315                      320 | | 960 |
| gaa cga ctg gaa cgg cgc act gtg aac aat aac gaa gcc att tta aaa<br>Glu Arg Leu Glu Arg Arg Thr Val Asn Asn Asn Glu Ala Ile Leu Lys<br>                    325                      330                      335 | | 1008 |
| atc gat tgt gcc ctc tcc ggt tta ccc cac ttc act gcc atg gcc ggg<br>Ile Asp Cys Ala Leu Ser Gly Leu Pro His Phe Thr Ala Met Ala Gly<br>                    340                      345                      350 | | 1056 |
| ccg gag gat cta acg gga act att ttg att gcc gac tcg gta cgc cat<br>Pro Glu Asp Leu Thr Gly Thr Ile Leu Ile Ala Asp Ser Val Arg His | | 1104 |

```
                355                 360                 365
gtc gag gaa gcc cac gcc ctc att gcc ttg ggg caa att ccc gat gct      1152
Val Glu Glu Ala His Ala Leu Ile Ala Leu Gly Gln Ile Pro Asp Ala
        370                 375                 380 aat ccg tct tta tat ttg gat att ccc act gta ttg gac ccc acc atg      1200
Asn Pro Ser Leu Tyr Leu Asp Ile Pro Thr Val Leu Asp Pro Thr Met
385                 390                 395                 400 gcc ccc cct ggg cag cac acc ctc tgg atc gaa ttt ttt gcc ccc tac      1248
Ala Pro Pro Gly Gln His Thr Leu Trp Ile Glu Phe Phe Ala Pro Tyr
                405                 410                 415 cgc atc gcc ggg ttg gaa ggg aca ggg tta atg ggc aca ggt tgg acc      1296
Arg Ile Ala Gly Leu Glu Gly Thr Gly Leu Met Gly Thr Gly Trp Thr
            420                 425                 430 gat gag tta aag gaa aaa gtg gcg gat cgg gtg att gat aaa tta acg      1344
Asp Glu Leu Lys Glu Lys Val Ala Asp Arg Val Ile Asp Lys Leu Thr
        435                 440                 445 gac tat gcc cct aac cta aaa tct ctg atc att ggt cgc cga gtg gaa      1392
Asp Tyr Ala Pro Asn Leu Lys Ser Leu Ile Ile Gly Arg Arg Val Glu
    450                 455                 460 agt ccc gcc gaa ctg gcc caa cgg ctg gga agt tac aac ggc aat gtc      1440
Ser Pro Ala Glu Leu Ala Gln Arg Leu Gly Ser Tyr Asn Gly Asn Val
465                 470                 475                 480 tat cat ctg gat atg agt ttg gac caa atg atg ttc ctc cgg cct cta      1488
Tyr His Leu Asp Met Ser Leu Asp Gln Met Met Phe Leu Arg Pro Leu
                485                 490                 495 ccg gaa att gcc aac tac caa acc ccc atc aaa aat ctt tac tta aca      1536
Pro Glu Ile Ala Asn Tyr Gln Thr Pro Ile Lys Asn Leu Tyr Leu Thr
            500                 505                 510 ggg gcg ggt acc cat ccc ggt ggc tcc ata tca ggt atg ccc ggt aga      1584
Gly Ala Gly Thr His Pro Gly Gly Ser Ile Ser Gly Met Pro Gly Arg
        515                 520                 525 aat tgc gct cgg gtc ttt tta aaa caa caa cgt cgt ttt tgg taa          1629
Asn Cys Ala Arg Val Phe Leu Lys Gln Gln Arg Arg Phe Trp
    530                 535                 540

<210> SEQ ID NO 12
<211> LENGTH: 542
<212> TYPE: PRT
<213> ORGANISM: Synechococcus sp.

<400> SEQUENCE: 12

Met Ile Thr Thr Asp Val Val Ile Ile Gly Ala Gly His Asn Gly Leu
1               5                   10                  15

Val Cys Ala Ala Tyr Leu Leu Gln Arg Gly Leu Gly Val Thr Leu Leu
            20                  25                  30

Glu Lys Arg Glu Val Pro Gly Gly Ala Ala Thr Thr Glu Ala Leu Met
        35                  40                  45

Pro Glu Leu Ser Pro Gln Phe Arg Phe Asn Arg Cys Ala Ile Asp His
    50                  55                  60

Glu Phe Ile Phe Leu Gly Pro Val Leu Gln Glu Leu Asn Leu Ala Gln
65                  70                  75                  80

Tyr Gly Leu Glu Tyr Leu Phe Cys Asp Pro Ser Val Phe Cys Pro Gly
                85                  90                  95

Leu Asp Gly Gln Ala Phe Met Ser Tyr Arg Ser Leu Glu Lys Thr Cys
            100                 105                 110

Ala His Ile Ala Thr Tyr Ser Pro Arg Asp Ala Glu Lys Tyr Arg Gln
        115                 120                 125

Phe Val Asn Tyr Trp Thr Asp Leu Leu Asn Ala Val Gln Pro Ala Phe
```

-continued

```
            130                 135                 140
Asn Ala Pro Pro Gln Ala Leu Leu Asp Leu Ala Leu Asn Tyr Gly Trp
145                 150                 155                 160

Glu Asn Leu Lys Ser Val Leu Ala Ile Ala Gly Ser Lys Thr Lys Ala
                165                 170                 175

Leu Asp Phe Ile Arg Thr Met Ile Gly Ser Pro Glu Asp Val Leu Asn
            180                 185                 190

Glu Trp Phe Asp Ser Glu Arg Val Lys Ala Pro Leu Ala Arg Leu Cys
        195                 200                 205

Ser Glu Ile Gly Ala Pro Pro Ser Gln Lys Gly Ser Ser Ser Gly Met
    210                 215                 220

Met Met Val Ala Met Arg His Leu Glu Gly Ile Ala Arg Pro Lys Gly
225                 230                 235                 240

Gly Thr Gly Ala Leu Thr Glu Ala Leu Val Lys Leu Val Gln Ala Gln
                245                 250                 255

Gly Gly Lys Ile Leu Thr Asp Gln Thr Val Lys Arg Val Leu Val Glu
            260                 265                 270

Asn Asn Gln Ala Ile Gly Val Glu Val Ala Asn Gly Glu Gln Tyr Arg
        275                 280                 285

Ala Lys Lys Gly Val Ile Ser Asn Ile Asp Ala Arg Arg Leu Phe Leu
    290                 295                 300

Gln Leu Val Glu Pro Gly Ala Leu Ala Lys Val Asn Gln Asn Leu Gly
305                 310                 315                 320

Glu Arg Leu Glu Arg Arg Thr Val Asn Asn Glu Ala Ile Leu Lys
                325                 330                 335

Ile Asp Cys Ala Leu Ser Gly Leu Pro His Phe Thr Ala Met Ala Gly
            340                 345                 350

Pro Glu Asp Leu Thr Gly Thr Ile Leu Ile Ala Asp Ser Val Arg His
        355                 360                 365

Val Glu Glu Ala His Ala Leu Ile Ala Leu Gly Gln Ile Pro Asp Ala
    370                 375                 380

Asn Pro Ser Leu Tyr Leu Asp Ile Pro Thr Val Leu Asp Pro Thr Met
385                 390                 395                 400

Ala Pro Pro Gly Gln His Thr Leu Trp Ile Glu Phe Phe Ala Pro Tyr
                405                 410                 415

Arg Ile Ala Gly Leu Glu Gly Thr Gly Leu Met Gly Thr Gly Trp Thr
            420                 425                 430

Asp Glu Leu Lys Glu Lys Val Ala Asp Arg Val Ile Asp Lys Leu Thr
        435                 440                 445

Asp Tyr Ala Pro Asn Leu Lys Ser Leu Ile Ile Gly Arg Arg Val Glu
    450                 455                 460

Ser Pro Ala Glu Leu Ala Gln Arg Leu Gly Ser Tyr Asn Gly Asn Val
465                 470                 475                 480

Tyr His Leu Asp Met Ser Leu Asp Gln Met Met Phe Leu Arg Pro Leu
                485                 490                 495

Pro Glu Ile Ala Asn Tyr Gln Thr Pro Ile Lys Asn Leu Tyr Leu Thr
            500                 505                 510

Gly Ala Gly Thr His Pro Gly Gly Ser Ile Ser Gly Met Pro Gly Arg
        515                 520                 525

Asn Cys Ala Arg Val Phe Leu Lys Gln Gln Arg Arg Phe Trp
    530                 535                 540
```

<210> SEQ ID NO 13

```
<211> LENGTH: 776
<212> TYPE: DNA
<213> ORGANISM: Bradyrhizobium sp.
<220> FEATURE:
<221> NAME/KEY: CDS
<222> LOCATION: (1)..(774)

<400> SEQUENCE: 13 atg cat gca gca acc gcc aag gct act gag ttc ggg gcc tct cgg cgc      48
Met His Ala Ala Thr Ala Lys Ala Thr Glu Phe Gly Ala Ser Arg Arg
1               5                  10                  15 gac gat gcg agg cag cgc cgc gtc ggt ctc acg ctg gcc gcg gtc atc      96
Asp Asp Ala Arg Gln Arg Arg Val Gly Leu Thr Leu Ala Ala Val Ile
            20                  25                  30 atc gcc gcc tgg ctg gtg ctg cat gtc ggt ctg atg ttc ttc tgg ccg     144
Ile Ala Ala Trp Leu Val Leu His Val Gly Leu Met Phe Phe Trp Pro
        35                  40                  45 ctg acc ctt cac agc ctg ctg ccg gct ttg cct ctg gtg gtg ctg cag     192
Leu Thr Leu His Ser Leu Leu Pro Ala Leu Pro Leu Val Val Leu Gln
    50                  55                  60 acc tgg ctc tat gta ggc ctg ttc atc atc gcg cat gac tgc atg cac     240
Thr Trp Leu Tyr Val Gly Leu Phe Ile Ile Ala His Asp Cys Met His
65                  70                  75                  80 ggc tcg ctg gtg ccg ttc aag ccg cag gtc aac cgc gtc atc gga cag     288
Gly Ser Leu Val Pro Phe Lys Pro Gln Val Asn Arg Val Ile Gly Gln
                85                  90                  95 ctc tgc ctg ttc ctc tat gcc ggg ttc tcc ttc gac gct ctc aat gtc     336
Leu Cys Leu Phe Leu Tyr Ala Gly Phe Ser Phe Asp Ala Leu Asn Val
            100                 105                 110 gag cac cac aag cat cac cgc cat ccc ggc acg gcc gag gat ccc gat     384
Glu His His Lys His His Arg His Pro Gly Thr Ala Glu Asp Pro Asp
        115                 120                 125 ttc gac gag gtg ccg ccg cac ggc ttc tgg cac tgg ttc gcc agc ttt     432
Phe Asp Glu Val Pro Pro His Gly Phe Trp His Trp Phe Ala Ser Phe
    130                 135                 140 ttc ctg cac tat ttc ggc tgg aag cag gtc gcg atc atc gca gcc gtc     480
Phe Leu His Tyr Phe Gly Trp Lys Gln Val Ala Ile Ile Ala Ala Val
145                 150                 155                 160 tcg ctg gtt tat cag ctc gtc ttc gcc gtt ccc ttg cag aac atc ctg     528
Ser Leu Val Tyr Gln Leu Val Phe Ala Val Pro Leu Gln Asn Ile Leu
                165                 170                 175 ctg ttc tgg gcg ctg ccc ggg ctg ctg tcg gcg ctg cag ctg ttc acc     576
Leu Phe Trp Ala Leu Pro Gly Leu Leu Ser Ala Leu Gln Leu Phe Thr
            180                 185                 190 ttc ggc acc tat ctg ccg cac aag ccg gcc acg cag ccc ttc gcc gat     624
Phe Gly Thr Tyr Leu Pro His Lys Pro Ala Thr Gln Pro Phe Ala Asp
        195                 200                 205 cgc cac aac gcg cgg acg agc gaa ttt ccc gcg tgg ctg tcg ctg ctg     672
Arg His Asn Ala Arg Thr Ser Glu Phe Pro Ala Trp Leu Ser Leu Leu
    210                 215                 220 acc tgc ttc cac ttc ggc ttt cat cac gag cat cat ctg cat ccc gat     720
Thr Cys Phe His Phe Gly Phe His His Glu His His Leu His Pro Asp
225                 230                 235                 240 gcg ccg tgg tgg cgg ctg ccg gag atc aag cgg cgg gcc ctg gaa agg     768
Ala Pro Trp Trp Arg Leu Pro Glu Ile Lys Arg Arg Ala Leu Glu Arg
                245                 250                 255 cgt gac ta                                                           776
Arg Asp

<210> SEQ ID NO 14
<211> LENGTH: 258
```

```
<212> TYPE: PRT
<213> ORGANISM: Bradyrhizobium sp.

<400> SEQUENCE: 14

Met His Ala Ala Thr Ala Lys Ala Thr Glu Phe Gly Ala Ser Arg Arg
1               5                   10                  15

Asp Asp Ala Arg Gln Arg Arg Val Gly Leu Thr Leu Ala Ala Val Ile
            20                  25                  30

Ile Ala Ala Trp Leu Val Leu His Val Gly Leu Met Phe Phe Trp Pro
        35                  40                  45

Leu Thr Leu His Ser Leu Leu Pro Ala Leu Pro Leu Val Val Leu Gln
    50                  55                  60

Thr Trp Leu Tyr Val Gly Leu Phe Ile Ile Ala His Asp Cys Met His
65                  70                  75                  80

Gly Ser Leu Val Pro Phe Lys Pro Gln Val Asn Arg Arg Ile Gly Gln
                85                  90                  95

Leu Cys Leu Phe Leu Tyr Ala Gly Phe Ser Phe Asp Ala Leu Asn Val
            100                 105                 110

Glu His His Lys His His Arg His Pro Gly Thr Ala Glu Asp Pro Asp
        115                 120                 125

Phe Asp Glu Val Pro Pro His Gly Phe Trp His Trp Phe Ala Ser Phe
    130                 135                 140

Phe Leu His Tyr Phe Gly Trp Lys Gln Val Ala Ile Ile Ala Ala Val
145                 150                 155                 160

Ser Leu Val Tyr Gln Leu Val Phe Ala Val Pro Leu Gln Asn Ile Leu
                165                 170                 175

Leu Phe Trp Ala Leu Pro Gly Leu Leu Ser Ala Leu Gln Leu Phe Thr
            180                 185                 190

Phe Gly Thr Tyr Leu Pro His Lys Pro Ala Thr Gln Pro Phe Ala Asp
        195                 200                 205

Arg His Asn Ala Arg Thr Ser Glu Phe Pro Ala Trp Leu Ser Leu Leu
    210                 215                 220

Thr Cys Phe His Phe Gly Phe His His Glu His His Leu His Pro Asp
225                 230                 235                 240

Ala Pro Trp Trp Arg Leu Pro Glu Ile Lys Arg Arg Ala Leu Glu Arg
                245                 250                 255

Arg Asp

<210> SEQ ID NO 15
<211> LENGTH: 777
<212> TYPE: DNA
<213> ORGANISM: Nostoc sp.
<220> FEATURE:
<221> NAME/KEY: CDS

<400> SEQUENCE: 15 atg gtt cag tgt caa cca tca tct ctg cat tca gaa aaa ctg gtg tta      48
Met Val Gln Cys Gln Pro Ser Ser Leu His Ser Glu Lys Leu Val Leu
1               5                   10                  15 ttg tca tcg aca atc aga gat gat aaa aat att aat aag ggt ata ttt      96
Leu Ser Ser Thr Ile Arg Asp Asp Lys Asn Ile Asn Lys Gly Ile Phe
            20                  25                  30 att gcc tgc ttt atc tta ttt tta tgg gca att agt tta atc tta tta    144
Ile Ala Cys Phe Ile Leu Phe Leu Trp Ala Ile Ser Leu Ile Leu Leu
        35                  40                  45 ctc tca ata gat aca tcc ata att cat aag agc tta tta ggt ata gcc    192
Leu Ser Ile Asp Thr Ser Ile Ile His Lys Ser Leu Leu Gly Ile Ala
```

```
            50                  55                  60
atg ctt tgg cag acc ttc tta tat aca ggt tta ttt att act gct cat    240
Met Leu Trp Gln Thr Phe Leu Tyr Thr Gly Leu Phe Ile Thr Ala His
 65                  70                  75                  80 gat gcc atg cac ggc gta gtt tat ccc aaa aat ccc aga ata aat aat    288
Asp Ala Met His Gly Val Val Tyr Pro Lys Asn Pro Arg Ile Asn Asn
                 85                  90                  95 ttt ata ggt aag ctc act cta atc ttg tat gga cta ctc cct tat aaa    336
Phe Ile Gly Lys Leu Thr Leu Ile Leu Tyr Gly Leu Leu Pro Tyr Lys
            100                 105                 110 gat tta ttg aaa aaa cat tgg tta cac cac gga cat cct ggt act gat    384
Asp Leu Leu Lys Lys His Trp Leu His His Gly His Pro Gly Thr Asp
        115                 120                 125 tta gac cct gat tat tac aat ggt cat ccc caa aac ttc ttt ctt tgg    432
Leu Asp Pro Asp Tyr Tyr Asn Gly His Pro Gln Asn Phe Phe Leu Trp
    130                 135                 140 tat cta cat ttt atg aag tct tat tgg cga tgg acg caa att ttc gga    480
Tyr Leu His Phe Met Lys Ser Tyr Trp Arg Trp Thr Gln Ile Phe Gly
145                 150                 155                 160 tta gtg atg att ttt cat gga ctt aaa aat ctg gtg cat ata cca gaa    528
Leu Val Met Ile Phe His Gly Leu Lys Asn Leu Val His Ile Pro Glu
                165                 170                 175 aat aat tta att ata ttt tgg atg ata cct tct att tta agt tca gta    576
Asn Asn Leu Ile Ile Phe Trp Met Ile Pro Ser Ile Leu Ser Ser Val
            180                 185                 190 caa cta ttt tat ttt ggt aca ttt ttg cct cat aaa aag cta gaa ggt    624
Gln Leu Phe Tyr Phe Gly Thr Phe Leu Pro His Lys Lys Leu Glu Gly
        195                 200                 205 ggt tat act aac ccc cat tgt gcg cgc agt atc cca tta cct ctt ttt    672
Gly Tyr Thr Asn Pro His Cys Ala Arg Ser Ile Pro Leu Pro Leu Phe
    210                 215                 220 tgg tct ttt gtt act tgt tat cac ttc ggc tac cac aag gaa cat cac    720
Trp Ser Phe Val Thr Cys Tyr His Phe Gly Tyr His Lys Glu His His
225                 230                 235                 240 gaa tac cct caa ctt cct tgg tgg aaa tta cct gaa gct cac aaa ata    768
Glu Tyr Pro Gln Leu Pro Trp Trp Lys Leu Pro Glu Ala His Lys Ile
                245                 250                 255 tct tta taa                                                        777
Ser Leu

<210> SEQ ID NO 16
<211> LENGTH: 258
<212> TYPE: PRT
<213> ORGANISM: Nostoc sp.

<400> SEQUENCE: 16

Met Val Gln Cys Gln Pro Ser Ser Leu His Ser Glu Lys Leu Val Leu
 1               5                  10                  15

Leu Ser Ser Thr Ile Arg Asp Asp Lys Asn Ile Asn Lys Gly Ile Phe
                20                  25                  30

Ile Ala Cys Phe Ile Leu Phe Leu Trp Ala Ile Ser Leu Ile Leu Leu
            35                  40                  45

Leu Ser Ile Asp Thr Ser Ile Ile His Lys Ser Leu Leu Gly Ile Ala
        50                  55                  60

Met Leu Trp Gln Thr Phe Leu Tyr Thr Gly Leu Phe Ile Thr Ala His
 65                  70                  75                  80

Asp Ala Met His Gly Val Val Tyr Pro Lys Asn Pro Arg Ile Asn Asn
                85                  90                  95
```

```
Phe Ile Gly Lys Leu Thr Leu Ile Leu Tyr Gly Leu Leu Pro Tyr Lys
            100                 105                 110

Asp Leu Leu Lys Lys His Trp Leu His His Gly His Pro Gly Thr Asp
            115                 120                 125

Leu Asp Pro Asp Tyr Tyr Asn Gly His Pro Gln Asn Phe Phe Leu Trp
    130                 135                 140

Tyr Leu His Phe Met Lys Ser Tyr Trp Arg Trp Thr Gln Ile Phe Gly
145                 150                 155                 160

Leu Val Met Ile Phe His Gly Leu Lys Asn Leu Val His Ile Pro Glu
                165                 170                 175

Asn Asn Leu Ile Ile Phe Trp Met Ile Pro Ser Ile Leu Ser Ser Val
                180                 185                 190

Gln Leu Phe Tyr Phe Gly Thr Phe Leu Pro His Lys Lys Leu Glu Gly
            195                 200                 205

Gly Tyr Thr Asn Pro His Cys Ala Arg Ser Ile Pro Leu Pro Leu Phe
    210                 215                 220

Trp Ser Phe Val Thr Cys Tyr His Phe Gly Tyr His Lys Glu His His
225                 230                 235                 240

Glu Tyr Pro Gln Leu Pro Trp Trp Lys Leu Pro Glu Ala His Lys Ile
                245                 250                 255

Ser Leu

<210> SEQ ID NO 17
<211> LENGTH: 1608
<212> TYPE: DNA
<213> ORGANISM: Haematococcus pluvialis
<220> FEATURE:
<221> NAME/KEY: CDS
<222> LOCATION: (3)..(971)

<400> SEQUENCE: 17 ct aca ttt cac aag ccc gtg agc ggt gca agc gct ctg ccc cac atc        47
   Thr Phe His Lys Pro Val Ser Gly Ala Ser Ala Leu Pro His Ile
    1               5                   10                  15 ggc cca cct cct cat ctc cat cgg tca ttt gct gct acc acg atg ctg       95
Gly Pro Pro Pro His Leu His Arg Ser Phe Ala Ala Thr Thr Met Leu
                20                  25                  30 tcg aag ctg cag tca atc agc gtc aag gcc cgc cgc gtt gaa cta gcc      143
Ser Lys Leu Gln Ser Ile Ser Val Lys Ala Arg Arg Val Glu Leu Ala
            35                  40                  45 cgc gac atc acg cgg ccc aaa gtc tgc ctg cat gct cag cgg tgc tcg      191
Arg Asp Ile Thr Arg Pro Lys Val Cys Leu His Ala Gln Arg Cys Ser
        50                  55                  60 tta gtt cgg ctg cga gtg gca gca cca cag aca gag gag gcg ctg gga      239
Leu Val Arg Leu Arg Val Ala Ala Pro Gln Thr Glu Glu Ala Leu Gly
65                  70                  75 acc gtg cag gct gcc ggc gcg ggc gat gag cac agc gcc gat gta gca      287
Thr Val Gln Ala Ala Gly Ala Gly Asp Glu His Ser Ala Asp Val Ala
80                  85                  90                  95 ctc cag cag ctt gac cgg gct atc gca gag cgt cgt gcc cgg cgc aaa      335
Leu Gln Gln Leu Asp Arg Ala Ile Ala Glu Arg Arg Ala Arg Arg Lys
                100                 105                 110 cgg gag cag ctg tca tac cag gct gcc gcc att gca gca tca att ggc      383
Arg Glu Gln Leu Ser Tyr Gln Ala Ala Ala Ile Ala Ala Ser Ile Gly
            115                 120                 125 gtg tca ggc att gcc atc ttc gcc acc tac ctg aga ttt gcc atg cac      431
Val Ser Gly Ile Ala Ile Phe Ala Thr Tyr Leu Arg Phe Ala Met His
        130                 135                 140
```

| | | |
|---|---|---|
| atg acc gtg ggc ggc gca gtg cca tgg ggt gaa gtg gct ggc act ctc<br>Met Thr Val Gly Gly Ala Val Pro Trp Gly Glu Val Ala Gly Thr Leu<br>145                             150                     155 | | 479 |
| ctc ttg gtg gtt ggt ggc gcg ctc ggc atg gag atg tat gcc cgc tat<br>Leu Leu Val Val Gly Gly Ala Leu Gly Met Glu Met Tyr Ala Arg Tyr<br>160                         165                   170                   175 | | 527 |
| gca cac aaa gcc atc tgg cat gag tcg cct ctg ggc tgg ctg ctg cac<br>Ala His Lys Ala Ile Trp His Glu Ser Pro Leu Gly Trp Leu Leu His<br>                 180                        185                   190 | | 575 |
| aag agc cac cac aca cct cgc act gga ccc ttt gaa gcc aac gac ttg<br>Lys Ser His His Thr Pro Arg Thr Gly Pro Phe Glu Ala Asn Asp Leu<br>                      195                      200                   205 | | 623 |
| ttt gca atc atc aat gga ctg ccc gcc atg ctc ctg tgt acc ttt ggc<br>Phe Ala Ile Ile Asn Gly Leu Pro Ala Met Leu Leu Cys Thr Phe Gly<br>210                             215                     220 | | 671 |
| ttc tgg ctg ccc aac gtc ctg ggg gcg gcc tgc ttt gga gcg ggg ctg<br>Phe Trp Leu Pro Asn Val Leu Gly Ala Ala Cys Phe Gly Ala Gly Leu<br>225                         230                     235 | | 719 |
| ggc atc acg cta tac ggc atg gca tat atg ttt gta cac gat ggc ctg<br>Gly Ile Thr Leu Tyr Gly Met Ala Tyr Met Phe Val His Asp Gly Leu<br>240                         245                   250                   255 | | 767 |
| gtg cac agg cgc ttt ccc acc ggg ccc atc gct ggc ctg ccc tac atg<br>Val His Arg Arg Phe Pro Thr Gly Pro Ile Ala Gly Leu Pro Tyr Met<br>                         260                   265                   270 | | 815 |
| aag cgc ctg aca gtg gcc cac cag cta cac cac agc ggc aag tac ggt<br>Lys Arg Leu Thr Val Ala His Gln Leu His His Ser Gly Lys Tyr Gly<br>                 275                        280                   285 | | 863 |
| ggc gcg ccc tgg ggt atg ttc ttg ggt cca cag gag ctg cag cac att<br>Gly Ala Pro Trp Gly Met Phe Leu Gly Pro Gln Glu Leu Gln His Ile<br>                      290                      295                   300 | | 911 |
| cca ggt gcg gcg gag gag gtg gag cga ctg gtc ctg gaa ctg gac tgg<br>Pro Gly Ala Ala Glu Glu Val Glu Arg Leu Val Leu Glu Leu Asp Trp<br>305                             310                     315 | | 959 |
| tcc aag cgg tag ggtgcggaac caggcacgct ggtttcacac ctcatgcctg<br>Ser Lys Arg<br>320 | | 1011 |
| tgataaggtg tggctagagc gatgcgtgtg agacgggtat gtcacggtcg actggtctga | | 1071 |
| tggccaatgg catcggccat gtctggtcat cacgggctgg ttgcctgggt gaaggtgatg | | 1131 |
| cacatcatca tgtgcggttg gaggggctgg cacagtgtgg gctgaactgg agcagttgtc | | 1191 |
| caggctggcg ttgaatcagt gagggtttgt gattggcggt tgtgaagcaa tgactccgcc | | 1251 |
| catattctat ttgtgggagc tgagatgatg gcatgcttgg gatgtgcatg gatcatggta | | 1311 |
| gtgcagcaaa ctatattcac ctagggctgt tggtaggatc aggtgaggcc ttgcacattg | | 1371 |
| catgatgtac tcgtcatggt gtgttggtga gaggatggat gtggatggat gtgtattctc | | 1431 |
| agacgtagac cttgactgga ggcttgatcg agagagtggg ccgtattctt tgagagggga | | 1491 |
| ggctcgtgcc agaaatggtg agtggatgac tgtgacgctg tacattgcag gcaggtgaga | | 1551 |
| tgcactgtct cgattgtaaa atacattcag atgcaaaaaa aaaaaaaaa aaaaaa | | 1608 |

<210> SEQ ID NO 18
<211> LENGTH: 322
<212> TYPE: PRT
<213> ORGANISM: Haematococcus pluvialis

<400> SEQUENCE: 18

Thr Phe His Lys Pro Val Ser Gly Ala Ser Ala Leu Pro His Ile Gly
1               5                   10                 15

```
Pro Pro Pro His Leu His Arg Ser Phe Ala Ala Thr Thr Met Leu Ser
            20                  25                  30

Lys Leu Gln Ser Ile Ser Val Lys Ala Arg Arg Val Glu Leu Ala Arg
        35                  40                  45

Asp Ile Thr Arg Pro Lys Val Cys Leu His Ala Gln Arg Cys Ser Leu
 50                  55                  60

Val Arg Leu Arg Val Ala Ala Pro Gln Thr Glu Glu Ala Leu Gly Thr
 65                  70                  75                  80

Val Gln Ala Ala Gly Ala Gly Asp Glu His Ser Ala Asp Val Ala Leu
                 85                  90                  95

Gln Gln Leu Asp Arg Ala Ile Ala Glu Arg Arg Ala Arg Arg Lys Arg
            100                 105                 110

Glu Gln Leu Ser Tyr Gln Ala Ala Ile Ala Ser Ile Gly Val
            115                 120                 125

Ser Gly Ile Ala Ile Phe Ala Thr Tyr Leu Arg Phe Ala Met His Met
130                 135                 140

Thr Val Gly Gly Ala Val Pro Trp Gly Glu Val Ala Gly Thr Leu Leu
145                 150                 155                 160

Leu Val Val Gly Gly Ala Leu Gly Met Glu Met Tyr Ala Arg Tyr Ala
                165                 170                 175

His Lys Ala Ile Trp His Glu Ser Pro Leu Gly Trp Leu Leu His Lys
            180                 185                 190

Ser His His Thr Pro Arg Thr Gly Pro Phe Glu Ala Asn Asp Leu Phe
            195                 200                 205

Ala Ile Ile Asn Gly Leu Pro Ala Met Leu Leu Cys Thr Phe Gly Phe
210                 215                 220

Trp Leu Pro Asn Val Leu Gly Ala Ala Cys Phe Gly Ala Gly Leu Gly
225                 230                 235                 240

Ile Thr Leu Tyr Gly Met Ala Tyr Met Phe Val His Asp Gly Leu Val
                245                 250                 255

His Arg Arg Phe Pro Thr Gly Pro Ile Ala Gly Leu Pro Tyr Met Lys
            260                 265                 270

Arg Leu Thr Val Ala His Gln Leu His Ser Gly Lys Tyr Gly Gly
            275                 280                 285

Ala Pro Trp Gly Met Phe Leu Gly Pro Gln Glu Leu Gln His Ile Pro
290                 295                 300

Gly Ala Ala Glu Glu Val Glu Arg Leu Val Leu Glu Leu Asp Trp Ser
305                 310                 315                 320

Lys Arg

<210> SEQ ID NO 19
<211> LENGTH: 1503
<212> TYPE: DNA
<213> ORGANISM: Tomato
<220> FEATURE:
<221> NAME/KEY: CDS

<400> SEQUENCE: 19 atg gat act ttg ttg aaa acc cca aat aac ctt gaa ttt ctg aac cca     48
Met Asp Thr Leu Leu Lys Thr Pro Asn Asn Leu Glu Phe Leu Asn Pro
 1               5                  10                  15 cat cat ggt ttt gct gtt aaa gct agt acc ttt aga tct gag aag cat     96
His His Gly Phe Ala Val Lys Ala Ser Thr Phe Arg Ser Glu Lys His
             20                  25                  30 cat aat ttt ggt tct agg aag ttt tgt gaa act ttg ggt aga agt gtt    144
His Asn Phe Gly Ser Arg Lys Phe Cys Glu Thr Leu Gly Arg Ser Val
```

-continued

```
             35                  40                  45
tgt gtt aag ggt agt agt agt gct ctt tta gag ctt gta cct gag acc      192
Cys Val Lys Gly Ser Ser Ser Ala Leu Leu Glu Leu Val Pro Glu Thr
 50                  55                  60 aaa aag gag aat ctt gat ttt gag ctt cct atg tat gac cct tca aaa      240
Lys Lys Glu Asn Leu Asp Phe Glu Leu Pro Met Tyr Asp Pro Ser Lys
 65                  70                  75                  80 ggg gtt gtt gtg gat ctt gct gtg gtt ggt ggt ggc cct gca gga ctt      288
Gly Val Val Val Asp Leu Ala Val Val Gly Gly Gly Pro Ala Gly Leu
                 85                  90                  95 gct gtt gca cag caa gtt tct gaa gca gga ctc tct gtt tgt tca att      336
Ala Val Ala Gln Gln Val Ser Glu Ala Gly Leu Ser Val Cys Ser Ile
            100                 105                 110 gat ccg aat cct aaa ttg ata tgg cct aat aac tat ggt gtt tgg gtg      384
Asp Pro Asn Pro Lys Leu Ile Trp Pro Asn Asn Tyr Gly Val Trp Val
        115                 120                 125 gat gaa ttt gag gct atg gac ttg tta gat tgt cta gat gct acc tgg      432
Asp Glu Phe Glu Ala Met Asp Leu Leu Asp Cys Leu Asp Ala Thr Trp
    130                 135                 140 tct ggt gca gca gtg tac att gat gat aat acg gct aaa gat ctt cat      480
Ser Gly Ala Ala Val Tyr Ile Asp Asp Asn Thr Ala Lys Asp Leu His
145                 150                 155                 160 aga cct tat gga agg gtt aac cgg aaa cag ctg aaa tcg aaa atg atg      528
Arg Pro Tyr Gly Arg Val Asn Arg Lys Gln Leu Lys Ser Lys Met Met
                165                 170                 175 cag aaa tgt ata atg aat ggt gtt aaa ttc cac caa gcc aaa gtt ata      576
Gln Lys Cys Ile Met Asn Gly Val Lys Phe His Gln Ala Lys Val Ile
            180                 185                 190 aag gtg att cat gag gaa tcg aaa tcc atg ttg ata tgc aat gat ggt      624
Lys Val Ile His Glu Glu Ser Lys Ser Met Leu Ile Cys Asn Asp Gly
        195                 200                 205 att act att cag gca acg gtg gtg ctc gat gca act ggc ttc tct aga      672
Ile Thr Ile Gln Ala Thr Val Val Leu Asp Ala Thr Gly Phe Ser Arg
    210                 215                 220 tct ctt gtt cag tat gat aag cct tat aac ccc ggg tat caa gtt gct      720
Ser Leu Val Gln Tyr Asp Lys Pro Tyr Asn Pro Gly Tyr Gln Val Ala
225                 230                 235                 240 tat ggc att ttg gct gaa gtg gaa gag cac ccc ttt gat gta aac aag      768
Tyr Gly Ile Leu Ala Glu Val Glu Glu His Pro Phe Asp Val Asn Lys
                245                 250                 255 atg gtt ttc atg gat tgg cga gat tct cat ttg aag aac aat act gat      816
Met Val Phe Met Asp Trp Arg Asp Ser His Leu Lys Asn Asn Thr Asp
            260                 265                 270 ctc aag gag aga aat agt aga ata cca act ttt ctt tat gca atg cca      864
Leu Lys Glu Arg Asn Ser Arg Ile Pro Thr Phe Leu Tyr Ala Met Pro
        275                 280                 285 ttt tca tcc aac agg ata ttt ctt gaa gaa aca tca ctc gta gct cgt      912
Phe Ser Ser Asn Arg Ile Phe Leu Glu Glu Thr Ser Leu Val Ala Arg
    290                 295                 300 cct ggc ttg cgt ata gat gat att caa gaa cga atg gtg gct cgt tta      960
Pro Gly Leu Arg Ile Asp Asp Ile Gln Glu Arg Met Val Ala Arg Leu
305                 310                 315                 320 aac cat ttg ggg ata aaa gtg aag agc att gaa gaa gat gaa cat tgt     1008
Asn His Leu Gly Ile Lys Val Lys Ser Ile Glu Glu Asp Glu His Cys
                325                 330                 335 cta ata cca atg ggt ggt cca ctt cca gta tta cct cag aga gtc gtt     1056
Leu Ile Pro Met Gly Gly Pro Leu Pro Val Leu Pro Gln Arg Val Val
            340                 345                 350 gga atc ggt ggt aca gct ggc atg gtt cat cca tcc acc ggt tat atg     1104
```

-continued

```
Gly Ile Gly Gly Thr Ala Gly Met Val His Pro Ser Thr Gly Tyr Met
            355                 360                 365 gtg gca agg aca cta gct gcg gct cct gtt gtt gcc aat gcc ata att    1152
Val Ala Arg Thr Leu Ala Ala Ala Pro Val Val Ala Asn Ala Ile Ile
    370                 375                 380 caa tac ctc ggt tct gaa aga agt cat tcg ggt aat gaa tta tcc aca    1200
Gln Tyr Leu Gly Ser Glu Arg Ser His Ser Gly Asn Glu Leu Ser Thr
385                 390                 395                 400 gct gtt tgg aaa gat ttg tgg cct ata gag agg aga cgt caa aga gag    1248
Ala Val Trp Lys Asp Leu Trp Pro Ile Glu Arg Arg Arg Gln Arg Glu
                405                 410                 415 ttc ttc tgc ttc ggt atg gat att ctt ctg aag ctt gat tta cct gct    1296
Phe Phe Cys Phe Gly Met Asp Ile Leu Leu Lys Leu Asp Leu Pro Ala
            420                 425                 430 aca aga agg ttc ttt gat gca ttc ttt gac tta gaa cct cgt tat tgg    1344
Thr Arg Arg Phe Phe Asp Ala Phe Phe Asp Leu Glu Pro Arg Tyr Trp
        435                 440                 445 cat ggc ttc tta tcg tct cga ttg ttt cta cct gaa ctc ata gtt ttt    1392
His Gly Phe Leu Ser Ser Arg Leu Phe Leu Pro Glu Leu Ile Val Phe
    450                 455                 460 ggg ctg tct cta ttc tct cat gct tca aat act tct aga ttt gag ata    1440
Gly Leu Ser Leu Phe Ser His Ala Ser Asn Thr Ser Arg Phe Glu Ile
465                 470                 475                 480 atg aca aag gga act gtt cca tta gta aat atg atc aac aat ttg tta    1488
Met Thr Lys Gly Thr Val Pro Leu Val Asn Met Ile Asn Asn Leu Leu
                485                 490                 495 cag gat aaa gaa tga                                                1503
Gln Asp Lys Glu
            500
```

<210> SEQ ID NO 20
<211> LENGTH: 500
<212> TYPE: PRT
<213> ORGANISM: Tomato

<400> SEQUENCE: 20

```
Met Asp Thr Leu Leu Lys Thr Pro Asn Asn Leu Glu Phe Leu Asn Pro
1               5                   10                  15

His His Gly Phe Ala Val Lys Ala Ser Thr Phe Arg Ser Glu Lys His
            20                  25                  30

His Asn Phe Gly Ser Arg Lys Phe Cys Glu Thr Leu Gly Arg Ser Val
        35                  40                  45

Cys Val Lys Gly Ser Ser Ala Leu Leu Glu Leu Val Pro Glu Thr
    50                  55                  60

Lys Lys Glu Asn Leu Asp Phe Glu Leu Pro Met Tyr Asp Pro Ser Lys
65                  70                  75                  80

Gly Val Val Asp Leu Ala Val Gly Gly Pro Ala Gly Leu
                85                  90                  95

Ala Val Ala Gln Val Ser Glu Ala Gly Leu Ser Val Cys Ser Ile
            100                 105                 110

Asp Pro Asn Pro Lys Leu Ile Trp Pro Asn Asn Tyr Gly Val Trp Val
        115                 120                 125

Asp Glu Phe Glu Ala Met Asp Leu Leu Asp Cys Leu Asp Ala Thr Trp
    130                 135                 140

Ser Gly Ala Ala Val Tyr Ile Asp Asp Asn Thr Ala Lys Asp Leu His
145                 150                 155                 160

Arg Pro Tyr Gly Arg Val Asn Arg Lys Gln Leu Lys Ser Lys Met Met
                165                 170                 175
```

```
Gln Lys Cys Ile Met Asn Gly Val Lys Phe His Gln Ala Lys Val Ile
            180                 185                 190

Lys Val Ile His Glu Glu Ser Lys Ser Met Leu Ile Cys Asn Asp Gly
        195                 200                 205

Ile Thr Ile Gln Ala Thr Val Val Leu Asp Ala Thr Gly Phe Ser Arg
        210                 215                 220

Ser Leu Val Gln Tyr Asp Lys Pro Tyr Asn Pro Gly Tyr Gln Val Ala
225                 230                 235                 240

Tyr Gly Ile Leu Ala Glu Val Glu His Pro Phe Asp Val Asn Lys
                245                 250                 255

Met Val Phe Met Asp Trp Arg Asp Ser His Leu Lys Asn Asn Thr Asp
                260                 265                 270

Leu Lys Glu Arg Asn Ser Arg Ile Pro Thr Phe Leu Tyr Ala Met Pro
            275                 280                 285

Phe Ser Ser Asn Arg Ile Phe Leu Glu Glu Thr Ser Leu Val Ala Arg
        290                 295                 300

Pro Gly Leu Arg Ile Asp Asp Ile Gln Glu Arg Met Val Ala Arg Leu
305                 310                 315                 320

Asn His Leu Gly Ile Lys Val Lys Ser Ile Glu Asp Glu His Cys
                325                 330                 335

Leu Ile Pro Met Gly Gly Pro Leu Pro Val Leu Pro Gln Arg Val Val
                340                 345                 350

Gly Ile Gly Gly Thr Ala Gly Met Val His Pro Ser Thr Gly Tyr Met
            355                 360                 365

Val Ala Arg Thr Leu Ala Ala Ala Pro Val Val Ala Asn Ala Ile Ile
        370                 375                 380

Gln Tyr Leu Gly Ser Glu Arg Ser His Ser Gly Asn Glu Leu Ser Thr
385                 390                 395                 400

Ala Val Trp Lys Asp Leu Trp Pro Ile Glu Arg Arg Gln Arg Glu
                405                 410                 415

Phe Phe Cys Phe Gly Met Asp Ile Leu Leu Lys Leu Asp Leu Pro Ala
                420                 425                 430

Thr Arg Arg Phe Phe Asp Ala Phe Asp Leu Glu Pro Arg Tyr Trp
            435                 440                 445

His Gly Phe Leu Ser Ser Arg Leu Phe Leu Pro Glu Leu Ile Val Phe
            450                 455                 460

Gly Leu Ser Leu Phe Ser His Ala Ser Asn Thr Ser Arg Phe Glu Ile
465                 470                 475                 480

Met Thr Lys Gly Thr Val Pro Leu Val Asn Met Ile Asn Asn Leu Leu
                485                 490                 495

Gln Asp Lys Glu
            500

<210> SEQ ID NO 21
<211> LENGTH: 195
<212> TYPE: DNA
<213> ORGANISM: Potato
<220> FEATURE:
<221> NAME/KEY: Intron

<400> SEQUENCE: 21
tacgtaagtt tctgcttcta cctttgatat atatataata attatcatta attagtagta      60
atataatatt tcaaatattt ttttcaaaat aaaagaatgt agtatatagc aattgctttt     120
ctgtagttta taagtgtgta tattttaatt tataacttt ctaatatatg accaaaattt     180
```

```
gttgatgtgc agctg                                                      195

<210> SEQ ID NO 22
<211> LENGTH: 1155
<212> TYPE: DNA
<213> ORGANISM: Haematococcus pluvialis
<220> FEATURE:
<221> NAME/KEY: CDS
<222> LOCATION: (6)..(995)

<400> SEQUENCE: 22 gaagc atg cag cta gca gcg aca gta atg ttg gag cag ctt acc gga agc     50
      Met Gln Leu Ala Ala Thr Val Met Leu Glu Gln Leu Thr Gly Ser
      1               5                   10                  15 gct gag gca ctc aag gag aag gag aag gag gtt gca ggc agc tct gac       98
Ala Glu Ala Leu Lys Glu Lys Glu Lys Glu Val Ala Gly Ser Ser Asp
                20                  25                  30 gtg ttg cgt aca tgg gcg acc cag tac tcg ctt ccg tca gag gag tca      146
Val Leu Arg Thr Trp Ala Thr Gln Tyr Ser Leu Pro Ser Glu Glu Ser
            35                  40                  45 gac gcg gcc cgc ccg gga ctg aag aat gcc tac aag cca cca cct tcc      194
Asp Ala Ala Arg Pro Gly Leu Lys Asn Ala Tyr Lys Pro Pro Pro Ser
        50                  55                  60 gac aca aag ggc atc aca atg gcg cta gct gtc atc ggc tcc tgg gcc      242
Asp Thr Lys Gly Ile Thr Met Ala Leu Ala Val Ile Gly Ser Trp Ala
    65                  70                  75 gca gtg ttc ctc cac gcc att ttt caa atc aag ctt ccg acc tcc ttg      290
Ala Val Phe Leu His Ala Ile Phe Gln Ile Lys Leu Pro Thr Ser Leu
80                  85                  90                  95 gac cag ctg cac tgg ctg ccc gtg tca gat gcc aca gct cag ctg gtt      338
Asp Gln Leu His Trp Leu Pro Val Ser Asp Ala Thr Ala Gln Leu Val
                100                 105                 110 agc ggc agc agc agc ctg ctg cac atc gtc gta gta ttc ttt gtc ctg      386
Ser Gly Ser Ser Ser Leu Leu His Ile Val Val Val Phe Phe Val Leu
            115                 120                 125 gag ttc ctg tac aca ggc ctt ttt atc acc acg cat gat gct atg cat      434
Glu Phe Leu Tyr Thr Gly Leu Phe Ile Thr Thr His Asp Ala Met His
        130                 135                 140 ggc acc atc gcc atg aga aac agg cag ctt aat gac ttc ttg ggc aga      482
Gly Thr Ile Ala Met Arg Asn Arg Gln Leu Asn Asp Phe Leu Gly Arg
    145                 150                 155 gta tgc atc tcc ttg tac gcc tgg ttt gat tac aac atg ctg cac cgc      530
Val Cys Ile Ser Leu Tyr Ala Trp Phe Asp Tyr Asn Met Leu His Arg
160                 165                 170                 175 aag cat tgg gag cac cac aac cac act ggc gag gtg ggc aag gac cct      578
Lys His Trp Glu His His Asn His Thr Gly Glu Val Gly Lys Asp Pro
                180                 185                 190 gac ttc cac agg gga aac cct ggc att gtg ccc tgg ttt gcc agc ttc      626
Asp Phe His Arg Gly Asn Pro Gly Ile Val Pro Trp Phe Ala Ser Phe
            195                 200                 205 atg tcc agc tac atg tcg atg tgg cag ttt gcg cgc ctc gca tgg tgg      674
Met Ser Ser Tyr Met Ser Met Trp Gln Phe Ala Arg Leu Ala Trp Trp
        210                 215                 220 acg gtg gtc atg cag ctg ctg ggt gcg cca atg gcg aac ctg ctg gtg      722
Thr Val Val Met Gln Leu Leu Gly Ala Pro Met Ala Asn Leu Leu Val
    225                 230                 235 ttc atg gcg gcc gcg ccc atc ctg tcc gcc ttc cgc ttg ttc tac ttt      770
Phe Met Ala Ala Ala Pro Ile Leu Ser Ala Phe Arg Leu Phe Tyr Phe
240                 245                 250                 255 ggc acg tac atg ccc cac aag cct gag cct ggc gcc gcg tca ggc tct      818
```

-continued

```
Gly Thr Tyr Met Pro His Lys Pro Glu Pro Gly Ala Ala Ser Gly Ser
                260                 265                 270 tca cca gcc gtc atg aac tgg tgg aag tcg cgc act agc cag gcg tcc      866
Ser Pro Ala Val Met Asn Trp Trp Lys Ser Arg Thr Ser Gln Ala Ser
        275                 280                 285 gac ctg gtc agc ttt ctg acc tgc tac cac ttc gac ctg cac tgg gag      914
Asp Leu Val Ser Phe Leu Thr Cys Tyr His Phe Asp Leu His Trp Glu
            290                 295                 300 cac cac cgc tgg ccc ttt gcc ccc tgg tgg gag ctg ccc aac tgc cgc      962
His His Arg Trp Pro Phe Ala Pro Trp Trp Glu Leu Pro Asn Cys Arg
305                 310                 315 cgc ctg tct ggc cga ggt ctg gtt cct gcc tag ctggacacac tgcagtgggc    1015
Arg Leu Ser Gly Arg Gly Leu Val Pro Ala
320                 325 cctgctgcca gctgggcatg caggttgtgg caggactggg tgaggtgaaa agctgcaggc    1075
gctgctgccg gacacgctgc atgggctacc ctgtgtagct gccgccacta ggggaggggg    1135
tttgtagctg tcgagcttgc                                                1155

<210> SEQ ID NO 23
<211> LENGTH: 329
<212> TYPE: PRT
<213> ORGANISM: Haematococcus pluvialis

<400> SEQUENCE: 23

Met Gln Leu Ala Ala Thr Val Met Leu Glu Gln Leu Thr Gly Ser Ala
1               5                   10                  15

Glu Ala Leu Lys Glu Lys Glu Lys Glu Val Ala Gly Ser Ser Asp Val
            20                  25                  30

Leu Arg Thr Trp Ala Thr Gln Tyr Ser Leu Pro Ser Glu Glu Ser Asp
        35                  40                  45

Ala Ala Arg Pro Gly Leu Lys Asn Ala Tyr Lys Pro Pro Ser Asp
    50                  55                  60

Thr Lys Gly Ile Thr Met Ala Leu Ala Val Ile Gly Ser Trp Ala Ala
65                  70                  75                  80

Val Phe Leu His Ala Ile Phe Gln Ile Lys Leu Pro Thr Ser Leu Asp
                85                  90                  95

Gln Leu His Trp Leu Pro Val Ser Asp Ala Thr Ala Gln Leu Val Ser
            100                 105                 110

Gly Ser Ser Ser Leu Leu His Ile Val Val Phe Val Leu Glu
        115                 120                 125

Phe Leu Tyr Thr Gly Leu Phe Ile Thr Thr His Asp Ala Met His Gly
    130                 135                 140

Thr Ile Ala Met Arg Asn Arg Gln Leu Asn Asp Phe Leu Gly Arg Val
145                 150                 155                 160

Cys Ile Ser Leu Tyr Ala Trp Phe Asp Tyr Asn Met Leu His Arg Lys
                165                 170                 175

His Trp Glu His His Asn His Thr Gly Glu Val Gly Lys Asp Pro Asp
            180                 185                 190

Phe His Arg Gly Asn Pro Gly Ile Val Pro Trp Phe Ala Ser Phe Met
        195                 200                 205

Ser Ser Tyr Met Ser Met Trp Gln Phe Ala Arg Leu Ala Trp Trp Thr
    210                 215                 220

Val Val Met Gln Leu Leu Gly Ala Pro Met Ala Asn Leu Leu Val Phe
225                 230                 235                 240

Met Ala Ala Ala Pro Ile Leu Ser Ala Phe Arg Leu Phe Tyr Phe Gly
```

```
                            245                 250                 255
Thr Tyr Met Pro His Lys Pro Glu Pro Gly Ala Ala Ser Gly Ser Ser
            260                 265                 270

Pro Ala Val Met Asn Trp Trp Lys Ser Arg Thr Ser Gln Ala Ser Asp
            275                 280                 285

Leu Val Ser Phe Leu Thr Cys Tyr His Phe Asp Leu His Trp Glu His
            290                 295                 300

His Arg Trp Pro Phe Ala Pro Trp Trp Glu Leu Pro Asn Cys Arg Arg
305                 310                 315                 320

Leu Ser Gly Arg Gly Leu Val Pro Ala
                325

<210> SEQ ID NO 24
<211> LENGTH: 1111
<212> TYPE: DNA
<213> ORGANISM: Haematococcus pluvialis
<220> FEATURE:
<221> NAME/KEY: CDS
<222> LOCATION: (4)..(951)

<400> SEQUENCE: 24 tgc atg cta gag gca ctc aag gag aag gag aag gag gtt gca ggc agc         48
    Met Leu Glu Ala Leu Lys Glu Lys Glu Lys Glu Val Ala Gly Ser
    1               5                   10                  15 tct gac gtg ttg cgt aca tgg gcg acc cag tac tcg ctt ccg tca gaa         96
Ser Asp Val Leu Arg Thr Trp Ala Thr Gln Tyr Ser Leu Pro Ser Glu
                20                  25                  30 gag tca gac gcg gcc cgc ccg gga ctg aag aat gcc tac aag cca cca        144
Glu Ser Asp Ala Ala Arg Pro Gly Leu Lys Asn Ala Tyr Lys Pro Pro
            35                  40                  45 cct tcc gac aca aag ggc atc aca atg gcg cta gct gtc atc ggc tcc        192
Pro Ser Asp Thr Lys Gly Ile Thr Met Ala Leu Ala Val Ile Gly Ser
        50                  55                  60 tgg gcc gca gtg ttc ctc cac gcc att ttt caa atc aag ctt ccg acc        240
Trp Ala Ala Val Phe Leu His Ala Ile Phe Gln Ile Lys Leu Pro Thr
65                  70                  75 tcc ttg gac cag ctg cac tgg ctg ccc gtg tca gat gcc aca gct cag        288
Ser Leu Asp Gln Leu His Trp Leu Pro Val Ser Asp Ala Thr Ala Gln
80                  85                  90                  95 ctg gtt agc ggc agc agc agc ctg ctg cac atc gtc gta gta ttc ttt        336
Leu Val Ser Gly Ser Ser Ser Leu Leu His Ile Val Val Val Phe Phe
                100                 105                 110 gtc ctg gag ttc ctg tac aca ggc ctt ttt atc acc acg cat gat gct        384
Val Leu Glu Phe Leu Tyr Thr Gly Leu Phe Ile Thr Thr His Asp Ala
            115                 120                 125 atg cat ggc acc atc gcc atg aga aac agg cag ctt aat gac ttc ttg        432
Met His Gly Thr Ile Ala Met Arg Asn Arg Gln Leu Asn Asp Phe Leu
        130                 135                 140 ggc aga gta tgc atc tcc ttg tac gcc tgg ttt gat tac aac atg ctg        480
Gly Arg Val Cys Ile Ser Leu Tyr Ala Trp Phe Asp Tyr Asn Met Leu
    145                 150                 155 cac cgc aag cat tgg gag cac cac aac cac act ggc gag gtg ggc aag        528
His Arg Lys His Trp Glu His His Asn His Thr Gly Glu Val Gly Lys
160                 165                 170                 175 gac cct gac ttc cac agg gga aac cct ggc att gtg ccc tgg ttt gcc        576
Asp Pro Asp Phe His Arg Gly Asn Pro Gly Ile Val Pro Trp Phe Ala
                180                 185                 190 agc ttc atg tcc agc tac atg tcg atg tgg cag ttt gcg cgc ctc gca        624
Ser Phe Met Ser Ser Tyr Met Ser Met Trp Gln Phe Ala Arg Leu Ala
            195                 200                 205
```

```
tgg tgg acg gtg gtc atg cag ctg ctg ggt gcg cca atg gcg aac ctg      672
Trp Trp Thr Val Val Met Gln Leu Leu Gly Ala Pro Met Ala Asn Leu
            210                 215                 220 ctg gtg ttc atg gcg gcc gcg ccc atc ctg tcc gcc ttc cgc ttg ttc      720
Leu Val Phe Met Ala Ala Ala Pro Ile Leu Ser Ala Phe Arg Leu Phe
        225                 230                 235 tac ttt ggc acg tac atg ccc cac aag cct gag cct ggc gcc gcg tca      768
Tyr Phe Gly Thr Tyr Met Pro His Lys Pro Glu Pro Gly Ala Ala Ser
240                 245                 250                 255 ggc tct tca cca gcc gtc atg aac tgg tgg aag tcg cgc act agc cag      816
Gly Ser Ser Pro Ala Val Met Asn Trp Trp Lys Ser Arg Thr Ser Gln
                260                 265                 270 gcg tcc gac ctg gtc agc ttt ctg acc tgc tac cac ttc gac ctg cac      864
Ala Ser Asp Leu Val Ser Phe Leu Thr Cys Tyr His Phe Asp Leu His
            275                 280                 285 tgg gag cac cac cgc tgg ccc ttc gcc ccc tgg tgg gag ctg ccc aac      912
Trp Glu His His Arg Trp Pro Phe Ala Pro Trp Trp Glu Leu Pro Asn
        290                 295                 300 tgc cgc cgc ctg tct ggc cga ggt ctg gtt cct gcc tag ctggacacac      961
Cys Arg Arg Leu Ser Gly Arg Gly Leu Val Pro Ala
305                 310                 315 tgcagtgggc cctgctgcca gctgggcatg caggttgtgg caggactggg tgaggtgaaa   1021
agctgcaggc gctgctgccg gacacgttgc atgggctacc ctgtgtagct gccgccacta   1081
ggggaggggg tttgtagctg tcgagcttgc                                    1111

<210> SEQ ID NO 25
<211> LENGTH: 315
<212> TYPE: PRT
<213> ORGANISM: Haematococcus pluvialis

<400> SEQUENCE: 25

Met Leu Glu Ala Leu Lys Glu Lys Glu Val Ala Gly Ser Ser
1               5                   10                  15

Asp Val Leu Arg Thr Trp Ala Thr Gln Tyr Ser Leu Pro Ser Glu Glu
            20                  25                  30

Ser Asp Ala Ala Arg Pro Gly Leu Lys Asn Ala Tyr Lys Pro Pro Pro
        35                  40                  45

Ser Asp Thr Lys Gly Ile Thr Met Ala Leu Ala Val Ile Gly Ser Trp
    50                  55                  60

Ala Ala Val Phe Leu His Ala Ile Phe Gln Ile Lys Leu Pro Thr Ser
65                  70                  75                  80

Leu Asp Gln Leu His Trp Leu Pro Val Ser Asp Ala Thr Ala Gln Leu
                85                  90                  95

Val Ser Gly Ser Ser Leu Leu His Ile Val Val Phe Phe Val
            100                 105                 110

Leu Glu Phe Leu Tyr Thr Gly Leu Phe Ile Thr Thr His Asp Ala Met
        115                 120                 125

His Gly Thr Ile Ala Met Arg Asn Arg Gln Leu Asn Asp Phe Leu Gly
    130                 135                 140

Arg Val Cys Ile Ser Leu Tyr Ala Trp Phe Asp Tyr Asn Met Leu His
145                 150                 155                 160

Arg Lys His Trp Glu His His Asn His Thr Gly Glu Val Gly Lys Asp
                165                 170                 175

Pro Asp Phe His Arg Gly Asn Pro Gly Ile Val Pro Trp Phe Ala Ser
            180                 185                 190
```

```
Phe Met Ser Ser Tyr Met Ser Met Trp Gln Phe Ala Arg Leu Ala Trp
            195                 200                 205

Trp Thr Val Val Met Gln Leu Leu Gly Ala Pro Met Ala Asn Leu Leu
    210                 215                 220

Val Phe Met Ala Ala Pro Ile Leu Ser Ala Phe Arg Leu Phe Tyr
225                 230                 235                 240

Phe Gly Thr Tyr Met Pro His Lys Pro Glu Pro Gly Ala Ala Ser Gly
                245                 250                 255

Ser Ser Pro Ala Val Met Asn Trp Trp Lys Ser Arg Thr Ser Gln Ala
            260                 265                 270

Ser Asp Leu Val Ser Phe Leu Thr Cys Tyr His Phe Asp Leu His Trp
        275                 280                 285

Glu His His Arg Trp Pro Phe Ala Pro Trp Trp Glu Leu Pro Asn Cys
    290                 295                 300

Arg Arg Leu Ser Gly Arg Gly Leu Val Pro Ala
305                 310                 315

<210> SEQ ID NO 26
<211> LENGTH: 1031
<212> TYPE: DNA
<213> ORGANISM: Haematococcus pluvialis
<220> FEATURE:
<221> NAME/KEY: CDS
<222> LOCATION: (6)..(1031)

<400> SEQUENCE: 26 gaagc atg cag cta gca gcg aca gta atg ttg gag cag ctt acc gga agc      50
      Met Gln Leu Ala Ala Thr Val Met Leu Glu Gln Leu Thr Gly Ser
       1               5                  10                  15 gct gag gca ctc aag gag aag gag aag gag gtt gca ggc agc tct gac       98
Ala Glu Ala Leu Lys Glu Lys Glu Lys Glu Val Ala Gly Ser Ser Asp
                 20                  25                  30 gtg ttg cgt aca tgg gcg acc cag tac tcg ctt ccg tca gag gag tca      146
Val Leu Arg Thr Trp Ala Thr Gln Tyr Ser Leu Pro Ser Glu Glu Ser
             35                  40                  45 gac gcg gcc cgc ccg gga ctg aag aat gcc tac aag cca cca cct tcc      194
Asp Ala Ala Arg Pro Gly Leu Lys Asn Ala Tyr Lys Pro Pro Pro Ser
         50                  55                  60 gac aca aag ggc atc aca atg gcg cta gct gtc atc ggc tcc tgg gct      242
Asp Thr Lys Gly Ile Thr Met Ala Leu Ala Val Ile Gly Ser Trp Ala
     65                  70                  75 gca gtg ttc ctc cac gcc att ttt caa atc aag ctt ccg acc tcc ttg      290
Ala Val Phe Leu His Ala Ile Phe Gln Ile Lys Leu Pro Thr Ser Leu
 80                  85                  90                  95 gac cag ctg cac tgg ctg ccc gtg tca gat gcc aca gct cag ctg gtt      338
Asp Gln Leu His Trp Leu Pro Val Ser Asp Ala Thr Ala Gln Leu Val
                100                 105                 110 agc ggc agc agc agc ctg ctg cac atc gtc gta gta ttc ttt gtc ctg      386
Ser Gly Ser Ser Ser Leu Leu His Ile Val Val Val Phe Phe Val Leu
            115                 120                 125 gag ttc ctg tac aca ggc ctt ttt atc acc acg cat gat gct atg cat      434
Glu Phe Leu Tyr Thr Gly Leu Phe Ile Thr Thr His Asp Ala Met His
        130                 135                 140 ggc acc atc gcc atg aga aac agg cag ctt aat gac ttc ttg ggc aga      482
Gly Thr Ile Ala Met Arg Asn Arg Gln Leu Asn Asp Phe Leu Gly Arg
    145                 150                 155 gta tgc atc tcc ttg tac gcc tgg ttt gat tac aac atg ctg cac cgc      530
Val Cys Ile Ser Leu Tyr Ala Trp Phe Asp Tyr Asn Met Leu His Arg
160                 165                 170                 175
```

```
aag cat tgg gag cac cac aac cac act ggc gag gtg ggc aag gac cct       578
Lys His Trp Glu His His Asn His Thr Gly Glu Val Gly Lys Asp Pro
                    180                 185                 190 gac ttc cac agg gga aac cct ggc att gtg ccc tgg ttt gcc agc ttc       626
Asp Phe His Arg Gly Asn Pro Gly Ile Val Pro Trp Phe Ala Ser Phe
            195                 200                 205 atg tcc agc tac atg tcg atg tgg cag ttt gcg cgc ctc gca tgg tgg       674
Met Ser Ser Tyr Met Ser Met Trp Gln Phe Ala Arg Leu Ala Trp Trp
        210                 215                 220 acg gtg gtc atg cag ctg ctg ggt gcg cca atg gcg aac ctg ctg gtg       722
Thr Val Val Met Gln Leu Leu Gly Ala Pro Met Ala Asn Leu Leu Val
    225                 230                 235 ttc atg gcg gcc gcg ccc atc ctg tcc gcc ttc cgc ttg ttc tac ttt       770
Phe Met Ala Ala Ala Pro Ile Leu Ser Ala Phe Arg Leu Phe Tyr Phe
240                 245                 250                 255 ggc acg tac atg ccc cac aag cct gag cct ggc gcc gcg tca ggc tct       818
Gly Thr Tyr Met Pro His Lys Pro Glu Pro Gly Ala Ala Ser Gly Ser
                    260                 265                 270 tca cca gcc gtc atg aac tgg tgg aag tcg cgc act agc cag gcg tcc       866
Ser Pro Ala Val Met Asn Trp Trp Lys Ser Arg Thr Ser Gln Ala Ser
            275                 280                 285 gac ctg gtc agc ttt ctg acc tgc tac cac ttc gac ctg cac tgg gag       914
Asp Leu Val Ser Phe Leu Thr Cys Tyr His Phe Asp Leu His Trp Glu
        290                 295                 300 cac cac cgc tgg ccc ttt gcc ccc tgg tgg gag ctg ccc aac tgc cgc       962
His His Arg Trp Pro Phe Ala Pro Trp Trp Glu Leu Pro Asn Cys Arg
    305                 310                 315 cgc ctg tct ggc cga ggt ctg gtt cct gcc gag caa aaa ctc atc tca      1010
Arg Leu Ser Gly Arg Gly Leu Val Pro Ala Glu Gln Lys Leu Ile Ser
320                 325                 330                 335 gaa gag gat ctg aat agc tag                                          1031
Glu Glu Asp Leu Asn Ser
                    340

<210> SEQ ID NO 27
<211> LENGTH: 341
<212> TYPE: PRT
<213> ORGANISM: Haematococcus pluvialis

<400> SEQUENCE: 27

Met Gln Leu Ala Ala Thr Val Met Leu Glu Gln Leu Thr Gly Ser Ala
1               5                   10                  15

Glu Ala Leu Lys Glu Lys Glu Lys Val Ala Gly Ser Ser Asp Val
            20                  25                  30

Leu Arg Thr Trp Ala Thr Gln Tyr Ser Leu Pro Ser Glu Glu Ser Asp
        35                  40                  45

Ala Ala Arg Pro Gly Leu Lys Asn Ala Tyr Lys Pro Pro Ser Asp
    50                  55                  60

Thr Lys Gly Ile Thr Met Ala Leu Ala Val Ile Gly Ser Trp Ala Ala
65                  70                  75                  80

Val Phe Leu His Ala Ile Phe Gln Ile Lys Leu Pro Thr Ser Leu Asp
                85                  90                  95

Gln Leu His Trp Leu Pro Val Ser Asp Ala Thr Ala Gln Leu Val Ser
            100                 105                 110

Gly Ser Ser Ser Leu Leu His Ile Val Val Phe Val Leu Glu
        115                 120                 125

Phe Leu Tyr Thr Gly Leu Phe Ile Thr Thr His Asp Ala Met His Gly
    130                 135                 140
```

-continued

```
Thr Ile Ala Met Arg Asn Arg Gln Leu Asn Asp Phe Leu Gly Arg Val
145                 150                 155                 160

Cys Ile Ser Leu Tyr Ala Trp Phe Asp Tyr Asn Met Leu His Arg Lys
                165                 170                 175

His Trp Glu His His Asn His Thr Gly Glu Val Gly Lys Asp Pro Asp
            180                 185                 190

Phe His Arg Gly Asn Pro Gly Ile Val Pro Trp Phe Ala Ser Phe Met
        195                 200                 205

Ser Ser Tyr Met Ser Met Trp Gln Phe Ala Arg Leu Ala Trp Trp Thr
    210                 215                 220

Val Val Met Gln Leu Leu Gly Ala Pro Met Ala Asn Leu Leu Val Phe
225                 230                 235                 240

Met Ala Ala Ala Pro Ile Leu Ser Ala Phe Arg Leu Phe Tyr Phe Gly
                245                 250                 255

Thr Tyr Met Pro His Lys Pro Glu Pro Gly Ala Ala Ser Gly Ser Ser
                260                 265                 270

Pro Ala Val Met Asn Trp Trp Lys Ser Arg Thr Ser Gln Ala Ser Asp
            275                 280                 285

Leu Val Ser Phe Leu Thr Cys Tyr His Phe Asp Leu His Trp Glu His
    290                 295                 300

His Arg Trp Pro Phe Ala Pro Trp Trp Glu Leu Pro Asn Cys Arg Arg
305                 310                 315                 320

Leu Ser Gly Arg Gly Leu Val Pro Ala Glu Gln Lys Leu Ile Ser Glu
                325                 330                 335

Glu Asp Leu Asn Ser
            340

<210> SEQ ID NO 28
<211> LENGTH: 777
<212> TYPE: DNA
<213> ORGANISM: Arabidopsis thaliana
<220> FEATURE:
<221> NAME/KEY: promoter

<400> SEQUENCE: 28
gagctcactc actgatttcc attgcttgaa aattgatgat gaactaagat caatccatgt    60
tagtttcaaa acaacagtaa ctgtggccaa cttagttttg aaacaacact aactggtcga   120
agcaaaaaga aaaagagtt tcatcatata tctgatttga tggactgttt ggagttagga    180
ccaaacatta tctacaaaca aagacttttc tcctaacttg tgattccttc ttaaacccta   240
ggggtaatat tctattttcc aaggatcttt agttaaaggc aaatccggga aattattgta   300
atcatttggg gaaacatata aaagatttga gttagatgga agtgacgatt aatccaaaca   360
tatatatctc tttcttctta tttcccaaat taacagacaa agtagaata ttggctttta    420
acaccaatat aaaaacttgc ttcacaccta aacacttttg tttactttag ggtaagtgca   480
aaaagccaac caaatccacc tgcactgatt tgacgtttac aaacgccgtt aagtcgatgt   540
ccgttgattt aaacagtgtc ttgtaattaa aaaaatcagt ttacataaat ggaaaattta   600
tcacttagtt ttcatcaact tctgaactta cctttcatgg attaggcaat actttccatt   660
tttagtaact caagtggacc ctttacttct tcaactccat ctctctcttt ctatttcact   720
tctttcttct cattatatct cttgtcctct ccaccaaatc tcttcaacaa aaagctt      777

<210> SEQ ID NO 29
<211> LENGTH: 22
<212> TYPE: DNA
```

<213> ORGANISM: Unknown
<220> FEATURE:
<221> NAME/KEY: primer_bind
<223> OTHER INFORMATION: Synthetic sequence

<400> SEQUENCE: 29
gcaagctcga cagctacaaa cc                                        22

<210> SEQ ID NO 30
<211> LENGTH: 24
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 30
gaagcatgca gctagcagcg acag                                      24

<210> SEQ ID NO 31
<211> LENGTH: 30
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 31
tgcatgctag aggcactcaa ggagaaggag                                30

<210> SEQ ID NO 32
<211> LENGTH: 59
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 32
ctagctattc agatcctctt ctgagatgag tttttgctcg gcaggaacca gacctcggc    59

<210> SEQ ID NO 33
<211> LENGTH: 28
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 33
gagctcactc actgatttcc attgcttg                                  28

<210> SEQ ID NO 34
<211> LENGTH: 37
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 34
cgccgttaag tcgatgtccg ttgatttaaa cagtgtc                        37

<210> SEQ ID NO 35
<211> LENGTH: 34
<212> TYPE: DNA
<213> ORGANISM: Unknown

```
<220> FEATURE:
<221> NAME/KEY: primer_bind
<223> OTHER INFORMATION: Synthetic sequence

<400> SEQUENCE: 35
atcaacggac atcgacttaa cggcgtttgt aaac                                    34

<210> SEQ ID NO 36
<211> LENGTH: 25
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 36
taagcttttt gttgaagaga tttgg                                              25

<210> SEQ ID NO 37
<211> LENGTH: 212
<212> TYPE: DNA
<213> ORGANISM: Unknown
<220> FEATURE:
<221> NAME/KEY: Intron
<223> OTHER INFORMATION: Synthetic sequence

<400> SEQUENCE: 37
gtcgactacg taagtttctg cttctacctt tgatatatat ataataatta tcattaatta        60
gtagtaatat aatatttcaa atattttttt caaaataaaa gaatgtagta tatagcaatt       120
gcttttctgt agtttataag tgtgtatatt ttaatttata acttttctaa tatatgacca       180
aaatttgttg atgtgcaggt atcaccggat cc                                     212

<210> SEQ ID NO 38
<211> LENGTH: 1830
<212> TYPE: DNA
<213> ORGANISM: Tagetes erecta
<220> FEATURE:
<221> NAME/KEY: CDS
<222> LOCATION: (141)..(1691)

<400> SEQUENCE: 38
ggcacgaggc aaagcaaagg ttgtttgttg ttgttgttga gagacactcc aatccaaaca        60
gatacaaggc gtgactggat atttctctct cgttcctaac aacagcaacg aagaagaaaa       120
agaatcatta ctaacaatca atg agt atg aga gct gga cac atg acg gca aca      173
                         Met Ser Met Arg Ala Gly His Met Thr Ala Thr
                           1               5                  10 atg gcg gct ttt aca tgc cct agg ttt atg act agc atc aga tac acg        221
Met Ala Ala Phe Thr Cys Pro Arg Phe Met Thr Ser Ile Arg Tyr Thr
             15                  20                  25 aag caa att aag tgc aac gct gct aaa agc cag cta gtc gtt aaa caa        269
Lys Gln Ile Lys Cys Asn Ala Ala Lys Ser Gln Leu Val Val Lys Gln
         30                  35                  40 gag att gag gag gaa gaa gat tat gtg aaa gcc ggt gga tcg gag ctg        317
Glu Ile Glu Glu Glu Glu Asp Tyr Val Lys Ala Gly Gly Ser Glu Leu
     45                  50                  55 ctt ttt gtt caa atg caa cag aat aag tcc atg gat gca cag tct agc        365
Leu Phe Val Gln Met Gln Gln Asn Lys Ser Met Asp Ala Gln Ser Ser
 60                  65                  70                  75 cta tcc caa aag ctc cca agg gta cca ata gga gga gga gga gac agt        413
Leu Ser Gln Lys Leu Pro Arg Val Pro Ile Gly Gly Gly Gly Asp Ser
                 80                  85                  90
```

```
aac tgt ata ctg gat ttg gtt gta att ggt tgt ggt cct gct ggc ctt      461
Asn Cys Ile Leu Asp Leu Val Val Ile Gly Cys Gly Pro Ala Gly Leu
            95                  100                 105 gct ctt gct gga gaa tca gcc aag cta ggc ttg aat gtc gca ctt atc      509
Ala Leu Ala Gly Glu Ser Ala Lys Leu Gly Leu Asn Val Ala Leu Ile
        110                 115                 120 ggc cct gat ctt cct ttt aca aat aac tat ggt gtt tgg gag gat gaa      557
Gly Pro Asp Leu Pro Phe Thr Asn Asn Tyr Gly Val Trp Glu Asp Glu
125                 130                 135 ttt ata ggt ctt gga ctt gag ggc tgt att gaa cat gtt tgg cga gat      605
Phe Ile Gly Leu Gly Leu Glu Gly Cys Ile Glu His Val Trp Arg Asp
140                 145                 150                 155 act gta gta tat ctt gat gac aac gat ccc att ctc ata ggt cgt gcc      653
Thr Val Val Tyr Leu Asp Asp Asn Asp Pro Ile Leu Ile Gly Arg Ala
            160                 165                 170 tat gga cga gtt agt cgt gat tta ctt cac gag gag ttg ttg act agg      701
Tyr Gly Arg Val Ser Arg Asp Leu Leu His Glu Glu Leu Leu Thr Arg
        175                 180                 185 tgc atg gag tca ggc gtt tca tat ctg agc tcc aaa gtg gaa cgg att      749
Cys Met Glu Ser Gly Val Ser Tyr Leu Ser Ser Lys Val Glu Arg Ile
        190                 195                 200 act gaa gct cca aat ggc cta agt ctc ata gag tgt gaa ggc aat atc      797
Thr Glu Ala Pro Asn Gly Leu Ser Leu Ile Glu Cys Glu Gly Asn Ile
205                 210                 215 aca att cca tgc agg ctt gct act gtc gct tct gga gca gct tct gga      845
Thr Ile Pro Cys Arg Leu Ala Thr Val Ala Ser Gly Ala Ala Ser Gly
220                 225                 230                 235 aaa ctt ttg cag tat gaa ctt ggc ggt ccc cgt gtt tgc gtt caa aca      893
Lys Leu Leu Gln Tyr Glu Leu Gly Gly Pro Arg Val Cys Val Gln Thr
            240                 245                 250 gct tat ggt ata gag gtt gag gtt gaa agc ata ccc tat gat cca agc      941
Ala Tyr Gly Ile Glu Val Glu Val Glu Ser Ile Pro Tyr Asp Pro Ser
        255                 260                 265 cta atg gtt ttc atg gat tat aga gac tac acc aaa cat aaa tct caa      989
Leu Met Val Phe Met Asp Tyr Arg Asp Tyr Thr Lys His Lys Ser Gln
        270                 275                 280 tca cta gaa gca caa tat cca aca ttt ttg tat gtc atg cca atg tct     1037
Ser Leu Glu Ala Gln Tyr Pro Thr Phe Leu Tyr Val Met Pro Met Ser
285                 290                 295 cca act aaa gta ttc ttt gag gaa act tgt ttg gct tca aaa gag gcc     1085
Pro Thr Lys Val Phe Phe Glu Glu Thr Cys Leu Ala Ser Lys Glu Ala
300                 305                 310                 315 atg cct ttt gag tta ttg aag aca aaa ctc atg tca aga tta aag act     1133
Met Pro Phe Glu Leu Leu Lys Thr Lys Leu Met Ser Arg Leu Lys Thr
            320                 325                 330 atg ggg atc cga ata acc aaa act tat gaa gag gaa tgg tca tat att     1181
Met Gly Ile Arg Ile Thr Lys Thr Tyr Glu Glu Glu Trp Ser Tyr Ile
        335                 340                 345 cca gta ggt gga tcc tta cca aat acc gag caa aag aac ctt gca ttt     1229
Pro Val Gly Gly Ser Leu Pro Asn Thr Glu Gln Lys Asn Leu Ala Phe
        350                 355                 360 ggt gct gct gct agc atg gtg cat cca gcc aca gga tat tcg gtt gta     1277
Gly Ala Ala Ala Ser Met Val His Pro Ala Thr Gly Tyr Ser Val Val
365                 370                 375 aga tca ctg tca gaa gct cct aat tat gca gca gta att gca aag att     1325
Arg Ser Leu Ser Glu Ala Pro Asn Tyr Ala Ala Val Ile Ala Lys Ile
380                 385                 390                 395 tta ggg aaa gga aat tca aaa cag atg ctt gat cat gga aga tac aca     1373
Leu Gly Lys Gly Asn Ser Lys Gln Met Leu Asp His Gly Arg Tyr Thr
            400                 405                 410
```

-continued

```
acc aac atc tca aag caa gct tgg gaa aca ctt tgg ccc ctt gaa agg       1421
Thr Asn Ile Ser Lys Gln Ala Trp Glu Thr Leu Trp Pro Leu Glu Arg
        415                 420                 425 aaa aga cag aga gca ttc ttt ctc ttt gga tta gca ctg att gtc cag       1469
Lys Arg Gln Arg Ala Phe Phe Leu Phe Gly Leu Ala Leu Ile Val Gln
    430                 435                 440 atg gat att gag ggg acc cgc aca ttc ttc cgg act ttc ttc cgc ttg       1517
Met Asp Ile Glu Gly Thr Arg Thr Phe Phe Arg Thr Phe Phe Arg Leu
445                 450                 455 ccc aca tgg atg tgg tgg ggg ttt ctt gga tct tcg tta tca tca act       1565
Pro Thr Trp Met Trp Trp Gly Phe Leu Gly Ser Ser Leu Ser Ser Thr
460                 465                 470                 475 gac ttg ata ata ttt gcg ttt tac atg ttt atc ata gca ccg cat agc       1613
Asp Leu Ile Ile Phe Ala Phe Tyr Met Phe Ile Ile Ala Pro His Ser
                480                 485                 490 ctg aga atg ggt ctg gtt aga cat ttg ctt tct gac ccg aca gga gga       1661
Leu Arg Met Gly Leu Val Arg His Leu Leu Ser Asp Pro Thr Gly Gly
            495                 500                 505 aca atg tta aaa gcg tat ctc acg ata taa ataactctag tcgcgatcag        1711
Thr Met Leu Lys Ala Tyr Leu Thr Ile
        510                 515 tttagattat aggcacatct tgcatatata tatgtataaa ccttatgtgt gctgtatcct    1771
tacatcaaca cagtcattaa ttgtatttct tggggtaatg ctgatgaagt attttctgg    1830
```

<210> SEQ ID NO 39
<211> LENGTH: 516
<212> TYPE: PRT
<213> ORGANISM: Tagetes erecta

<400> SEQUENCE: 39

```
Met Ser Met Arg Ala Gly His Met Thr Ala Thr Met Ala Ala Phe Thr
1               5                   10                  15

Cys Pro Arg Phe Met Thr Ser Ile Arg Tyr Thr Lys Gln Ile Lys Cys
            20                  25                  30

Asn Ala Ala Lys Ser Gln Leu Val Val Lys Gln Glu Ile Glu Glu Glu
        35                  40                  45

Glu Asp Tyr Val Lys Ala Gly Gly Ser Glu Leu Leu Phe Val Gln Met
    50                  55                  60

Gln Gln Asn Lys Ser Met Asp Ala Gln Ser Ser Leu Ser Gln Lys Leu
65                  70                  75                  80

Pro Arg Val Pro Ile Gly Gly Gly Gly Asp Ser Asn Cys Ile Leu Asp
                85                  90                  95

Leu Val Val Ile Gly Cys Gly Pro Ala Gly Leu Ala Leu Ala Gly Glu
            100                 105                 110

Ser Ala Lys Leu Gly Leu Asn Val Ala Leu Ile Gly Pro Asp Leu Pro
        115                 120                 125

Phe Thr Asn Asn Tyr Gly Val Trp Glu Asp Glu Phe Ile Gly Leu Gly
    130                 135                 140

Leu Glu Gly Cys Ile Glu His Val Trp Arg Asp Thr Val Tyr Leu
145                 150                 155                 160

Asp Asp Asn Asp Pro Ile Leu Ile Gly Arg Ala Tyr Gly Arg Val Ser
                165                 170                 175

Arg Asp Leu Leu His Glu Glu Leu Leu Thr Arg Cys Met Glu Ser Gly
            180                 185                 190

Val Ser Tyr Leu Ser Ser Lys Val Glu Arg Ile Thr Glu Ala Pro Asn
        195                 200                 205
```

Gly Leu Ser Leu Ile Glu Cys Glu Gly Asn Ile Thr Ile Pro Cys Arg
    210                 215                 220

Leu Ala Thr Val Ala Ser Gly Ala Ala Ser Gly Lys Leu Leu Gln Tyr
225                 230                 235                 240

Glu Leu Gly Gly Pro Arg Val Cys Val Gln Thr Ala Tyr Gly Ile Glu
                245                 250                 255

Val Glu Val Glu Ser Ile Pro Tyr Asp Pro Ser Leu Met Val Phe Met
            260                 265                 270

Asp Tyr Arg Asp Tyr Thr Lys His Lys Ser Gln Ser Leu Glu Ala Gln
        275                 280                 285

Tyr Pro Thr Phe Leu Tyr Val Met Pro Met Ser Pro Thr Lys Val Phe
    290                 295                 300

Phe Glu Glu Thr Cys Leu Ala Ser Lys Glu Ala Met Pro Phe Glu Leu
305                 310                 315                 320

Leu Lys Thr Lys Leu Met Ser Arg Leu Lys Thr Met Gly Ile Arg Ile
                325                 330                 335

Thr Lys Thr Tyr Glu Glu Glu Trp Ser Tyr Ile Pro Val Gly Gly Ser
            340                 345                 350

Leu Pro Asn Thr Glu Gln Lys Asn Leu Ala Phe Gly Ala Ala Ala Ser
        355                 360                 365

Met Val His Pro Ala Thr Gly Tyr Ser Val Val Arg Ser Leu Ser Glu
    370                 375                 380

Ala Pro Asn Tyr Ala Ala Val Ile Ala Lys Ile Leu Gly Lys Gly Asn
385                 390                 395                 400

Ser Lys Gln Met Leu Asp His Gly Arg Tyr Thr Thr Asn Ile Ser Lys
                405                 410                 415

Gln Ala Trp Glu Thr Leu Trp Pro Leu Glu Arg Lys Arg Gln Arg Ala
            420                 425                 430

Phe Phe Leu Phe Gly Leu Ala Leu Ile Val Gln Met Asp Ile Glu Gly
        435                 440                 445

Thr Arg Thr Phe Phe Arg Thr Phe Arg Leu Pro Thr Trp Met Trp
    450                 455                 460

Trp Gly Phe Leu Gly Ser Ser Leu Ser Ser Thr Asp Leu Ile Ile Phe
465                 470                 475                 480

Ala Phe Tyr Met Phe Ile Ile Ala Pro His Ser Leu Arg Met Gly Leu
                485                 490                 495

Val Arg His Leu Leu Ser Asp Pro Thr Gly Gly Thr Met Leu Lys Ala
            500                 505                 510

Tyr Leu Thr Ile
    515

<210> SEQ ID NO 40
<211> LENGTH: 445
<212> TYPE: DNA
<213> ORGANISM: Tagetes erecta
<220> FEATURE:
<221> NAME/KEY: misc_feature
<222> LOCATION: (1)..(445)
<223> OTHER INFORMATION: Sense Fragment

<400> SEQUENCE: 40
aagcttgcac gaggcaaagc aaaggttgtt tgttgttgtt gttgagagac actccaatcc      60
aaacagatac aaggcgtgac tggatatttc tctctcgttc ctaacaacag caacgaagaa     120
gaaaaagaat cattactaac aatcaatgag tatgagagct ggacacatga cggcaacaat     180

```
ggcggctttt acatgccctc ggtttatgac tagcatcaga tacacgaagc aaattaagtg    240
caacgctgct aaaagccagc tagtcgttaa acaagagatt gaggaggaag aagattatgt    300
gaaagccggt ggatcggagc tgctttttgt tcaaatgcaa cagaataagt ccatggatgc    360
acagtctagc ctatcccaaa agctcccaag ggtaccaata ggaggaggag agacagtaa     420 ctgtatactg gatttggttg tcgac                                         445
```

```
<210> SEQ ID NO 41
<211> LENGTH: 446
<212> TYPE: DNA
<213> ORGANISM: Tagetes erecta
<220> FEATURE:
<221> NAME/KEY: misc_feature
<223> OTHER INFORMATION: Antisense Fragment

<400> SEQUENCE: 41
gaattcgcac gaggcaaagc aaaggttgtt tgttgttgtt gttgagagac actccaatcc    60
aaacagatac aaggcgtgac tggatatttc tctctcgttc ctaacaacag caacgaagaa   120
gaaaaagaat cattactaac aatcaatgag tatgagagct ggacacatga cggcaacaat   180
ggcggctttt acatgccctc ggtttatgac tagcatcaga tacacgaagc aaattaagtg   240
caacgctgct aaaagccagc tagtcgttaa acaagagatt gaggaggaag aagattatgt   300
gaaagccggt ggatcggagc tgctttttgt tcaaatgcaa cagaataagt ccatggatgc   360
acagtctagc ctatcccaaa agctcccaag ggtaccaata ggaggaggag agacagtaa    420 ctgtatactg gatttggttg gatcct                                        446
```

```
<210> SEQ ID NO 42
<211> LENGTH: 393
<212> TYPE: DNA
<213> ORGANISM: Tagetes erecta
<220> FEATURE:
<221> NAME/KEY: misc_feature
<223> OTHER INFORMATION: Sense Fragment

<400> SEQUENCE: 42
aagctttgga ttagcactga ttgtccagat ggatattgag gggacccgca cattcttccg    60
gactttcttc cgcttgccca catggatgtg gtggggtttc ttggatcttc gttatcatc    120 aactgacttg ataatatttg cgttttacat gtttatcata gcaccgcata gcctgagaat   180
gggtctggtt agacatttgc tttctgaccc gacaggagga acaatgttaa aagcgtatct   240
cacgatataa ataactctag tcgcgatcag tttagattat aggcacatct tgcatatata   300
tatgtataaa ccttatgtgt gctgtatcct tacatcaaca cagtcattaa ttgtatttct   360
tggggtaatg ctgatgaagt attttctgtc gac                                393
```

```
<210> SEQ ID NO 43
<211> LENGTH: 397
<212> TYPE: DNA
<213> ORGANISM: Tagetes erecta
<220> FEATURE:
<221> NAME/KEY: misc_feature
<223> OTHER INFORMATION: Antisense Fragment

<400> SEQUENCE: 43
gaattctctt tggattagca ctgattgtcc agatggatat tgaggggacc cgcacattct    60
tccggacttt cttccgcttg cccacatgga tgtggtgggg gtttcttgga tcttcgttat   120
catcaactga cttgataata tttgcgtttt acatgtttat catagcaccg catagcctga   180
```

```
gaatgggtct ggttagacat ttgctttctg acccgacagg aggaacaatg ttaaaagcgt      240
atctcacgat ataaataact ctagtcgcga tcagtttaga ttataggcac atcttgcata      300
tatatatgta taaaccttat gtgtgctgta tccttacatc aacacagtca ttaattgtat      360
ttcttggggt aatgctgatg aagtattttc tggatcc                               397

<210> SEQ ID NO 44
<211> LENGTH: 1537
<212> TYPE: DNA
<213> ORGANISM: Unknown
<220> FEATURE:
<221> NAME/KEY: promoter
<223> OTHER INFORMATION: Promoter sequence

<400> SEQUENCE: 44
gagctctaca aattagggtt actttattca ttttcatcca ttctctttat tgttaaattt       60
tgtacattta ttcaataata ttatatgttt attacaaatt ctcactttct tattcatacc     120
tattcactca agcctttacc atcttccttt tctatttcaa tactatttct acttcatttt     180
tcacgttttt aacatctttc tttatttctt gtccacttcg tttagggatg cctaatgtcc     240
caaatttcat ctctcgtagt aacacaaaac caatgtaatg ctacttctct ctacattttt     300
aatacaaata aagtgaaaca aaatatctat aaataaacaa atatatatat tttgttagac     360
gctgtctcaa cccatcaatt aaaaaatttt gttatatttc tactttaccr actaaatttg     420
tttctcatat ttacctttta accccacaa aaaaaaatta taaaaagaa agaaaaaagc      480 taaaccctat ttaaatagct aactataaga tcttaaaatt atcctcatca gtgtatagtt     540
taattggtta ttaacttata acattatata tctatgacat atactctctc ctagctattt     600
ctcacatttt ttaacttaag aaaatagtca taacatagtc taaaattcaa acatccacat     660
gctctaattt gattaacaaa aagttagaaa tatttattta aataaaaaag actaataaat     720
atataaaatg aatgttcata cgcagaccca tttagagatg agtatgcttt cacatgctga     780
gattattttc aaaactaagg ttgtagcaat attaaatcaa taaaattatt ataaataaca     840
aaattaacct gctcgtgttt gctgtatatg ggaggctaca aaataaatta aactaaagat     900
gattatgttt tagacatttt ttctatctgt attagtttat acatattaat tcaggagctg     960
cacaacccaa ttctattttc gttccttggt ggctgggttt ctcacaaggt tcaatagtca    1020
atattaggtt ttattggact tttaatagta tcaaacaaat ctatgtgtga acttaaaaat    1080
tgtattaaat atttagggta acctgttgcc gtttttagaa taatgttttct tcttaataca    1140 cgaaagcgta ttgtgtattc attcatttgg cgcctcacat gcttcggttg gctcgcttta    1200
gtctctgcct tctttgtata ttgtactccc cctcttccta tgccacgtgt tctgagctta    1260
acaagccacg ttgcgtgcca ttgccaaaca agtcatttta acttcacaag gtccgatttg    1320
acctccaaaa caacgacaag tttccgaaca gtcgcgaaga tcaagggtat aatcgtcttt    1380
ttgaattcta tttctcttta tttaatagtc cctctcgtgt gatagttttt aaaagatttt    1440
taaaacgtag ctgctgttta agtaaatccc agtccttcag tttgtgcttt tgtgtgtttt    1500
gtttctctga tttacggaat ttggaaataa taagctt                              1537

<210> SEQ ID NO 45
<211> LENGTH: 734
<212> TYPE: DNA
<213> ORGANISM: Unknown
<220> FEATURE:
<221> NAME/KEY: variation
<223> OTHER INFORMATION: synthetic sequence
```

```
<400> SEQUENCE: 45
ctaacaatca atgagtagag agctggacac atgacggcaa caatggcggc ttttacatgc      60
cctaggttta tgactagcat cagatacacg aagcaaatta agtgcaacgc tgctaaaagc     120
cagctagtcg ttaaacaaga gattgaggag gaagaagatt atgtgaaagc cggtggatcg     180
gagctgcttt ttgttcaaat gcaacagaat aagtccatgg atgcacagtc tagcctatcc     240
caaaaggtca ctccagactt aattgcttat aaataaataa atatgttttt taggaataat     300
gatatttaga tagattagct atcacctgtg ctgtggtgtg cagctcccaa gggtcttacc     360
gatagtaaaa tcgttagtta tgattaatac ttgggaggtg ggggattata ggctttgttg     420
tgagaatgtt gagaaagagg tttgacaaat cggtgtttga atgaggttaa atggagttta     480
attaaaataa agagaagaga aagattaaga gggtgatggg gatattaaag acggscaata     540
tagtgatgcc acgtagaaaa aggtaagtga aacatacaa cgtggcttta aaagatggct     600
tggctgctaa tcaactcaac tcaactcata tcctatccat tcaaattcaa ttcaattcta     660
ttgaatgcaa agcaaagcaa aggttgtttg ttgttgttgt tgagagacac tccaatccaa     720
acagatacaa ggcg                                                      734

<210> SEQ ID NO 46
<211> LENGTH: 280
<212> TYPE: DNA
<213> ORGANISM: Unknown
<220> FEATURE:
<221> NAME/KEY: variation
<223> OTHER INFORMATION: Synthetic sequence

<400> SEQUENCE: 46
gtcgagtatg gagttcaatt aaaataaaga gaagaraaag attaagaggg tgatggggat      60
attaaagacg gccaatrtag tgatgccacg taagaaaaag gtaagtgaaa acatacaacg     120
tggctttaaa agatggcttg gctgctaatc aactcaactc aactcatatc ctatccattc     180
aaattcaatt caattctatt gaatgcaaag caaagcaaag caaaggttgt tgttgttgt      240 tgttgagaga cactccaatc caaacagata caaggcgtga                          280

<210> SEQ ID NO 47
<211> LENGTH: 358
<212> TYPE: DNA
<213> ORGANISM: Tagetes erecta
<220> FEATURE:
<221> NAME/KEY: Promoter
<223> OTHER INFORMATION: Sense Promoter

<400> SEQUENCE: 47
aagcttaccg atagtaaaat cgttagttat gattaatact tgggaggtgg gggattatag      60
gctttgttgt gagaatgttg agaaagaggt ttgacaaatc ggtgtttgaa tgaggttaaa     120
tggagtttaa ttaaaataaa gagaagagaa agattaagag ggtgatgggg atattaaaga     180
cggccaatat agtgatgcca cgtagaaaaa ggtaagtgaa acatacaac gtggctttaa     240 aagatggctt ggctgctaat caactcaact caactcatat cctatccatt caaattcaat     300
tcaattctat tgaatgcaaa gcaaagcaaa gcaaaggttg tttgttgttg ttgtcgac      358

<210> SEQ ID NO 48
<211> LENGTH: 361
<212> TYPE: DNA
<213> ORGANISM: Tagetes erecta
<220> FEATURE:
```

-continued

```
<221> NAME/KEY: Promoter
<223> OTHER INFORMATION: Antisense Promoter

<400> SEQUENCE: 48
ctcgagctta ccgatagtaa aatcgttagt tatgattaat acttgggagg tggggatta      60 taggctttgt tgtgagaatg ttgagaaaga ggtttgacaa atcggtgttt gaatgaggtt    120
aaatggagtt taattaaaat aaagagaaga gaaagattaa gagggtgatg gggatattaa    180
agacggccaa tatagtgatg ccacgtagaa aaaggtaagt gaaaacatac aacgtggctt    240
taaaagatgg cttggctgct aatcaactca actcaactca tatcctatcc attcaaattc    300
aattcaattc tattgaatgc aaagcaaagc aaagcaaagg ttgtttgttg ttgttggatc    360
c                                                                    361

<210> SEQ ID NO 49
<211> LENGTH: 28
<212> TYPE: DNA
<213> ORGANISM: Artificial sequence
<220> FEATURE:
<223> OTHER INFORMATION: primer

<400> SEQUENCE: 49
gagctcactc actgatttcc attgcttg                                        28

<210> SEQ ID NO 50
<211> LENGTH: 37
<212> TYPE: DNA
<213> ORGANISM: Artificial sequence
<220> FEATURE:
<223> OTHER INFORMATION: primer

<400> SEQUENCE: 50
cgccgttaag tcgatgtccg ttgatttaaa cagtgtc                              37

<210> SEQ ID NO 51
<211> LENGTH: 34
<212> TYPE: DNA
<213> ORGANISM: Artificial sequence
<220> FEATURE:
<223> OTHER INFORMATION: primer

<400> SEQUENCE: 51
atcaacggac atcgacttaa cggcgtttgt aaac                                 34

<210> SEQ ID NO 52
<211> LENGTH: 25
<212> TYPE: DNA
<213> ORGANISM: Artificial sequence
<220> FEATURE:
<223> OTHER INFORMATION: primer

<400> SEQUENCE: 52
taagcttttt gttgaagaga tttgg                                           25

<210> SEQ ID NO 53
<211> LENGTH: 23
<212> TYPE: DNA
<213> ORGANISM: Artificial sequence
<220> FEATURE:
<223> OTHER INFORMATION: primer

<400> SEQUENCE: 53
gaaaatactt catcagcatt acc                                             23
```

<210> SEQ ID NO 54
<211> LENGTH: 28
<212> TYPE: DNA
<213> ORGANISM: Artificial sequence
<220> FEATURE:
<223> OTHER INFORMATION: primer

<400> SEQUENCE: 54
gtcgactacg taagtttctg cttctacc                                28

<210> SEQ ID NO 55
<211> LENGTH: 26
<212> TYPE: DNA
<213> ORGANISM: Artificial sequence
<220> FEATURE:
<223> OTHER INFORMATION: primer

<400> SEQUENCE: 55
ggatccggtg atacctgcac atcaac                                  26

<210> SEQ ID NO 56
<211> LENGTH: 28
<212> TYPE: DNA
<213> ORGANISM: Artificial sequence
<220> FEATURE:
<223> OTHER INFORMATION: primer

<400> SEQUENCE: 56
aagcttgcac gaggcaaagc aaaggttg                                28

<210> SEQ ID NO 57
<211> LENGTH: 29
<212> TYPE: DNA
<213> ORGANISM: Artificial sequence
<220> FEATURE:
<223> OTHER INFORMATION: primer

<400> SEQUENCE: 57
gtcgacaacc aaatccagta tacagttac                               29

<210> SEQ ID NO 58
<211> LENGTH: 30
<212> TYPE: DNA
<213> ORGANISM: Artificial sequence
<220> FEATURE:
<223> OTHER INFORMATION: primer

<400> SEQUENCE: 58
aggatccaac caaatccagt atacagttac                              30

<210> SEQ ID NO 59
<211> LENGTH: 28
<212> TYPE: DNA
<213> ORGANISM: Artificial sequence
<220> FEATURE:
<223> OTHER INFORMATION: primer

<400> SEQUENCE: 59
gaattcgcac gaggcaaagc aaaggttg                                28

<210> SEQ ID NO 60
<211> LENGTH: 25
<212> TYPE: DNA
<213> ORGANISM: Artificial sequence
<220> FEATURE:
<223> OTHER INFORMATION: primer

```
<400> SEQUENCE: 60
aagctttgga ttagcactga ttgtc                                    25

<210> SEQ ID NO 61
<211> LENGTH: 29
<212> TYPE: DNA
<213> ORGANISM: Artificial sequence
<220> FEATURE:
<223> OTHER INFORMATION: primer

<400> SEQUENCE: 61
gtcgacagaa aatacttcat cagcattac                                29

<210> SEQ ID NO 62
<211> LENGTH: 29
<212> TYPE: DNA
<213> ORGANISM: Artificial sequence
<220> FEATURE:
<223> OTHER INFORMATION: primer

<400> SEQUENCE: 62
ggatccagaa aatacttcat cagcattac                                29

<210> SEQ ID NO 63
<211> LENGTH: 27
<212> TYPE: DNA
<213> ORGANISM: Artificial sequence
<220> FEATURE:
<223> OTHER INFORMATION: primer

<400> SEQUENCE: 63
gaattctctt tggattagca ctgattg                                  27

<210> SEQ ID NO 64
<211> LENGTH: 23
<212> TYPE: DNA
<213> ORGANISM: Artificial sequence
<220> FEATURE:
<223> OTHER INFORMATION: primer

<400> SEQUENCE: 64
cgccttgtat ctgtttggat tgg                                      23

<210> SEQ ID NO 65
<211> LENGTH: 24
<212> TYPE: DNA
<213> ORGANISM: Artificial sequence
<220> FEATURE:
<223> OTHER INFORMATION: primer

<400> SEQUENCE: 65
ctaacaatca atgagtatga gagc                                     24

<210> SEQ ID NO 66
<211> LENGTH: 26
<212> TYPE: DNA
<213> ORGANISM: Artificial sequence
<220> FEATURE:
<223> OTHER INFORMATION: primer

<400> SEQUENCE: 66
agagcaaggc cagcaggacc acaacc                                   26

<210> SEQ ID NO 67
```

```
<211> LENGTH: 26
<212> TYPE: DNA
<213> ORGANISM: Artificial sequence
<220> FEATURE:
<223> OTHER INFORMATION: primer

<400> SEQUENCE: 67
ccttgggagc ttttgggata ggctag                                              26

<210> SEQ ID NO 68
<211> LENGTH: 26
<212> TYPE: DNA
<213> ORGANISM: Artificial sequence
<220> FEATURE:
<223> OTHER INFORMATION: primer

<400> SEQUENCE: 68
tcacgccttg tatctgtttg gattgg                                              26

<210> SEQ ID NO 69
<211> LENGTH: 15
<212> TYPE: DNA
<213> ORGANISM: Artificial sequence
<220> FEATURE:
<223> OTHER INFORMATION: primer

<400> SEQUENCE: 69
gtcgagtatg gagtt                                                          15

<210> SEQ ID NO 70
<211> LENGTH: 28
<212> TYPE: DNA
<213> ORGANISM: Artificial sequence
<220> FEATURE:
<223> OTHER INFORMATION: primer

<400> SEQUENCE: 70
aagcttaccg atagtaaaat cgttagtt                                            28

<210> SEQ ID NO 71
<211> LENGTH: 31
<212> TYPE: DNA
<213> ORGANISM: Artificial sequence
<220> FEATURE:
<223> OTHER INFORMATION: primer

<400> SEQUENCE: 71
ctcgagctta ccgatagtaa aatcgttagt t                                        31

<210> SEQ ID NO 72
<211> LENGTH: 28
<212> TYPE: DNA
<213> ORGANISM: Artificial sequence
<220> FEATURE:
<223> OTHER INFORMATION: Synthetic sequence

<400> SEQUENCE: 72
gtcgacaaca acaacaaaca acctttgc                                            28

<210> SEQ ID NO 73
<211> LENGTH: 28
<212> TYPE: DNA
<213> ORGANISM: Artificial sequence
<220> FEATURE:
<223> OTHER INFORMATION: primer

<400> SEQUENCE: 73
```

```
ggatccaaca acaacaaaca acctttgc                                              28

<210> SEQ ID NO 74
<211> LENGTH: 28
<212> TYPE: DNA
<213> ORGANISM: Artificial sequence
<220> FEATURE:
<223> OTHER INFORMATION: primer

<400> SEQUENCE: 74
gtcgactttt tgttgaagag atttggtg                                              28

<210> SEQ ID NO 75
<211> LENGTH: 28
<212> TYPE: DNA
<213> ORGANISM: Artificial sequence
<220> FEATURE:
<223> OTHER INFORMATION: primer

<400> SEQUENCE: 75
ctcgagactc actgatttcc attgcttg                                              28

<210> SEQ ID NO 76
<211> LENGTH: 22
<212> TYPE: DNA
<213> ORGANISM: Artificial sequence
<220> FEATURE:
<223> OTHER INFORMATION: primer

<400> SEQUENCE: 76
gagctctaca aattagggtt ac                                                    22

<210> SEQ ID NO 77
<211> LENGTH: 23
<212> TYPE: DNA
<213> ORGANISM: Artificial sequence
<220> FEATURE:
<223> OTHER INFORMATION: primer

<400> SEQUENCE: 77
aagcttatta tttccaaatt ccg                                                   23

<210> SEQ ID NO 78
<211> LENGTH: 50
<212> TYPE: DNA
<213> ORGANISM: Artificial sequence
<220> FEATURE:
<223> OTHER INFORMATION: primer

<400> SEQUENCE: 78
aagctttgca attcatacag aagtgagaaa aatgcagcta gcagcgacag                      50

<210> SEQ ID NO 79
<211> LENGTH: 1062
<212> TYPE: DNA
<213> ORGANISM: Haematococcus pluvialis
<220> FEATURE:
<221> NAME/KEY: CDS
<222> LOCATION: (32)..(1021)

<400> SEQUENCE: 79
aagctttgca attcatacag aagtgagaaa a atg cag cta gca gcg aca gta              52
                                  Met Gln Leu Ala Ala Thr Val
                                   1               5 atg ttg gag cag ctt acc gga agc gct gag gca ctc aag gag aag gag            100
```

```
                  Met Leu Glu Gln Leu Thr Gly Ser Ala Glu Ala Leu Lys Glu Lys Glu
                          10                  15                  20 aag gag gtt gca ggc agc tct gac gtg ttg cgt aca tgg gcg acc cag      148
Lys Glu Val Ala Gly Ser Ser Asp Val Leu Arg Thr Trp Ala Thr Gln
    25                  30                  35 tac tcg ctt ccg tca gag gag tca gac gcg gcc cgc ccg gga ctg aag      196
Tyr Ser Leu Pro Ser Glu Glu Ser Asp Ala Ala Arg Pro Gly Leu Lys
40                  45                  50                  55 aat gcc tac aag cca cca cct tcc gac aca aag ggc atc aca atg gcg      244
Asn Ala Tyr Lys Pro Pro Pro Ser Asp Thr Lys Gly Ile Thr Met Ala
                60                  65                  70 cta gct gtc atc ggc tcc tgg gcc gca gtg ttc ctc cac gcc att ttt      292
Leu Ala Val Ile Gly Ser Trp Ala Ala Val Phe Leu His Ala Ile Phe
            75                  80                  85 caa atc aag ctt ccg acc tcc ttg gac cag ctg cac tgg ctg ccc gtg      340
Gln Ile Lys Leu Pro Thr Ser Leu Asp Gln Leu His Trp Leu Pro Val
        90                  95                  100 tca gat gcc aca gct cag ctg gtt agc ggc agc agc agc ctg ctg cac      388
Ser Asp Ala Thr Ala Gln Leu Val Ser Gly Ser Ser Ser Leu Leu His
    105                 110                 115 atc gtc gta gta ttc ttt gtc ctg gag ttc ctg tac aca ggc ctt ttt      436
Ile Val Val Val Phe Phe Val Leu Glu Phe Leu Tyr Thr Gly Leu Phe
120                 125                 130                 135 atc acc acg cat gat gct atg cat ggc acc atc gcc atg aga aac agg      484
Ile Thr Thr His Asp Ala Met His Gly Thr Ile Ala Met Arg Asn Arg
                140                 145                 150 cag ctt aat gac ttc ttg ggc aga gta tgc atc tcc ttg tac gcc tgg      532
Gln Leu Asn Asp Phe Leu Gly Arg Val Cys Ile Ser Leu Tyr Ala Trp
            155                 160                 165 ttt gat tac aac atg ctg cac cgc aag cat tgg gag cac cac aac cac      580
Phe Asp Tyr Asn Met Leu His Arg Lys His Trp Glu His His Asn His
        170                 175                 180 act ggc gag gtg ggc aag gac cct gac ttc cac agg gga aac cct ggc      628
Thr Gly Glu Val Gly Lys Asp Pro Asp Phe His Arg Gly Asn Pro Gly
    185                 190                 195 att gtg ccc tgg ttt gcc agc ttc atg tcc agc tac atg tcg atg tgg      676
Ile Val Pro Trp Phe Ala Ser Phe Met Ser Ser Tyr Met Ser Met Trp
200                 205                 210                 215 cag ttt gcg cgc ctc gca tgg tgg acg gtg gtc atg cag ctg ctg ggt      724
Gln Phe Ala Arg Leu Ala Trp Trp Thr Val Val Met Gln Leu Leu Gly
                220                 225                 230 gcg cca atg gcg aac ctg ctg gtg ttc atg gcg gcc gcg ccc atc ctg      772
Ala Pro Met Ala Asn Leu Leu Val Phe Met Ala Ala Ala Pro Ile Leu
            235                 240                 245 tcc gcc ttc cgc ttg ttc tac ttt ggc acg tac atg ccc cac aag cct      820
Ser Ala Phe Arg Leu Phe Tyr Phe Gly Thr Tyr Met Pro His Lys Pro
        250                 255                 260 gag cct ggc gcc gcg tca ggc tct tca cca gcc gtc atg aac tgg tgg      868
Glu Pro Gly Ala Ala Ser Gly Ser Ser Pro Ala Val Met Asn Trp Trp
    265                 270                 275 aag tcg cgc act agc cag gcg tcc gac ctg gtc agc ttt ctg acc tgc      916
Lys Ser Arg Thr Ser Gln Ala Ser Asp Leu Val Ser Phe Leu Thr Cys
280                 285                 290                 295 tac cac ttc gac ctg cac tgg gag cac cac cgc tgg ccc ttt gcc ccc      964
Tyr His Phe Asp Leu His Trp Glu His His Arg Trp Pro Phe Ala Pro
                300                 305                 310 tgg tgg gag ctg ccc aac tgc cgc cgc ctg tct ggc cga ggt ctg gtt     1012
Trp Trp Glu Leu Pro Asn Cys Arg Arg Leu Ser Gly Arg Gly Leu Val
            315                 320                 325
```

```
cct gcc tag ctggacacac tgcagtgggc cctgctgcca gctgggcatg c            1062
Pro Ala
```

<210> SEQ ID NO 80
<211> LENGTH: 329
<212> TYPE: PRT
<213> ORGANISM: Haematococcus pluvialis

<400> SEQUENCE: 80

```
Met Gln Leu Ala Ala Thr Val Met Leu Glu Gln Leu Thr Gly Ser Ala
1               5                   10                  15

Glu Ala Leu Lys Glu Lys Glu Lys Val Ala Gly Ser Ser Asp Val
            20                  25                  30

Leu Arg Thr Trp Ala Thr Gln Tyr Ser Leu Pro Ser Glu Glu Ser Asp
        35                  40                  45

Ala Ala Arg Pro Gly Leu Lys Asn Ala Tyr Lys Pro Pro Ser Asp
    50                  55                  60

Thr Lys Gly Ile Thr Met Ala Leu Ala Val Ile Gly Ser Trp Ala Ala
65                  70                  75                  80

Val Phe Leu His Ala Ile Phe Gln Ile Lys Leu Pro Thr Ser Leu Asp
                85                  90                  95

Gln Leu His Trp Leu Pro Val Ser Asp Ala Thr Ala Gln Leu Val Ser
            100                 105                 110

Gly Ser Ser Leu Leu His Ile Val Val Phe Val Leu Glu
        115                 120                 125

Phe Leu Tyr Thr Gly Leu Phe Ile Thr Thr His Asp Ala Met His Gly
    130                 135                 140

Thr Ile Ala Met Arg Asn Arg Gln Leu Asn Asp Phe Leu Gly Arg Val
145                 150                 155                 160

Cys Ile Ser Leu Tyr Ala Trp Phe Asp Tyr Asn Met Leu His Arg Lys
                165                 170                 175

His Trp Glu His His Asn His Thr Gly Glu Val Gly Lys Asp Pro Asp
            180                 185                 190

Phe His Arg Gly Asn Pro Gly Ile Val Pro Trp Phe Ala Ser Phe Met
        195                 200                 205

Ser Ser Tyr Met Ser Met Trp Gln Phe Ala Arg Leu Ala Trp Trp Thr
    210                 215                 220

Val Val Met Gln Leu Leu Gly Ala Pro Met Ala Asn Leu Leu Val Phe
225                 230                 235                 240

Met Ala Ala Ala Pro Ile Leu Ser Ala Phe Arg Leu Phe Tyr Phe Gly
                245                 250                 255

Thr Tyr Met Pro His His Lys Pro Glu Pro Gly Ala Ala Ser Gly Ser Ser
            260                 265                 270

Pro Ala Val Met Asn Trp Trp Lys Ser Arg Thr Ser Gln Ala Ser Asp
        275                 280                 285

Leu Val Ser Phe Leu Thr Cys Tyr His Phe Asp Leu His Trp Glu His
    290                 295                 300

His Arg Trp Pro Phe Ala Pro Trp Trp Glu Leu Pro Asn Cys Arg Arg
305                 310                 315                 320

Leu Ser Gly Arg Gly Leu Val Pro Ala
                325
```

<210> SEQ ID NO 81
<211> LENGTH: 789
<212> TYPE: DNA
<213> ORGANISM: Nostoc punctiforme

```
<220> FEATURE:
<221> NAME/KEY: CDS

<400> SEQUENCE: 81 ttg aat ttt tgt gat aaa cca gtt agc tat tat gtt gca ata gag caa      48
Leu Asn Phe Cys Asp Lys Pro Val Ser Tyr Tyr Val Ala Ile Glu Gln
  1               5                  10                  15 tta agt gct aaa gaa gat act gtt tgg ggg ctg gtg att gtc ata gta      96
Leu Ser Ala Lys Glu Asp Thr Val Trp Gly Leu Val Ile Val Ile Val
             20                  25                  30 att att agt ctt tgg gta gct agt ttg gct ttt tta cta gct att aat     144
Ile Ile Ser Leu Trp Val Ala Ser Leu Ala Phe Leu Leu Ala Ile Asn
         35                  40                  45 tat gcc aaa gtc cca att tgg ttg ata cct att gca ata gtt tgg caa     192
Tyr Ala Lys Val Pro Ile Trp Leu Ile Pro Ile Ala Ile Val Trp Gln
 50                  55                  60 atg ttc ctt tat aca ggg cta ttt att act gca cat gat gct atg cat     240
Met Phe Leu Tyr Thr Gly Leu Phe Ile Thr Ala His Asp Ala Met His
 65                  70                  75                  80 ggg tca gtt tat cgt aaa aat ccc aaa att aat aat ttt atc ggt tca     288
Gly Ser Val Tyr Arg Lys Asn Pro Lys Ile Asn Asn Phe Ile Gly Ser
                 85                  90                  95 cta gct gta gcg ctt tac gct gtg ttt cca tat caa cag atg tta aag     336
Leu Ala Val Ala Leu Tyr Ala Val Phe Pro Tyr Gln Gln Met Leu Lys
            100                 105                 110 aat cat tgc tta cat cat cgt cat cct gct agc gaa gtt gac cca gat     384
Asn His Cys Leu His His Arg His Pro Ala Ser Glu Val Asp Pro Asp
        115                 120                 125 ttt cat gat ggt aag aga aca aac gct att ttc tgg tat ctc cat ttc     432
Phe His Asp Gly Lys Arg Thr Asn Ala Ile Phe Trp Tyr Leu His Phe
    130                 135                 140 atg ata gaa tac tcc agt tgg caa cag tta ata gta cta act atc cta     480
Met Ile Glu Tyr Ser Ser Trp Gln Gln Leu Ile Val Leu Thr Ile Leu
145                 150                 155                 160 ttt aat tta gct aaa tac gtt ttg cac atc cat caa ata aat ctc atc     528
Phe Asn Leu Ala Lys Tyr Val Leu His Ile His Gln Ile Asn Leu Ile
                165                 170                 175 tta ttt tgg agt att cct cca att tta agt tcc att caa ctg ttt tat     576
Leu Phe Trp Ser Ile Pro Pro Ile Leu Ser Ser Ile Gln Leu Phe Tyr
            180                 185                 190 ttc gga aca ttt ttg cct cat cga gaa ccc aag aaa gga tat gtt tat     624
Phe Gly Thr Phe Leu Pro His Arg Glu Pro Lys Lys Gly Tyr Val Tyr
        195                 200                 205 ccc cat tgc agc caa aca ata aaa ttg cca act ttt ttg tca ttt atc     672
Pro His Cys Ser Gln Thr Ile Lys Leu Pro Thr Phe Leu Ser Phe Ile
    210                 215                 220 gct tgc tac cac ttt ggt tat cat gaa gaa cat cat gag tat ccc cat     720
Ala Cys Tyr His Phe Gly Tyr His Glu Glu His His Glu Tyr Pro His
225                 230                 235                 240 gta cct tgg tgg caa ctt cca tct gta tat aag cag aga gta ttc aac     768
Val Pro Trp Trp Gln Leu Pro Ser Val Tyr Lys Gln Arg Val Phe Asn
                245                 250                 255 aat tca gta acc aat tcg taa                                         789
Asn Ser Val Thr Asn Ser
            260

<210> SEQ ID NO 82
<211> LENGTH: 262
<212> TYPE: PRT
<213> ORGANISM: Nostoc punctiforme
```

-continued

```
<400> SEQUENCE: 82

Leu Asn Phe Cys Asp Lys Pro Val Ser Tyr Tyr Val Ala Ile Glu Gln
1               5                   10                  15

Leu Ser Ala Lys Glu Asp Thr Val Trp Gly Leu Val Ile Val Ile Val
            20                  25                  30

Ile Ile Ser Leu Trp Val Ala Ser Leu Ala Phe Leu Leu Ala Ile Asn
        35                  40                  45

Tyr Ala Lys Val Pro Ile Trp Leu Ile Pro Ile Ala Ile Val Trp Gln
    50                  55                  60

Met Phe Leu Tyr Thr Gly Leu Phe Ile Thr Ala His Asp Ala Met His
65                  70                  75                  80

Gly Ser Val Tyr Arg Lys Asn Pro Lys Ile Asn Asn Phe Ile Gly Ser
                85                  90                  95

Leu Ala Val Ala Leu Tyr Ala Val Phe Pro Tyr Gln Gln Met Leu Lys
            100                 105                 110

Asn His Cys Leu His His Arg His Pro Ala Ser Glu Val Asp Pro Asp
        115                 120                 125

Phe His Asp Gly Lys Arg Thr Asn Ala Ile Phe Trp Tyr Leu His Phe
    130                 135                 140

Met Ile Glu Tyr Ser Ser Trp Gln Gln Leu Ile Val Leu Thr Ile Leu
145                 150                 155                 160

Phe Asn Leu Ala Lys Tyr Val Leu His Ile His Gln Ile Asn Leu Ile
                165                 170                 175

Leu Phe Trp Ser Ile Pro Pro Ile Leu Ser Ser Ile Gln Leu Phe Tyr
            180                 185                 190

Phe Gly Thr Phe Leu Pro His Arg Glu Pro Lys Lys Gly Tyr Val Tyr
        195                 200                 205

Pro His Cys Ser Gln Thr Ile Lys Leu Pro Thr Phe Leu Ser Phe Ile
    210                 215                 220

Ala Cys Tyr His Phe Gly Tyr His Glu Glu His Glu Tyr Pro His
225                 230                 235                 240

Val Pro Trp Trp Gln Leu Pro Ser Val Tyr Lys Gln Arg Val Phe Asn
                245                 250                 255

Asn Ser Val Thr Asn Ser
            260

<210> SEQ ID NO 83
<211> LENGTH: 762
<212> TYPE: DNA
<213> ORGANISM: Nostoc punctiforme
<220> FEATURE:
<221> NAME/KEY: CDS

<400> SEQUENCE: 83 gtg atc cag tta gaa caa cca ctc agt cat caa gca aaa ctg act cca      48
Val Ile Gln Leu Glu Gln Pro Leu Ser His Gln Ala Lys Leu Thr Pro
1               5                   10                  15 gta ctg aga agt aaa tct cag ttt aag ggg ctt ttc att gct att gtc      96
Val Leu Arg Ser Lys Ser Gln Phe Lys Gly Leu Phe Ile Ala Ile Val
            20                  25                  30 att gtt agc gca tgg gtc att agc ctg agt tta tta ctt tcc ctt gac     144
Ile Val Ser Ala Trp Val Ile Ser Leu Ser Leu Leu Leu Ser Leu Asp
        35                  40                  45 atc tca aag cta aaa ttt tgg atg tta ttg cct gtt ata cta tgg caa     192
Ile Ser Lys Leu Lys Phe Trp Met Leu Leu Pro Val Ile Leu Trp Gln
    50                  55                  60
```

```
aca ttt tta tat acg gga tta ttt att aca tct cat gat gcc atg cat        240
Thr Phe Leu Tyr Thr Gly Leu Phe Ile Thr Ser His Asp Ala Met His
 65                  70                  75                  80 ggc gta gta ttt ccc caa aac acc aag att aat cat ttg att gga aca        288
Gly Val Val Phe Pro Gln Asn Thr Lys Ile Asn His Leu Ile Gly Thr
                 85                  90                  95 ttg acc cta tcc ctt tat ggt ctt tta cca tat caa aaa cta ttg aaa        336
Leu Thr Leu Ser Leu Tyr Gly Leu Leu Pro Tyr Gln Lys Leu Leu Lys
            100                 105                 110 aaa cat tgg tta cac cac cac aat cca gca agc tca ata gac ccg gat        384
Lys His Trp Leu His His His Asn Pro Ala Ser Ser Ile Asp Pro Asp
        115                 120                 125 ttt cac aat ggt aaa cac caa agt ttc ttt gct tgg tat ttt cat ttt        432
Phe His Asn Gly Lys His Gln Ser Phe Phe Ala Trp Tyr Phe His Phe
    130                 135                 140 atg aaa ggt tac tgg agt tgg ggg caa ata att gcg ttg act att att        480
Met Lys Gly Tyr Trp Ser Trp Gly Gln Ile Ile Ala Leu Thr Ile Ile
145                 150                 155                 160 tat aac ttt gct aaa tac ata ctc cat atc cca agt gat aat cta act        528
Tyr Asn Phe Ala Lys Tyr Ile Leu His Ile Pro Ser Asp Asn Leu Thr
                165                 170                 175 tac ttt tgg gtg cta ccc tcg ctt tta agt tca tta caa tta ttc tat        576
Tyr Phe Trp Val Leu Pro Ser Leu Leu Ser Ser Leu Gln Leu Phe Tyr
            180                 185                 190 ttt ggt act ttt tta ccc cat agt gaa cca ata ggg ggt tat gtt cag        624
Phe Gly Thr Phe Leu Pro His Ser Glu Pro Ile Gly Gly Tyr Val Gln
        195                 200                 205 cct cat tgt gcc caa aca att agc cgt cct att tgg tgg tca ttt atc        672
Pro His Cys Ala Gln Thr Ile Ser Arg Pro Ile Trp Trp Ser Phe Ile
    210                 215                 220 acg tgc tat cat ttt ggc tac cac gag gaa cat cac gaa tat cct cat        720
Thr Cys Tyr His Phe Gly Tyr His Glu Glu His His Glu Tyr Pro His
225                 230                 235                 240 att tct tgg tgg cag tta cca gaa att tac aaa gca aaa tag               762
Ile Ser Trp Trp Gln Leu Pro Glu Ile Tyr Lys Ala Lys
                245                 250

<210> SEQ ID NO 84
<211> LENGTH: 253
<212> TYPE: PRT
<213> ORGANISM: Nostoc punctiforme

<400> SEQUENCE: 84

Val Ile Gln Leu Glu Gln Pro Leu Ser His Gln Ala Lys Leu Thr Pro
  1               5                  10                  15

Val Leu Arg Ser Lys Ser Gln Phe Lys Gly Leu Phe Ile Ala Ile Val
             20                  25                  30

Ile Val Ser Ala Trp Val Ile Ser Leu Ser Leu Leu Ser Leu Asp
         35                  40                  45

Ile Ser Lys Leu Lys Phe Trp Met Leu Leu Pro Val Ile Leu Trp Gln
     50                  55                  60

Thr Phe Leu Tyr Thr Gly Leu Phe Ile Thr Ser His Asp Ala Met His
 65                  70                  75                  80

Gly Val Val Phe Pro Gln Asn Thr Lys Ile Asn His Leu Ile Gly Thr
                 85                  90                  95

Leu Thr Leu Ser Leu Tyr Gly Leu Leu Pro Tyr Gln Lys Leu Leu Lys
            100                 105                 110

Lys His Trp Leu His His His Asn Pro Ala Ser Ser Ile Asp Pro Asp
        115                 120                 125
```

```
Phe His Asn Gly Lys His Gln Ser Phe Phe Ala Trp Tyr Phe His Phe
        130                 135                 140

Met Lys Gly Tyr Trp Ser Trp Gly Gln Ile Ile Ala Leu Thr Ile Ile
145                 150                 155                 160

Tyr Asn Phe Ala Lys Tyr Ile Leu His Ile Pro Ser Asp Asn Leu Thr
                165                 170                 175

Tyr Phe Trp Val Leu Pro Ser Leu Leu Ser Ser Leu Gln Leu Phe Tyr
            180                 185                 190

Phe Gly Thr Phe Leu Pro His Ser Glu Pro Ile Gly Gly Tyr Val Gln
        195                 200                 205

Pro His Cys Ala Gln Thr Ile Ser Arg Pro Ile Trp Trp Ser Phe Ile
    210                 215                 220

Thr Cys Tyr His Phe Gly Tyr His Glu Glu His Glu Tyr Pro His
225                 230                 235                 240

Ile Ser Trp Trp Gln Leu Pro Glu Ile Tyr Lys Ala Lys
                245                 250

<210> SEQ ID NO 85
<211> LENGTH: 804
<212> TYPE: DNA
<213> ORGANISM: Synechococcus WH8102
<220> FEATURE:
<221> NAME/KEY: CDS

<400> SEQUENCE: 85 atg aaa acg aca aga tct att tcg tgg cca tcg act tgc tgg cat cac      48
Met Lys Thr Thr Arg Ser Ile Ser Trp Pro Ser Thr Cys Trp His His
1               5                   10                  15 cag ccg agt tgc tca agc tgg gtg gca aat gag ttc agc cct cag gcc      96
Gln Pro Ser Cys Ser Ser Trp Val Ala Asn Glu Phe Ser Pro Gln Ala
                20                  25                  30 ctc aaa ggg ttg gct ctg gct ggt ctg att gga tca gcc tgg ctg ctc     144
Leu Lys Gly Leu Ala Leu Ala Gly Leu Ile Gly Ser Ala Trp Leu Leu
            35                  40                  45 tcc ctg ggc ctg agc tac acc ctg cca ctt gat cag acg cct ggg ctg     192
Ser Leu Gly Leu Ser Tyr Thr Leu Pro Leu Asp Gln Thr Pro Gly Leu
        50                  55                  60 ttg att ggc agc ttg att ctg ctc aga gca ttt ctg cac acc ggg ctg     240
Leu Ile Gly Ser Leu Ile Leu Leu Arg Ala Phe Leu His Thr Gly Leu
65                  70                  75                  80 ttc atc gtt gcc cac gat tcc atg cac gcc agt ctg gtt ccg ggt cat     288
Phe Ile Val Ala His Asp Ser Met His Ala Ser Leu Val Pro Gly His
                85                  90                  95 ccc gga ttg aac cgc tgg atc ggc aaa gtg tat ttg ttg gtg tat gca     336
Pro Gly Leu Asn Arg Trp Ile Gly Lys Val Tyr Leu Leu Val Tyr Ala
            100                 105                 110 ggc ttg tct tat gag cgt tgt tcc cgc aac cac aga cgt cat cac ctg     384
Gly Leu Ser Tyr Glu Arg Cys Ser Arg Asn His Arg Arg His His Leu
        115                 120                 125 gca ccg gag acg ttc cag gat cct gac tac caa cgt tgc acc aat aac     432
Ala Pro Glu Thr Phe Gln Asp Pro Asp Tyr Gln Arg Cys Thr Asn Asn
130                 135                 140 aac atc cta gat tgg tat gtt cac ttc atg ggc aac tat ctg ggc atg     480
Asn Ile Leu Asp Trp Tyr Val His Phe Met Gly Asn Tyr Leu Gly Met
145                 150                 155                 160 cgg caa ctg tta aat cta agc tgt ctt tgg ctg gcg cta atc att ctc     528
Arg Gln Leu Leu Asn Leu Ser Cys Leu Trp Leu Ala Leu Ile Ile Leu
                165                 170                 175
```

```
aac ggt tct gat ctc cct gct cag atc atg cat ctg ctg ttg ttc agc       576
Asn Gly Ser Asp Leu Pro Ala Gln Ile Met His Leu Leu Leu Phe Ser
            180                 185                 190 gtt ctg ccg ttg atc atc agt tcc tgt caa ttg ttt cta gtg gga acc       624
Val Leu Pro Leu Ile Ile Ser Ser Cys Gln Leu Phe Leu Val Gly Thr
        195                 200                 205 tgg tta ccc cac cga cgt ggg gcc acg aca cga ccg gcg gtg aca acg       672
Trp Leu Pro His Arg Arg Gly Ala Thr Thr Arg Pro Gly Val Thr Thr
    210                 215                 220 cgc agc ctg gct ttg cat cca gcc ctc tct ttc gca gct tgt tac aac       720
Arg Ser Leu Ala Leu His Pro Ala Leu Ser Phe Ala Ala Cys Tyr Asn
225                 230                 235                 240 ttt ggc tat cat cgt gaa cat cat gaa tcg cct tcc aca ccc tgg ttt       768
Phe Gly Tyr His Arg Glu His His Glu Ser Pro Ser Thr Pro Trp Phe
                245                 250                 255 cag ctg cca caa ctt cga aat gaa tca ttc act tga                       804
Gln Leu Pro Gln Leu Arg Asn Glu Ser Phe Thr
            260                 265

<210> SEQ ID NO 86
<211> LENGTH: 267
<212> TYPE: PRT
<213> ORGANISM: Synechococcus WH8102

<400> SEQUENCE: 86

Met Lys Thr Thr Arg Ser Ile Ser Trp Pro Ser Thr Cys Trp His His
1               5                   10                  15

Gln Pro Ser Cys Ser Ser Trp Val Ala Asn Glu Phe Ser Pro Gln Ala
            20                  25                  30

Leu Lys Gly Leu Ala Leu Ala Gly Leu Ile Gly Ser Ala Trp Leu Leu
        35                  40                  45

Ser Leu Gly Leu Ser Tyr Thr Leu Pro Leu Asp Gln Thr Pro Gly Leu
    50                  55                  60

Leu Ile Gly Ser Leu Ile Leu Leu Arg Ala Phe Leu His Thr Gly Leu
65                  70                  75                  80

Phe Ile Val Ala His Asp Ser Met His Ala Ser Leu Val Pro Gly His
                85                  90                  95

Pro Gly Leu Asn Arg Trp Ile Gly Lys Val Tyr Leu Val Tyr Ala
            100                 105                 110

Gly Leu Ser Tyr Glu Arg Cys Ser Arg Asn His Arg His His Leu
        115                 120                 125

Ala Pro Glu Thr Phe Gln Asp Pro Asp Tyr Gln Arg Cys Thr Asn Asn
    130                 135                 140

Asn Ile Leu Asp Trp Tyr Val His Phe Met Gly Asn Tyr Leu Gly Met
145                 150                 155                 160

Arg Gln Leu Leu Asn Leu Ser Cys Leu Trp Leu Ala Leu Ile Ile Leu
                165                 170                 175

Asn Gly Ser Asp Leu Pro Ala Gln Ile Met His Leu Leu Leu Phe Ser
            180                 185                 190

Val Leu Pro Leu Ile Ile Ser Ser Cys Gln Leu Phe Leu Val Gly Thr
        195                 200                 205

Trp Leu Pro His Arg Arg Gly Ala Thr Thr Arg Pro Gly Val Thr Thr
    210                 215                 220

Arg Ser Leu Ala Leu His Pro Ala Leu Ser Phe Ala Ala Cys Tyr Asn
225                 230                 235                 240

Phe Gly Tyr His Arg Glu His His Glu Ser Pro Ser Thr Pro Trp Phe
                245                 250                 255
```

Gln Leu Pro Gln Leu Arg Asn Glu Ser Phe Thr
          260                 265

<210> SEQ ID NO 87
<211> LENGTH: 33
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 87
gcatgctcta gaccttataa agatattttg tga                                33

<210> SEQ ID NO 88
<211> LENGTH: 33
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 88
gcatgcatct agaaatggtt cagtgtcaac cat                                33

<210> SEQ ID NO 89
<211> LENGTH: 805
<212> TYPE: DNA
<213> ORGANISM: Nostoc sp. Strain PCC7120
<220> FEATURE:
<221> NAME/KEY: variation

<400> SEQUENCE: 89
gcatgcatct agaaatggtt cagtgtcaac catcatctct gcattcagaa aaactggtgt     60
tattgtcatc gacaatcaga gatgataaaa atattaataa gggtatattt attgcctgct    120
ttatcttatt tttatgggca attagtttaa tcttattact ctcaatagat acatccataa    180
ttcataagag cttattaggt atagccatgc tttggcagac cttcttatat acaggtttat    240
ttattactgc tcatgatgcc atgcacggcg tagtttatcc caaaaatccc agaataaata    300
attttatagg taagctcact ctaatcttgt atggactact cccttataaa gatttattga    360
aaaaacattg gttacaccac ggacatcctg gtactgattt agaccctgat tattacaatg    420
gtcatcccca aaacttcttt ctttggtatc tacattttat gaagtcttat ggcgatggaa    480
cgcaaatttt cggattagtg atgattttte atggacttaa aaatctggtg catataccag    540
aaaataattt aattatattt tggatgatac cttctatttt aagttcagta caactatttt    600
attttggtac attttttgcct cataaaaagc tagaaggtgg ttatactaac ccccattgtg    660
cgcgcagtat cccattacct cttttttggt cttttgttac ttgttatcac ttcggctacc    720
acaaggaaca tcacgaatac cctcaacttc cttggtggaa attacctgaa gctcacaaaa    780
tatctttata aggtctagag catgc                                          805

<210> SEQ ID NO 90
<211> LENGTH: 35
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 90

```
gagctcttca ttatttcgat tttgatttcg tgacc                                  35
```

<210> SEQ ID NO 91
<211> LENGTH: 44
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 91

```
aagcttgagc tcggttgatc agaagaagaa gaagaagatg aact                        44
```

<210> SEQ ID NO 92
<211> LENGTH: 653
<212> TYPE: DNA
<213> ORGANISM: Arabidopsis thaliana
<220> FEATURE:
<221> NAME/KEY: promoter

<400> SEQUENCE: 92

```
gagctcttca ttatttcgat tttgatttcg tgaccagcga acgcagaata ccttgttgtg       60
taatacttta cccgtgtaaa tcaaaaacaa aaaggctttt gagcttttg tagttgaatt       120
tctctggctg atcttttctg tacagattca tatatctgca gagacgatat cattgattat      180
ttgagcttct tttgaactat ttcgtgtaat ttgggatgag agctctatgt atgtgtgtaa      240
actttgaaga caacaagaaa ggtaacaagt gagggaggga tgactccatg tcaaaataga      300
tgtcataaga ggcccatcaa taagtgcttg agcccattag ctagcccagt aactaccaga      360
ttgtgagatg gatgtgtgaa cagttttttt tttgatgtag gactgaaatg tgaacaacag      420
gcgcatgaaa ggctaaatta ggacaatgat aagcagaaat aacttatcct ctctaacact      480
tggcctcaca ttgcccttca cacaatccac acacatccaa tcacaacctc atcatatatc      540
tcccgctaat cttttttttct tgatcttttt tttttttgct tattattttt ttgactttga      600
tctcccatca gttcatcttc ttcttcttct tctgatcaac cgagctcaag ctt             653
```

<210> SEQ ID NO 93
<211> LENGTH: 28
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 93

```
gagctcactc actgatttcc attgcttg                                          28
```

<210> SEQ ID NO 94
<211> LENGTH: 30
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 94

```
aagcttgagc tctttgttga agagatttgg                                        30
```

<210> SEQ ID NO 95
<211> LENGTH: 37
<212> TYPE: DNA
<213> ORGANISM: Unknown
<220> FEATURE:

```
-continued

<221> NAME/KEY: primer_bind
<223> OTHER INFORMATION: Synthetic sequence

<400> SEQUENCE: 95
cgccgttaag tcgatgtccg ttgatttaaa cagtgtc                                37

<210> SEQ ID NO 96
<211> LENGTH: 34
<212> TYPE: DNA
<213> ORGANISM: Unknown
<220> FEATURE:
<221> NAME/KEY: primer_bind
<223> OTHER INFORMATION: Synthetic sequence

<400> SEQUENCE: 96
atcaacggac atcgacttaa cggcgtttgt aaac                                   34

<210> SEQ ID NO 97
<211> LENGTH: 831
<212> TYPE: DNA
<213> ORGANISM: Haematococcus pluvialis
<220> FEATURE:
<221> NAME/KEY: CDS

<400> SEQUENCE: 97 atg cca tcc gag tcg tca gac gca gct cgt cct gtg ttg aag cac gcc        48
Met Pro Ser Glu Ser Ser Asp Ala Ala Arg Pro Val Leu Lys His Ala
1               5                   10                  15 tat aaa cct cca gca tct gac gcc aag ggc atc act atg gcg ctg acc        96
Tyr Lys Pro Pro Ala Ser Asp Ala Lys Gly Ile Thr Met Ala Leu Thr
            20                  25                  30 atc att ggc acc tgg acc gca gtg ttt tta cac gca ata ttc caa atc       144
Ile Ile Gly Thr Trp Thr Ala Val Phe Leu His Ala Ile Phe Gln Ile
        35                  40                  45 agg cta ccg aca tcc atg gac cag ctt cac tgg ttg cct gtg tcc gaa       192
Arg Leu Pro Thr Ser Met Asp Gln Leu His Trp Leu Pro Val Ser Glu
    50                  55                  60 gcc aca gcc cag ctg ttg ggc gga agc agc agc cta ttg cac atc gcc       240
Ala Thr Ala Gln Leu Leu Gly Gly Ser Ser Ser Leu Leu His Ile Ala
65                  70                  75                  80 gca gtc ttc att gta ctt gag ttt ctg tac act ggt cta ttc atc acc       288
Ala Val Phe Ile Val Leu Glu Phe Leu Tyr Thr Gly Leu Phe Ile Thr
                85                  90                  95 acg cat gat gca atg cat ggc acc ata gct ttg agg aac agg cag ctc       336
Thr His Asp Ala Met His Gly Thr Ile Ala Leu Arg Asn Arg Gln Leu
            100                 105                 110 aat gat ctc ctt ggc aac atc tgc ata tca ctg tac gcc tgg ttt gac       384
Asn Asp Leu Leu Gly Asn Ile Cys Ile Ser Leu Tyr Ala Trp Phe Asp
        115                 120                 125 tac agc atg cac tgg gag cac cac aac cat act ggc gaa gtg ggg aaa       432
Tyr Ser Met His Trp Glu His His Asn His Thr Gly Glu Val Gly Lys
    130                 135                 140 gac cct gac ttc cac aaa gga aat cct ggc ctt gtc ccc tgg ttc gcc       480
Asp Pro Asp Phe His Lys Gly Asn Pro Gly Leu Val Pro Trp Phe Ala
145                 150                 155                 160 agc ttc atg tcc agc tac atg tcc ctg tgg cag ttt gcc cgg ctg gca       528
Ser Phe Met Ser Ser Tyr Met Ser Leu Trp Gln Phe Ala Arg Leu Ala
                165                 170                 175 tgg tgg gca gtg gtg atg caa acg ttg ggg gcc ccc atg gcg aat ctc       576
Trp Trp Ala Val Val Met Gln Thr Leu Gly Ala Pro Met Ala Asn Leu
            180                 185                 190 cta gtc ttc atg gct gca gcc cca atc ttg tca gca ttc gcc ctc ttc       624
```

```
                    Leu Val Phe Met Ala Ala Ala Pro Ile Leu Ser Ala Phe Arg Leu Phe
                                    195                 200                 205 tac ttc ggc act tac ctg cca cac aag cct gag cca ggc cct gca gca          672
Tyr Phe Gly Thr Tyr Leu Pro His Lys Pro Glu Pro Gly Pro Ala Ala
    210                 215                 220 ggc tct cag gtc atg tct tgg ttc agg gcc aag aca agt gag gca tct          720
Gly Ser Gln Val Met Ser Trp Phe Arg Ala Lys Thr Ser Glu Ala Ser
225                 230                 235                 240 gat gtg atg agc ttc ctg aca tgc tac cac ttt gac ctg ttt gcc ccc          768
Asp Val Met Ser Phe Leu Thr Cys Tyr His Phe Asp Leu Phe Ala Pro
                    245                 250                 255 tgg tgg cag ctg ccc cac tgc cgc cgc ctg tct ggg cgt ggc ctg gtg          816
Trp Trp Gln Leu Pro His Cys Arg Arg Leu Ser Gly Arg Gly Leu Val
                260                 265                 270 cct gcc ttg gca tga                                                      831
Pro Ala Leu Ala
        275

<210> SEQ ID NO 98
<211> LENGTH: 276
<212> TYPE: PRT
<213> ORGANISM: Haematococcus pluvialis

<400> SEQUENCE: 98

Met Pro Ser Glu Ser Ser Asp Ala Ala Arg Pro Val Leu Lys His Ala
1               5                   10                  15

Tyr Lys Pro Pro Ala Ser Asp Ala Lys Gly Ile Thr Met Ala Leu Thr
            20                  25                  30

Ile Ile Gly Thr Trp Thr Ala Val Phe Leu His Ala Ile Phe Gln Ile
        35                  40                  45

Arg Leu Pro Thr Ser Met Asp Gln Leu His Trp Leu Pro Val Ser Glu
    50                  55                  60

Ala Thr Ala Gln Leu Leu Gly Gly Ser Ser Leu Leu His Ile Ala
65                  70                  75                  80

Ala Val Phe Ile Val Leu Glu Phe Leu Tyr Thr Gly Leu Phe Ile Thr
                85                  90                  95

Thr His Asp Ala Met His Gly Thr Ile Ala Leu Arg Asn Arg Gln Leu
            100                 105                 110

Asn Asp Leu Leu Gly Asn Ile Cys Ile Ser Leu Tyr Ala Trp Phe Asp
        115                 120                 125

Tyr Ser Met His Trp Glu His His Asn His Thr Gly Glu Val Gly Lys
    130                 135                 140

Asp Pro Asp Phe His Lys Gly Asn Pro Gly Leu Val Pro Trp Phe Ala
145                 150                 155                 160

Ser Phe Met Ser Ser Tyr Met Ser Leu Trp Gln Phe Ala Arg Leu Ala
                165                 170                 175

Trp Trp Ala Val Val Met Gln Thr Leu Gly Ala Pro Met Ala Asn Leu
            180                 185                 190

Leu Val Phe Met Ala Ala Ala Pro Ile Leu Ser Ala Phe Arg Leu Phe
        195                 200                 205

Tyr Phe Gly Thr Tyr Leu Pro His Lys Pro Glu Pro Gly Pro Ala Ala
    210                 215                 220

Gly Ser Gln Val Met Ser Trp Phe Arg Ala Lys Thr Ser Glu Ala Ser
225                 230                 235                 240

Asp Val Met Ser Phe Leu Thr Cys Tyr His Phe Asp Leu Phe Ala Pro
                245                 250                 255
```

```
Trp Trp Gln Leu Pro His Cys Arg Arg Leu Ser Gly Arg Gly Leu Val
            260                 265                 270

Pro Ala Leu Ala
        275

<210> SEQ ID NO 99
<211> LENGTH: 729
<212> TYPE: DNA
<213> ORGANISM: Paracoccus sp. MBIC1143
<220> FEATURE:
<221> NAME/KEY: CDS

<400> SEQUENCE: 99 atg agc gca cat gcc ctg ccc aag gca gat ctg acc gcc acc agc ctg        48
Met Ser Ala His Ala Leu Pro Lys Ala Asp Leu Thr Ala Thr Ser Leu
1               5                  10                  15 atc gtc tcg ggc ggc atc atc gcc gct tgg ctg gcc ctg cat gtg cat        96
Ile Val Ser Gly Gly Ile Ile Ala Ala Trp Leu Ala Leu His Val His
                20                  25                  30 gcg ctg tgg ttt ctg gac gca gcg gcg cat ccc atc ctg gcg atc gca       144
Ala Leu Trp Phe Leu Asp Ala Ala Ala His Pro Ile Leu Ala Ile Ala
            35                  40                  45 aat ttc ctg ggg ctg acc tgg ctg tcg gtc gga ttg ttc atc atc gcg       192
Asn Phe Leu Gly Leu Thr Trp Leu Ser Val Gly Leu Phe Ile Ile Ala
        50                  55                  60 cat gac gcg atg cac ggg tcg gtg gtg ccg ggg cgt ccg cgc gcc aat       240
His Asp Ala Met His Gly Ser Val Val Pro Gly Arg Pro Arg Ala Asn
65                  70                  75                  80 gcg gcg atg ggc cag ctt gtc ctg tgg ctg tat gcc gga ttt tcg tgg       288
Ala Ala Met Gly Gln Leu Val Leu Trp Leu Tyr Ala Gly Phe Ser Trp
                85                  90                  95 cgc aag atg atc gtc aag cac atg gcc cat cac cgc cat gcc gga acc       336
Arg Lys Met Ile Val Lys His Met Ala His His Arg His Ala Gly Thr
                100                 105                 110 gac gac gac ccc gat ttc gac cat ggc ggc ccg gtc cgc tgg tac gcc       384
Asp Asp Asp Pro Asp Phe Asp His Gly Gly Pro Val Arg Trp Tyr Ala
            115                 120                 125 cgc ttc atc ggc acc tat ttc ggc tgg cgc gag ggg ctg ctg ctg ccc       432
Arg Phe Ile Gly Thr Tyr Phe Gly Trp Arg Glu Gly Leu Leu Leu Pro
        130                 135                 140 gtc atc gtg acg gtc tat gcg ctg atc ctt ggg gat cgc tgg atg tac       480
Val Ile Val Thr Val Tyr Ala Leu Ile Leu Gly Asp Arg Trp Met Tyr
145                 150                 155                 160 gtg gtc ttc tgg ccg ctg ccg tcg atc ctg gcg tcg atc cag ctg ttc       528
Val Val Phe Trp Pro Leu Pro Ser Ile Leu Ala Ser Ile Gln Leu Phe
                165                 170                 175 gtg ttc ggc acc tgg ctg ccg cac cgc ccc ggc cac gac gcg ttc ccg       576
Val Phe Gly Thr Trp Leu Pro His Arg Pro Gly His Asp Ala Phe Pro
            180                 185                 190 gac cgc cac aat gcg cgg tcg tcg cgg atc agc gac ccc gtg tcg ctg       624
Asp Arg His Asn Ala Arg Ser Ser Arg Ile Ser Asp Pro Val Ser Leu
        195                 200                 205 ctg acc tgc ttt cac ttt ggc ggt tat cat cac gaa cac cac ctg cac       672
Leu Thr Cys Phe His Phe Gly Gly Tyr His His Glu His His Leu His
210                 215                 220 ccg acg gtg ccg tgg tgg cgc ctg ccc agc acc cgc acc aag ggg gac       720
Pro Thr Val Pro Trp Trp Arg Leu Pro Ser Thr Arg Thr Lys Gly Asp
225                 230                 235                 240 acc gca tga                                                            729
Thr Ala
```

<210> SEQ ID NO 100
<211> LENGTH: 242
<212> TYPE: PRT
<213> ORGANISM: Paracoccus sp. MBIC1143

<400> SEQUENCE: 100

```
Met Ser Ala His Ala Leu Pro Lys Ala Asp Leu Thr Ala Thr Ser Leu
1               5                   10                  15

Ile Val Ser Gly Gly Ile Ile Ala Ala Trp Leu Ala Leu His Val His
            20                  25                  30

Ala Leu Trp Phe Leu Asp Ala Ala His Pro Ile Leu Ala Ile Ala
            35                  40                  45

Asn Phe Leu Gly Leu Thr Trp Leu Ser Val Gly Leu Phe Ile Ile Ala
    50                  55                  60

His Asp Ala Met His Gly Ser Val Val Pro Gly Arg Pro Arg Ala Asn
65                  70                  75                  80

Ala Ala Met Gly Gln Leu Val Leu Trp Leu Tyr Ala Gly Phe Ser Trp
                85                  90                  95

Arg Lys Met Ile Val Lys His Met Ala His His Arg His Ala Gly Thr
            100                 105                 110

Asp Asp Asp Pro Asp Phe Asp His Gly Gly Pro Val Arg Trp Tyr Ala
            115                 120                 125

Arg Phe Ile Gly Thr Tyr Phe Gly Trp Arg Glu Gly Leu Leu Leu Pro
    130                 135                 140

Val Ile Val Thr Val Tyr Ala Leu Ile Leu Gly Asp Arg Trp Met Tyr
145                 150                 155                 160

Val Val Phe Trp Pro Leu Pro Ser Ile Leu Ala Ser Ile Gln Leu Phe
                165                 170                 175

Val Phe Gly Thr Trp Leu Pro His Arg Pro Gly His Asp Ala Phe Pro
            180                 185                 190

Asp Arg His Asn Ala Arg Ser Ser Arg Ile Ser Asp Pro Val Ser Leu
            195                 200                 205

Leu Thr Cys Phe His Phe Gly Gly Tyr His His Glu His His Leu His
    210                 215                 220

Pro Thr Val Pro Trp Trp Arg Leu Pro Ser Thr Arg Thr Lys Gly Asp
225                 230                 235                 240

Thr Ala
```

<210> SEQ ID NO 101
<211> LENGTH: 735
<212> TYPE: DNA
<213> ORGANISM: Brevundimonas aurantiaca
<220> FEATURE:
<221> NAME/KEY: CDS

<400> SEQUENCE: 101

```
atg acc gcc gcc gtc gcc gag cca cgc acc gtc ccg cgc cag acc tgg        48
Met Thr Ala Ala Val Ala Glu Pro Arg Thr Val Pro Arg Gln Thr Trp
1               5                   10                  15 atc ggt ctg acc ctg gcg gga atg atc gtg gcg gga tgg gcg gtt ctg        96
Ile Gly Leu Thr Leu Ala Gly Met Ile Val Ala Gly Trp Ala Val Leu
            20                  25                  30 cat gtc tac ggc gtc tat ttt cac cga tgg ggg ccg ttg acc ctg gtg       144
His Val Tyr Gly Val Tyr Phe His Arg Trp Gly Pro Leu Thr Leu Val
            35                  40                  45 atc gcc ccg gcg atc gtg gcg gtc cag acc tgg ttg tcg gtc ggc ctt       192
Ile Ala Pro Ala Ile Val Ala Val Gln Thr Trp Leu Ser Val Gly Leu
```

```
          50                      55                      60
ttc atc gtc gcc cat gac gcc atg tac ggc tcc ctg gcg ccg gga cgg      240
Phe Ile Val Ala His Asp Ala Met Tyr Gly Ser Leu Ala Pro Gly Arg
 65                  70                  75                  80 ccg cgg ctg aac gcc gca gtc ggc cgg ctg acc ctg ggg ctc tat gcg      288
Pro Arg Leu Asn Ala Ala Val Gly Arg Leu Thr Leu Gly Leu Tyr Ala
                 85                  90                  95 ggc ttc cgc ttc gat cgg ctg aag acg gcg cac cac gcc cac cac gcc      336
Gly Phe Arg Phe Asp Arg Leu Lys Thr Ala His His Ala His His Ala
                100                 105                 110 gcg ccc ggc acg gcc gac gac ccg gat ttt cac gcc ccg gcc ccc cgc      384
Ala Pro Gly Thr Ala Asp Asp Pro Asp Phe His Ala Pro Ala Pro Arg
            115                 120                 125 gcc ttc ctt ccc tgg ttc ctg aac ttc ttt cgc acc tat ttc ggc tgg      432
Ala Phe Leu Pro Trp Phe Leu Asn Phe Phe Arg Thr Tyr Phe Gly Trp
            130                 135                 140 cgc gag atg gcg gtc ctg acc gcc ctg gtc ctg atc gcc ctc ttc ggc      480
Arg Glu Met Ala Val Leu Thr Ala Leu Val Leu Ile Ala Leu Phe Gly
145                 150                 155                 160 ctg ggg gcg cgg ccg gcc aat ctc ctg acc ttc tgg gcc gcg ccg gcc      528
Leu Gly Ala Arg Pro Ala Asn Leu Leu Thr Phe Trp Ala Ala Pro Ala
                165                 170                 175 ctg ctt tca gcg ctt cag ctc ttc acc ttc ggc acc tgg ctg ccg cac      576
Leu Leu Ser Ala Leu Gln Leu Phe Thr Phe Gly Thr Trp Leu Pro His
                180                 185                 190 cgc cac acc gac cag ccg ttc gcc gac gcg cac cac gcc cgc agc agc      624
Arg His Thr Asp Gln Pro Phe Ala Asp Ala His His Ala Arg Ser Ser
            195                 200                 205 ggc tac ggc ccc gtg ctt tcc ctg ctc acc tgt ttc cac ttc ggc cgc      672
Gly Tyr Gly Pro Val Leu Ser Leu Leu Thr Cys Phe His Phe Gly Arg
210                 215                 220 cac cac gaa cac cat ctg agc ccc tgg cgg ccc tgg tgg cgt ctg tgg      720
His His Glu His His Leu Ser Pro Trp Arg Pro Trp Trp Arg Leu Trp
225                 230                 235                 240 cgc ggc gag tct tga                                                   735
Arg Gly Glu Ser <210> SEQ ID NO 102
<211> LENGTH: 244
<212> TYPE: PRT
<213> ORGANISM: Brevundimonas aurantiaca

<400> SEQUENCE: 102

Met Thr Ala Ala Val Ala Glu Pro Arg Thr Val Pro Arg Gln Thr Trp
 1               5                  10                  15

Ile Gly Leu Thr Leu Ala Gly Met Ile Val Ala Gly Trp Ala Val Leu
                20                  25                  30

His Val Tyr Gly Val Tyr Phe His Arg Trp Gly Pro Leu Thr Leu Val
            35                  40                  45

Ile Ala Pro Ala Ile Val Ala Val Gln Thr Trp Leu Ser Val Gly Leu
        50                  55                  60

Phe Ile Val Ala His Asp Ala Met Tyr Gly Ser Leu Ala Pro Gly Arg
 65                  70                  75                  80

Pro Arg Leu Asn Ala Ala Val Gly Arg Leu Thr Leu Gly Leu Tyr Ala
                85                  90                  95

Gly Phe Arg Phe Asp Arg Leu Lys Thr Ala His His Ala His His Ala
                100                 105                 110

Ala Pro Gly Thr Ala Asp Asp Pro Asp Phe His Ala Pro Ala Pro Arg
```

```
                115                 120                 125
Ala Phe Leu Pro Trp Phe Leu Asn Phe Phe Arg Thr Tyr Phe Gly Trp
    130                 135                 140

Arg Glu Met Ala Val Leu Thr Ala Leu Val Leu Ile Ala Leu Phe Gly
145                 150                 155                 160

Leu Gly Ala Arg Pro Ala Asn Leu Leu Thr Phe Trp Ala Ala Pro Ala
                165                 170                 175

Leu Leu Ser Ala Leu Gln Leu Phe Thr Phe Gly Thr Trp Leu Pro His
            180                 185                 190

Arg His Thr Asp Gln Pro Phe Ala Asp Ala His His Ala Arg Ser Ser
                195                 200                 205

Gly Tyr Gly Pro Val Leu Ser Leu Leu Thr Cys Phe His Phe Gly Arg
        210                 215                 220

His His Glu His His Leu Ser Pro Trp Arg Pro Trp Trp Arg Leu Trp
225                 230                 235                 240

Arg Gly Glu Ser

<210> SEQ ID NO 103
<211> LENGTH: 690
<212> TYPE: DNA
<213> ORGANISM: Nodularia spumigena NSOR10
<220> FEATURE:
<221> NAME/KEY: CDS

<400> SEQUENCE: 103
```

| | | | | | | | | | | | | | | | | |
|---|---|---|---|---|---|---|---|---|---|---|---|---|---|---|---|---|
| atg | gcg | atc | gcc | att | att | agt | ata | tgg | gct | atc | agc | cta | ggt | ttg | tta | 48 |
| Met | Ala | Ile | Ala | Ile | Ile | Ser | Ile | Trp | Ala | Ile | Ser | Leu | Gly | Leu | Leu | |
| 1 | | | | 5 | | | | | 10 | | | | | 15 | | |

```
ctt tat att gat ata tcc caa ttc aag ttt tgg atg ttg tta ccg ctc    96
Leu Tyr Ile Asp Ile Ser Gln Phe Lys Phe Trp Met Leu Leu Pro Leu
                20                  25                  30 ata ttt tgg caa aca ttt tta tat acg gga tta ttt att aca gct cat   144
Ile Phe Trp Gln Thr Phe Leu Tyr Thr Gly Leu Phe Ile Thr Ala His
        35                  40                  45 gat gcc atg cat ggg gta gtt ttt ccc aaa aat ccc aaa atc aac cat   192
Asp Ala Met His Gly Val Val Phe Pro Lys Asn Pro Lys Ile Asn His
50                  55                  60 ttc att ggc tca ttg tgc ctg ttt ctt tat ggt ctt tta cct tat caa   240
Phe Ile Gly Ser Leu Cys Leu Phe Leu Tyr Gly Leu Leu Pro Tyr Gln
65                  70                  75                  80 aaa ctt tta aaa aag cat tgg cta cat cac cat aat cca gcc agt gaa   288
Lys Leu Leu Lys Lys His Trp Leu His His His Asn Pro Ala Ser Glu
                85                  90                  95 aca gat cca gat ttt cac aac ggg aag cag aaa aac ttt ttt gct tgg   336
Thr Asp Pro Asp Phe His Asn Gly Lys Gln Lys Asn Phe Phe Ala Trp
            100                 105                 110 tat tta tat ttt atg aag cgt tac tgg agt tgg tta caa att atc aca   384
Tyr Leu Tyr Phe Met Lys Arg Tyr Trp Ser Trp Leu Gln Ile Ile Thr
        115                 120                 125 tta atg att att tat aac tta cta aaa tat ata tgg cat ttt cca gag   432
Leu Met Ile Ile Tyr Asn Leu Leu Lys Tyr Ile Trp His Phe Pro Glu
130                 135                 140 gat aat atg act tat ttt tgg gta gtt ccc tca att tta agt tct tta   480
Asp Asn Met Thr Tyr Phe Trp Val Val Pro Ser Ile Leu Ser Ser Leu
145                 150                 155                 160 caa tta ttt tat ttt gga act ttt cta ccc cac agt gag cct gta gaa   528
Gln Leu Phe Tyr Phe Gly Thr Phe Leu Pro His Ser Glu Pro Val Glu
                165                 170                 175
```

| | | | | | | | | | | | | | | | | |
|---|---|---|---|---|---|---|---|---|---|---|---|---|---|---|---|---|
| ggt | tat | aaa | gag | cct | cat | cgt | tcc | caa | act | att | agc | cgt | ccc | att | tgg | 576 |
| Gly | Tyr | Lys | Glu | Pro | His | Arg | Ser | Gln | Thr | Ile | Ser | Arg | Pro | Ile | Trp | |
| | | | 180 | | | | | 185 | | | | | 190 | | | |
| tgg | tca | ttt | ata | act | tgt | tac | cat | ttt | ggt | tat | cat | tac | gaa | cat | cat | 624 |
| Trp | Ser | Phe | Ile | Thr | Cys | Tyr | His | Phe | Gly | Tyr | His | Tyr | Glu | His | His | |
| | | 195 | | | | | 200 | | | | | 205 | | | | |
| gaa | tac | ccc | cat | gtt | cct | tgg | tgg | caa | tta | cca | gaa | att | tat | aaa | atg | 672 |
| Glu | Tyr | Pro | His | Val | Pro | Trp | Trp | Gln | Leu | Pro | Glu | Ile | Tyr | Lys | Met | |
| | 210 | | | | | 215 | | | | | 220 | | | | | |
| tct | aaa | tca | aat | ttg | tga | | | | | | | | | | | 690 |
| Ser | Lys | Ser | Asn | Leu | | | | | | | | | | | | |
| 225 | | | | | | | | | | | | | | | | |

<210> SEQ ID NO 104
<211> LENGTH: 229
<212> TYPE: PRT
<213> ORGANISM: Nodularia spumigena NSOR10

<400> SEQUENCE: 104

Met Ala Ile Ala Ile Ile Ser Ile Trp Ala Ile Ser Leu Gly Leu Leu
1               5                   10                  15

Leu Tyr Ile Asp Ile Ser Gln Phe Lys Phe Trp Met Leu Leu Pro Leu
            20                  25                  30

Ile Phe Trp Gln Thr Phe Leu Tyr Thr Gly Leu Phe Ile Thr Ala His
        35                  40                  45

Asp Ala Met His Gly Val Val Phe Pro Lys Asn Pro Lys Ile Asn His
    50                  55                  60

Phe Ile Gly Ser Leu Cys Leu Phe Leu Tyr Gly Leu Leu Pro Tyr Gln
65                  70                  75                  80

Lys Leu Leu Lys Lys His Trp Leu His His Asn Pro Ala Ser Glu
                85                  90                  95

Thr Asp Pro Asp Phe His Asn Gly Lys Gln Lys Asn Phe Phe Ala Trp
            100                 105                 110

Tyr Leu Tyr Phe Met Lys Arg Tyr Trp Ser Trp Leu Gln Ile Ile Thr
        115                 120                 125

Leu Met Ile Ile Tyr Asn Leu Leu Lys Tyr Ile Trp His Phe Pro Glu
130                 135                 140

Asp Asn Met Thr Tyr Phe Trp Val Val Pro Ser Ile Leu Ser Ser Leu
145                 150                 155                 160

Gln Leu Phe Tyr Phe Gly Thr Phe Leu Pro His Ser Glu Pro Val Glu
                165                 170                 175

Gly Tyr Lys Glu Pro His Arg Ser Gln Thr Ile Ser Arg Pro Ile Trp
            180                 185                 190

Trp Ser Phe Ile Thr Cys Tyr His Phe Gly Tyr His Tyr Glu His His
        195                 200                 205

Glu Tyr Pro His Val Pro Trp Trp Gln Leu Pro Glu Ile Tyr Lys Met
    210                 215                 220

Ser Lys Ser Asn Leu
225

<210> SEQ ID NO 105
<211> LENGTH: 1536
<212> TYPE: DNA
<213> ORGANISM: Deinococcus radiodurans R1
<220> FEATURE:
<221> NAME/KEY: CDS

<400> SEQUENCE: 105

-continued

| | |
|---|---|
| atg ccg gat tac gac ctg atc gtc atg ggc gcg ggc cac aac gcg ctg<br>Met Pro Asp Tyr Asp Leu Ile Val Met Gly Ala Gly His Asn Ala Leu<br>1               5                   10                  15 | 48 |
| gtg act gct gcc tac gcc gcc cgg gcg ggc ctg aaa gtc ggc gtg ttc<br>Val Thr Ala Ala Tyr Ala Ala Arg Ala Gly Leu Lys Val Gly Val Phe<br>            20                  25                  30 | 96 |
| gag cgg cgg cac ctc gtc ggc ggg gcg gtc agc acc gag gag gtc gtg<br>Glu Arg Arg His Leu Val Gly Gly Ala Val Ser Thr Glu Glu Val Val<br>        35                  40                  45 | 144 |
| ccc ggt tac cgc ttc gac tac ggc ggc agc gcc cac atc ctg att cgg<br>Pro Gly Tyr Arg Phe Asp Tyr Gly Gly Ser Ala His Ile Leu Ile Arg<br>    50                  55                  60 | 192 |
| atg acg ccc atc gtg cgc gaa ctc gaa ctc acg cgg cac ggg ctg cat<br>Met Thr Pro Ile Val Arg Glu Leu Glu Leu Thr Arg His Gly Leu His<br>65                  70                  75                  80 | 240 |
| tac ctc gaa gtg gac cct atg ttt cac gct tcc gac ggt gaa acg ccc<br>Tyr Leu Glu Val Asp Pro Met Phe His Ala Ser Asp Gly Glu Thr Pro<br>                85                  90                  95 | 288 |
| tgg ttc att cac cgc gac gcc ggg cgg acc atc cgc gaa ctg gac gaa<br>Trp Phe Ile His Arg Asp Ala Gly Arg Thr Ile Arg Glu Leu Asp Glu<br>            100                 105                 110 | 336 |
| aag ttt ccc ggg cag ggc gac gcc tac ggg cgc ttt ctc gac gat tgg<br>Lys Phe Pro Gly Gln Gly Asp Ala Tyr Gly Arg Phe Leu Asp Asp Trp<br>        115                 120                 125 | 384 |
| aca ccc ttc gcg cgc gcc gtg gcc gac ctg ttc aac tcg gcg ccg ggg<br>Thr Pro Phe Ala Arg Ala Val Ala Asp Leu Phe Asn Ser Ala Pro Gly<br>    130                 135                 140 | 432 |
| ccg ctc gac ctg ggc aaa atg gtg atg cgc agc ggc cag ggc aag gac<br>Pro Leu Asp Leu Gly Lys Met Val Met Arg Ser Gly Gln Gly Lys Asp<br>145                 150                 155                 160 | 480 |
| tgg aac gag cag ctc ccg cgc atc ctg cgg ccc tac ggc gac gtg gcg<br>Trp Asn Glu Gln Leu Pro Arg Ile Leu Arg Pro Tyr Gly Asp Val Ala<br>                165                 170                 175 | 528 |
| cgc gag tac ttc agc gag gag cgc gtg cgg gct ccc ctg acc tgg atg<br>Arg Glu Tyr Phe Ser Glu Glu Arg Val Arg Ala Pro Leu Thr Trp Met<br>            180                 185                 190 | 576 |
| gcg gcc cag agc ggc ccc cca ccc tcg gac ccg ctg agc gcg ccc ttt<br>Ala Ala Gln Ser Gly Pro Pro Pro Ser Asp Pro Leu Ser Ala Pro Phe<br>        195                 200                 205 | 624 |
| ttg ctg tgg cac ccg ctc tac cac gaa ggc ggc gtg gcg cgg ccc aaa<br>Leu Leu Trp His Pro Leu Tyr His Glu Gly Gly Val Ala Arg Pro Lys<br>    210                 215                 220 | 672 |
| ggc ggc agc ggc ggc ctg acc aaa gcc ctg cgc cgg gcc acc gag gcc<br>Gly Gly Ser Gly Gly Leu Thr Lys Ala Leu Arg Arg Ala Thr Glu Ala<br>225                 230                 235                 240 | 720 |
| gaa ggc ggc gag gtc ttc acc gac gcg ccg gtc aag gaa att ctg gtc<br>Glu Gly Gly Glu Val Phe Thr Asp Ala Pro Val Lys Glu Ile Leu Val<br>                245                 250                 255 | 768 |
| aag gac ggc aag gcg cag ggc atc cgg ctg gaa agc ggc gag acg tac<br>Lys Asp Gly Lys Ala Gln Gly Ile Arg Leu Glu Ser Gly Glu Thr Tyr<br>            260                 265                 270 | 816 |
| acc gcc cgc gcc gtc gtg tcg ggc gtc cac atc ctg acc act gcg aat<br>Thr Ala Arg Ala Val Val Ser Gly Val His Ile Leu Thr Thr Ala Asn<br>        275                 280                 285 | 864 |
| gcc ctg ccc gcc gaa tat gtc cct agc gcc gcc agg aat gtg cgc gtg<br>Ala Leu Pro Ala Glu Tyr Val Pro Ser Ala Ala Arg Asn Val Arg Val<br>    290                 295                 300 | 912 |
| ggc aac ggc ttc ggc atg att ttg cgc ctc gcc ctc agt gaa aaa gtc<br>Gly Asn Gly Phe Gly Met Ile Leu Arg Leu Ala Leu Ser Glu Lys Val<br>305                 310                 315                 320 | 960 |

```
aaa tac cgt cac cac acc gag ccc gac tca cgc atc ggc ctg gga ttg      1008
Lys Tyr Arg His His Thr Glu Pro Asp Ser Arg Ile Gly Leu Gly Leu
                325                 330                 335 ctg atc aaa aac gag cgg caa atc atg cag ggc tac ggc gaa tac ctc      1056
Leu Ile Lys Asn Glu Arg Gln Ile Met Gln Gly Tyr Gly Glu Tyr Leu
            340                 345                 350 gcc ggg cag ccc acc acc gac ccg ccc ctc gtc gcc atg agc ttc agc      1104
Ala Gly Gln Pro Thr Thr Asp Pro Pro Leu Val Ala Met Ser Phe Ser
        355                 360                 365 gcg gtg gac gac tcg ctc gcc cca ccg aac ggc gac gtg ttg tgg ctg      1152
Ala Val Asp Asp Ser Leu Ala Pro Pro Asn Gly Asp Val Leu Trp Leu
    370                 375                 380 tgg gcg cag tac tac ccc ttc gag ctc gcc acc ggg agc tgg gaa acg      1200
Trp Ala Gln Tyr Tyr Pro Phe Glu Leu Ala Thr Gly Ser Trp Glu Thr
385                 390                 395                 400 cgc acc gcc gaa gcg cgg gag aac atc ctg cgg gcc ttt gag cac tac      1248
Arg Thr Ala Glu Ala Arg Glu Asn Ile Leu Arg Ala Phe Glu His Tyr
                405                 410                 415 gcg ccg ggc acc cgc gac acg att gtg ggc gaa ctc gtg cag acg ccg      1296
Ala Pro Gly Thr Arg Asp Thr Ile Val Gly Glu Leu Val Gln Thr Pro
            420                 425                 430 cag tgg ctg gaa acc aac ctc ggc ctg cac cgg ggc aac gtg atg cac      1344
Gln Trp Leu Glu Thr Asn Leu Gly Leu His Arg Gly Asn Val Met His
        435                 440                 445 ctg gaa atg tcc ttc gac cag atg ttc tcc ttc cgc ccc tgg ctg aaa      1392
Leu Glu Met Ser Phe Asp Gln Met Phe Ser Phe Arg Pro Trp Leu Lys
    450                 455                 460 gcg agc cag tac cgc tgg ccg ggc gtg cag ggg ctg tac ctc acc ggc      1440
Ala Ser Gln Tyr Arg Trp Pro Gly Val Gln Gly Leu Tyr Leu Thr Gly
465                 470                 475                 480 gcc agc acc cac ccc ggc gga ggc atc atg ggc gcc tcg gga cgc aac      1488
Ala Ser Thr His Pro Gly Gly Gly Ile Met Gly Ala Ser Gly Arg Asn
                485                 490                 495 gcg gcg cgg gtc atc gtg aag gac ctg acg cgg agg cgc tgg aaa tga      1536
Ala Ala Arg Val Ile Val Lys Asp Leu Thr Arg Arg Arg Trp Lys
            500                 505                 510

<210> SEQ ID NO 106
<211> LENGTH: 511
<212> TYPE: PRT
<213> ORGANISM: Deinococcus radiodurans R1

<400> SEQUENCE: 106

Met Pro Asp Tyr Asp Leu Ile Val Met Gly Ala Gly His Asn Ala Leu
1               5                   10                  15

Val Thr Ala Ala Tyr Ala Ala Arg Ala Gly Leu Lys Val Gly Val Phe
            20                  25                  30

Glu Arg Arg His Leu Val Gly Gly Ala Val Ser Thr Glu Glu Val Val
        35                  40                  45

Pro Gly Tyr Arg Phe Asp Tyr Gly Gly Ser Ala His Ile Leu Ile Arg
    50                  55                  60

Met Thr Pro Ile Val Arg Glu Leu Glu Leu Thr Arg His Gly Leu His
65                  70                  75                  80

Tyr Leu Glu Val Asp Pro Met Phe His Ala Ser Asp Gly Glu Thr Pro
                85                  90                  95

Trp Phe Ile His Arg Asp Ala Gly Arg Thr Ile Arg Glu Leu Asp Glu
            100                 105                 110

Lys Phe Pro Gly Gln Gly Asp Ala Tyr Gly Arg Phe Leu Asp Asp Trp
```

```
                115                 120                 125
Thr Pro Phe Ala Arg Ala Val Ala Asp Leu Phe Asn Ser Ala Pro Gly
    130                 135                 140
Pro Leu Asp Leu Gly Lys Met Val Met Arg Ser Gly Gln Gly Lys Asp
145                 150                 155                 160
Trp Asn Glu Gln Leu Pro Arg Ile Leu Arg Pro Tyr Gly Asp Val Ala
                165                 170                 175
Arg Glu Tyr Phe Ser Glu Arg Val Arg Ala Pro Leu Thr Trp Met
                180                 185                 190
Ala Ala Gln Ser Gly Pro Pro Ser Asp Pro Leu Ser Ala Pro Phe
                195                 200                 205
Leu Leu Trp His Pro Leu Tyr His Glu Gly Val Ala Arg Pro Lys
    210                 215                 220
Gly Gly Ser Gly Gly Leu Thr Lys Ala Leu Arg Arg Ala Thr Glu Ala
225                 230                 235                 240
Glu Gly Gly Glu Val Phe Thr Asp Ala Pro Val Lys Glu Ile Leu Val
                245                 250                 255
Lys Asp Gly Lys Ala Gln Gly Ile Arg Leu Glu Ser Gly Glu Thr Tyr
                260                 265                 270
Thr Ala Arg Ala Val Val Ser Gly Val His Ile Leu Thr Thr Ala Asn
                275                 280                 285
Ala Leu Pro Ala Glu Tyr Val Pro Ser Ala Ala Arg Asn Val Arg Val
    290                 295                 300
Gly Asn Gly Phe Gly Met Ile Leu Arg Leu Ala Leu Ser Glu Lys Val
305                 310                 315                 320
Lys Tyr Arg His His Thr Glu Pro Asp Ser Arg Ile Gly Leu Gly Leu
                325                 330                 335
Leu Ile Lys Asn Glu Arg Gln Ile Met Gln Gly Tyr Gly Glu Tyr Leu
                340                 345                 350
Ala Gly Gln Pro Thr Thr Asp Pro Leu Val Ala Met Ser Phe Ser
                355                 360                 365
Ala Val Asp Asp Ser Leu Ala Pro Pro Asn Gly Asp Val Leu Trp Leu
    370                 375                 380
Trp Ala Gln Tyr Tyr Pro Phe Glu Leu Ala Thr Gly Ser Trp Glu Thr
385                 390                 395                 400
Arg Thr Ala Glu Ala Arg Glu Asn Ile Leu Arg Ala Phe Glu His Tyr
                405                 410                 415
Ala Pro Gly Thr Arg Asp Thr Ile Val Gly Glu Leu Val Gln Thr Pro
                420                 425                 430
Gln Trp Leu Glu Thr Asn Leu Gly Leu His Arg Gly Asn Val Met His
                435                 440                 445
Leu Glu Met Ser Phe Asp Gln Met Phe Ser Phe Arg Pro Trp Leu Lys
    450                 455                 460
Ala Ser Gln Tyr Arg Trp Pro Gly Val Gln Gly Leu Tyr Leu Thr Gly
465                 470                 475                 480
Ala Ser Thr His Pro Gly Gly Ile Met Gly Ala Ser Gly Arg Asn
                485                 490                 495
Ala Ala Arg Val Ile Val Lys Asp Leu Thr Arg Arg Trp Lys
                500                 505                 510

<210> SEQ ID NO 107
<211> LENGTH: 1666
<212> TYPE: DNA
<213> ORGANISM: Lycopersicon esculentum
```

```
<220> FEATURE:
<221> NAME/KEY: CDS
<222> LOCATION: (1)..(1494)

<400> SEQUENCE: 107 atg gaa gct ctt ctc aag cct ttt cca tct ctt tta ctt tcc tct cct        48
Met Glu Ala Leu Leu Lys Pro Phe Pro Ser Leu Leu Leu Ser Ser Pro
1               5                   10                  15 aca ccc cat agg tct att ttc caa caa aat ccc tct ttt cta agt ccc        96
Thr Pro His Arg Ser Ile Phe Gln Gln Asn Pro Ser Phe Leu Ser Pro
            20                  25                  30 acc acc aaa aaa aaa tca aga aaa tgt ctt ctt aga aac aaa agt agt       144
Thr Thr Lys Lys Lys Ser Arg Lys Cys Leu Leu Arg Asn Lys Ser Ser
        35                  40                  45 aaa ctt ttt tgt agc ttt ctt gat tta gca ccc aca tca aag cca gag       192
Lys Leu Phe Cys Ser Phe Leu Asp Leu Ala Pro Thr Ser Lys Pro Glu
    50                  55                  60 tct tta gat gtt aac atc tca tgg gtt gat cct aat tcg aat cgg gct       240
Ser Leu Asp Val Asn Ile Ser Trp Val Asp Pro Asn Ser Asn Arg Ala
65                  70                  75                  80 caa ttc gac gtg atc att atc gga gct ggc cct gct ggg ctc agg cta       288
Gln Phe Asp Val Ile Ile Ile Gly Ala Gly Pro Ala Gly Leu Arg Leu
                85                  90                  95 gct gaa caa gtt tct aaa tat ggt att aag gta tgt tgt gtt gac cct       336
Ala Glu Gln Val Ser Lys Tyr Gly Ile Lys Val Cys Cys Val Asp Pro
            100                 105                 110 tca cca ctc tcc atg tgg cca aat aat tat ggt gtt tgg gtt gat gag       384
Ser Pro Leu Ser Met Trp Pro Asn Asn Tyr Gly Val Trp Val Asp Glu
        115                 120                 125 ttt gag aat tta gga ctg gaa aat tgt tta gat cat aaa tgg cct atg       432
Phe Glu Asn Leu Gly Leu Glu Asn Cys Leu Asp His Lys Trp Pro Met
    130                 135                 140 act tgt gtg cat ata aat gat aac aaa act aag tat ttg gga aga cca       480
Thr Cys Val His Ile Asn Asp Asn Lys Thr Lys Tyr Leu Gly Arg Pro
145                 150                 155                 160 tat ggt aga gtt agt aga aag aag ctg aag ttg aaa ttg tta aat agt       528
Tyr Gly Arg Val Ser Arg Lys Lys Leu Lys Leu Lys Leu Leu Asn Ser
                165                 170                 175 tgt gtt gag aac aga gtg aag ttt tat aaa gct aag gtt tgg aaa gtg       576
Cys Val Glu Asn Arg Val Lys Phe Tyr Lys Ala Lys Val Trp Lys Val
            180                 185                 190 gaa cat gaa gaa ttt gag tct tca att gtt tgt gat gat ggt aag aag       624
Glu His Glu Glu Phe Glu Ser Ser Ile Val Cys Asp Asp Gly Lys Lys
        195                 200                 205 ata aga ggt agt ttg gtt gtg gat gca agt ggt ttt gct agt gat ttt       672
Ile Arg Gly Ser Leu Val Val Asp Ala Ser Gly Phe Ala Ser Asp Phe
    210                 215                 220 ata gag tat gac agg cca aga aac cat ggt tat caa att gct cat ggg       720
Ile Glu Tyr Asp Arg Pro Arg Asn His Gly Tyr Gln Ile Ala His Gly
225                 230                 235                 240 gtt tta gta gaa gtt gat aat cat cca ttt gat ttg gat aaa atg gtg       768
Val Leu Val Glu Val Asp Asn His Pro Phe Asp Leu Asp Lys Met Val
                245                 250                 255 ctt atg gat tgg agg gat tct cat ttg ggt aat gag cca tat tta agg       816
Leu Met Asp Trp Arg Asp Ser His Leu Gly Asn Glu Pro Tyr Leu Arg
            260                 265                 270 gtg aat aat gct aaa gaa cca aca ttc ttg tat gca atg cca ttt gat       864
Val Asn Asn Ala Lys Glu Pro Thr Phe Leu Tyr Ala Met Pro Phe Asp
        275                 280                 285 aga gat ttg gtt ttc ttg gaa gag act tct ttg gtg agt cgt cct gtt       912
```

-continued

| | | | | | | | | | | | | |
|---|---|---|---|---|---|---|---|---|---|---|---|---|
| Arg | Asp | Leu | Val | Phe | Leu | Glu | Glu | Thr | Ser | Leu | Val | Ser | Arg | Pro | Val |
| | 290 | | | | 295 | | | | | 300 | | |

```
tta tcg tat atg gaa gta aaa aga agg atg gtg gca aga tta agg cat      960
Leu Ser Tyr Met Glu Val Lys Arg Arg Met Val Ala Arg Leu Arg His
305             310                 315                 320 ttg ggg atc aaa gtg aaa agt gtt att gag gaa gag aaa tgt gtg atc     1008
Leu Gly Ile Lys Val Lys Ser Val Ile Glu Glu Glu Lys Cys Val Ile
            325                 330                 335 cct atg gga gga cca ctt ccg cgg att cct caa aat gtt atg gct att     1056
Pro Met Gly Gly Pro Leu Pro Arg Ile Pro Gln Asn Val Met Ala Ile
            340                 345                 350 ggt ggg aat tca ggg ata gtt cat cca tca aca ggg tac atg gtg gct     1104
Gly Gly Asn Ser Gly Ile Val His Pro Ser Thr Gly Tyr Met Val Ala
            355                 360             365 agg agc atg gct tta gca cca gta cta gct gaa gcc atc gtc gag ggg     1152
Arg Ser Met Ala Leu Ala Pro Val Leu Ala Glu Ala Ile Val Glu Gly
        370                 375                 380 ctt ggc tca aca aga atg ata aga ggg tct caa ctt tac cat aga gtt     1200
Leu Gly Ser Thr Arg Met Ile Arg Gly Ser Gln Leu Tyr His Arg Val
385                 390                 395                 400 tgg aat ggt ttg tgg cct ttg gat aga aga tgt gtt aga gaa tgt tat     1248
Trp Asn Gly Leu Trp Pro Leu Asp Arg Arg Cys Val Arg Glu Cys Tyr
                405                 410                 415 tca ttt ggg atg gag aca ttg ttg aag ctt gat ttg aaa ggg act agg     1296
Ser Phe Gly Met Glu Thr Leu Leu Lys Leu Asp Leu Lys Gly Thr Arg
            420                 425                 430 aga ttg ttt gac gct ttc ttt gat ctt gat cct aaa tac tgg caa ggg     1344
Arg Leu Phe Asp Ala Phe Phe Asp Leu Asp Pro Lys Tyr Trp Gln Gly
        435                 440                 445 ttc ctt tct tca aga ttg tct gtc aaa gaa ctt ggt tta ctc agc ttg     1392
Phe Leu Ser Ser Arg Leu Ser Val Lys Glu Leu Gly Leu Leu Ser Leu
    450                 455                 460 tgt ctt ttc gga cat ggc tca aac atg act agg ttg gat att gtt aca     1440
Cys Leu Phe Gly His Gly Ser Asn Met Thr Arg Leu Asp Ile Val Thr
465                 470                 475                 480 aaa tgt cct ctt cct ttg gtt aga ctg att ggc aat cta gca ata gag     1488
Lys Cys Pro Leu Pro Leu Val Arg Leu Ile Gly Asn Leu Ala Ile Glu
                485                 490                 495 agc ctt tgaatgtgaa aagtttgaat cattttcttc attttaattt ctttgattat     1544
Ser Leu tttcatattt tctcaattgc aaaagtgaga taagagctac atactgtcaa caaataaact  1604
actattggaa agttaaaata tgtgtttgtt gtatgttatt ctaatggaat ggattttgta  1664
aa                                                                 1666

<210> SEQ ID NO 108
<211> LENGTH: 498
<212> TYPE: PRT
<213> ORGANISM: Lycopersicon esculentum

<400> SEQUENCE: 108

Met Glu Ala Leu Leu Lys Pro Phe Pro Ser Leu Leu Ser Ser Pro
1               5                   10                  15

Thr Pro His Arg Ser Ile Phe Gln Gln Asn Pro Ser Phe Leu Ser Pro
            20                  25                  30

Thr Thr Lys Lys Lys Ser Arg Lys Cys Leu Leu Arg Asn Lys Ser Ser
        35                  40                  45

Lys Leu Phe Cys Ser Phe Leu Asp Leu Ala Pro Thr Ser Lys Pro Glu
    50                  55                  60
```

-continued

```
Ser Leu Asp Val Asn Ile Ser Trp Val Asp Pro Asn Ser Asn Arg Ala
 65                  70                  75                  80

Gln Phe Asp Val Ile Ile Ile Gly Ala Gly Pro Ala Gly Leu Arg Leu
                 85                  90                  95

Ala Glu Gln Val Ser Lys Tyr Gly Ile Lys Val Cys Cys Val Asp Pro
            100                 105                 110

Ser Pro Leu Ser Met Trp Pro Asn Asn Tyr Gly Val Trp Val Asp Glu
        115                 120                 125

Phe Glu Asn Leu Gly Leu Glu Asn Cys Leu Asp His Lys Trp Pro Met
    130                 135                 140

Thr Cys Val His Ile Asn Asp Asn Lys Thr Lys Tyr Leu Gly Arg Pro
145                 150                 155                 160

Tyr Gly Arg Val Ser Arg Lys Lys Leu Lys Leu Lys Leu Leu Asn Ser
                165                 170                 175

Cys Val Glu Asn Arg Val Lys Phe Tyr Lys Ala Lys Val Trp Lys Val
            180                 185                 190

Glu His Glu Glu Phe Glu Ser Ser Ile Val Cys Asp Asp Gly Lys Lys
        195                 200                 205

Ile Arg Gly Ser Leu Val Val Asp Ala Ser Gly Phe Ala Ser Asp Phe
210                 215                 220

Ile Glu Tyr Asp Arg Pro Arg Asn His Gly Tyr Gln Ile Ala His Gly
225                 230                 235                 240

Val Leu Val Glu Val Asp Asn His Pro Phe Asp Leu Asp Lys Met Val
                245                 250                 255

Leu Met Asp Trp Arg Asp Ser His Leu Gly Asn Glu Pro Tyr Leu Arg
            260                 265                 270

Val Asn Asn Ala Lys Glu Pro Thr Phe Leu Tyr Ala Met Pro Phe Asp
        275                 280                 285

Arg Asp Leu Val Phe Leu Glu Glu Thr Ser Leu Val Ser Arg Pro Val
290                 295                 300

Leu Ser Tyr Met Glu Val Lys Arg Arg Met Val Ala Arg Leu Arg His
305                 310                 315                 320

Leu Gly Ile Lys Val Lys Ser Val Ile Glu Glu Lys Cys Val Ile
                325                 330                 335

Pro Met Gly Gly Pro Leu Pro Arg Ile Pro Gln Asn Val Met Ala Ile
            340                 345                 350

Gly Gly Asn Ser Gly Ile Val His Pro Ser Thr Gly Tyr Met Val Ala
        355                 360                 365

Arg Ser Met Ala Leu Ala Pro Val Leu Ala Glu Ala Ile Val Glu Gly
370                 375                 380

Leu Gly Ser Thr Arg Met Ile Arg Gly Ser Gln Leu Tyr His Arg Val
385                 390                 395                 400

Trp Asn Gly Leu Trp Pro Leu Asp Arg Arg Cys Val Arg Glu Cys Tyr
                405                 410                 415

Ser Phe Gly Met Glu Thr Leu Leu Lys Leu Asp Leu Lys Gly Thr Arg
            420                 425                 430

Arg Leu Phe Asp Ala Phe Phe Asp Leu Asp Pro Lys Tyr Trp Gln Gly
        435                 440                 445

Phe Leu Ser Ser Arg Leu Ser Val Lys Glu Leu Gly Leu Leu Ser Leu
450                 455                 460

Cys Leu Phe Gly His Gly Ser Asn Met Thr Arg Leu Asp Ile Val Thr
465                 470                 475                 480
```

```
Lys Cys Pro Leu Pro Leu Val Arg Leu Ile Gly Asn Leu Ala Ile Glu
            485                 490                 495
Ser Leu

<210> SEQ ID NO 109
<211> LENGTH: 1125
<212> TYPE: DNA
<213> ORGANISM: Lycopersicon esculentum
<220> FEATURE:
<221> NAME/KEY: CDS
<222> LOCATION: (20)..(946)

<400> SEQUENCE: 109
ttggtcatct ccacaatca atg gct gcc gcc gcc aga atc tcc gcc tcc tct          52
                    Met Ala Ala Ala Ala Arg Ile Ser Ala Ser Ser
                      1               5                  10 acc tca cga act ttt tat ttc cgt cat tca ccg ttt ctt ggc cca aaa          100
Thr Ser Arg Thr Phe Tyr Phe Arg His Ser Pro Phe Leu Gly Pro Lys
                15                  20                  25 cct act tcg aca acc tca cat gtt tct cca atc tct cct ttt tct ctt         148
Pro Thr Ser Thr Thr Ser His Val Ser Pro Ile Ser Pro Phe Ser Leu
         30                  35                  40 aat cta ggc cca att ttg agg tct aga aga aaa ccc agt ttc act gtt         196
Asn Leu Gly Pro Ile Leu Arg Ser Arg Arg Lys Pro Ser Phe Thr Val
     45                  50                  55 tgc ttt gtt ctc gag gat gag aag ctg aaa cct caa ttt gac gat gag         244
Cys Phe Val Leu Glu Asp Glu Lys Leu Lys Pro Gln Phe Asp Asp Glu
 60                  65                  70                  75 gct gag gat ttt gaa aag aag att gag gaa cag atc tta gct act cgc         292
Ala Glu Asp Phe Glu Lys Lys Ile Glu Glu Gln Ile Leu Ala Thr Arg
                 80                  85                  90 ttg gcg gag aaa ctg gct agg aag aaa tcg gag agg ttt act tat ctt         340
Leu Ala Glu Lys Leu Ala Arg Lys Lys Ser Glu Arg Phe Thr Tyr Leu
             95                 100                 105 gtg gct gct ata atg tct agt ttt ggg att act tct atg gct gtt atg         388
Val Ala Ala Ile Met Ser Ser Phe Gly Ile Thr Ser Met Ala Val Met
        110                 115                 120 gct gtt tat tac aga ttt tcg tgg caa atg gag gga gga gaa gtt cct         436
Ala Val Tyr Tyr Arg Phe Ser Trp Gln Met Glu Gly Gly Glu Val Pro
    125                 130                 135 gta acc gaa atg ttg ggt aca ttt gct ctc tct gtt ggt gct gct gta         484
Val Thr Glu Met Leu Gly Thr Phe Ala Leu Ser Val Gly Ala Ala Val
140                 145                 150                 155 gga atg gag ttt tgg gcg aga tgg gca cac aaa gca ctg tgg cat gct         532
Gly Met Glu Phe Trp Ala Arg Trp Ala His Lys Ala Leu Trp His Ala
                160                 165                 170 tca cta tgg cac atg cat gag tca cac cac aaa cca aga gaa gga cct         580
Ser Leu Trp His Met His Glu Ser His His Lys Pro Arg Glu Gly Pro
            175                 180                 185 ttt gag ctg aac gac gtt ttc gcc ata aca aac gct gtt cca gca ata         628
Phe Glu Leu Asn Asp Val Phe Ala Ile Thr Asn Ala Val Pro Ala Ile
        190                 195                 200 gcc ctc ctc aac tat ggt ttc ttc cat aaa ggc ctc att gcc gga cta         676
Ala Leu Leu Asn Tyr Gly Phe Phe His Lys Gly Leu Ile Ala Gly Leu
    205                 210                 215 tgc ttc ggt gct ggg cta ggg atc aca gta ttt gga atg gca tac atg         724
Cys Phe Gly Ala Gly Leu Gly Ile Thr Val Phe Gly Met Ala Tyr Met
220                 225                 230                 235 ttt gtt cac gat ggt ttg gtt cac aag aga ttc cca gtt gga cct gta         772
Phe Val His Asp Gly Leu Val His Lys Arg Phe Pro Val Gly Pro Val
                240                 245                 250
```

-continued

```
gcc aat gta cct tat ctt agg aag gtg gct gct gct cat tcg ctt cat      820
Ala Asn Val Pro Tyr Leu Arg Lys Val Ala Ala Ala His Ser Leu His
        255                 260                 265 cac tca gag aag ttc aat ggt gtc cca tat ggc ttg ttc ttc gga cct      868
His Ser Glu Lys Phe Asn Gly Val Pro Tyr Gly Leu Phe Phe Gly Pro
        270                 275                 280 aag gaa ctg gaa gaa gta gga ggg acg gaa gag ttg gaa aag gaa gtg      916
Lys Glu Leu Glu Glu Val Gly Gly Thr Glu Glu Leu Glu Lys Glu Val
285                 290                 295 ata cga agg acg aga ctt tcg aaa gga tca tgaacgattg ttcataaaca        966
Ile Arg Arg Thr Arg Leu Ser Lys Gly Ser
300                 305 tagaatgtca ttttacactt cttatcaatg aggaagggtg atttttgatg tatttgatag   1026
tagagaaaaa tgtagctctc ttgatgaaat gaatttgtat ttatgtaggc tcttcttatt   1086
cagtaagatt ttttcttttt tttgatctcg tgccgaatt                          1125
```

<210> SEQ ID NO 110
<211> LENGTH: 309
<212> TYPE: PRT
<213> ORGANISM: Lycopersicon esculentum

<400> SEQUENCE: 110

```
Met Ala Ala Ala Arg Ile Ser Ala Ser Thr Ser Arg Thr Phe
1               5                   10                  15

Tyr Phe Arg His Ser Pro Phe Leu Gly Pro Lys Pro Thr Ser Thr Thr
            20                  25                  30

Ser His Val Ser Pro Ile Ser Pro Phe Ser Leu Asn Leu Gly Pro Ile
        35                  40                  45

Leu Arg Ser Arg Arg Lys Pro Ser Phe Thr Val Cys Phe Val Leu Glu
    50                  55                  60

Asp Glu Lys Leu Lys Pro Gln Phe Asp Asp Glu Ala Glu Asp Phe Glu
65                  70                  75                  80

Lys Lys Ile Glu Glu Gln Ile Leu Ala Thr Arg Leu Ala Glu Lys Leu
                85                  90                  95

Ala Arg Lys Lys Ser Glu Arg Phe Thr Tyr Leu Val Ala Ala Ile Met
            100                 105                 110

Ser Ser Phe Gly Ile Thr Ser Met Ala Val Met Ala Val Tyr Tyr Arg
        115                 120                 125

Phe Ser Trp Gln Met Glu Gly Gly Glu Val Pro Val Thr Glu Met Leu
    130                 135                 140

Gly Thr Phe Ala Leu Ser Val Gly Ala Ala Val Gly Met Glu Phe Trp
145                 150                 155                 160

Ala Arg Trp Ala His Lys Ala Leu Trp His Ala Ser Leu Trp His Met
                165                 170                 175

His Glu Ser His His Lys Pro Arg Glu Gly Pro Phe Glu Leu Asn Asp
            180                 185                 190

Val Phe Ala Ile Thr Asn Ala Val Pro Ala Ile Ala Leu Leu Asn Tyr
        195                 200                 205

Gly Phe Phe His Lys Gly Leu Ile Ala Gly Leu Cys Phe Gly Ala Gly
    210                 215                 220

Leu Gly Ile Thr Val Phe Gly Met Ala Tyr Met Phe Val His Asp Gly
225                 230                 235                 240

Leu Val His Lys Arg Phe Pro Val Gly Pro Val Ala Asn Val Pro Tyr
                245                 250                 255
```

```
Leu Arg Lys Val Ala Ala His Ser Leu His His Ser Glu Lys Phe
            260                 265                 270

Asn Gly Val Pro Tyr Gly Leu Phe Phe Gly Pro Lys Glu Leu Glu Glu
            275                 280                 285

Val Gly Gly Thr Glu Glu Leu Glu Lys Glu Val Ile Arg Arg Thr Arg
            290                 295                 300

Leu Ser Lys Gly Ser
305

<210> SEQ ID NO 111
<211> LENGTH: 1779
<212> TYPE: DNA
<213> ORGANISM: Arabidopsis thaliana
<220> FEATURE:
<221> NAME/KEY: CDS

<400> SEQUENCE: 111
```

| | | | | | | | | | | | | | | | | |
|---|---|---|---|---|---|---|---|---|---|---|---|---|---|---|---|---|
| atg gat ctc cgt cgg agg cct cct aaa cca ccg gtt acc aac aac aac | | | | | | | | | | | | | | | | 48 |
| Met Asp Leu Arg Arg Arg Pro Pro Lys Pro Pro Val Thr Asn Asn Asn | | | | | | | | | | | | | | | | |
| 1 | | | 5 | | | | | 10 | | | | | 15 | | | |
| aac tcc aac gga tct ttc cgt tct tat cag cct cgc act tcc gat gac | | | | | | | | | | | | | | | | 96 |
| Asn Ser Asn Gly Ser Phe Arg Ser Tyr Gln Pro Arg Thr Ser Asp Asp | | | | | | | | | | | | | | | | |
| | | | 20 | | | | | 25 | | | | | 30 | | | |
| gat cat cgt cgc cgg gct aca aca att gct cct cca ccg aaa gca tcc | | | | | | | | | | | | | | | | 144 |
| Asp His Arg Arg Arg Ala Thr Thr Ile Ala Pro Pro Pro Lys Ala Ser | | | | | | | | | | | | | | | | |
| | | 35 | | | | | 40 | | | | | 45 | | | | |
| gac gcg ctt cct ctt ccg tta tat ctc aca aac gcc gtt ttc ttc acg | | | | | | | | | | | | | | | | 192 |
| Asp Ala Leu Pro Leu Pro Leu Tyr Leu Thr Asn Ala Val Phe Phe Thr | | | | | | | | | | | | | | | | |
| 50 | | | | | 55 | | | | | 60 | | | | | | |
| ctc ttc ttc tcc gtc gcg tat tac ctc ctc cac cgg tgg cgt gac aag | | | | | | | | | | | | | | | | 240 |
| Leu Phe Phe Ser Val Ala Tyr Tyr Leu Leu His Arg Trp Arg Asp Lys | | | | | | | | | | | | | | | | |
| 65 | | | | | 70 | | | | | 75 | | | | | 80 | |
| atc cgt tac aat acg cct ctt cac gtc gtc act atc aca gaa ctc ggc | | | | | | | | | | | | | | | | 288 |
| Ile Arg Tyr Asn Thr Pro Leu His Val Val Thr Ile Thr Glu Leu Gly | | | | | | | | | | | | | | | | |
| | | | | 85 | | | | | 90 | | | | | 95 | | |
| gcc att att gct ctc atc gct tcg ttt atc tat ctc cta ggg ttt ttt | | | | | | | | | | | | | | | | 336 |
| Ala Ile Ile Ala Leu Ile Ala Ser Phe Ile Tyr Leu Leu Gly Phe Phe | | | | | | | | | | | | | | | | |
| | | | 100 | | | | | 105 | | | | | 110 | | | |
| ggt att gac ttt gtt cag tca ttt atc tca cgt gcc tct ggt gat gct | | | | | | | | | | | | | | | | 384 |
| Gly Ile Asp Phe Val Gln Ser Phe Ile Ser Arg Ala Ser Gly Asp Ala | | | | | | | | | | | | | | | | |
| | | | 115 | | | | | 120 | | | | | 125 | | | |
| tgg gat ctc gcc gat acg atc gat gat gat gac cac cgc ctt gtc acg | | | | | | | | | | | | | | | | 432 |
| Trp Asp Leu Ala Asp Thr Ile Asp Asp Asp Asp His Arg Leu Val Thr | | | | | | | | | | | | | | | | |
| | | 130 | | | | | 135 | | | | | 140 | | | | |
| tgc tct cca ccg act ccg atc gtt tcc gtt gct aaa tta cct aat ccg | | | | | | | | | | | | | | | | 480 |
| Cys Ser Pro Pro Thr Pro Ile Val Ser Val Ala Lys Leu Pro Asn Pro | | | | | | | | | | | | | | | | |
| 145 | | | | | 150 | | | | | 155 | | | | | 160 | |
| gaa cct att gtt acc gaa tcg ctt cct gag gaa gac gag gag att gtg | | | | | | | | | | | | | | | | 528 |
| Glu Pro Ile Val Thr Glu Ser Leu Pro Glu Glu Asp Glu Glu Ile Val | | | | | | | | | | | | | | | | |
| | | | | 165 | | | | | 170 | | | | | 175 | | |
| aaa tcg gtt atc gac gga gtt att cca tcg tac tcg ctt gaa tct cgt | | | | | | | | | | | | | | | | 576 |
| Lys Ser Val Ile Asp Gly Val Ile Pro Ser Tyr Ser Leu Glu Ser Arg | | | | | | | | | | | | | | | | |
| | | | 180 | | | | | 185 | | | | | 190 | | | |
| ctc ggt gat tgc aaa aga gcg gcg tcg att cgt cgt gag gcg ttg cag | | | | | | | | | | | | | | | | 624 |
| Leu Gly Asp Cys Lys Arg Ala Ala Ser Ile Arg Arg Glu Ala Leu Gln | | | | | | | | | | | | | | | | |
| | | | 195 | | | | | 200 | | | | | 205 | | | |
| aga gtc acc ggg aga tcg att gaa ggg tta ccg ttg gat gga ttt gat | | | | | | | | | | | | | | | | 672 |
| Arg Val Thr Gly Arg Ser Ile Glu Gly Leu Pro Leu Asp Gly Phe Asp | | | | | | | | | | | | | | | | |
| | | 210 | | | | | 215 | | | | | 220 | | | | |
| tat gaa tcg att ttg ggg caa tgc tgt gag atg cct gtt gga tac att | | | | | | | | | | | | | | | | 720 |

```
              Tyr Glu Ser Ile Leu Gly Gln Cys Cys Glu Met Pro Val Gly Tyr Ile
              225                 230                 235                 240 cag att cct gtt ggg att gct ggt cca ttg ttg ctt gat ggt tat gag        768
Gln Ile Pro Val Gly Ile Ala Gly Pro Leu Leu Leu Asp Gly Tyr Glu
                245                 250                 255 tac tct gtt cct atg gct aca acc gaa ggt tgt ttg gtt gct agc act        816
Tyr Ser Val Pro Met Ala Thr Thr Glu Gly Cys Leu Val Ala Ser Thr
                260                 265                 270 aac aga ggc tgc aag gct atg ttt atc tct ggt ggc gcc acc agt acc        864
Asn Arg Gly Cys Lys Ala Met Phe Ile Ser Gly Gly Ala Thr Ser Thr
                275                 280                 285 gtt ctt aag gac ggt atg acc cga gca cct gtt gtt cgg ttc gct tcg        912
Val Leu Lys Asp Gly Met Thr Arg Ala Pro Val Val Arg Phe Ala Ser
                290                 295                 300 gcg aga cga gct tcg gag ctt aag ttt ttc ttg gag aat cca gag aac        960
Ala Arg Arg Ala Ser Glu Leu Lys Phe Phe Leu Glu Asn Pro Glu Asn
305                 310                 315                 320 ttt gat act ttg gca gta gtc ttc aac agg tcg agt aga ttt gca aga       1008
Phe Asp Thr Leu Ala Val Val Phe Asn Arg Ser Ser Arg Phe Ala Arg
                325                 330                 335 ctg caa agt gtt aaa tgc aca atc gcg ggg aag aat gct tat gta agg       1056
Leu Gln Ser Val Lys Cys Thr Ile Ala Gly Lys Asn Ala Tyr Val Arg
                340                 345                 350 ttc tgt tgt agt act ggt gat gct atg ggg atg aat atg gtt tct aaa       1104
Phe Cys Cys Ser Thr Gly Asp Ala Met Gly Met Asn Met Val Ser Lys
                355                 360                 365 ggt gtg cag aat gtt ctt gag tat ctt acc gat gat ttc cct gac atg       1152
Gly Val Gln Asn Val Leu Glu Tyr Leu Thr Asp Asp Phe Pro Asp Met
370                 375                 380 gat gtg att gga atc tct ggt aac ttc tgt tcg gac aag aaa cct gct       1200
Asp Val Ile Gly Ile Ser Gly Asn Phe Cys Ser Asp Lys Lys Pro Ala
385                 390                 395                 400 gct gtg aac tgg att gag gga cgt ggt aaa tca gtt gtt tgc gag gct       1248
Ala Val Asn Trp Ile Glu Gly Arg Gly Lys Ser Val Val Cys Glu Ala
                405                 410                 415 gta atc aga gga gag atc gtg aac aag gtc ttg aaa acg agc gtg gct       1296
Val Ile Arg Gly Glu Ile Val Asn Lys Val Leu Lys Thr Ser Val Ala
                420                 425                 430 gct tta gtc gag ctc aac atg ctc aag aac cta gct ggc tct gct gtt       1344
Ala Leu Val Glu Leu Asn Met Leu Lys Asn Leu Ala Gly Ser Ala Val
                435                 440                 445 gca ggc tct cta ggt gga ttc aac gct cat gcc agt aac ata gtg tct       1392
Ala Gly Ser Leu Gly Gly Phe Asn Ala His Ala Ser Asn Ile Val Ser
450                 455                 460 gct gta ttc ata gct act ggc caa gat cca gct caa aac gtg gag agt       1440
Ala Val Phe Ile Ala Thr Gly Gln Asp Pro Ala Gln Asn Val Glu Ser
465                 470                 475                 480 tct caa tgc atc acc atg atg gaa gct att aat gac ggc aaa gat atc       1488
Ser Gln Cys Ile Thr Met Met Glu Ala Ile Asn Asp Gly Lys Asp Ile
                485                 490                 495 cat atc tca gtc act atg cca tct atc gag gtg ggg aca gtg gga gga       1536
His Ile Ser Val Thr Met Pro Ser Ile Glu Val Gly Thr Val Gly Gly
                500                 505                 510 gga aca cag ctt gca tct caa tca gcg tgt tta aac ctg ctc gga gtt       1584
Gly Thr Gln Leu Ala Ser Gln Ser Ala Cys Leu Asn Leu Leu Gly Val
                515                 520                 525 aaa gga gca agc aca gag tcg ccg gga atg aac gca agg agg cta gcg       1632
Lys Gly Ala Ser Thr Glu Ser Pro Gly Met Asn Ala Arg Arg Leu Ala
530                 535                 540
```

```
acg atc gta gcc gga gca gtt tta gct gga gag tta tct tta atg tca    1680
Thr Ile Val Ala Gly Ala Val Leu Ala Gly Glu Leu Ser Leu Met Ser
545                 550                 555                 560 gca att gca gct gga cag ctt gtg aga agt cac atg aaa tac aat aga    1728
Ala Ile Ala Ala Gly Gln Leu Val Arg Ser His Met Lys Tyr Asn Arg
                565                 570                 575 tcc agc cga gac atc tct gga gca acg aca acg aca aca aca aca       1776
Ser Ser Arg Asp Ile Ser Gly Ala Thr Thr Thr Thr Thr Thr Thr
                580                 585                 590 tga                                                                1779
```

```
<210> SEQ ID NO 112
<211> LENGTH: 592
<212> TYPE: PRT
<213> ORGANISM: Arabidopsis thaliana

<400> SEQUENCE: 112
```

Met Asp Leu Arg Arg Arg Pro Lys Pro Val Thr Asn Asn
1               5                   10              15

Asn Ser Asn Gly Ser Phe Arg Ser Tyr Gln Pro Arg Thr Ser Asp Asp
            20                  25                  30

Asp His Arg Arg Ala Thr Thr Ile Ala Pro Pro Lys Ala Ser
        35                  40                  45

Asp Ala Leu Pro Leu Pro Leu Tyr Leu Thr Asn Ala Val Phe Phe Thr
    50                  55                  60

Leu Phe Phe Ser Val Ala Tyr Tyr Leu Leu His Arg Trp Arg Asp Lys
65                  70                  75                  80

Ile Arg Tyr Asn Thr Pro Leu His Val Val Thr Ile Thr Glu Leu Gly
                85                  90                  95

Ala Ile Ile Ala Leu Ile Ala Ser Phe Ile Tyr Leu Leu Gly Phe Phe
            100                 105                 110

Gly Ile Asp Phe Val Gln Ser Phe Ile Ser Arg Ala Ser Gly Asp Ala
        115                 120                 125

Trp Asp Leu Ala Asp Thr Ile Asp Asp Asp His Arg Leu Val Thr
    130                 135                 140

Cys Ser Pro Pro Thr Pro Ile Val Ser Val Ala Lys Leu Pro Asn Pro
145                 150                 155                 160

Glu Pro Ile Val Thr Glu Ser Leu Pro Glu Glu Asp Glu Ile Val
                165                 170                 175

Lys Ser Val Ile Asp Gly Val Ile Pro Ser Tyr Ser Leu Glu Ser Arg
            180                 185                 190

Leu Gly Asp Cys Lys Arg Ala Ala Ser Ile Arg Arg Glu Ala Leu Gln
        195                 200                 205

Arg Val Thr Gly Arg Ser Ile Glu Gly Leu Pro Leu Asp Gly Phe Asp
    210                 215                 220

Tyr Glu Ser Ile Leu Gly Gln Cys Cys Glu Met Pro Val Gly Tyr Ile
225                 230                 235                 240

Gln Ile Pro Val Gly Ile Ala Gly Pro Leu Leu Leu Asp Gly Tyr Glu
                245                 250                 255

Tyr Ser Val Pro Met Ala Thr Thr Glu Gly Cys Leu Val Ala Ser Thr
            260                 265                 270

Asn Arg Gly Cys Lys Ala Met Phe Ile Ser Gly Gly Ala Thr Ser Thr
        275                 280                 285

Val Leu Lys Asp Gly Met Thr Arg Ala Pro Val Val Arg Phe Ala Ser
    290                 295                 300

-continued

```
Ala Arg Arg Ala Ser Glu Leu Lys Phe Phe Leu Glu Asn Pro Glu Asn
305                 310                 315                 320

Phe Asp Thr Leu Ala Val Val Phe Asn Arg Ser Ser Arg Phe Ala Arg
            325                 330                 335

Leu Gln Ser Val Lys Cys Thr Ile Ala Gly Lys Asn Ala Tyr Val Arg
        340                 345                 350

Phe Cys Cys Ser Thr Gly Asp Ala Met Gly Met Asn Met Val Ser Lys
    355                 360                 365

Gly Val Gln Asn Val Leu Glu Tyr Leu Thr Asp Asp Phe Pro Asp Met
370                 375                 380

Asp Val Ile Gly Ile Ser Gly Asn Phe Cys Ser Asp Lys Lys Pro Ala
385                 390                 395                 400

Ala Val Asn Trp Ile Glu Gly Arg Gly Lys Ser Val Val Cys Glu Ala
            405                 410                 415

Val Ile Arg Gly Glu Ile Val Asn Lys Val Leu Lys Thr Ser Val Ala
        420                 425                 430

Ala Leu Val Glu Leu Asn Met Leu Lys Asn Leu Ala Gly Ser Ala Val
    435                 440                 445

Ala Gly Ser Leu Gly Gly Phe Asn Ala His Ala Ser Asn Ile Val Ser
450                 455                 460

Ala Val Phe Ile Ala Thr Gly Gln Asp Pro Ala Gln Asn Val Glu Ser
465                 470                 475                 480

Ser Gln Cys Ile Thr Met Met Glu Ala Ile Asn Asp Gly Lys Asp Ile
            485                 490                 495

His Ile Ser Val Thr Met Pro Ser Ile Glu Val Gly Thr Val Gly Gly
        500                 505                 510

Gly Thr Gln Leu Ala Ser Gln Ser Ala Cys Leu Asn Leu Leu Gly Val
    515                 520                 525

Lys Gly Ala Ser Thr Glu Ser Pro Gly Met Asn Ala Arg Arg Leu Ala
530                 535                 540

Thr Ile Val Ala Gly Ala Val Leu Ala Gly Glu Leu Ser Leu Met Ser
545                 550                 555                 560

Ala Ile Ala Ala Gly Gln Leu Val Arg Ser His Met Lys Tyr Asn Arg
            565                 570                 575

Ser Ser Arg Asp Ile Ser Gly Ala Thr Thr Thr Thr Thr Thr Thr Thr
        580                 585                 590
```

<210> SEQ ID NO 113
<211> LENGTH: 1401
<212> TYPE: DNA
<213> ORGANISM: Arabidopsis thaliana ISPH
<220> FEATURE:
<221> NAME/KEY: CDS

<400> SEQUENCE: 113

```
atg gct gtt gcg ctc caa ttc agc cga tta tgc gtt cga ccg gat act    48
Met Ala Val Ala Leu Gln Phe Ser Arg Leu Cys Val Arg Pro Asp Thr
1               5                   10                  15 ttc gtg cgg gag aat cat ctc tct gga tcc gga tct ctc cgc cgc cgg    96
Phe Val Arg Glu Asn His Leu Ser Gly Ser Gly Ser Leu Arg Arg Arg
            20                  25                  30 aaa gct tta tca gtc cgg tgc tcg tct ggc gat gag aac gct cct tcg   144
Lys Ala Leu Ser Val Arg Cys Ser Ser Gly Asp Glu Asn Ala Pro Ser
        35                  40                  45 cca tcg gtg gtg atg gac tcc gat ttc gac gcc aag gtg ttc cgt aag   192
Pro Ser Val Val Met Asp Ser Asp Phe Asp Ala Lys Val Phe Arg Lys
    50                  55                  60
```

-continued

| | |
|---|---|
| aac ttg acg aga agc gat aat tac aat cgt aaa ggg ttc ggt cat aag<br>Asn Leu Thr Arg Ser Asp Asn Tyr Asn Arg Lys Gly Phe Gly His Lys<br>65                    70                      75                    80 | 240 |
| gag gag aca ctc aag ctc atg aat cga gag tac acc agt gat ata ttg<br>Glu Glu Thr Leu Lys Leu Met Asn Arg Glu Tyr Thr Ser Asp Ile Leu<br>                    85                      90                      95 | 288 |
| gag aca ctg aaa aca aat ggg tat act tat tct tgg gga gat gtt act<br>Glu Thr Leu Lys Thr Asn Gly Tyr Thr Tyr Ser Trp Gly Asp Val Thr<br>100                      105                    110 | 336 |
| gtg aaa ctc gct aaa gca tat ggt ttt tgc tgg ggt gtt gag cgt gct<br>Val Lys Leu Ala Lys Ala Tyr Gly Phe Cys Trp Gly Val Glu Arg Ala<br>          115                      120                    125 | 384 |
| gtt cag att gca tat gaa gca cga aag cag ttt cca gag gag agg ctt<br>Val Gln Ile Ala Tyr Glu Ala Arg Lys Gln Phe Pro Glu Glu Arg Leu<br>130                      135                    140 | 432 |
| tgg att act aac gaa atc att cat aac ccg acc gtc aat aag agg ttg<br>Trp Ile Thr Asn Glu Ile Ile His Asn Pro Thr Val Asn Lys Arg Leu<br>145                    150                    155                    160 | 480 |
| gaa gat atg gat gtt aaa att att ccg gtt gag gat tca aag aaa cag<br>Glu Asp Met Asp Val Lys Ile Ile Pro Val Glu Asp Ser Lys Lys Gln<br>                    165                      170                    175 | 528 |
| ttt gat gta gta gag aaa gat gat gtg gtt atc ctt cct gcg ttt gga<br>Phe Asp Val Val Glu Lys Asp Asp Val Val Ile Leu Pro Ala Phe Gly<br>          180                      185                    190 | 576 |
| gct ggt gtt gac gag atg tat gtt ctt aat gat aaa aag gtg caa att<br>Ala Gly Val Asp Glu Met Tyr Val Leu Asn Asp Lys Lys Val Gln Ile<br>195                      200                    205 | 624 |
| gtt gac acg act tgt cct tgg gtg aca aag gtc tgg aac acg gtt gag<br>Val Asp Thr Thr Cys Pro Trp Val Thr Lys Val Trp Asn Thr Val Glu<br>210                      215                    220 | 672 |
| aag cac aag aag ggg gaa tac aca tca gta atc cat ggt aaa tat aat<br>Lys His Lys Lys Gly Glu Tyr Thr Ser Val Ile His Gly Lys Tyr Asn<br>225                    230                    235                    240 | 720 |
| cat gaa gag acg att gca act gcg tct ttt gca gga aag tac atc att<br>His Glu Glu Thr Ile Ala Thr Ala Ser Phe Ala Gly Lys Tyr Ile Ile<br>                    245                      250                    255 | 768 |
| gta aag aac atg aaa gag gca aat tac gtt tgt gat tac att ctc ggt<br>Val Lys Asn Met Lys Glu Ala Asn Tyr Val Cys Asp Tyr Ile Leu Gly<br>          260                      265                    270 | 816 |
| ggc caa tac gat gga tct agc tcc aca aaa gag gag ttc atg gag aaa<br>Gly Gln Tyr Asp Gly Ser Ser Ser Thr Lys Glu Glu Phe Met Glu Lys<br>275                      280                    285 | 864 |
| ttc aaa tac gca att tcg aag ggt ttc gat ccc gac aat gac ctt gtc<br>Phe Lys Tyr Ala Ile Ser Lys Gly Phe Asp Pro Asp Asn Asp Leu Val<br>290                      295                    300 | 912 |
| aaa gtt ggt att gca aac caa aca acg atg cta aag gga gaa aca gag<br>Lys Val Gly Ile Ala Asn Gln Thr Thr Met Leu Lys Gly Glu Thr Glu<br>305                      310                    315                    320 | 960 |
| gag ata gga aga tta ctc gag aca aca atg atg cgc aag tat gga gtg<br>Glu Ile Gly Arg Leu Leu Glu Thr Thr Met Met Arg Lys Tyr Gly Val<br>                    325                      330                    335 | 1008 |
| gaa aat gta agc gga cat ttc atc agc ttc aac aca ata tgc gac gct<br>Glu Asn Val Ser Gly His Phe Ile Ser Phe Asn Thr Ile Cys Asp Ala<br>          340                      345                    350 | 1056 |
| act caa gag cga caa gac gca atc tat gag cta gtg gaa gag aag att<br>Thr Gln Glu Arg Gln Asp Ala Ile Tyr Glu Leu Val Glu Glu Lys Ile<br>355                      360                    365 | 1104 |
| gac ctc atg cta gtg gtt ggc gga tgg aat tca agt aac acc tct cac<br>Asp Leu Met Leu Val Val Gly Gly Trp Asn Ser Ser Asn Thr Ser His | 1152 |

```
                370             375             380
ctt cag gaa atc tca gag gca cgg gga atc cca tct tac tgg atc gat    1200
Leu Gln Glu Ile Ser Glu Ala Arg Gly Ile Pro Ser Tyr Trp Ile Asp
385                 390                 395                 400 agt gag aaa cgg ata gga cct ggg aat aaa ata gcc tat aag ctc cac    1248
Ser Glu Lys Arg Ile Gly Pro Gly Asn Lys Ile Ala Tyr Lys Leu His
                405                 410                 415 tat gga gaa ctg gtc gag aag gaa aac ttt ctc cca aag gga cca ata    1296
Tyr Gly Glu Leu Val Glu Lys Glu Asn Phe Leu Pro Lys Gly Pro Ile
            420                 425                 430 aca atc ggt gtg aca tca ggt gca tca acc ccg gat aag gtc gtg gaa    1344
Thr Ile Gly Val Thr Ser Gly Ala Ser Thr Pro Asp Lys Val Val Glu
        435                 440                 445 gat gct ttg gtg aag gtg ttc gac att aaa cgt gaa gag tta ttg cag    1392
Asp Ala Leu Val Lys Val Phe Asp Ile Lys Arg Glu Glu Leu Leu Gln
    450                 455                 460 ctg gct tga                                                         1401
Leu Ala
465

<210> SEQ ID NO 114
<211> LENGTH: 466
<212> TYPE: PRT
<213> ORGANISM: Arabidopsis thaliana ISPH

<400> SEQUENCE: 114

Met Ala Val Ala Leu Gln Phe Ser Arg Leu Cys Val Arg Pro Asp Thr
1               5                   10                  15

Phe Val Arg Glu Asn His Leu Ser Gly Ser Gly Ser Leu Arg Arg Arg
                20                  25                  30

Lys Ala Leu Ser Val Arg Cys Ser Ser Gly Asp Glu Asn Ala Pro Ser
            35                  40                  45

Pro Ser Val Val Met Asp Ser Asp Phe Asp Ala Lys Val Phe Arg Lys
        50                  55                  60

Asn Leu Thr Arg Ser Asp Asn Tyr Asn Arg Lys Gly Phe Gly His Lys
65              70                  75                  80

Glu Glu Thr Leu Lys Leu Met Asn Arg Glu Tyr Thr Ser Asp Ile Leu
                85                  90                  95

Glu Thr Leu Lys Thr Asn Gly Tyr Thr Tyr Ser Trp Gly Asp Val Thr
            100                 105                 110

Val Lys Leu Ala Lys Ala Tyr Gly Phe Cys Trp Gly Val Glu Arg Ala
        115                 120                 125

Val Gln Ile Ala Tyr Glu Ala Arg Lys Gln Phe Pro Glu Glu Arg Leu
    130                 135                 140

Trp Ile Thr Asn Glu Ile Ile His Asn Pro Thr Val Asn Lys Arg Leu
145             150                 155                 160

Glu Asp Met Asp Val Lys Ile Ile Pro Val Glu Asp Ser Lys Lys Gln
                165                 170                 175

Phe Asp Val Val Glu Lys Asp Val Val Ile Leu Pro Ala Phe Gly
            180                 185                 190

Ala Gly Val Asp Glu Met Tyr Val Leu Asn Asp Lys Val Gln Ile
        195                 200                 205

Val Asp Thr Thr Cys Pro Trp Val Thr Lys Val Trp Asn Thr Val Glu
    210                 215                 220

Lys His Lys Lys Gly Glu Tyr Thr Ser Val Ile His Gly Lys Tyr Asn
225             230                 235                 240
```

```
His Glu Glu Thr Ile Ala Thr Ala Ser Phe Ala Gly Lys Tyr Ile Ile
            245                 250                 255

Val Lys Asn Met Lys Glu Ala Asn Tyr Val Cys Asp Tyr Ile Leu Gly
            260                 265                 270

Gly Gln Tyr Asp Gly Ser Ser Thr Lys Glu Glu Phe Met Glu Lys
            275                 280                 285

Phe Lys Tyr Ala Ile Ser Lys Gly Phe Asp Pro Asp Asn Asp Leu Val
            290                 295                 300

Lys Val Gly Ile Ala Asn Gln Thr Thr Met Leu Lys Gly Glu Thr Glu
305                 310                 315                 320

Glu Ile Gly Arg Leu Glu Thr Thr Met Arg Lys Tyr Gly Val
            325                 330                 335

Glu Asn Val Ser Gly His Phe Ile Ser Phe Asn Thr Ile Cys Asp Ala
            340                 345                 350

Thr Gln Glu Arg Gln Asp Ala Ile Tyr Glu Leu Val Glu Lys Ile
            355                 360                 365

Asp Leu Met Leu Val Val Gly Gly Trp Asn Ser Ser Asn Thr Ser His
370                 375                 380

Leu Gln Glu Ile Ser Glu Ala Arg Gly Ile Pro Ser Tyr Trp Ile Asp
385                 390                 395                 400

Ser Glu Lys Arg Ile Gly Pro Gly Asn Lys Ile Ala Tyr Lys Leu His
            405                 410                 415

Tyr Gly Glu Leu Val Glu Lys Glu Asn Phe Leu Pro Lys Gly Pro Ile
            420                 425                 430

Thr Ile Gly Val Thr Ser Gly Ala Ser Thr Pro Asp Lys Val Val Glu
            435                 440                 445

Asp Ala Leu Val Lys Val Phe Asp Ile Lys Arg Glu Glu Leu Leu Gln
450                 455                 460

Leu Ala
465

<210> SEQ ID NO 115
<211> LENGTH: 2160
<212> TYPE: DNA
<213> ORGANISM: Lycopersicon esculentum
<220> FEATURE:
<221> NAME/KEY: CDS

<400> SEQUENCE: 115 atg gct ttg tgt gct tat gca ttt cct ggg att ttg aac agg act ggt     48
Met Ala Leu Cys Ala Tyr Ala Phe Pro Gly Ile Leu Asn Arg Thr Gly
1               5                   10                  15 gtg gtt tca gat tct tct aag gca acc cct ttg ttc tct gga tgg att     96
Val Val Ser Asp Ser Ser Lys Ala Thr Pro Leu Phe Ser Gly Trp Ile
            20                  25                  30 cat gga aca gat ctg cag ttt ttg ttc caa cac aag ctt act cat gag    144
His Gly Thr Asp Leu Gln Phe Leu Phe Gln His Lys Leu Thr His Glu
        35                  40                  45 gtc aag aaa agg tca cgt gtg gtt cag gct tcc tta tca gaa tct gga    192
Val Lys Lys Arg Ser Arg Val Val Gln Ala Ser Leu Ser Glu Ser Gly
    50                  55                  60 gaa tac tac aca cag aga ccg cca acg cct att ttg gac act gtg aac    240
Glu Tyr Tyr Thr Gln Arg Pro Pro Thr Pro Ile Leu Asp Thr Val Asn
65                  70                  75                  80 tat ccc att cat atg aaa aat ctg tct ctg aag gaa ctt aaa caa cta    288
Tyr Pro Ile His Met Lys Asn Leu Ser Leu Lys Glu Leu Lys Gln Leu
                85                  90                  95
```

```
gca gat gaa cta agg tca gat aca att ttc aat gta tca aag act ggg        336
Ala Asp Glu Leu Arg Ser Asp Thr Ile Phe Asn Val Ser Lys Thr Gly
        100                 105                 110 ggt cac ctt ggc tca agt ctt ggt gtt gtt gag ctg act gtt gct ctt        384
Gly His Leu Gly Ser Ser Leu Gly Val Val Glu Leu Thr Val Ala Leu
    115                 120                 125 cat tat gtc ttc aat gca ccg caa gat agg att ctc tgg gat gtt ggt        432
His Tyr Val Phe Asn Ala Pro Gln Asp Arg Ile Leu Trp Asp Val Gly
130                 135                 140 cat cag tct tat cct cac aaa atc ttg act ggt aga agg gac aag atg        480
His Gln Ser Tyr Pro His Lys Ile Leu Thr Gly Arg Arg Asp Lys Met
145                 150                 155                 160 tcg aca tta agg cag aca gat ggt ctt gca gga ttt act aag cga tcg        528
Ser Thr Leu Arg Gln Thr Asp Gly Leu Ala Gly Phe Thr Lys Arg Ser
            165                 170                 175 gag agt gaa tat gat tgc ttt ggc acc ggc cac agt tcc acc acc atc        576
Glu Ser Glu Tyr Asp Cys Phe Gly Thr Gly His Ser Ser Thr Thr Ile
        180                 185                 190 tca gca ggc cta ggg atg gct gtt ggt aga gat cta aaa gga aga aac        624
Ser Ala Gly Leu Gly Met Ala Val Gly Arg Asp Leu Lys Gly Arg Asn
    195                 200                 205 aac aat gtt att gcc gta ata ggt gat ggt gcc atg aca gca ggt caa        672
Asn Asn Val Ile Ala Val Ile Gly Asp Gly Ala Met Thr Ala Gly Gln
210                 215                 220 gct tat gaa gcc atg aat aat gct ggt tac ctg gac tct gac atg att        720
Ala Tyr Glu Ala Met Asn Asn Ala Gly Tyr Leu Asp Ser Asp Met Ile
225                 230                 235                 240 gtt atc tta aac gac aat aga caa gtt tct tta cct act gct act ctg        768
Val Ile Leu Asn Asp Asn Arg Gln Val Ser Leu Pro Thr Ala Thr Leu
            245                 250                 255 gat ggg cca gtt gct cct gtt gga gct cta agt agt gct ttg agc agg        816
Asp Gly Pro Val Ala Pro Val Gly Ala Leu Ser Ser Ala Leu Ser Arg
        260                 265                 270 tta cag tct aat agg cct ctc aga gaa cta aga gaa gtc gca aag gga        864
Leu Gln Ser Asn Arg Pro Leu Arg Glu Leu Arg Glu Val Ala Lys Gly
    275                 280                 285 gtt act aag cag att ggt ggt cct atg cat gag ctt gct gca aaa gtt        912
Val Thr Lys Gln Ile Gly Gly Pro Met His Glu Leu Ala Ala Lys Val
290                 295                 300 gat gaa tat gct cgt ggc atg att agt ggt tct gga tca aca ttg ttt        960
Asp Glu Tyr Ala Arg Gly Met Ile Ser Gly Ser Gly Ser Thr Leu Phe
305                 310                 315                 320 gaa gaa ctt gga ctt tac tat att ggt cct gtg gat ggt cac aac att       1008
Glu Glu Leu Gly Leu Tyr Tyr Ile Gly Pro Val Asp Gly His Asn Ile
            325                 330                 335 gat gat cta att gcg att ctc aaa gag gtt aga agt act aaa aca aca       1056
Asp Asp Leu Ile Ala Ile Leu Lys Glu Val Arg Ser Thr Lys Thr Thr
        340                 345                 350 ggt cca gta ctg atc cat gtt gtc act gag aaa ggc aga ggt tat cca       1104
Gly Pro Val Leu Ile His Val Val Thr Glu Lys Gly Arg Gly Tyr Pro
    355                 360                 365 tat gct gag aga gct gca gat aag tat cat gga gtt gcc aag ttt gat       1152
Tyr Ala Glu Arg Ala Ala Asp Lys Tyr His Gly Val Ala Lys Phe Asp
370                 375                 380 cca gca aca gga aag caa ttc aaa gcc agt gcc aag aca cag tcc tat       1200
Pro Ala Thr Gly Lys Gln Phe Lys Ala Ser Ala Lys Thr Gln Ser Tyr
385                 390                 395                 400 aca aca tat ttt gcc gag gct tta att gca gaa gca gaa gca gat aaa       1248
Thr Thr Tyr Phe Ala Glu Ala Leu Ile Ala Glu Ala Glu Ala Asp Lys
            405                 410                 415
```

```
gac att gtt gca atc cat gct gcc atg ggg ggt ggg acc gga atg aac          1296
Asp Ile Val Ala Ile His Ala Ala Met Gly Gly Gly Thr Gly Met Asn
            420                 425                 430 ctt ttc cat cgt cgc ttc cca aca agg tgt ttt gat gtt gga ata gca          1344
Leu Phe His Arg Arg Phe Pro Thr Arg Cys Phe Asp Val Gly Ile Ala
            435                 440                 445 gaa caa cat gca gta acc ttt gct gct gga ttg gct tgt gaa ggc att          1392
Glu Gln His Ala Val Thr Phe Ala Ala Gly Leu Ala Cys Glu Gly Ile
        450                 455                 460 aaa cct ttc tgt gca atc tat tcg tct ttc atg cag agg gct tat gac          1440
Lys Pro Phe Cys Ala Ile Tyr Ser Ser Phe Met Gln Arg Ala Tyr Asp
465                 470                 475                 480 cag gta gtg cat gac gtt gat ttg caa aag ctg ccc gtg agg ttt gca          1488
Gln Val Val His Asp Val Asp Leu Gln Lys Leu Pro Val Arg Phe Ala
                485                 490                 495 atg gac aga gca ggt ctt gtt gga gca gat ggt cca aca cat tgt ggt          1536
Met Asp Arg Ala Gly Leu Val Gly Ala Asp Gly Pro Thr His Cys Gly
            500                 505                 510 gca ttt gat gtt act tac atg gca tgt ctt cct aac atg gtt gta atg          1584
Ala Phe Asp Val Thr Tyr Met Ala Cys Leu Pro Asn Met Val Val Met
            515                 520                 525 gct cct tct gat gaa gcg gag cta ttt cac atg gta gca act gct gcc          1632
Ala Pro Ser Asp Glu Ala Glu Leu Phe His Met Val Ala Thr Ala Ala
        530                 535                 540 gcc att gat gac aga cca agt tgt ttt aga tac cca aga gga aat ggg          1680
Ala Ile Asp Asp Arg Pro Ser Cys Phe Arg Tyr Pro Arg Gly Asn Gly
545                 550                 555                 560 atc ggt gta gag ctt ccg gct gga aac aaa gga att cct ctt gag gtt          1728
Ile Gly Val Glu Leu Pro Ala Gly Asn Lys Gly Ile Pro Leu Glu Val
                565                 570                 575 ggt aaa ggt agg ata ttg att gag ggg gag aga gtg gct cta ttg gga          1776
Gly Lys Gly Arg Ile Leu Ile Glu Gly Glu Arg Val Ala Leu Leu Gly
            580                 585                 590 tat ggc tca gca gtg cag aac tgt ttg gat gct gct att gtg cta gaa          1824
Tyr Gly Ser Ala Val Gln Asn Cys Leu Asp Ala Ala Ile Val Leu Glu
            595                 600                 605 tcc cgc ggc tta caa gta aca gtt gca gat gca cgt ttc tgc aaa cca          1872
Ser Arg Gly Leu Gln Val Thr Val Ala Asp Ala Arg Phe Cys Lys Pro
        610                 615                 620 ctg gac cat gcc ctc ata agg agc ctt gca aaa tca cat gaa gtg cta          1920
Leu Asp His Ala Leu Ile Arg Ser Leu Ala Lys Ser His Glu Val Leu
625                 630                 635                 640 atc act gtc gaa gaa gga tca att gga ggt ttt gga tct cat gtt gtt          1968
Ile Thr Val Glu Glu Gly Ser Ile Gly Gly Phe Gly Ser His Val Val
                645                 650                 655 cag ttc atg gcc tta gat ggg ctt ctt gat ggc aag ttg aag tgg aga          2016
Gln Phe Met Ala Leu Asp Gly Leu Leu Asp Gly Lys Leu Lys Trp Arg
            660                 665                 670 cca ata gtt ctt cct gat cga tac att gac cat gga tct cct gtt gat          2064
Pro Ile Val Leu Pro Asp Arg Tyr Ile Asp His Gly Ser Pro Val Asp
            675                 680                 685 cag ttg gcg gaa gct ggc cta aca cca tct cac att gca gca aca gta          2112
Gln Leu Ala Glu Ala Gly Leu Thr Pro Ser His Ile Ala Ala Thr Val
        690                 695                 700 ttt aac ata ctt gga caa acc aga gag gct cta gag gtc atg aca taa          2160
Phe Asn Ile Leu Gly Gln Thr Arg Glu Ala Leu Glu Val Met Thr
705                 710                 715
```

<210> SEQ ID NO 116

```
<211> LENGTH: 719
<212> TYPE: PRT
<213> ORGANISM: Lycopersicon esculentum

<400> SEQUENCE: 116

Met Ala Leu Cys Ala Tyr Ala Phe Pro Gly Ile Leu Asn Arg Thr Gly
1               5                   10                  15

Val Val Ser Asp Ser Ser Lys Ala Thr Pro Leu Phe Ser Gly Trp Ile
            20                  25                  30

His Gly Thr Asp Leu Gln Phe Leu Phe Gln His Lys Leu Thr His Glu
        35                  40                  45

Val Lys Lys Arg Ser Arg Val Val Gln Ala Ser Leu Ser Glu Ser Gly
    50                  55                  60

Glu Tyr Tyr Thr Gln Arg Pro Pro Thr Pro Ile Leu Asp Thr Val Asn
65                  70                  75                  80

Tyr Pro Ile His Met Lys Asn Leu Ser Leu Lys Glu Leu Lys Gln Leu
                85                  90                  95

Ala Asp Glu Leu Arg Ser Asp Thr Ile Phe Asn Val Ser Lys Thr Gly
            100                 105                 110

Gly His Leu Gly Ser Ser Leu Gly Val Val Glu Leu Thr Val Ala Leu
        115                 120                 125

His Tyr Val Phe Asn Ala Pro Gln Asp Arg Ile Leu Trp Asp Val Gly
130                 135                 140

His Gln Ser Tyr Pro His Lys Ile Leu Thr Gly Arg Arg Asp Lys Met
145                 150                 155                 160

Ser Thr Leu Arg Gln Thr Asp Gly Leu Ala Gly Phe Thr Lys Arg Ser
                165                 170                 175

Glu Ser Glu Tyr Asp Cys Phe Gly Thr Gly His Ser Ser Thr Thr Ile
            180                 185                 190

Ser Ala Gly Leu Gly Met Ala Val Gly Arg Asp Leu Lys Gly Arg Asn
        195                 200                 205

Asn Asn Val Ile Ala Val Ile Gly Asp Gly Ala Met Thr Ala Gly Gln
    210                 215                 220

Ala Tyr Glu Ala Met Asn Asn Ala Gly Tyr Leu Asp Ser Asp Met Ile
225                 230                 235                 240

Val Ile Leu Asn Asp Asn Arg Gln Val Ser Leu Pro Thr Ala Thr Leu
                245                 250                 255

Asp Gly Pro Val Ala Pro Val Gly Ala Leu Ser Ser Ala Leu Ser Arg
            260                 265                 270

Leu Gln Ser Asn Arg Pro Leu Arg Glu Leu Arg Glu Val Ala Lys Gly
        275                 280                 285

Val Thr Lys Gln Ile Gly Gly Pro Met His Glu Leu Ala Ala Lys Val
    290                 295                 300

Asp Glu Tyr Ala Arg Gly Met Ile Ser Gly Ser Gly Ser Thr Leu Phe
305                 310                 315                 320

Glu Glu Leu Gly Leu Tyr Tyr Ile Gly Pro Val Asp Gly His Asn Ile
                325                 330                 335

Asp Asp Leu Ile Ala Ile Leu Lys Glu Val Arg Ser Thr Lys Thr Thr
            340                 345                 350

Gly Pro Val Leu Ile His Val Val Thr Glu Lys Gly Arg Gly Tyr Pro
        355                 360                 365

Tyr Ala Glu Arg Ala Ala Asp Lys Tyr His Gly Val Ala Lys Phe Asp
    370                 375                 380

Pro Ala Thr Gly Lys Gln Phe Lys Ala Ser Ala Lys Thr Gln Ser Tyr
```

```
                385                 390                 395                 400
Thr Thr Tyr Phe Ala Glu Ala Leu Ile Ala Glu Ala Glu Ala Asp Lys
                405                 410                 415
Asp Ile Val Ala Ile His Ala Ala Met Gly Gly Gly Thr Gly Met Asn
                420                 425                 430
Leu Phe His Arg Arg Phe Pro Thr Arg Cys Phe Asp Val Gly Ile Ala
                435                 440                 445
Glu Gln His Ala Val Thr Phe Ala Ala Gly Leu Ala Cys Glu Gly Ile
                450                 455                 460
Lys Pro Phe Cys Ala Ile Tyr Ser Ser Phe Met Gln Arg Ala Tyr Asp
465                 470                 475                 480
Gln Val Val His Asp Val Asp Leu Gln Lys Leu Pro Val Arg Phe Ala
                485                 490                 495
Met Asp Arg Ala Gly Leu Val Gly Ala Asp Gly Pro Thr His Cys Gly
                500                 505                 510
Ala Phe Asp Val Thr Tyr Met Ala Cys Leu Pro Asn Met Val Val Met
                515                 520                 525
Ala Pro Ser Asp Glu Ala Glu Leu Phe His Met Val Ala Thr Ala Ala
                530                 535                 540
Ala Ile Asp Asp Arg Pro Ser Cys Phe Arg Tyr Pro Arg Gly Asn Gly
545                 550                 555                 560
Ile Gly Val Glu Leu Pro Ala Gly Asn Lys Gly Ile Pro Leu Glu Val
                565                 570                 575
Gly Lys Gly Arg Ile Leu Ile Glu Gly Glu Arg Val Ala Leu Leu Gly
                580                 585                 590
Tyr Gly Ser Ala Val Gln Asn Cys Leu Asp Ala Ala Ile Val Leu Glu
                595                 600                 605
Ser Arg Gly Leu Gln Val Thr Val Ala Asp Ala Arg Phe Cys Lys Pro
                610                 615                 620
Leu Asp His Ala Leu Ile Arg Ser Leu Ala Lys Ser His Glu Val Leu
625                 630                 635                 640
Ile Thr Val Glu Glu Gly Ser Ile Gly Gly Phe Gly Ser His Val Val
                645                 650                 655
Gln Phe Met Ala Leu Asp Gly Leu Leu Asp Gly Lys Leu Lys Trp Arg
                660                 665                 670
Pro Ile Val Leu Pro Asp Arg Tyr Ile Asp His Gly Ser Pro Val Asp
                675                 680                 685
Gln Leu Ala Glu Ala Gly Leu Thr Pro Ser His Ile Ala Ala Thr Val
                690                 695                 700
Phe Asn Ile Leu Gly Gln Thr Arg Glu Ala Leu Glu Val Met Thr
705                 710                 715

<210> SEQ ID NO 117
<211> LENGTH: 1434
<212> TYPE: DNA
<213> ORGANISM: Arabidopsis thaliana
<220> FEATURE:
<221> NAME/KEY: CDS

<400> SEQUENCE: 117 atg atg aca tta aac tca cta tct cca gct gaa tcc aaa gct att tct      48
Met Met Thr Leu Asn Ser Leu Ser Pro Ala Glu Ser Lys Ala Ile Ser
1               5                   10                  15 ttc ttg gat acc tcc agg ttc aat cca atc cct aaa ctc tca ggt ggg      96
Phe Leu Asp Thr Ser Arg Phe Asn Pro Ile Pro Lys Leu Ser Gly Gly
                20                  25                  30
```

| | | |
|---|---|---|
| ttt agt ttg agg agg agg aat caa ggg aga ggt ttt gga aaa ggt gtt<br>Phe Ser Leu Arg Arg Arg Asn Gln Gly Arg Gly Phe Gly Lys Gly Val<br>35                           40                       45 | | 144 |
| aag tgt tca gtg aaa gtg cag cag caa caa caa cct cct cca gca tgg<br>Lys Cys Ser Val Lys Val Gln Gln Gln Gln Gln Pro Pro Pro Ala Trp<br>50                           55                       60 | | 192 |
| cct ggg aga gct gtc cct gag gcg cct cgt caa tct tgg gat gga cca<br>Pro Gly Arg Ala Val Pro Glu Ala Pro Arg Gln Ser Trp Asp Gly Pro<br>65                         70                      75                     80 | | 240 |
| aaa ccc atc tct atc gtt gga tct act ggt tct att ggc act cag aca<br>Lys Pro Ile Ser Ile Val Gly Ser Thr Gly Ser Ile Gly Thr Gln Thr<br>                      85                      90                      95 | | 288 |
| ttg gat att gtg gct gag aat cct gac aaa ttc aga gtt gtg gct cta<br>Leu Asp Ile Val Ala Glu Asn Pro Asp Lys Phe Arg Val Val Ala Leu<br>100                        105                     110 | | 336 |
| gct gct ggt tcg aat gtt act cta ctt gct gat cag gta agg aga ttt<br>Ala Ala Gly Ser Asn Val Thr Leu Leu Ala Asp Gln Val Arg Arg Phe<br>               115                     120                     125 | | 384 |
| aag cct gca ttg gtt gct gtt aga aac gag tca ctg att aat gag ctt<br>Lys Pro Ala Leu Val Ala Val Arg Asn Glu Ser Leu Ile Asn Glu Leu<br>130                        135                     140 | | 432 |
| aaa gag gct tta gct gat ttg gac tat aaa ctc gag att att cca gga<br>Lys Glu Ala Leu Ala Asp Leu Asp Tyr Lys Leu Glu Ile Ile Pro Gly<br>145                        150                     155                     160 | | 480 |
| gag caa gga gtg att gag gtt gcc cga cat cct gaa gct gta acc gtt<br>Glu Gln Gly Val Ile Glu Val Ala Arg His Pro Glu Ala Val Thr Val<br>               165                     170                     175 | | 528 |
| gtt acc gga ata gta ggt tgt gcg gga cta aag cct acg gtt gct gca<br>Val Thr Gly Ile Val Gly Cys Ala Gly Leu Lys Pro Thr Val Ala Ala<br>                  180                     185                     190 | | 576 |
| att gaa gca gga aag gac att gct ctt gca aac aaa gag aca tta atc<br>Ile Glu Ala Gly Lys Asp Ile Ala Leu Ala Asn Lys Glu Thr Leu Ile<br>               195                     200                     205 | | 624 |
| gca ggt ggt cct ttc gtg ctt ccg ctt gcc aac aaa cat aat gta aag<br>Ala Gly Gly Pro Phe Val Leu Pro Leu Ala Asn Lys His Asn Val Lys<br>210                        215                     220 | | 672 |
| att ctt ccg gca gat tca gaa cat tct gcc ata ttt cag tgt att caa<br>Ile Leu Pro Ala Asp Ser Glu His Ser Ala Ile Phe Gln Cys Ile Gln<br>225                        230                     235                     240 | | 720 |
| ggt ttg cct gaa ggc gct ctg cgc aag ata atc ttg act gca tct ggt<br>Gly Leu Pro Glu Gly Ala Leu Arg Lys Ile Ile Leu Thr Ala Ser Gly<br>                  245                     250                     255 | | 768 |
| gga gct ttt agg gat tgg cct gtc gaa aag cta aag gaa gtt aaa gta<br>Gly Ala Phe Arg Asp Trp Pro Val Glu Lys Leu Lys Glu Val Lys Val<br>260                        265                     270 | | 816 |
| gcg gat gcg ttg aag cat cca aac tgg aac atg gga aag aaa atc act<br>Ala Asp Ala Leu Lys His Pro Asn Trp Asn Met Gly Lys Lys Ile Thr<br>275                        280                     285 | | 864 |
| gtg gac tct gct acg ctt ttc aac aag ggt ctt gag gtc att gaa gcg<br>Val Asp Ser Ala Thr Leu Phe Asn Lys Gly Leu Glu Val Ile Glu Ala<br>290                        295                     300 | | 912 |
| cat tat ttg ttt gga gct gag tat gac gat ata gag att gtc att cat<br>His Tyr Leu Phe Gly Ala Glu Tyr Asp Asp Ile Glu Ile Val Ile His<br>305                        310                     315                     320 | | 960 |
| ccg caa agt atc ata cat tcc atg att gaa aca cag gat tca tct gtg<br>Pro Gln Ser Ile Ile His Ser Met Ile Glu Thr Gln Asp Ser Ser Val<br>                      325                     330                     335 | | 1008 |
| ctt gct caa ttg ggt tgg cct gat atg cgt tta ccg att ctc tac acc<br>Leu Ala Gln Leu Gly Trp Pro Asp Met Arg Leu Pro Ile Leu Tyr Thr | | 1056 |

```
                340              345              350
atg tca tgg ccc gat aga gtt cct tgt tct gaa gta act tgg cca aga    1104
Met Ser Trp Pro Asp Arg Val Pro Cys Ser Glu Val Thr Trp Pro Arg
        355              360              365 ctt gac ctt tgc aaa ctc ggt tca ttg act ttc aag aaa cca gac aat    1152
Leu Asp Leu Cys Lys Leu Gly Ser Leu Thr Phe Lys Lys Pro Asp Asn
370              375              380 gtg aaa tac cca tcc atg gat ctt gct tat gct gct gga cga gct gga    1200
Val Lys Tyr Pro Ser Met Asp Leu Ala Tyr Ala Ala Gly Arg Ala Gly
385              390              395              400 ggc aca atg act gga gtt ctc agc gcc gcc aat gag aaa gct gtt gaa    1248
Gly Thr Met Thr Gly Val Leu Ser Ala Ala Asn Glu Lys Ala Val Glu
                405              410              415 atg ttc att gat gaa aag ata agc tat ttg gat atc ttc aag gtt gtg    1296
Met Phe Ile Asp Glu Lys Ile Ser Tyr Leu Asp Ile Phe Lys Val Val
            420              425              430 gaa tta aca tgc gat aaa cat cga aac gag ttg gta aca tca ccg tct    1344
Glu Leu Thr Cys Asp Lys His Arg Asn Glu Leu Val Thr Ser Pro Ser
        435              440              445 ctt gaa gag att gtt cac tat gac ttg tgg gca cgt gaa tat gcc gcg    1392
Leu Glu Glu Ile Val His Tyr Asp Leu Trp Ala Arg Glu Tyr Ala Ala
    450              455              460 aat gtg cag ctt tct tct ggt gct agg cca gtt cat gca tga            1434
Asn Val Gln Leu Ser Ser Gly Ala Arg Pro Val His Ala
465              470              475

<210> SEQ ID NO 118
<211> LENGTH: 477
<212> TYPE: PRT
<213> ORGANISM: Arabidopsis thaliana

<400> SEQUENCE: 118

Met Met Thr Leu Asn Ser Leu Ser Pro Ala Glu Ser Lys Ala Ile Ser
1               5                   10                  15

Phe Leu Asp Thr Ser Arg Phe Asn Pro Ile Pro Lys Leu Ser Gly Gly
            20                  25                  30

Phe Ser Leu Arg Arg Arg Asn Gln Gly Arg Gly Phe Gly Lys Gly Val
        35                  40                  45

Lys Cys Ser Val Lys Val Gln Gln Gln Gln Pro Pro Ala Trp
    50                  55                  60

Pro Gly Arg Ala Val Pro Glu Ala Pro Arg Gln Ser Trp Asp Gly Pro
65                  70                  75                  80

Lys Pro Ile Ser Ile Val Gly Ser Thr Gly Ser Ile Gly Thr Gln Thr
                85                  90                  95

Leu Asp Ile Val Ala Glu Asn Pro Asp Lys Phe Arg Val Val Ala Leu
            100                 105                 110

Ala Ala Gly Ser Asn Val Thr Leu Leu Ala Asp Gln Val Arg Arg Phe
        115                 120                 125

Lys Pro Ala Leu Val Ala Val Arg Asn Glu Ser Leu Ile Asn Glu Leu
    130                 135                 140

Lys Glu Ala Leu Ala Asp Leu Asp Tyr Lys Leu Glu Ile Ile Pro Gly
145                 150                 155                 160

Glu Gln Gly Val Ile Glu Val Ala Arg His Pro Glu Ala Val Thr Val
                165                 170                 175

Val Thr Gly Ile Val Gly Cys Ala Gly Leu Lys Pro Thr Val Ala Ala
            180                 185                 190

Ile Glu Ala Gly Lys Asp Ile Ala Leu Ala Asn Lys Glu Thr Leu Ile
```

```
                195                 200                 205
Ala Gly Gly Pro Phe Val Leu Pro Leu Ala Asn Lys His Asn Val Lys
    210                 215                 220

Ile Leu Pro Ala Asp Ser Glu His Ser Ala Ile Phe Gln Cys Ile Gln
225                 230                 235                 240

Gly Leu Pro Glu Gly Ala Leu Arg Lys Ile Ile Leu Thr Ala Ser Gly
                245                 250                 255

Gly Ala Phe Arg Asp Trp Pro Val Glu Lys Leu Lys Glu Val Lys Val
                    260                 265                 270

Ala Asp Ala Leu Lys His Pro Asn Trp Asn Met Gly Lys Lys Ile Thr
                275                 280                 285

Val Asp Ser Ala Thr Leu Phe Asn Lys Gly Leu Glu Val Ile Glu Ala
    290                 295                 300

His Tyr Leu Phe Gly Ala Glu Tyr Asp Asp Ile Glu Ile Val Ile His
305                 310                 315                 320

Pro Gln Ser Ile Ile His Ser Met Ile Glu Thr Gln Asp Ser Ser Val
                325                 330                 335

Leu Ala Gln Leu Gly Trp Pro Asp Met Arg Leu Pro Ile Leu Tyr Thr
                    340                 345                 350

Met Ser Trp Pro Asp Arg Val Pro Cys Ser Glu Val Thr Trp Pro Arg
        355                 360                 365

Leu Asp Leu Cys Lys Leu Gly Ser Leu Thr Phe Lys Lys Pro Asp Asn
    370                 375                 380

Val Lys Tyr Pro Ser Met Asp Leu Ala Tyr Ala Ala Gly Arg Ala Gly
385                 390                 395                 400

Gly Thr Met Thr Gly Val Leu Ser Ala Ala Asn Glu Lys Ala Val Glu
                    405                 410                 415

Met Phe Ile Asp Glu Lys Ile Ser Tyr Leu Asp Ile Phe Lys Val Val
                420                 425                 430

Glu Leu Thr Cys Asp Lys His Arg Asn Glu Leu Val Thr Ser Pro Ser
            435                 440                 445

Leu Glu Glu Ile Val His Tyr Asp Leu Trp Ala Arg Glu Tyr Ala Ala
    450                 455                 460

Asn Val Gln Leu Ser Ser Gly Ala Arg Pro Val His Ala
465                 470                 475

<210> SEQ ID NO 119
<211> LENGTH: 884
<212> TYPE: DNA
<213> ORGANISM: Adonis palaestina clone ApIPI28
<220> FEATURE:
<221> NAME/KEY: CDS
<222> LOCATION: (180)..(884)

<400> SEQUENCE: 119
cgtcgatcag gattaatcct ttatatagta tcttctccac caccactaaa acattatcag      60
cttcgtgttc ttctcccgct gttcatcttc agcagcgttg tcgtactctt tctatttctt     120
cttccatcac taacagtcct cgccgagggt tgaatcggct gttcgcctca acgtcgact      179 atg ggt gaa gtc gct gat gct ggt atg gat gcc gtc cag aag cgg ctt     227
Met Gly Glu Val Ala Asp Ala Gly Met Asp Ala Val Gln Lys Arg Leu
1               5                   10                  15 atg ttc gac gat gaa tgt att ttg gtg gat gag aat gac aag gtc gtc     275
Met Phe Asp Asp Glu Cys Ile Leu Val Asp Glu Asn Asp Lys Val Val
                20                  25                  30 gga cat gat tcc aaa tac aac tgt cat ttg atg gaa aag ata gag gca     323
```

```
                Gly His Asp Ser Lys Tyr Asn Cys His Leu Met Glu Lys Ile Glu Ala
                         35                  40                  45 gaa aac ttg ctt cac aga gcc ttc agt gtt ttc tta ttc aac tca aaa              371
Glu Asn Leu Leu His Arg Ala Phe Ser Val Phe Leu Phe Asn Ser Lys
     50                  55                  60 tac gag ttg ctt ctt cag caa cga tct gca acg aag gta aca ttc ccg              419
Tyr Glu Leu Leu Leu Gln Gln Arg Ser Ala Thr Lys Val Thr Phe Pro
65                  70                  75                  80 ctc gta tgg aca aac acc tgt tgc agc cat ccc ctc ttc cgt gat tcc              467
Leu Val Trp Thr Asn Thr Cys Cys Ser His Pro Leu Phe Arg Asp Ser
                 85                  90                  95 gaa ctc ata gaa gaa aat ttt ctc ggg gta cga aac gct gca caa agg              515
Glu Leu Ile Glu Glu Asn Phe Leu Gly Val Arg Asn Ala Ala Gln Arg
         100                 105                 110 aag ctt tta gac gag cta ggc att cca gct gaa gac gta cca gtt gat              563
Lys Leu Leu Asp Glu Leu Gly Ile Pro Ala Glu Asp Val Pro Val Asp
     115                 120                 125 gaa ttc act cct ctt ggt cgc att ctt tac aaa gct cca tct gac gga              611
Glu Phe Thr Pro Leu Gly Arg Ile Leu Tyr Lys Ala Pro Ser Asp Gly
130                 135                 140 aaa tgg gga gag cac gaa ctg gac tat ctt ctg ttt att gtc cga gat              659
Lys Trp Gly Glu His Glu Leu Asp Tyr Leu Leu Phe Ile Val Arg Asp
145                 150                 155                 160 gtg aaa tac gat cca aac cca gat gaa gtt gct gac gct aag tac gtt              707
Val Lys Tyr Asp Pro Asn Pro Asp Glu Val Ala Asp Ala Lys Tyr Val
                 165                 170                 175 aat cgc gag gag ttg aaa gag ata ctg aga aaa gct gat gca ggt gaa              755
Asn Arg Glu Glu Leu Lys Glu Ile Leu Arg Lys Ala Asp Ala Gly Glu
         180                 185                 190 gag gga ata aag ttg tct cct tgg ttt aga ttg gtt gtg gat aac ttt              803
Glu Gly Ile Lys Leu Ser Pro Trp Phe Arg Leu Val Val Asp Asn Phe
     195                 200                 205 ttg ttc aag tgg tgg gat cat gta gag gag ggg aag att aag gac gtc              851
Leu Phe Lys Trp Trp Asp His Val Glu Glu Gly Lys Ile Lys Asp Val
210                 215                 220 gcc gac atg aaa act atc cac aag ttg act taa                                  884
Ala Asp Met Lys Thr Ile His Lys Leu Thr
225                 230

<210> SEQ ID NO 120
<211> LENGTH: 234
<212> TYPE: PRT
<213> ORGANISM: Adonis palaestina clone ApIPI28

<400> SEQUENCE: 120

Met Gly Glu Val Ala Asp Ala Gly Met Asp Ala Val Gln Lys Arg Leu
1               5                   10                  15

Met Phe Asp Asp Glu Cys Ile Leu Val Asp Glu Asn Asp Lys Val Val
                20                  25                  30

Gly His Asp Ser Lys Tyr Asn Cys His Leu Met Glu Lys Ile Glu Ala
         35                  40                  45

Glu Asn Leu Leu His Arg Ala Phe Ser Val Phe Leu Phe Asn Ser Lys
     50                  55                  60

Tyr Glu Leu Leu Leu Gln Gln Arg Ser Ala Thr Lys Val Thr Phe Pro
65                  70                  75                  80

Leu Val Trp Thr Asn Thr Cys Cys Ser His Pro Leu Phe Arg Asp Ser
                 85                  90                  95

Glu Leu Ile Glu Glu Asn Phe Leu Gly Val Arg Asn Ala Ala Gln Arg
         100                 105                 110
```

```
Lys Leu Leu Asp Glu Leu Gly Ile Pro Ala Glu Asp Val Pro Val Asp
            115                 120                 125

Glu Phe Thr Pro Leu Gly Arg Ile Leu Tyr Lys Ala Pro Ser Asp Gly
    130                 135                 140

Lys Trp Gly Glu His Glu Leu Asp Tyr Leu Leu Phe Ile Val Arg Asp
145                 150                 155                 160

Val Lys Tyr Asp Pro Asn Pro Asp Glu Val Ala Asp Ala Lys Tyr Val
                165                 170                 175

Asn Arg Glu Glu Leu Lys Glu Ile Leu Arg Lys Ala Asp Ala Gly Glu
            180                 185                 190

Glu Gly Ile Lys Leu Ser Pro Trp Phe Arg Leu Val Val Asp Asn Phe
        195                 200                 205

Leu Phe Lys Trp Trp Asp His Val Glu Glu Gly Lys Ile Lys Asp Val
    210                 215                 220

Ala Asp Met Lys Thr Ile His Lys Leu Thr
225                 230
```

<210> SEQ ID NO 121
<211> LENGTH: 1402
<212> TYPE: DNA
<213> ORGANISM: Arabidopsis thaliana
<220> FEATURE:
<221> NAME/KEY: CDS
<222> LOCATION: (52)..(1317)

<400> SEQUENCE: 121

```
aagtctttgc ctctttggtt tactttcctc tgttttcgat ccatttagaa a atg tta       57
                                                         Met Leu
                                                           1 ttc acg agg agt gtt gct cgg att tct tct aag ttt ctg aga aac cgt      105
Phe Thr Arg Ser Val Ala Arg Ile Ser Ser Lys Phe Leu Arg Asn Arg
        5                  10                  15 agc ttc tat ggc tcc tct caa tct ctc gcc tct cat cgg ttc gca atc      153
Ser Phe Tyr Gly Ser Ser Gln Ser Leu Ala Ser His Arg Phe Ala Ile
     20                  25                  30 att ccc gat cag ggt cac tct tgt tct gac tct cca cac aag ggt tac      201
Ile Pro Asp Gln Gly His Ser Cys Ser Asp Ser Pro His Lys Gly Tyr
35                  40                  45                  50 gtt tgc aga aca act tat tca ttg aaa tct ccg gtt ttt ggt gga ttt      249
Val Cys Arg Thr Thr Tyr Ser Leu Lys Ser Pro Val Phe Gly Gly Phe
                 55                  60                  65 agt cat caa ctc tat cac cag agt agc tcc ttg gtt gag gag gag ctt      297
Ser His Gln Leu Tyr His Gln Ser Ser Ser Leu Val Glu Glu Glu Leu
             70                  75                  80 gac cca ttt tcg ctt gtt gcc gat gag ctg tca ctt ctt agt aat aag      345
Asp Pro Phe Ser Leu Val Ala Asp Glu Leu Ser Leu Leu Ser Asn Lys
         85                  90                  95 ttg aga gag atg gta ctt gcc gag gtt cca aag ctt gcc tct gct gct      393
Leu Arg Glu Met Val Leu Ala Glu Val Pro Lys Leu Ala Ser Ala Ala
    100                 105                 110 gag tac ttc ttc aaa agg ggt gtg caa gga aaa cag ttt cgt tca act      441
Glu Tyr Phe Phe Lys Arg Gly Val Gln Gly Lys Gln Phe Arg Ser Thr
115                 120                 125                 130 att ttg ctg ctg atg gcg aca gct ctg gat gta cga gtt cca gaa gca      489
Ile Leu Leu Leu Met Ala Thr Ala Leu Asp Val Arg Val Pro Glu Ala
                135                 140                 145 ttg att ggg gaa tca aca gat ata gtc aca tca gaa tta cgc gta agg      537
Leu Ile Gly Glu Ser Thr Asp Ile Val Thr Ser Glu Leu Arg Val Arg
            150                 155                 160
```

| | | | | | | | | | | | | | | | | |
|---|---|---|---|---|---|---|---|---|---|---|---|---|---|---|---|---|
| caa | cgg | ggt | att | gct | gaa | atc | act | gaa | atg | ata | cac | gtc | gca | agt | cta | 585 |
| Gln | Arg | Gly | Ile | Ala | Glu | Ile | Thr | Glu | Met | Ile | His | Val | Ala | Ser | Leu | |
| | 165 | | | | | 170 | | | | | 175 | | | | | |
| ctg | cac | gat | gat | gtc | ttg | gat | gat | gcc | gat | aca | agg | cgt | ggt | gtt | ggt | 633 |
| Leu | His | Asp | Asp | Val | Leu | Asp | Asp | Ala | Asp | Thr | Arg | Arg | Gly | Val | Gly | |
| 180 | | | | | 185 | | | | | 190 | | | | | | |
| tcc | tta | aat | gtt | gta | atg | ggt | aac | aag | atg | tcg | gta | tta | gca | gga | gac | 681 |
| Ser | Leu | Asn | Val | Val | Met | Gly | Asn | Lys | Met | Ser | Val | Leu | Ala | Gly | Asp | |
| 195 | | | | | 200 | | | | | 205 | | | | | 210 | |
| ttc | ttg | ctc | tcc | cgg | gct | tgt | ggg | gct | ctc | gct | gct | tta | aag | aac | aca | 729 |
| Phe | Leu | Leu | Ser | Arg | Ala | Cys | Gly | Ala | Leu | Ala | Ala | Leu | Lys | Asn | Thr | |
| | | | | 215 | | | | | 220 | | | | | 225 | | |
| gag | gtt | gta | gca | tta | ctt | gca | act | gct | gta | gaa | cat | ctt | gtt | acc | ggt | 777 |
| Glu | Val | Val | Ala | Leu | Leu | Ala | Thr | Ala | Val | Glu | His | Leu | Val | Thr | Gly | |
| | | | 230 | | | | | 235 | | | | | 240 | | | |
| gaa | acc | atg | gag | ata | act | agt | tca | acc | gag | cag | cgt | tat | agt | atg | gac | 825 |
| Glu | Thr | Met | Glu | Ile | Thr | Ser | Ser | Thr | Glu | Gln | Arg | Tyr | Ser | Met | Asp | |
| | | 245 | | | | | 250 | | | | | 255 | | | | |
| tac | tac | atg | cag | aag | aca | tat | tat | aag | aca | gca | tcg | cta | atc | tct | aac | 873 |
| Tyr | Tyr | Met | Gln | Lys | Thr | Tyr | Tyr | Lys | Thr | Ala | Ser | Leu | Ile | Ser | Asn | |
| | 260 | | | | | 265 | | | | | 270 | | | | | |
| agc | tgc | aaa | gct | gtt | gcc | gtt | ctc | act | gga | caa | aca | gca | gaa | gtt | gcc | 921 |
| Ser | Cys | Lys | Ala | Val | Ala | Val | Leu | Thr | Gly | Gln | Thr | Ala | Glu | Val | Ala | |
| 275 | | | | | 280 | | | | | 285 | | | | | 290 | |
| gtg | tta | gct | ttt | gag | tat | ggg | agg | aat | ctg | ggt | tta | gca | ttc | caa | tta | 969 |
| Val | Leu | Ala | Phe | Glu | Tyr | Gly | Arg | Asn | Leu | Gly | Leu | Ala | Phe | Gln | Leu | |
| | | | | 295 | | | | | 300 | | | | | 305 | | |
| ata | gac | gac | att | ctt | gat | ttc | acg | ggc | aca | tct | gcc | tct | ctc | gga | aag | 1017 |
| Ile | Asp | Asp | Ile | Leu | Asp | Phe | Thr | Gly | Thr | Ser | Ala | Ser | Leu | Gly | Lys | |
| | | | 310 | | | | | 315 | | | | | 320 | | | |
| gga | tcg | ttg | tca | gat | att | cgc | cat | gga | gtc | ata | aca | gcc | cca | atc | ctc | 1065 |
| Gly | Ser | Leu | Ser | Asp | Ile | Arg | His | Gly | Val | Ile | Thr | Ala | Pro | Ile | Leu | |
| | | 325 | | | | | 330 | | | | | 335 | | | | |
| ttt | gcc | atg | gaa | gag | ttt | cct | caa | cta | cgc | gaa | gtt | gtt | gat | caa | gtt | 1113 |
| Phe | Ala | Met | Glu | Glu | Phe | Pro | Gln | Leu | Arg | Glu | Val | Val | Asp | Gln | Val | |
| | 340 | | | | | 345 | | | | | 350 | | | | | |
| gaa | aaa | gat | cct | agg | aat | gtt | gac | att | gct | tta | gag | tat | ctt | ggg | aag | 1161 |
| Glu | Lys | Asp | Pro | Arg | Asn | Val | Asp | Ile | Ala | Leu | Glu | Tyr | Leu | Gly | Lys | |
| 355 | | | | | 360 | | | | | 365 | | | | | 370 | |
| agc | aag | gga | ata | cag | agg | gca | aga | gaa | tta | gcc | atg | gaa | cat | gcg | aat | 1209 |
| Ser | Lys | Gly | Ile | Gln | Arg | Ala | Arg | Glu | Leu | Ala | Met | Glu | His | Ala | Asn | |
| | | | | 375 | | | | | 380 | | | | | 385 | | |
| cta | gca | gca | gct | gca | atc | ggg | tct | cta | cct | gaa | aca | gac | aat | gaa | gat | 1257 |
| Leu | Ala | Ala | Ala | Ala | Ile | Gly | Ser | Leu | Pro | Glu | Thr | Asp | Asn | Glu | Asp | |
| | | | 390 | | | | | 395 | | | | | 400 | | | |
| gtc | aaa | aga | tcg | agg | cgg | gca | ctt | att | gac | ttg | acc | cat | aga | gtc | atc | 1305 |
| Val | Lys | Arg | Ser | Arg | Arg | Ala | Leu | Ile | Asp | Leu | Thr | His | Arg | Val | Ile | |
| | | 405 | | | | | 410 | | | | | 415 | | | | |
| acc | aga | aac | aag | tgagattaag | taatgtttct | ctctatacac | caaaacattc | | | | | | | | | 1357 |
| Thr | Arg | Asn | Lys | | | | | | | | | | | | | |
| | 420 | | | | | | | | | | | | | | | | ctcatttcat ttgtaggatt ttgttggtcc aattcgtttc acgaa 1402

<210> SEQ ID NO 122
<211> LENGTH: 422
<212> TYPE: PRT
<213> ORGANISM: Arabidopsis thaliana

<400> SEQUENCE: 122

-continued

```
Met Leu Phe Thr Arg Ser Val Ala Arg Ile Ser Ser Lys Phe Leu Arg
1               5                   10                  15

Asn Arg Ser Phe Tyr Gly Ser Ser Gln Ser Leu Ala Ser His Arg Phe
                20                  25                  30

Ala Ile Ile Pro Asp Gln Gly His Ser Cys Ser Asp Ser Pro His Lys
            35                  40                  45

Gly Tyr Val Cys Arg Thr Thr Tyr Ser Leu Lys Ser Pro Val Phe Gly
        50                  55                  60

Gly Phe Ser His Gln Leu Tyr His Gln Ser Ser Ser Leu Val Glu Glu
65                  70                  75                  80

Glu Leu Asp Pro Phe Ser Leu Val Ala Asp Glu Leu Ser Leu Leu Ser
                85                  90                  95

Asn Lys Leu Arg Glu Met Val Leu Ala Glu Val Pro Lys Leu Ala Ser
                100                 105                 110

Ala Ala Glu Tyr Phe Phe Lys Arg Gly Val Gln Gly Lys Gln Phe Arg
            115                 120                 125

Ser Thr Ile Leu Leu Leu Met Ala Thr Ala Leu Asp Val Arg Val Pro
        130                 135                 140

Glu Ala Leu Ile Gly Ser Thr Asp Ile Val Thr Ser Glu Leu Arg
145                 150                 155                 160

Val Arg Gln Arg Gly Ile Ala Glu Ile Thr Glu Met Ile His Val Ala
                165                 170                 175

Ser Leu Leu His Asp Asp Val Leu Asp Asp Ala Asp Thr Arg Arg Gly
            180                 185                 190

Val Gly Ser Leu Asn Val Val Met Gly Asn Lys Met Ser Val Leu Ala
        195                 200                 205

Gly Asp Phe Leu Leu Ser Arg Ala Cys Gly Ala Leu Ala Ala Leu Lys
210                 215                 220

Asn Thr Glu Val Val Ala Leu Leu Ala Thr Ala Val Glu His Leu Val
225                 230                 235                 240

Thr Gly Glu Thr Met Glu Ile Thr Ser Ser Thr Gln Arg Tyr Ser
                245                 250                 255

Met Asp Tyr Tyr Met Gln Lys Thr Tyr Tyr Lys Thr Ala Ser Leu Ile
            260                 265                 270

Ser Asn Ser Cys Lys Ala Val Ala Val Leu Thr Gly Gln Thr Ala Glu
        275                 280                 285

Val Ala Val Leu Ala Phe Glu Tyr Gly Arg Asn Leu Gly Leu Ala Phe
290                 295                 300

Gln Leu Ile Asp Asp Ile Leu Asp Phe Thr Gly Thr Ser Ala Ser Leu
305                 310                 315                 320

Gly Lys Gly Ser Leu Ser Asp Ile Arg His Gly Val Ile Thr Ala Pro
                325                 330                 335

Ile Leu Phe Ala Met Glu Glu Phe Pro Gln Leu Arg Glu Val Val Asp
            340                 345                 350

Gln Val Glu Lys Asp Pro Arg Asn Val Asp Ile Ala Leu Glu Tyr Leu
        355                 360                 365

Gly Lys Ser Lys Gly Ile Gln Arg Ala Arg Glu Leu Ala Met Glu His
370                 375                 380

Ala Asn Leu Ala Ala Ala Ile Gly Ser Leu Pro Glu Thr Asp Asn
385                 390                 395                 400

Glu Asp Val Lys Arg Ser Arg Arg Ala Leu Ile Asp Leu Thr His Arg
                405                 410                 415

Val Ile Thr Arg Asn Lys
```

```
<210> SEQ ID NO 123
<211> LENGTH: 1155
<212> TYPE: DNA
<213> ORGANISM: Arabidopsis thaliana
<220> FEATURE:
<221> NAME/KEY: CDS

<400> SEQUENCE: 123 atg agt gtg agt tgt tgt tgt agg aat ctg ggc aag aca ata aaa aag      48
Met Ser Val Ser Cys Cys Cys Arg Asn Leu Gly Lys Thr Ile Lys Lys
1               5                   10                  15 gca ata cct tca cat cat ttg cat ctg aga agt ctt ggt ggg agt ctc      96
Ala Ile Pro Ser His His Leu His Leu Arg Ser Leu Gly Gly Ser Leu
            20                  25                  30 tat cgt cgt cgt atc caa agc tct tca atg gag acc gat ctc aag tca     144
Tyr Arg Arg Arg Ile Gln Ser Ser Ser Met Glu Thr Asp Leu Lys Ser
        35                  40                  45 acc ttt ctc aac gtt tat tct gtt ctc aag tct gac ctt ctt cat gac     192
Thr Phe Leu Asn Val Tyr Ser Val Leu Lys Ser Asp Leu Leu His Asp
50                  55                  60 cct tcc ttc gaa ttc acc aat gaa tct cgt ctc tgg gtt gat cgg atg     240
Pro Ser Phe Glu Phe Thr Asn Glu Ser Arg Leu Trp Val Asp Arg Met
65                  70                  75                  80 ctg gac tac aat gta cgt gga ggg aaa ctc aat cgg ggt ctc tct gtt     288
Leu Asp Tyr Asn Val Arg Gly Gly Lys Leu Asn Arg Gly Leu Ser Val
                85                  90                  95 gtt gac agt ttc aaa ctt ttg aag caa ggc aat gat ttg act gag caa     336
Val Asp Ser Phe Lys Leu Leu Lys Gln Gly Asn Asp Leu Thr Glu Gln
            100                 105                 110 gag gtt ttc ctc tct tgt gct ctc ggt tgg tgc att gaa tgg ctc caa     384
Glu Val Phe Leu Ser Cys Ala Leu Gly Trp Cys Ile Glu Trp Leu Gln
        115                 120                 125 gct tat ttc ctt gtg ctt gat gat att atg gat aac tct gtc act cgc     432
Ala Tyr Phe Leu Val Leu Asp Asp Ile Met Asp Asn Ser Val Thr Arg
    130                 135                 140 cgt ggt caa cct tgc tgg ttc aga gtt cct cag gtt ggt atg gtt gcc     480
Arg Gly Gln Pro Cys Trp Phe Arg Val Pro Gln Val Gly Met Val Ala
145                 150                 155                 160 atc aat gat ggg att cta ctt cgc aat cac atc cac agg att ctc aaa     528
Ile Asn Asp Gly Ile Leu Leu Arg Asn His Ile His Arg Ile Leu Lys
                165                 170                 175 aag cat ttc cgt gat aag cct tac tat gtt gac ctt gtt gat ttg ttt     576
Lys His Phe Arg Asp Lys Pro Tyr Tyr Val Asp Leu Val Asp Leu Phe
            180                 185                 190 aat gag gtt gag ttg caa aca gct tgt ggc cag atg ata gat ttg atc     624
Asn Glu Val Glu Leu Gln Thr Ala Cys Gly Gln Met Ile Asp Leu Ile
        195                 200                 205 acc acc ttt gaa gga gaa aag gat ttg gcc aag tac tca ttg tca atc     672
Thr Thr Phe Glu Gly Glu Lys Asp Leu Ala Lys Tyr Ser Leu Ser Ile
    210                 215                 220 cac cgt cgt att gtc cag tac aaa acg gct tat tac tca ttt tat ctc     720
His Arg Arg Ile Val Gln Tyr Lys Thr Ala Tyr Tyr Ser Phe Tyr Leu
225                 230                 235                 240 cct gtt gct tgt gcg ttg ctt atg gcg ggc gaa aat ttg gaa aac cat     768
Pro Val Ala Cys Ala Leu Leu Met Ala Gly Glu Asn Leu Glu Asn His
                245                 250                 255 att gac gtg aaa aat gtt ctt gtt gac atg gga atc tac ttc caa gtg     816
Ile Asp Val Lys Asn Val Leu Val Asp Met Gly Ile Tyr Phe Gln Val
            260                 265                 270
```

```
cag gat gat tat ctg gat tgt ttt gct gat ccc gag acg ctt ggc aag      864
Gln Asp Asp Tyr Leu Asp Cys Phe Ala Asp Pro Glu Thr Leu Gly Lys
        275                 280                 285 ata gga aca gat ata gaa gat ttc aaa tgc tcg tgg ttg gtg gtt aag      912
Ile Gly Thr Asp Ile Glu Asp Phe Lys Cys Ser Trp Leu Val Val Lys
    290                 295                 300 gca tta gag cgc tgc agc gaa gaa caa act aag ata tta tat gag aac      960
Ala Leu Glu Arg Cys Ser Glu Glu Gln Thr Lys Ile Leu Tyr Glu Asn
305                 310                 315                 320 tat ggt aaa ccc gac cca tcg aac gtt gct aaa gtg aag gat ctc tac     1008
Tyr Gly Lys Pro Asp Pro Ser Asn Val Ala Lys Val Lys Asp Leu Tyr
                325                 330                 335 aaa gag ctg gat ctt gag gga gtt ttc atg gag tat gag agc aaa agc     1056
Lys Glu Leu Asp Leu Glu Gly Val Phe Met Glu Tyr Glu Ser Lys Ser
            340                 345                 350 tac gag aag ctg act gga gcg att gag gga cac caa agt aaa gca atc     1104
Tyr Glu Lys Leu Thr Gly Ala Ile Glu Gly His Gln Ser Lys Ala Ile
        355                 360                 365 caa gca gtg cta aaa tcc ttc ttg gct aag atc tac aag agg cag aag     1152
Gln Ala Val Leu Lys Ser Phe Leu Ala Lys Ile Tyr Lys Arg Gln Lys
    370                 375                 380 tag                                                                 1155

<210> SEQ ID NO 124
<211> LENGTH: 384
<212> TYPE: PRT
<213> ORGANISM: Arabidopsis thaliana

<400> SEQUENCE: 124

Met Ser Val Ser Cys Cys Cys Arg Asn Leu Gly Lys Thr Ile Lys Lys
1               5                   10                  15

Ala Ile Pro Ser His His Leu His Leu Arg Ser Leu Gly Gly Ser Leu
            20                  25                  30

Tyr Arg Arg Arg Ile Gln Ser Ser Met Glu Thr Asp Leu Lys Ser
        35                  40                  45

Thr Phe Leu Asn Val Tyr Ser Val Leu Lys Ser Asp Leu Leu His Asp
    50                  55                  60

Pro Ser Phe Glu Phe Thr Asn Glu Ser Arg Leu Trp Val Asp Arg Met
65                  70                  75                  80

Leu Asp Tyr Asn Val Arg Gly Gly Lys Leu Asn Arg Gly Leu Ser Val
                85                  90                  95

Val Asp Ser Phe Lys Leu Leu Lys Gln Gly Asn Asp Leu Thr Glu Gln
            100                 105                 110

Glu Val Phe Leu Ser Cys Ala Leu Gly Trp Cys Ile Glu Trp Leu Gln
        115                 120                 125

Ala Tyr Phe Leu Val Leu Asp Asp Ile Met Asp Asn Ser Val Thr Arg
    130                 135                 140

Arg Gly Gln Pro Cys Trp Phe Arg Val Pro Gln Val Gly Met Val Ala
145                 150                 155                 160

Ile Asn Asp Gly Ile Leu Leu Arg Asn His Ile His Arg Ile Leu Lys
                165                 170                 175

Lys His Phe Arg Asp Lys Pro Tyr Tyr Val Asp Leu Val Asp Leu Phe
            180                 185                 190

Asn Glu Val Glu Leu Gln Thr Ala Cys Gly Gln Met Ile Asp Leu Ile
        195                 200                 205

Thr Thr Phe Glu Gly Glu Lys Asp Leu Ala Lys Tyr Ser Leu Ser Ile
```

```
              210                 215                 220
His Arg Arg Ile Val Gln Tyr Lys Thr Ala Tyr Tyr Ser Phe Tyr Leu
225                 230                 235                 240

Pro Val Ala Cys Ala Leu Leu Met Ala Gly Glu Asn Leu Glu Asn His
                245                 250                 255

Ile Asp Val Lys Asn Val Leu Val Asp Met Gly Ile Tyr Phe Gln Val
                260                 265                 270

Gln Asp Tyr Leu Asp Cys Phe Ala Asp Pro Glu Thr Leu Gly Lys
            275                 280                 285

Ile Gly Thr Asp Ile Glu Asp Phe Lys Cys Ser Trp Leu Val Val Lys
290                 295                 300

Ala Leu Glu Arg Cys Ser Glu Glu Gln Thr Lys Ile Leu Tyr Glu Asn
305                 310                 315                 320

Tyr Gly Lys Pro Asp Pro Ser Asn Val Ala Lys Val Lys Asp Leu Tyr
                325                 330                 335

Lys Glu Leu Asp Leu Glu Gly Val Phe Met Glu Tyr Glu Ser Lys Ser
                340                 345                 350

Tyr Glu Lys Leu Thr Gly Ala Ile Glu Gly His Gln Ser Lys Ala Ile
            355                 360                 365

Gln Ala Val Leu Lys Ser Phe Leu Ala Lys Ile Tyr Lys Arg Gln Lys
        370                 375                 380

<210> SEQ ID NO 125
<211> LENGTH: 1101
<212> TYPE: DNA
<213> ORGANISM: Sinabs alba
<220> FEATURE:
<221> NAME/KEY: CDS

<400> SEQUENCE: 125 atg gct tct tca gtg act cct cta ggt tca tgg gtt ctt ctt cac cat        48
Met Ala Ser Ser Val Thr Pro Leu Gly Ser Trp Val Leu Leu His His
1               5                   10                  15 cat cct tca act atc tta acc caa tcc aga tcc aga tct cct cct tct        96
His Pro Ser Thr Ile Leu Thr Gln Ser Arg Ser Arg Ser Pro Pro Ser
                20                  25                  30 ctc atc acc ctt aaa ccc atc tcc ctc act cca aaa cgc acc gtt tcg        144
Leu Ile Thr Leu Lys Pro Ile Ser Leu Thr Pro Lys Arg Thr Val Ser
            35                  40                  45 tct tct tcc tcc tct tcc ctc atc acc aaa gaa gac aac aac ctc aaa        192
Ser Ser Ser Ser Ser Ser Leu Ile Thr Lys Glu Asp Asn Asn Leu Lys
50                  55                  60 tcc tct tcc tct tcc ttc gat ttc atg tct tac atc atc cgc aaa gcc        240
Ser Ser Ser Ser Ser Phe Asp Phe Met Ser Tyr Ile Ile Arg Lys Ala
65                  70                  75                  80 gac tcc gtc aac aaa gcc tta gac tcc gcc gtc cct ctc cgg gag cca        288
Asp Ser Val Asn Lys Ala Leu Asp Ser Ala Val Pro Leu Arg Glu Pro
                85                  90                  95 ctc aag atc cac gaa gcg atg cgt tac tct ctc ctc gcc gga gga aaa        336
Leu Lys Ile His Glu Ala Met Arg Tyr Ser Leu Leu Ala Gly Gly Lys
            100                 105                 110 cgc gtc aga cca gtt ctc tgc atc gcc gcg tgc gag cta gtc gga gga        384
Arg Val Arg Pro Val Leu Cys Ile Ala Ala Cys Glu Leu Val Gly Gly
        115                 120                 125 gaa gag tct tta gct atg ccg gcg cgt tgc gcc gtg gaa atg atc cac        432
Glu Glu Ser Leu Ala Met Pro Ala Arg Cys Ala Val Glu Met Ile His
130                 135                 140 acc atg tcg ttg atc cac gac gac ttg cct tgt atg gat aac gac gat        480
Thr Met Ser Leu Ile His Asp Asp Leu Pro Cys Met Asp Asn Asp Asp
```

```
Thr Met Ser Leu Ile His Asp Asp Leu Pro Cys Met Asp Asn Asp Asp
145                 150                 155                 160 ctc cgc cgc gga aag ccc acg aat cac aaa gtt tac ggc gaa gac gtg          528
Leu Arg Arg Gly Lys Pro Thr Asn His Lys Val Tyr Gly Glu Asp Val
                165                 170                 175 gcg gtt tta gcc gga gac gcg ctt ctt tcg ttc gcc ttc gag cat tta          576
Ala Val Leu Ala Gly Asp Ala Leu Leu Ser Phe Ala Phe Glu His Leu
            180                 185                 190 gcg tcg gct acg agc tcg gag gtt tct ccg gcg aga gtg gtt aga gct          624
Ala Ser Ala Thr Ser Ser Glu Val Ser Pro Ala Arg Val Val Arg Ala
        195                 200                 205 gtg gga gag ttg gct aaa gcc atc ggc acc gaa ggg ctc gtg gcg gga          672
Val Gly Glu Leu Ala Lys Ala Ile Gly Thr Glu Gly Leu Val Ala Gly
    210                 215                 220 caa gtg gtg gat ata agc agt gaa ggg ttg gac tta aac aac gtc gga          720
Gln Val Val Asp Ile Ser Ser Glu Gly Leu Asp Leu Asn Asn Val Gly
225                 230                 235                 240 ttg gag cat ttg aag ttt ata cat ttg cat aaa acg gcg gcg ttg ctt          768
Leu Glu His Leu Lys Phe Ile His Leu His Lys Thr Ala Ala Leu Leu
                245                 250                 255 gaa gct tca gcg gtt ttg ggt ggg atc atc ggt gga ggg agt gat gaa          816
Glu Ala Ser Ala Val Leu Gly Gly Ile Ile Gly Gly Gly Ser Asp Glu
            260                 265                 270 gag atc gag agg ctg agg aag ttc gcg agg tgt att ggg ttg ttg ttt          864
Glu Ile Glu Arg Leu Arg Lys Phe Ala Arg Cys Ile Gly Leu Leu Phe
        275                 280                 285 cag gtg gtt gat gat atc ttg gac gtg acg aaa tcg tct caa gaa ctg          912
Gln Val Val Asp Asp Ile Leu Asp Val Thr Lys Ser Ser Gln Glu Leu
    290                 295                 300 ggg aaa acc gct ggg aaa gat ttg att gct gat aag ttg act tat ccg          960
Gly Lys Thr Ala Gly Lys Asp Leu Ile Ala Asp Lys Leu Thr Tyr Pro
305                 310                 315                 320 aag ctc atg ggt ttg gag aaa tcg aga gag ttc gct gag aag ttg aat         1008
Lys Leu Met Gly Leu Glu Lys Ser Arg Glu Phe Ala Glu Lys Leu Asn
                325                 330                 335 aca gag gca cgt gat cag ctt tta ggg ttt gat tcc gac aag gtt gct         1056
Thr Glu Ala Arg Asp Gln Leu Leu Gly Phe Asp Ser Asp Lys Val Ala
            340                 345                 350 cct ttg ttg gct ttg gct aat tac att gcc aat aga cag aac tga             1101
Pro Leu Leu Ala Leu Ala Asn Tyr Ile Ala Asn Arg Gln Asn
        355                 360                 365

<210> SEQ ID NO 126
<211> LENGTH: 366
<212> TYPE: PRT
<213> ORGANISM: Sinabs alba

<400> SEQUENCE: 126

Met Ala Ser Ser Val Thr Pro Leu Gly Ser Trp Val Leu Leu His His
1               5                   10                  15

His Pro Ser Thr Ile Leu Thr Gln Ser Arg Ser Arg Ser Pro Pro Ser
                20                  25                  30

Leu Ile Thr Leu Lys Pro Ile Ser Leu Thr Pro Lys Arg Thr Val Ser
            35                  40                  45

Ser Ser Ser Ser Ser Leu Ile Thr Lys Glu Asp Asn Asn Leu Lys
        50                  55                  60

Ser Ser Ser Ser Phe Asp Phe Met Ser Tyr Ile Ile Arg Lys Ala
65                  70                  75                  80

Asp Ser Val Asn Lys Ala Leu Asp Ser Ala Val Pro Leu Arg Glu Pro
```

```
                    85                  90                  95
Leu Lys Ile His Glu Ala Met Arg Tyr Ser Leu Leu Ala Gly Gly Lys
            100                 105                 110
Arg Val Arg Pro Val Leu Cys Ile Ala Ala Cys Glu Leu Val Gly Gly
            115                 120                 125
Glu Glu Ser Leu Ala Met Pro Ala Arg Cys Ala Val Glu Met Ile His
            130                 135                 140
Thr Met Ser Leu Ile His Asp Asp Leu Pro Cys Met Asp Asn Asp Asp
145                 150                 155                 160
Leu Arg Arg Gly Lys Pro Thr Asn His Lys Val Tyr Gly Glu Asp Val
                165                 170                 175
Ala Val Leu Ala Gly Asp Ala Leu Leu Ser Phe Ala Phe Glu His Leu
            180                 185                 190
Ala Ser Ala Thr Ser Ser Glu Val Ser Pro Ala Arg Val Val Arg Ala
            195                 200                 205
Val Gly Glu Leu Ala Lys Ala Ile Gly Thr Glu Gly Leu Val Ala Gly
            210                 215                 220
Gln Val Val Asp Ile Ser Ser Glu Gly Leu Asp Leu Asn Asn Val Gly
225                 230                 235                 240
Leu Glu His Leu Lys Phe Ile His Leu His Lys Thr Ala Ala Leu Leu
                245                 250                 255
Glu Ala Ser Ala Val Leu Gly Gly Ile Ile Gly Gly Gly Ser Asp Glu
            260                 265                 270
Glu Ile Glu Arg Leu Arg Lys Phe Ala Arg Cys Ile Gly Leu Leu Phe
            275                 280                 285
Gln Val Val Asp Asp Ile Leu Asp Val Thr Lys Ser Ser Gln Glu Leu
290                 295                 300
Gly Lys Thr Ala Gly Lys Asp Leu Ile Ala Asp Lys Leu Thr Tyr Pro
305                 310                 315                 320
Lys Leu Met Gly Leu Glu Lys Ser Arg Glu Phe Ala Glu Lys Leu Asn
                325                 330                 335
Thr Glu Ala Arg Asp Gln Leu Leu Gly Phe Asp Ser Asp Lys Val Ala
            340                 345                 350
Pro Leu Leu Ala Leu Ala Asn Tyr Ile Ala Asn Arg Gln Asn
            355                 360                 365

<210> SEQ ID NO 127
<211> LENGTH: 930
<212> TYPE: DNA
<213> ORGANISM: Erwinia uredovora
<220> FEATURE:
<221> NAME/KEY: CDS

<400> SEQUENCE: 127 atg aat aat ccg tcg tta ctc aat cat gcg gtc gaa acg atg gca gtt       48
Met Asn Asn Pro Ser Leu Leu Asn His Ala Val Glu Thr Met Ala Val
1               5                   10                  15 ggc tcg aaa agt ttt gcg aca gcc tca aag tta ttt gat gca aaa acc       96
Gly Ser Lys Ser Phe Ala Thr Ala Ser Lys Leu Phe Asp Ala Lys Thr
            20                  25                  30 cgg cgc agc gta ctg atg ctc tac gcc tgg tgc cgc cat tgt gac gat      144
Arg Arg Ser Val Leu Met Leu Tyr Ala Trp Cys Arg His Cys Asp Asp
        35                  40                  45 gtt att gac gat cag acg ctg ggc ttt cag gcc cgg cag cct gcc tta      192
Val Ile Asp Asp Gln Thr Leu Gly Phe Gln Ala Arg Gln Pro Ala Leu
    50                  55                  60
```

```
caa acg ccc gaa caa cgt ctg atg caa ctt gag atg aaa acg cgc cag      240
Gln Thr Pro Glu Gln Arg Leu Met Gln Leu Glu Met Lys Thr Arg Gln
 65                  70                  75                  80 gcc tat gca gga tcg cag atg cac gaa ccg gcg ttt gcg gct ttt cag      288
Ala Tyr Ala Gly Ser Gln Met His Glu Pro Ala Phe Ala Ala Phe Gln
                 85                  90                  95 gaa gtg gct atg gct cat gat atc gcc ccg gct tac gcg ttt gat cat      336
Glu Val Ala Met Ala His Asp Ile Ala Pro Ala Tyr Ala Phe Asp His
            100                 105                 110 ctg gaa ggc ttc gcc atg gat gta cgc gaa gcg caa tac agc caa ctg      384
Leu Glu Gly Phe Ala Met Asp Val Arg Glu Ala Gln Tyr Ser Gln Leu
        115                 120                 125 gat gat acg ctg cgc tat tgc tat cac gtt gca ggc gtt gtc ggc ttg      432
Asp Asp Thr Leu Arg Tyr Cys Tyr His Val Ala Gly Val Val Gly Leu
130                 135                 140 atg atg gcg caa atc atg ggc gtg cgg gat aac gcc acg ctg gac cgc      480
Met Met Ala Gln Ile Met Gly Val Arg Asp Asn Ala Thr Leu Asp Arg
145                 150                 155                 160 gcc tgt gac ctt ggg ctg gca ttt cag ttg acc aat att gct cgc gat      528
Ala Cys Asp Leu Gly Leu Ala Phe Gln Leu Thr Asn Ile Ala Arg Asp
                165                 170                 175 att gtg gac gat gcg cat gcg ggc cgc tgt tat ctg ccg gca agc tgg      576
Ile Val Asp Asp Ala His Ala Gly Arg Cys Tyr Leu Pro Ala Ser Trp
            180                 185                 190 ctg gag cat gaa ggt ctg aac aaa gag aat tat gcg gca cct gaa aac      624
Leu Glu His Glu Gly Leu Asn Lys Glu Asn Tyr Ala Ala Pro Glu Asn
        195                 200                 205 cgt cag gcg ctg agc cgt atc gcc cgt cgt ttg gtg cag gaa gca gaa      672
Arg Gln Ala Leu Ser Arg Ile Ala Arg Arg Leu Val Gln Glu Ala Glu
    210                 215                 220 cct tac tat ttg tct gcc aca gcc ggc ctg gca ggg ttg ccc ctg cgt      720
Pro Tyr Tyr Leu Ser Ala Thr Ala Gly Leu Ala Gly Leu Pro Leu Arg
225                 230                 235                 240 tcc gcc tgg gca atc gct acg gcg aag cag gtt tac cgg aaa ata ggt      768
Ser Ala Trp Ala Ile Ala Thr Ala Lys Gln Val Tyr Arg Lys Ile Gly
                245                 250                 255 gtc aaa gtt gaa cag gcc ggt cag caa gcc tgg gat cag cgg cag tca      816
Val Lys Val Glu Gln Ala Gly Gln Gln Ala Trp Asp Gln Arg Gln Ser
            260                 265                 270 acg acc acg ccc gaa aaa tta acg ctg ctg ctg gcc gcc tct ggt cag      864
Thr Thr Thr Pro Glu Lys Leu Thr Leu Leu Leu Ala Ala Ser Gly Gln
        275                 280                 285 gcc ctt act tcc cgg atg cgg gct cat cct ccc cgc cct gcg cat ctc      912
Ala Leu Thr Ser Arg Met Arg Ala His Pro Pro Arg Pro Ala His Leu
    290                 295                 300 tgg cag cgc ccg ctc tag                                              930
Trp Gln Arg Pro Leu
305

<210> SEQ ID NO 128
<211> LENGTH: 309
<212> TYPE: PRT
<213> ORGANISM: Erwinia uredovora

<400> SEQUENCE: 128

Met Asn Asn Pro Ser Leu Leu Asn His Ala Val Glu Thr Met Ala Val
1               5                   10                  15

Gly Ser Lys Ser Phe Ala Thr Ala Ser Lys Leu Phe Asp Ala Lys Thr
            20                  25                  30

Arg Arg Ser Val Leu Met Leu Tyr Ala Trp Cys Arg His Cys Asp Asp
```

```
                    35                  40                  45
Val Ile Asp Asp Gln Thr Leu Gly Phe Gln Ala Arg Gln Pro Ala Leu
     50                  55                  60

Gln Thr Pro Glu Gln Arg Leu Met Gln Leu Glu Met Lys Thr Arg Gln
 65                  70                  75                  80

Ala Tyr Ala Gly Ser Gln Met His Glu Pro Ala Phe Ala Ala Phe Gln
                 85                  90                  95

Glu Val Ala Met Ala His Asp Ile Ala Pro Tyr Ala Phe Asp His
                100                 105                 110

Leu Glu Gly Phe Ala Met Asp Val Arg Glu Ala Gln Tyr Ser Gln Leu
            115                 120                 125

Asp Asp Thr Leu Arg Tyr Cys Tyr His Val Ala Gly Val Val Gly Leu
    130                 135                 140

Met Met Ala Gln Ile Met Gly Val Arg Asp Asn Ala Thr Leu Asp Arg
145                 150                 155                 160

Ala Cys Asp Leu Gly Leu Ala Phe Gln Leu Thr Asn Ile Ala Arg Asp
                165                 170                 175

Ile Val Asp Asp Ala His Ala Gly Arg Cys Tyr Leu Pro Ala Ser Trp
            180                 185                 190

Leu Glu His Glu Gly Leu Asn Lys Glu Asn Tyr Ala Ala Pro Glu Asn
        195                 200                 205

Arg Gln Ala Leu Ser Arg Ile Ala Arg Arg Leu Val Gln Glu Ala Glu
    210                 215                 220

Pro Tyr Tyr Leu Ser Ala Thr Ala Gly Leu Ala Gly Leu Pro Leu Arg
225                 230                 235                 240

Ser Ala Trp Ala Ile Ala Thr Ala Lys Gln Val Tyr Arg Lys Ile Gly
                245                 250                 255

Val Lys Val Glu Gln Ala Gly Gln Gln Ala Trp Asp Gln Arg Gln Ser
            260                 265                 270

Thr Thr Thr Pro Glu Lys Leu Thr Leu Leu Ala Ala Ser Gly Gln
        275                 280                 285

Ala Leu Thr Ser Arg Met Arg Ala His Pro Pro Arg Pro Ala His Leu
    290                 295                 300

Trp Gln Arg Pro Leu
305

<210> SEQ ID NO 129
<211> LENGTH: 1479
<212> TYPE: DNA
<213> ORGANISM: Erwinia uredovora
<220> FEATURE:
<221> NAME/KEY: CDS

<400> SEQUENCE: 129 atg aaa cca act acg gta att ggt gca ggc ttc ggt ggc ctg gca ctg      48
Met Lys Pro Thr Thr Val Ile Gly Ala Gly Phe Gly Gly Leu Ala Leu
 1               5                  10                  15 gca att cgt cta caa gct gcg ggg atc ccc gtc tta ctg ctt gaa caa      96
Ala Ile Arg Leu Gln Ala Ala Gly Ile Pro Val Leu Leu Leu Glu Gln
             20                  25                  30 cgt gat aaa ccc ggc ggt cgg gct tat gtc tac gag gat cag ggg ttt     144
Arg Asp Lys Pro Gly Gly Arg Ala Tyr Val Tyr Glu Asp Gln Gly Phe
         35                  40                  45 acc ttt gat gca ggc ccg acg gtt atc acc gat ccc agt gcc att gaa     192
Thr Phe Asp Ala Gly Pro Thr Val Ile Thr Asp Pro Ser Ala Ile Glu
     50                  55                  60
```

-continued

| | | |
|---|---|---|
| gaa ctg ttt gca ctg gca gga aaa cag tta aaa gag tat gtc gaa ctg<br>Glu Leu Phe Ala Leu Ala Gly Lys Gln Leu Lys Glu Tyr Val Glu Leu<br>65                            70                      75                   80 | 240 |
| ctg ccg gtt acg ccg ttt tac cgc ctg tgt tgg gag tca ggg aag gtc<br>Leu Pro Val Thr Pro Phe Tyr Arg Leu Cys Trp Glu Ser Gly Lys Val<br>                      85                      90                      95 | 288 |
| ttt aat tac gat aac gat caa acc cgg ctc gaa gcg cag att cag cag<br>Phe Asn Tyr Asp Asn Asp Gln Thr Arg Leu Glu Ala Gln Ile Gln Gln<br>              100                    105                    110 | 336 |
| ttt aat ccc cgc gat gtc gaa ggt tat cgt cag ttt ctg gac tat tca<br>Phe Asn Pro Arg Asp Val Glu Gly Tyr Arg Gln Phe Leu Asp Tyr Ser<br>            115                    120                    125 | 384 |
| cgc gcg gtg ttt aaa gaa ggc tat cta aag ctc ggt act gtc cct ttt<br>Arg Ala Val Phe Lys Glu Gly Tyr Leu Lys Leu Gly Thr Val Pro Phe<br>130                           135                    140 | 432 |
| tta tcg ttc aga gac atg ctt cgc gcc gca cct caa ctg gcg aaa ctg<br>Leu Ser Phe Arg Asp Met Leu Arg Ala Ala Pro Gln Leu Ala Lys Leu<br>145                           150                    155                  160 | 480 |
| cag gca tgg aga agc gtt tac agt aag gtt gcc agt tac atc gaa gat<br>Gln Ala Trp Arg Ser Val Tyr Ser Lys Val Ala Ser Tyr Ile Glu Asp<br>                 165                    170                    175 | 528 |
| gaa cat ctg cgc cag gcg ttt tct ttc cac tcg ctg ttg gtg ggc ggc<br>Glu His Leu Arg Gln Ala Phe Ser Phe His Ser Leu Leu Val Gly Gly<br>                180                    185                    190 | 576 |
| aat ccc ttc gcc acc tca tcc att tat acg ttg ata cac gcg ctg gag<br>Asn Pro Phe Ala Thr Ser Ser Ile Tyr Thr Leu Ile His Ala Leu Glu<br>            195                    200                    205 | 624 |
| cgt gag tgg ggc gtc tgg ttt ccg cgt ggc ggc acc ggc gca tta gtt<br>Arg Glu Trp Gly Val Trp Phe Pro Arg Gly Gly Thr Gly Ala Leu Val<br>210                         215                    220 | 672 |
| cag ggg atg ata aag ctg ttt cag gat ctg ggt ggc gaa gtc gtg tta<br>Gln Gly Met Ile Lys Leu Phe Gln Asp Leu Gly Gly Glu Val Val Leu<br>225                         230                    235                  240 | 720 |
| aac gcc aga gtc agc cat atg gaa acg aca gga aac aag att gaa gcc<br>Asn Ala Arg Val Ser His Met Glu Thr Thr Gly Asn Lys Ile Glu Ala<br>                245                    250                    255 | 768 |
| gtg cat tta gag gac ggt cgc agg ttc ctg acg caa gcc gtc gcg tca<br>Val His Leu Glu Asp Gly Arg Arg Phe Leu Thr Gln Ala Val Ala Ser<br>            260                    265                    270 | 816 |
| aat gca gat gtg gtt cat acc tat cgc gac ctg tta agc cag cac cct<br>Asn Ala Asp Val Val His Thr Tyr Arg Asp Leu Leu Ser Gln His Pro<br>            275                    280                    285 | 864 |
| gcc gcg gtt aag cag tcc aac aaa ctg cag act aag cgc atg agt aac<br>Ala Ala Val Lys Gln Ser Asn Lys Leu Gln Thr Lys Arg Met Ser Asn<br>290                         295                    300 | 912 |
| tct ctg ttt gtg ctc tat ttt ggt ttg aat cac cat cat gat cag ctc<br>Ser Leu Phe Val Leu Tyr Phe Gly Leu Asn His His His Asp Gln Leu<br>305                         310                    315                  320 | 960 |
| gcg cat cac acg gtt tgt ttc ggc ccg cgt tac cgc gag ctg att gac<br>Ala His His Thr Val Cys Phe Gly Pro Arg Tyr Arg Glu Leu Ile Asp<br>                325                    330                    335 | 1008 |
| gaa att ttt aat cat gat ggc ctc gca gag gac ttc tca ctt tat ctg<br>Glu Ile Phe Asn His Asp Gly Leu Ala Glu Asp Phe Ser Leu Tyr Leu<br>            340                    345                    350 | 1056 |
| cac gcg ccc tgt gtc acg gat tcg tca ctg gcg cct gaa ggt tgc ggc<br>His Ala Pro Cys Val Thr Asp Ser Ser Leu Ala Pro Glu Gly Cys Gly<br>            355                    360                    365 | 1104 |
| agt tac tat gtg ttg gcg ccg gtg ccg cat tta ggc acc gcg aac ctc<br>Ser Tyr Tyr Val Leu Ala Pro Val Pro His Leu Gly Thr Ala Asn Leu<br>370                         375                    380 | 1152 |

-continued

```
gac tgg acg gtt gag ggg cca aaa cta cgc gac cgt att ttt gcg tac       1200
Asp Trp Thr Val Glu Gly Pro Lys Leu Arg Asp Arg Ile Phe Ala Tyr
385                 390                 395                 400 ctt gag cag cat tac atg cct ggc tta cgg agt cag ctg gtc acg cac       1248
Leu Glu Gln His Tyr Met Pro Gly Leu Arg Ser Gln Leu Val Thr His
                405                 410                 415 cgg atg ttt acg ccg ttt gat ttt cgc gac cag ctt aat gcc tat cat       1296
Arg Met Phe Thr Pro Phe Asp Phe Arg Asp Gln Leu Asn Ala Tyr His
            420                 425                 430 ggc tca gcc ttt tct gtg gag ccc gtt ctt acc cag agc gcc tgg ttt       1344
Gly Ser Ala Phe Ser Val Glu Pro Val Leu Thr Gln Ser Ala Trp Phe
        435                 440                 445 cgg ccg cat aac cgc gat aaa acc att act aat ctc tac ctg gtc ggc       1392
Arg Pro His Asn Arg Asp Lys Thr Ile Thr Asn Leu Tyr Leu Val Gly
    450                 455                 460 gca ggc acg cat ccc ggc gca ggc att cct ggc gtc atc ggc tcg gca       1440
Ala Gly Thr His Pro Gly Ala Gly Ile Pro Gly Val Ile Gly Ser Ala
465                 470                 475                 480 aaa gca aca gca ggt ttg atg ctg gag gat ctg ata tga                   1479
Lys Ala Thr Ala Gly Leu Met Leu Glu Asp Leu Ile
                485                 490
```

<210> SEQ ID NO 130
<211> LENGTH: 492
<212> TYPE: PRT
<213> ORGANISM: Erwinia uredovora

<400> SEQUENCE: 130

```
Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
                20                  25                  30

Arg Asp Lys Pro Gly Gly Arg Ala Tyr Val Tyr Glu Asp Gln Gly Phe
            35                  40                  45

Thr Phe Asp Ala Gly Pro Thr Val Ile Thr Asp Pro Ser Ala Ile Glu
        50                  55                  60

Glu Leu Phe Ala Leu Ala Gly Lys Gln Leu Lys Glu Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Thr Arg Leu Glu Ala Gln Ile Gln Gln
            100                 105                 110

Phe Asn Pro Arg Asp Val Glu Gly Tyr Arg Gln Phe Leu Asp Tyr Ser
        115                 120                 125

Arg Ala Val Phe Lys Glu Gly Tyr Leu Lys Leu Gly Thr Val Pro Phe
    130                 135                 140

Leu Ser Phe Arg Asp Met Leu Arg Ala Ala Pro Gln Leu Ala Lys Leu
145                 150                 155                 160

Gln Ala Trp Arg Ser Val Tyr Ser Lys Val Ala Ser Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
    210                 215                 220
```

```
Gln Gly Met Ile Lys Leu Phe Gln Asp Leu Gly Gly Glu Val Val Leu
225                 230                 235                 240

Asn Ala Arg Val Ser His Met Glu Thr Thr Gly Asn Lys Ile Glu Ala
            245                 250                 255

Val His Leu Glu Asp Gly Arg Arg Phe Leu Thr Gln Ala Val Ala Ser
        260                 265                 270

Asn Ala Asp Val Val His Thr Tyr Arg Asp Leu Leu Ser Gln His Pro
    275                 280                 285

Ala Ala Val Lys Gln Ser Asn Lys Leu Gln Thr Lys Arg Met Ser Asn
290                 295                 300

Ser Leu Phe Val Leu Tyr Phe Gly Leu Asn His His Asp Gln Leu
305                 310                 315                 320

Ala His His Thr Val Cys Phe Gly Pro Arg Tyr Arg Glu Leu Ile Asp
            325                 330                 335

Glu Ile Phe Asn His Asp Gly Leu Ala Glu Asp Phe Ser Leu Tyr Leu
        340                 345                 350

His Ala Pro Cys Val Thr Asp Ser Ser Leu Ala Pro Glu Gly Cys Gly
    355                 360                 365

Ser Tyr Tyr Val Leu Ala Pro Val Pro His Leu Gly Thr Ala Asn Leu
370                 375                 380

Asp Trp Thr Val Glu Gly Pro Lys Leu Arg Asp Arg Ile Phe Ala Tyr
385                 390                 395                 400

Leu Glu Gln His Tyr Met Pro Gly Leu Arg Ser Gln Leu Val Thr His
            405                 410                 415

Arg Met Phe Thr Pro Phe Asp Phe Arg Asp Gln Leu Asn Ala Tyr His
        420                 425                 430

Gly Ser Ala Phe Ser Val Glu Pro Val Leu Thr Gln Ser Ala Trp Phe
    435                 440                 445

Arg Pro His Asn Arg Asp Lys Thr Ile Thr Asn Leu Tyr Leu Val Gly
450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
            485                 490

<210> SEQ ID NO 131
<211> LENGTH: 1725
<212> TYPE: DNA
<213> ORGANISM: Narcissus pseudonarcissus
<220> FEATURE:
<221> NAME/KEY: CDS

<400> SEQUENCE: 131
```

| | | | | | | | | | | | | | | | | |
|---|---|---|---|---|---|---|---|---|---|---|---|---|---|---|---|---|
| atg | gct | tct | tcc | act | tgt | tta | att | cat | tct | tcc | tct | ttt | ggg | gtt | gga | 48 |
| Met | Ala | Ser | Ser | Thr | Cys | Leu | Ile | His | Ser | Ser | Ser | Phe | Gly | Val | Gly | |
| 1 | | | | 5 | | | | | 10 | | | | | 15 | | |
| gga | aag | aaa | gtg | aag | atg | aac | acg | atg | att | cga | tcg | aag | ttg | ttt | tca | 96 |
| Gly | Lys | Lys | Val | Lys | Met | Asn | Thr | Met | Ile | Arg | Ser | Lys | Leu | Phe | Ser | |
| | | | 20 | | | | | 25 | | | | | 30 | | | |
| att | cgg | tcg | gct | ttg | gac | act | aag | gtg | tct | gat | atg | agc | gtc | aat | gct | 144 |
| Ile | Arg | Ser | Ala | Leu | Asp | Thr | Lys | Val | Ser | Asp | Met | Ser | Val | Asn | Ala | |
| | | 35 | | | | | 40 | | | | | 45 | | | | |
| cca | aaa | gga | ttg | ttt | cca | cca | gag | cct | gag | cac | tac | agg | ggg | cca | aag | 192 |
| Pro | Lys | Gly | Leu | Phe | Pro | Pro | Glu | Pro | Glu | His | Tyr | Arg | Gly | Pro | Lys | |
| | 50 | | | | | 55 | | | | | 60 | | | | | |
| ctt | aaa | gtg | gct | atc | att | gga | gct | ggg | ctc | gct | ggc | atg | tca | act | gca | 240 |
| Leu | Lys | Val | Ala | Ile | Ile | Gly | Ala | Gly | Leu | Ala | Gly | Met | Ser | Thr | Ala | |

```
                65                  70                  75                  80
gtg gag ctt ttg gat caa ggg cat gag gtt gac ata tat gaa tcc aga       288
Val Glu Leu Leu Asp Gln Gly His Glu Val Asp Ile Tyr Glu Ser Arg
                        85                  90                  95 caa ttt att ggt ggt aaa gtc ggt tct ttt gta gat aag cgt gga aac       336
Gln Phe Ile Gly Gly Lys Val Gly Ser Phe Val Asp Lys Arg Gly Asn
                100                 105                 110 cat att gaa atg gga ctc cat gtg ttt ttt ggt tgc tat aac aat ctt       384
His Ile Glu Met Gly Leu His Val Phe Phe Gly Cys Tyr Asn Asn Leu
                115                 120                 125 ttc aga ctt atg aaa aag gta ggt gca gat gaa aat tta ctg gtg aag       432
Phe Arg Leu Met Lys Lys Val Gly Ala Asp Glu Asn Leu Leu Val Lys
            130                 135                 140 gat cat act cat acc ttt gta aac cga ggt gga gaa att ggt gaa ctt       480
Asp His Thr His Thr Phe Val Asn Arg Gly Gly Glu Ile Gly Glu Leu
145                 150                 155                 160 gat ttc cga ctt ccg atg ggt gca cca tta cat ggt att cgt gca ttt       528
Asp Phe Arg Leu Pro Met Gly Ala Pro Leu His Gly Ile Arg Ala Phe
                    165                 170                 175 cta aca act aat caa ctg aag cct tat gat aaa gca agg aat gct gtg       576
Leu Thr Thr Asn Gln Leu Lys Pro Tyr Asp Lys Ala Arg Asn Ala Val
                180                 185                 190 gct ctt gcc ctt agc cca gtt gta cgt gct ctt att gat cca aat ggt       624
Ala Leu Ala Leu Ser Pro Val Val Arg Ala Leu Ile Asp Pro Asn Gly
                195                 200                 205 gca atg cag gat ata agg aac tta gat aat att agc ttt tct gat tgg       672
Ala Met Gln Asp Ile Arg Asn Leu Asp Asn Ile Ser Phe Ser Asp Trp
210                 215                 220 ttc tta tcc aaa ggc ggt acc cgc atg agc atc caa agg atg tgg gat       720
Phe Leu Ser Lys Gly Gly Thr Arg Met Ser Ile Gln Arg Met Trp Asp
225                 230                 235                 240 cca gtt gct tat gcc ctc gga ttt att gac tgt gat aat atc agt gcc       768
Pro Val Ala Tyr Ala Leu Gly Phe Ile Asp Cys Asp Asn Ile Ser Ala
                    245                 250                 255 cgt tgt atg ctt act ata ttt tct cta ttt gct act aag aca gaa gct       816
Arg Cys Met Leu Thr Ile Phe Ser Leu Phe Ala Thr Lys Thr Glu Ala
                260                 265                 270 tct ctg ttg cgt atg ttg aag ggt tcg cct gat gtt tac tta agc ggt       864
Ser Leu Leu Arg Met Leu Lys Gly Ser Pro Asp Val Tyr Leu Ser Gly
                275                 280                 285 cct ata aga aag tat att aca gat aaa ggt gga agg ttt cac cta agg       912
Pro Ile Arg Lys Tyr Ile Thr Asp Lys Gly Gly Arg Phe His Leu Arg
290                 295                 300 tgg ggg tgt aga gag ata ctt tat gat gaa cta tca aat ggc gac aca       960
Trp Gly Cys Arg Glu Ile Leu Tyr Asp Glu Leu Ser Asn Gly Asp Thr
305                 310                 315                 320 tat atc aca ggc att gca atg tcg aag gct acc aat aaa aaa ctt gtg      1008
Tyr Ile Thr Gly Ile Ala Met Ser Lys Ala Thr Asn Lys Lys Leu Val
                    325                 330                 335 aaa gct gac gtg tat gtt gca gca tgt gat gtt cct gga ata aaa agg      1056
Lys Ala Asp Val Tyr Val Ala Ala Cys Asp Val Pro Gly Ile Lys Arg
                340                 345                 350 ttg atc cca tcg gag tgg aga gaa tgg gat cta ttt gac aat atc tat      1104
Leu Ile Pro Ser Glu Trp Arg Glu Trp Asp Leu Phe Asp Asn Ile Tyr
                355                 360                 365 aaa cta gtt gga gtt cca gtt gtc act gtt cag ctt agg tac aat ggt      1152
Lys Leu Val Gly Val Pro Val Val Thr Val Gln Leu Arg Tyr Asn Gly
370                 375                 380 tgg gtg aca gag atg caa gat ctg gaa aaa tca agg cag ttg aga gct      1200
```

```
Trp Val Thr Glu Met Gln Asp Leu Glu Lys Ser Arg Gln Leu Arg Ala
385                 390                 395                 400 gca gta gga ttg gat aat ctt ctt tat act cca gat gca gac ttt tct    1248
Ala Val Gly Leu Asp Asn Leu Leu Tyr Thr Pro Asp Ala Asp Phe Ser
                405                 410                 415 tgt ttt tct gat ctt gca ctc tcg tcg cct gaa gat tat tat att gaa    1296
Cys Phe Ser Asp Leu Ala Leu Ser Ser Pro Glu Asp Tyr Tyr Ile Glu
                420                 425                 430 gga caa ggg tcc cta ata cag gct gtt ctc acg cca ggg gat cca tac    1344
Gly Gln Gly Ser Leu Ile Gln Ala Val Leu Thr Pro Gly Asp Pro Tyr
                435                 440                 445 atg ccc cta cct aat gat gca att ata gaa aga gtt cgg aaa cag gtt    1392
Met Pro Leu Pro Asn Asp Ala Ile Ile Glu Arg Val Arg Lys Gln Val
        450                 455                 460 ttg gat tta ttc cca tcc tct caa ggc ctg gaa gtt cta tgg tct tcg    1440
Leu Asp Leu Phe Pro Ser Ser Gln Gly Leu Glu Val Leu Trp Ser Ser
465                 470                 475                 480 gtg gtt aaa atc gga caa tcc cta tat cgg gag ggg cct gga aag gac    1488
Val Val Lys Ile Gly Gln Ser Leu Tyr Arg Glu Gly Pro Gly Lys Asp
                485                 490                 495 cca ttc aga cct gat cag aag aca cca gta aaa aat ttc ttc ctt gca    1536
Pro Phe Arg Pro Asp Gln Lys Thr Pro Val Lys Asn Phe Phe Leu Ala
                500                 505                 510 ggt tca tac acc aaa cag gat tac att gac agt atg gaa gga gcg acc    1584
Gly Ser Tyr Thr Lys Gln Asp Tyr Ile Asp Ser Met Glu Gly Ala Thr
                515                 520                 525 cta tcg ggg aga caa gca gct gca tat atc tgc agc gcc ggt gaa gat    1632
Leu Ser Gly Arg Gln Ala Ala Ala Tyr Ile Cys Ser Ala Gly Glu Asp
530                 535                 540 ctg gca gca ctt cgc aag aag atc gct gct gat cat cca gag caa ctg    1680
Leu Ala Ala Leu Arg Lys Lys Ile Ala Ala Asp His Pro Glu Gln Leu
545                 550                 555                 560 atc aac aaa gat tct aac gtg tcg gat gaa ctg agt ctc gta taa        1725
Ile Asn Lys Asp Ser Asn Val Ser Asp Glu Leu Ser Leu Val
                565                 570

<210> SEQ ID NO 132
<211> LENGTH: 574
<212> TYPE: PRT
<213> ORGANISM: Narcissus pseudonarcissus

<400> SEQUENCE: 132

Met Ala Ser Ser Thr Cys Leu Ile His Ser Ser Phe Gly Val Gly
1               5                   10                  15

Gly Lys Lys Val Lys Met Asn Thr Met Ile Arg Ser Lys Leu Phe Ser
                20                  25                  30

Ile Arg Ser Ala Leu Asp Thr Lys Val Ser Asp Met Ser Val Asn Ala
            35                  40                  45

Pro Lys Gly Leu Phe Pro Pro Glu Pro Glu His Tyr Arg Gly Pro Lys
        50                  55                  60

Leu Lys Val Ala Ile Ile Gly Ala Gly Leu Ala Gly Met Ser Thr Ala
65                  70                  75                  80

Val Glu Leu Leu Asp Gln Gly His Glu Val Asp Ile Tyr Glu Ser Arg
                85                  90                  95

Gln Phe Ile Gly Gly Lys Val Gly Ser Phe Val Asp Lys Arg Gly Asn
            100                 105                 110

His Ile Glu Met Gly Leu His Val Phe Phe Gly Cys Tyr Asn Asn Leu
        115                 120                 125
```

-continued

```
Phe Arg Leu Met Lys Val Gly Ala Asp Glu Asn Leu Val Lys
    130                 135                 140

Asp His Thr His Thr Phe Val Asn Arg Gly Glu Ile Gly Glu Leu
145                 150                 155                 160

Asp Phe Arg Leu Pro Met Gly Ala Pro Leu His Gly Ile Arg Ala Phe
                165                 170                 175

Leu Thr Thr Asn Gln Leu Lys Pro Tyr Asp Lys Ala Arg Asn Ala Val
                180                 185                 190

Ala Leu Ala Leu Ser Pro Val Arg Ala Leu Ile Asp Pro Asn Gly
            195                 200                 205

Ala Met Gln Asp Ile Arg Asn Leu Asp Asn Ile Ser Phe Ser Asp Trp
    210                 215                 220

Phe Leu Ser Lys Gly Gly Thr Arg Met Ser Ile Gln Arg Met Trp Asp
225                 230                 235                 240

Pro Val Ala Tyr Ala Leu Gly Phe Ile Asp Cys Asp Asn Ile Ser Ala
                245                 250                 255

Arg Cys Met Leu Thr Ile Phe Ser Leu Phe Ala Thr Lys Thr Glu Ala
                260                 265                 270

Ser Leu Leu Arg Met Leu Lys Gly Ser Pro Asp Val Tyr Leu Ser Gly
            275                 280                 285

Pro Ile Arg Lys Tyr Ile Thr Asp Lys Gly Arg Phe His Leu Arg
    290                 295                 300

Trp Gly Cys Arg Glu Ile Leu Tyr Asp Glu Leu Ser Asn Gly Asp Thr
305                 310                 315                 320

Tyr Ile Thr Gly Ile Ala Met Ser Lys Ala Thr Asn Lys Lys Leu Val
                325                 330                 335

Lys Ala Asp Val Tyr Val Ala Ala Cys Asp Val Pro Gly Ile Lys Arg
            340                 345                 350

Leu Ile Pro Ser Glu Trp Arg Glu Trp Asp Leu Phe Asp Asn Ile Tyr
    355                 360                 365

Lys Leu Val Gly Val Pro Val Val Thr Val Gln Leu Arg Tyr Asn Gly
    370                 375                 380

Trp Val Thr Glu Met Gln Asp Leu Glu Lys Ser Arg Gln Leu Arg Ala
385                 390                 395                 400

Ala Val Gly Leu Asp Asn Leu Leu Tyr Thr Pro Asp Ala Asp Phe Ser
                405                 410                 415

Cys Phe Ser Asp Leu Ala Leu Ser Ser Pro Glu Asp Tyr Tyr Ile Glu
                420                 425                 430

Gly Gln Gly Ser Leu Ile Gln Ala Val Leu Thr Pro Gly Asp Pro Tyr
            435                 440                 445

Met Pro Leu Pro Asn Asp Ala Ile Ile Glu Arg Val Arg Lys Gln Val
    450                 455                 460

Leu Asp Leu Phe Pro Ser Ser Gln Gly Leu Glu Val Leu Trp Ser Ser
465                 470                 475                 480

Val Val Lys Ile Gly Gln Ser Leu Tyr Arg Glu Gly Pro Gly Lys Asp
                485                 490                 495

Pro Phe Arg Pro Asp Gln Lys Thr Pro Val Lys Asn Phe Phe Leu Ala
                500                 505                 510

Gly Ser Tyr Thr Lys Gln Asp Tyr Ile Asp Ser Met Glu Gly Ala Thr
            515                 520                 525

Leu Ser Gly Arg Gln Ala Ala Ala Tyr Ile Cys Ser Ala Gly Glu Asp
    530                 535                 540

Leu Ala Ala Leu Arg Lys Lys Ile Ala Ala Asp His Pro Glu Gln Leu
```

-continued

```
         545                 550                 555                 560
Ile Asn Lys Asp Ser Asn Val Ser Asp Glu Leu Ser Leu Val
                565                 570

<210> SEQ ID NO 133
<211> LENGTH: 1848
<212> TYPE: DNA
<213> ORGANISM: Lycopersicon esculentum
<220> FEATURE:
<221> NAME/KEY: CDS

<400> SEQUENCE: 133 atg tgt acc ttg agt ttt atg tat cct aat tca ctt ctt gat ggt acc      48
Met Cys Thr Leu Ser Phe Met Tyr Pro Asn Ser Leu Leu Asp Gly Thr
1               5                  10                  15 tgc aag act gta gct ttg ggt gat agc aaa cca aga tac aat aaa cag      96
Cys Lys Thr Val Ala Leu Gly Asp Ser Lys Pro Arg Tyr Asn Lys Gln
            20                  25                  30 aga agt tct tgt ttt gac cct ttg ata att gga aat tgt act gat cag     144
Arg Ser Ser Cys Phe Asp Pro Leu Ile Ile Gly Asn Cys Thr Asp Gln
        35                  40                  45 cag cag ctt tgt ggc ttg agt tgg ggg gtg gac aag gct aag gga aga     192
Gln Gln Leu Cys Gly Leu Ser Trp Gly Val Asp Lys Ala Lys Gly Arg
    50                  55                  60 aga ggg ggt act gtt tcc aat ttg aaa gca gtt gta gat gta gac aaa     240
Arg Gly Gly Thr Val Ser Asn Leu Lys Ala Val Val Asp Val Asp Lys
65                  70                  75                  80 aga gtg gag agc tat ggc agt agt gat gta gaa gga aat gag agt ggc     288
Arg Val Glu Ser Tyr Gly Ser Ser Asp Val Glu Gly Asn Glu Ser Gly
                85                  90                  95 agc tat gat gcc att gtt ata ggt tca gga ata ggt gga ttg gtg gca     336
Ser Tyr Asp Ala Ile Val Ile Gly Ser Gly Ile Gly Gly Leu Val Ala
            100                 105                 110 gcg acg cag ctg gcg gtt aag gga gct aag gtt tta gtt ctg gag aag     384
Ala Thr Gln Leu Ala Val Lys Gly Ala Lys Val Leu Val Leu Glu Lys
        115                 120                 125 tat gtt att cct ggt gga agc tct ggc ttt tac gag agg gat ggt tat     432
Tyr Val Ile Pro Gly Gly Ser Ser Gly Phe Tyr Glu Arg Asp Gly Tyr
    130                 135                 140 aag ttt gat gtt ggt tca tca gtg atg ttt gga ttc agt gat aag gga     480
Lys Phe Asp Val Gly Ser Ser Val Met Phe Gly Phe Ser Asp Lys Gly
145                 150                 155                 160 aac ctc aat tta att act caa gca ttg gca gca gta gga cgt aaa tta     528
Asn Leu Asn Leu Ile Thr Gln Ala Leu Ala Ala Val Gly Arg Lys Leu
                165                 170                 175 gaa gtt ata cct gac cca aca act gta cat ttc cac ctg cca aat gac     576
Glu Val Ile Pro Asp Pro Thr Thr Val His Phe His Leu Pro Asn Asp
            180                 185                 190 ctt tct gtt cgt ata cac cga gag tat gat gac ttc att gaa gag ctt     624
Leu Ser Val Arg Ile His Arg Glu Tyr Asp Asp Phe Ile Glu Glu Leu
        195                 200                 205 gtg agt aaa ttt cca cat gaa aag gaa ggg att atc aaa ttt tac agt     672
Val Ser Lys Phe Pro His Glu Lys Glu Gly Ile Ile Lys Phe Tyr Ser
    210                 215                 220 gaa tgc tgg aag atc ttt aat tct ctg aat tca ttg gaa ctg aag tct     720
Glu Cys Trp Lys Ile Phe Asn Ser Leu Asn Ser Leu Glu Leu Lys Ser
225                 230                 235                 240 ttg gag gaa ccc atc tac ctt ttt ggc cag ttc ttt aag aag ccc ctt     768
Leu Glu Glu Pro Ile Tyr Leu Phe Gly Gln Phe Phe Lys Lys Pro Leu
                245                 250                 255
```

```
                                                         -continued gaa tgc ttg act ctt gcc tac tat ttg ccc cag aat gct ggt agc atc    816
Glu Cys Leu Thr Leu Ala Tyr Tyr Leu Pro Gln Asn Ala Gly Ser Ile
        260                 265                 270 gct cgg aag tat ata aga gat cct ggg ttg ctg tct ttt ata gat gca    864
Ala Arg Lys Tyr Ile Arg Asp Pro Gly Leu Leu Ser Phe Ile Asp Ala
275                 280                 285 gag tgc ttt atc gtg agt aca gtt aat gca tta caa aca cca atg atc    912
Glu Cys Phe Ile Val Ser Thr Val Asn Ala Leu Gln Thr Pro Met Ile
    290                 295                 300 aat gca agc atg gtt cta tgt gac aga cat ttt ggc gga atc aac tac    960
Asn Ala Ser Met Val Leu Cys Asp Arg His Phe Gly Gly Ile Asn Tyr
305                 310                 315                 320 ccc gtt ggt gga gtt ggc gag atc gcc aaa tcc tta gca aaa ggc ttg   1008
Pro Val Gly Gly Val Gly Glu Ile Ala Lys Ser Leu Ala Lys Gly Leu
                325                 330                 335 gat gat cac gga agt cag ata ctt tat agg gca aat gtt aca agt atc   1056
Asp Asp His Gly Ser Gln Ile Leu Tyr Arg Ala Asn Val Thr Ser Ile
            340                 345                 350 att ttg gac aat ggc aaa gct gtg gga gtg aag ctt tct gac ggg agg   1104
Ile Leu Asp Asn Gly Lys Ala Val Gly Val Lys Leu Ser Asp Gly Arg
        355                 360                 365 aag ttt tat gct aaa acc ata gta tcg aat gct acc aga tgg gat act   1152
Lys Phe Tyr Ala Lys Thr Ile Val Ser Asn Ala Thr Arg Trp Asp Thr
370                 375                 380 ttt gga aag ctt tta aaa gct gag aat ctg cca aaa gaa gaa gaa aat   1200
Phe Gly Lys Leu Leu Lys Ala Glu Asn Leu Pro Lys Glu Glu Glu Asn
385                 390                 395                 400 ttc cag aaa gct tat gta aaa gca cct tct ttt ctt tct att cat atg   1248
Phe Gln Lys Ala Tyr Val Lys Ala Pro Ser Phe Leu Ser Ile His Met
                405                 410                 415 gga gtt aaa gca gat gta ctc cca cca gac aca gat tgt cac cat ttt   1296
Gly Val Lys Ala Asp Val Leu Pro Pro Asp Thr Asp Cys His His Phe
            420                 425                 430 gtc ctc gag gat gat tgg aca aat ttg gag aaa cca tat gga agt ata   1344
Val Leu Glu Asp Asp Trp Thr Asn Leu Glu Lys Pro Tyr Gly Ser Ile
        435                 440                 445 ttc ttg agt att cca aca gtt ctt gat tcc tca ttg gcc cca gaa gga   1392
Phe Leu Ser Ile Pro Thr Val Leu Asp Ser Ser Leu Ala Pro Glu Gly
450                 455                 460 cac cat att ctt cac att ttt aca aca tcg agc att gaa gat tgg gag   1440
His His Ile Leu His Ile Phe Thr Thr Ser Ser Ile Glu Asp Trp Glu
465                 470                 475                 480 gga ctc tct ccg aaa gac tat gaa gcg aag aaa gag gtt gtt gct gaa   1488
Gly Leu Ser Pro Lys Asp Tyr Glu Ala Lys Lys Glu Val Val Ala Glu
                485                 490                 495 agg att ata agc aga ctt gaa aaa aca ctc ttc cca ggg ctt aag tca   1536
Arg Ile Ile Ser Arg Leu Glu Lys Thr Leu Phe Pro Gly Leu Lys Ser
            500                 505                 510 tct att ctc ttt aag gag gtg gga act cca aag acc cac aga cga tac   1584
Ser Ile Leu Phe Lys Glu Val Gly Thr Pro Lys Thr His Arg Arg Tyr
        515                 520                 525 ctt gct cgt gat agt ggt acc tat gga cca atg cca cgc gga aca cct   1632
Leu Ala Arg Asp Ser Gly Thr Tyr Gly Pro Met Pro Arg Gly Thr Pro
530                 535                 540 aag gga ctc ctg gga atg cct ttc aat acc act gct ata gat ggt cta   1680
Lys Gly Leu Leu Gly Met Pro Phe Asn Thr Thr Ala Ile Asp Gly Leu
545                 550                 555                 560 tat tgt gtt ggc gat agt tgc ttc cca gga caa ggt gtt ata gct gta   1728
Tyr Cys Val Gly Asp Ser Cys Phe Pro Gly Gln Gly Val Ile Ala Val
                565                 570                 575
```

```
gcc ttt tca gga gta atg tgc gct cat cgt gtt gca gct gac tta ggg    1776
Ala Phe Ser Gly Val Met Cys Ala His Arg Val Ala Ala Asp Leu Gly
        580                 585                 590 ttt gaa aaa aaa tca gat gtg ctg gac agt gct ctt ctt aga cta ctt    1824
Phe Glu Lys Lys Ser Asp Val Leu Asp Ser Ala Leu Leu Arg Leu Leu
        595                 600                 605 ggt tgg tta agg aca cta gca tga                                    1848
Gly Trp Leu Arg Thr Leu Ala
        610             615
```

<210> SEQ ID NO 134
<211> LENGTH: 615
<212> TYPE: PRT
<213> ORGANISM: Lycopersicon esculentum

<400> SEQUENCE: 134

```
Met Cys Thr Leu Ser Phe Met Tyr Pro Asn Ser Leu Leu Asp Gly Thr
1               5                   10                  15

Cys Lys Thr Val Ala Leu Gly Asp Ser Lys Pro Arg Tyr Asn Lys Gln
            20                  25                  30

Arg Ser Ser Cys Phe Asp Pro Leu Ile Ile Gly Asn Cys Thr Asp Gln
        35                  40                  45

Gln Gln Leu Cys Gly Leu Ser Trp Gly Val Asp Lys Ala Lys Gly Arg
    50                  55                  60

Arg Gly Gly Thr Val Ser Asn Leu Lys Ala Val Val Asp Val Asp Lys
65                  70                  75                  80

Arg Val Glu Ser Tyr Gly Ser Ser Asp Val Glu Asn Glu Ser Gly
                85                  90                  95

Ser Tyr Asp Ala Ile Val Ile Gly Ser Gly Ile Gly Gly Leu Val Ala
            100                 105                 110

Ala Thr Gln Leu Ala Val Lys Gly Ala Lys Val Leu Val Leu Glu Lys
        115                 120                 125

Tyr Val Ile Pro Gly Gly Ser Ser Gly Phe Tyr Glu Arg Asp Gly Tyr
    130                 135                 140

Lys Phe Asp Val Gly Ser Ser Val Met Phe Gly Phe Ser Asp Lys Gly
145                 150                 155                 160

Asn Leu Asn Leu Ile Thr Gln Ala Leu Ala Ala Val Gly Arg Lys Leu
                165                 170                 175

Glu Val Ile Pro Asp Pro Thr Thr Val His Phe His Leu Pro Asn Asp
            180                 185                 190

Leu Ser Val Arg Ile His Arg Glu Tyr Asp Asp Phe Ile Glu Glu Leu
        195                 200                 205

Val Ser Lys Phe Pro His Glu Lys Glu Gly Ile Ile Lys Phe Tyr Ser
    210                 215                 220

Glu Cys Trp Lys Ile Phe Asn Ser Leu Asn Ser Leu Glu Leu Lys Ser
225                 230                 235                 240

Leu Glu Glu Pro Ile Tyr Leu Phe Gly Gln Phe Phe Lys Lys Pro Leu
                245                 250                 255

Glu Cys Leu Thr Leu Ala Tyr Tyr Leu Pro Gln Asn Ala Gly Ser Ile
            260                 265                 270

Ala Arg Lys Tyr Ile Arg Asp Pro Gly Leu Leu Ser Phe Ile Asp Ala
        275                 280                 285

Glu Cys Phe Ile Val Ser Thr Val Asn Ala Leu Gln Thr Pro Met Ile
    290                 295                 300

Asn Ala Ser Met Val Leu Cys Asp Arg His Phe Gly Gly Ile Asn Tyr
```

```
                305                 310                 315                 320
Pro Val Gly Gly Val Gly Glu Ile Ala Lys Ser Leu Ala Lys Gly Leu
                    325                 330                 335

Asp Asp His Gly Ser Gln Ile Leu Tyr Arg Ala Asn Val Thr Ser Ile
                340                 345                 350

Ile Leu Asp Asn Gly Lys Ala Val Gly Val Lys Leu Ser Asp Gly Arg
                355                 360                 365

Lys Phe Tyr Ala Lys Thr Ile Val Ser Asn Ala Thr Arg Trp Asp Thr
    370                 375                 380

Phe Gly Lys Leu Lys Ala Glu Asn Leu Pro Lys Glu Glu Asn
385                 390                 395                 400

Phe Gln Lys Ala Tyr Val Lys Ala Pro Ser Phe Leu Ser Ile His Met
                405                 410                 415

Gly Val Lys Ala Asp Val Leu Pro Pro Asp Thr Asp Cys His His Phe
                420                 425                 430

Val Leu Glu Asp Asp Trp Thr Asn Leu Glu Lys Pro Tyr Gly Ser Ile
            435                 440                 445

Phe Leu Ser Ile Pro Thr Val Leu Asp Ser Ser Leu Ala Pro Glu Gly
    450                 455                 460

His His Ile Leu His Ile Phe Thr Thr Ser Ser Ile Glu Asp Trp Glu
465                 470                 475                 480

Gly Leu Ser Pro Lys Asp Tyr Glu Ala Lys Lys Glu Val Val Ala Glu
                485                 490                 495

Arg Ile Ile Ser Arg Leu Glu Lys Thr Leu Phe Pro Gly Leu Lys Ser
            500                 505                 510

Ser Ile Leu Phe Lys Glu Val Gly Thr Pro Lys Thr His Arg Arg Tyr
        515                 520                 525

Leu Ala Arg Asp Ser Gly Thr Tyr Gly Pro Met Pro Arg Gly Thr Pro
    530                 535                 540

Lys Gly Leu Leu Gly Met Pro Phe Asn Thr Thr Ala Ile Asp Gly Leu
545                 550                 555                 560

Tyr Cys Val Gly Asp Ser Cys Phe Pro Gly Gln Gly Val Ile Ala Val
                565                 570                 575

Ala Phe Ser Gly Val Met Cys Ala His Arg Val Ala Ala Asp Leu Gly
                580                 585                 590

Phe Glu Lys Lys Ser Asp Val Leu Asp Ser Ala Leu Leu Arg Leu Leu
        595                 600                 605

Gly Trp Leu Arg Thr Leu Ala
        610                 615

<210> SEQ ID NO 135
<211> LENGTH: 1233
<212> TYPE: DNA
<213> ORGANISM: Tagetes erecta
<220> FEATURE:
<221> NAME/KEY: CDS

<400> SEQUENCE: 135 atg gcc aca cac aaa ctc ctt caa ttc acc acc aat ctc cca cca tct     48
Met Ala Thr His Lys Leu Leu Gln Phe Thr Thr Asn Leu Pro Pro Ser
1               5                   10                  15 tct tct tca atc tct act ggc tgt tca ctc tcc ccc ttc ttc ctc aaa     96
Ser Ser Ser Ile Ser Thr Gly Cys Ser Leu Ser Pro Phe Phe Leu Lys
            20                  25                  30 tca tct tct cat tcc cct aac cct cgc cga cac cgc cgc tcc gcc gta    144
Ser Ser Ser His Ser Pro Asn Pro Arg Arg His Arg Arg Ser Ala Val
```

-continued

|   |   |   |   | 35 |   |   |   | 40 |   |   |   | 45 |   |   |   |      |
|---|---|---|---|----|---|---|---|----|---|---|---|----|---|---|---|------|
| tgc | tgc | tct | ttc | gcc | tca | ctc | gac | tct | gca | aaa | atc | aaa | gtc | gtt | ggc | 192 |
| Cys | Cys | Ser | Phe | Ala | Ser | Leu | Asp | Ser | Ala | Lys | Ile | Lys | Val | Val | Gly |   |
|   | 50 |   |   |   | 55 |   |   |   | 60 |   |   |   |   |   |   |   |

| gtc | ggt | ggt | ggt | ggc | aac | aat | gcc | gtt | aac | cgc | atg | att | ggt | agc | ggc | 240 |
|---|---|---|---|---|---|---|---|---|---|---|---|---|---|---|---|---|
| Val | Gly | Gly | Gly | Gly | Asn | Asn | Ala | Val | Asn | Arg | Met | Ile | Gly | Ser | Gly |   |
| 65 |   |   |   |   | 70 |   |   |   | 75 |   |   |   |   | 80 |   |   |

| tta | cag | ggt | gtt | gat | ttt | tac | gcc | att | aac | acg | gac | tca | caa | gcg | ctt | 288 |
|---|---|---|---|---|---|---|---|---|---|---|---|---|---|---|---|---|
| Leu | Gln | Gly | Val | Asp | Phe | Tyr | Ala | Ile | Asn | Thr | Asp | Ser | Gln | Ala | Leu |   |
|   |   |   |   | 85 |   |   |   |   | 90 |   |   |   |   | 95 |   |   |

| ctg | caa | tct | gtt | gca | cat | aac | cct | att | caa | att | ggg | gag | ctt | ttg | act | 336 |
|---|---|---|---|---|---|---|---|---|---|---|---|---|---|---|---|---|
| Leu | Gln | Ser | Val | Ala | His | Asn | Pro | Ile | Gln | Ile | Gly | Glu | Leu | Leu | Thr |   |
|   |   | 100 |   |   |   |   | 105 |   |   |   |   | 110 |   |   |   |   |

| cgt | gga | tta | ggt | act | ggt | ggg | aac | ccg | ctt | ttg | gga | gaa | cag | gct | gcg | 384 |
|---|---|---|---|---|---|---|---|---|---|---|---|---|---|---|---|---|
| Arg | Gly | Leu | Gly | Thr | Gly | Gly | Asn | Pro | Leu | Leu | Gly | Glu | Gln | Ala | Ala |   |
|   |   | 115 |   |   |   |   | 120 |   |   |   |   | 125 |   |   |   |   |

| gag | gag | tcg | aag | gaa | gcg | att | ggg | aat | gcg | ctt | aaa | ggg | tcg | gat | ctt | 432 |
|---|---|---|---|---|---|---|---|---|---|---|---|---|---|---|---|---|
| Glu | Glu | Ser | Lys | Glu | Ala | Ile | Gly | Asn | Ala | Leu | Lys | Gly | Ser | Asp | Leu |   |
|   | 130 |   |   |   |   | 135 |   |   |   |   | 140 |   |   |   |   |   |

| gtg | ttt | ata | aca | gca | ggt | atg | ggt | ggt | ggg | acg | ggt | tcg | ggt | gct | gct | 480 |
|---|---|---|---|---|---|---|---|---|---|---|---|---|---|---|---|---|
| Val | Phe | Ile | Thr | Ala | Gly | Met | Gly | Gly | Gly | Thr | Gly | Ser | Gly | Ala | Ala |   |
| 145 |   |   |   |   | 150 |   |   |   | 155 |   |   |   |   | 160 |   |   |

| cca | gtt | gta | gcg | cag | ata | gcg | aaa | gaa | gca | ggg | tat | tta | act | gtt | ggt | 528 |
|---|---|---|---|---|---|---|---|---|---|---|---|---|---|---|---|---|
| Pro | Val | Val | Ala | Gln | Ile | Ala | Lys | Glu | Ala | Gly | Tyr | Leu | Thr | Val | Gly |   |
|   |   |   | 165 |   |   |   |   | 170 |   |   |   |   | 175 |   |   |   |

| gtt | gta | acg | tac | cca | ttc | agc | ttt | gaa | ggc | cgt | aaa | aga | tca | gta | cag | 576 |
|---|---|---|---|---|---|---|---|---|---|---|---|---|---|---|---|---|
| Val | Val | Thr | Tyr | Pro | Phe | Ser | Phe | Glu | Gly | Arg | Lys | Arg | Ser | Val | Gln |   |
|   |   | 180 |   |   |   |   | 185 |   |   |   |   | 190 |   |   |   |   |

| gcg | tta | gag | gct | att | gag | aag | ctg | caa | aag | aac | gtt | gac | aca | ctt | ata | 624 |
|---|---|---|---|---|---|---|---|---|---|---|---|---|---|---|---|---|
| Ala | Leu | Glu | Ala | Ile | Glu | Lys | Leu | Gln | Lys | Asn | Val | Asp | Thr | Leu | Ile |   |
|   |   | 195 |   |   |   |   | 200 |   |   |   |   | 205 |   |   |   |   |

| gtg | att | cca | aat | gac | cgt | ttg | ctg | gat | att | gct | gat | gaa | aac | acg | cct | 672 |
|---|---|---|---|---|---|---|---|---|---|---|---|---|---|---|---|---|
| Val | Ile | Pro | Asn | Asp | Arg | Leu | Leu | Asp | Ile | Ala | Asp | Glu | Asn | Thr | Pro |   |
|   | 210 |   |   |   |   | 215 |   |   |   |   | 220 |   |   |   |   |   |

| ctt | cag | gat | gct | ttt | ctt | ctt | gct | gat | gat | gta | ctc | cgc | caa | gga | gtt | 720 |
|---|---|---|---|---|---|---|---|---|---|---|---|---|---|---|---|---|
| Leu | Gln | Asp | Ala | Phe | Leu | Leu | Ala | Asp | Asp | Val | Leu | Arg | Gln | Gly | Val |   |
| 225 |   |   |   |   | 230 |   |   |   |   | 235 |   |   |   |   | 240 |   |

| caa | gga | atc | tca | gat | ata | att | aca | ata | cct | ggg | ctg | gta | aat | gtg | gac | 768 |
|---|---|---|---|---|---|---|---|---|---|---|---|---|---|---|---|---|
| Gln | Gly | Ile | Ser | Asp | Ile | Ile | Thr | Ile | Pro | Gly | Leu | Val | Asn | Val | Asp |   |
|   |   |   | 245 |   |   |   |   | 250 |   |   |   |   | 255 |   |   |   |

| ttt | gca | gac | gtt | aaa | gca | gtc | atg | aaa | gat | tct | gga | act | gca | atg | ctt | 816 |
|---|---|---|---|---|---|---|---|---|---|---|---|---|---|---|---|---|
| Phe | Ala | Asp | Val | Lys | Ala | Val | Met | Lys | Asp | Ser | Gly | Thr | Ala | Met | Leu |   |
|   |   |   | 260 |   |   |   |   | 265 |   |   |   |   | 270 |   |   |   |

| ggt | gtc | ggt | gtt | tcc | tca | agt | aaa | aac | cga | gct | gaa | gaa | gca | gct | gaa | 864 |
|---|---|---|---|---|---|---|---|---|---|---|---|---|---|---|---|---|
| Gly | Val | Gly | Val | Ser | Ser | Ser | Lys | Asn | Arg | Ala | Glu | Glu | Ala | Ala | Glu |   |
|   |   | 275 |   |   |   |   | 280 |   |   |   |   | 285 |   |   |   |   |

| caa | gca | act | ctt | gct | cct | ttg | att | gga | tca | tca | att | caa | tct | gct | aca | 912 |
|---|---|---|---|---|---|---|---|---|---|---|---|---|---|---|---|---|
| Gln | Ala | Thr | Leu | Ala | Pro | Leu | Ile | Gly | Ser | Ser | Ile | Gln | Ser | Ala | Thr |   |
|   | 290 |   |   |   |   | 295 |   |   |   |   | 300 |   |   |   |   |   |

| ggt | gtt | gtt | tat | aat | att | acc | gga | ggg | aag | gac | ata | act | cta | caa | gaa | 960 |
|---|---|---|---|---|---|---|---|---|---|---|---|---|---|---|---|---|
| Gly | Val | Val | Tyr | Asn | Ile | Thr | Gly | Gly | Lys | Asp | Ile | Thr | Leu | Gln | Glu |   |
| 305 |   |   |   |   | 310 |   |   |   |   | 315 |   |   |   |   | 320 |   |

| gtc | aac | agg | gtt | tct | cag | gtg | gta | aca | agt | ttg | gca | gat | cca | tca | gca | 1008 |
|---|---|---|---|---|---|---|---|---|---|---|---|---|---|---|---|---|
| Val | Asn | Arg | Val | Ser | Gln | Val | Val | Thr | Ser | Leu | Ala | Asp | Pro | Ser | Ala |   |
|   |   |   | 325 |   |   |   |   | 330 |   |   |   |   | 335 |   |   |   |

| aac | att | ata | ttc | ggg | gca | gtg | gta | gat | gag | aga | tac | aac | ggg | gag | att | 1056 |
|---|---|---|---|---|---|---|---|---|---|---|---|---|---|---|---|---|
| Asn | Ile | Ile | Phe | Gly | Ala | Val | Val | Asp | Glu | Arg | Tyr | Asn | Gly | Glu | Ile |   |
|   |   |   | 340 |   |   |   |   | 345 |   |   |   |   | 350 |   |   |   |

| cat | gtg | acc | att | gtt | gct | act | ggc | ttt | gcc | cag | tcg | ttt | cag | aaa | tct | 1104 |

```
His Val Thr Ile Val Ala Thr Gly Phe Ala Gln Ser Phe Gln Lys Ser
            355                 360                 365 ctt ctt gct gac ccg aaa gga gca aaa ctt gtt gat aga aat caa gaa    1152
Leu Leu Ala Asp Pro Lys Gly Ala Lys Leu Val Asp Arg Asn Gln Glu
        370                 375                 380 cct aca caa cct ttg act tcc gcg aga tct ttg aca aca cct tct cct    1200
Pro Thr Gln Pro Leu Thr Ser Ala Arg Ser Leu Thr Thr Pro Ser Pro
385                 390                 395                 400 gct ccg tct cgg tct agg aaa ctc ttc ttt taa                        1233
Ala Pro Ser Arg Ser Arg Lys Leu Phe Phe
                405                 410

<210> SEQ ID NO 136
<211> LENGTH: 410
<212> TYPE: PRT
<213> ORGANISM: Tagetes erecta

<400> SEQUENCE: 136

Met Ala Thr His Lys Leu Leu Gln Phe Thr Thr Asn Leu Pro Pro Ser
1               5                   10                  15

Ser Ser Ser Ile Ser Thr Gly Cys Ser Leu Ser Pro Phe Phe Leu Lys
            20                  25                  30

Ser Ser Ser His Ser Pro Asn Pro Arg Arg His Arg Arg Ser Ala Val
        35                  40                  45

Cys Cys Ser Phe Ala Ser Leu Asp Ser Ala Lys Ile Lys Val Val Gly
    50                  55                  60

Val Gly Gly Gly Gly Asn Asn Ala Val Asn Arg Met Ile Gly Ser Gly
65                  70                  75                  80

Leu Gln Gly Val Asp Phe Tyr Ala Ile Asn Thr Asp Ser Gln Ala Leu
                85                  90                  95

Leu Gln Ser Val Ala His Asn Pro Ile Gln Ile Gly Glu Leu Leu Thr
            100                 105                 110

Arg Gly Leu Gly Thr Gly Gly Asn Pro Leu Leu Gly Glu Gln Ala Ala
        115                 120                 125

Glu Glu Ser Lys Glu Ala Ile Gly Asn Ala Leu Lys Gly Ser Asp Leu
    130                 135                 140

Val Phe Ile Thr Ala Gly Met Gly Gly Gly Thr Gly Ser Gly Ala Ala
145                 150                 155                 160

Pro Val Val Ala Gln Ile Ala Lys Glu Ala Gly Tyr Leu Thr Val Gly
                165                 170                 175

Val Val Thr Tyr Pro Phe Ser Phe Glu Gly Arg Lys Arg Ser Val Gln
            180                 185                 190

Ala Leu Glu Ala Ile Glu Lys Leu Gln Lys Asn Val Asp Thr Leu Ile
        195                 200                 205

Val Ile Pro Asn Asp Arg Leu Leu Asp Ile Ala Asp Glu Asn Thr Pro
    210                 215                 220

Leu Gln Asp Ala Phe Leu Leu Ala Asp Val Leu Arg Gln Gly Val
225                 230                 235                 240

Gln Gly Ile Ser Asp Ile Ile Thr Ile Pro Gly Leu Val Asn Val Asp
                245                 250                 255

Phe Ala Asp Val Lys Ala Val Met Lys Asp Ser Gly Thr Ala Met Leu
            260                 265                 270

Gly Val Gly Val Ser Ser Ser Lys Asn Arg Ala Glu Glu Ala Ala Glu
        275                 280                 285

Gln Ala Thr Leu Ala Pro Leu Ile Gly Ser Ser Ile Gln Ser Ala Thr
    290                 295                 300
```

```
Gly Val Val Tyr Asn Ile Thr Gly Gly Lys Asp Ile Thr Leu Gln Glu
305                 310                 315                 320

Val Asn Arg Val Ser Gln Val Val Thr Ser Leu Ala Asp Pro Ser Ala
            325                 330                 335

Asn Ile Ile Phe Gly Ala Val Val Asp Glu Arg Tyr Asn Gly Glu Ile
                340                 345                 350

His Val Thr Ile Val Ala Thr Gly Phe Ala Gln Ser Phe Gln Lys Ser
            355                 360                 365

Leu Leu Ala Asp Pro Lys Gly Ala Lys Leu Val Asp Arg Asn Gln Glu
        370                 375                 380

Pro Thr Gln Pro Leu Thr Ser Ala Arg Ser Leu Thr Thr Pro Ser Pro
385                 390                 395                 400

Ala Pro Ser Arg Ser Arg Lys Leu Phe Phe
                405                 410

<210> SEQ ID NO 137
<211> LENGTH: 891
<212> TYPE: DNA
<213> ORGANISM: Tagetes erecta
<220> FEATURE:
<221> NAME/KEY: CDS

<400> SEQUENCE: 137 atg aca tcc ctg agg ttt cta aca gaa ccc tca ctt gta tgc tca tcc      48
Met Thr Ser Leu Arg Phe Leu Thr Glu Pro Ser Leu Val Cys Ser Ser
1               5                   10                  15 act ttc ccc aca ttc aat ccc cta cac aaa acc cta act aaa cca aca      96
Thr Phe Pro Thr Phe Asn Pro Leu His Lys Thr Leu Thr Lys Pro Thr
                20                  25                  30 cca aaa ccc tac cca aag cca cca cca att cgc tcc gtc ctt caa tac     144
Pro Lys Pro Tyr Pro Lys Pro Pro Pro Ile Arg Ser Val Leu Gln Tyr
            35                  40                  45 aat cgc aaa cca gag ctc gcc gga gac act cca cga gtc gtc gca atc     192
Asn Arg Lys Pro Glu Leu Ala Gly Asp Thr Pro Arg Val Val Ala Ile
        50                  55                  60 gac gcc gac gtt ggt cta cgt aac ctc gat ctt ctt ctc ggt ctc gaa     240
Asp Ala Asp Val Gly Leu Arg Asn Leu Asp Leu Leu Leu Gly Leu Glu
65                  70                  75                  80 aac cgc gtc aat tac acc gtc gtt gaa gtt ctc aac ggc gat tgc aga     288
Asn Arg Val Asn Tyr Thr Val Val Glu Val Leu Asn Gly Asp Cys Arg
                85                  90                  95 ctc gac caa gcc cta gtt cgt gat aaa cgc tgg tca aat ttc gaa ttg     336
Leu Asp Gln Ala Leu Val Arg Asp Lys Arg Trp Ser Asn Phe Glu Leu
            100                 105                 110 ctt tgt att tca aaa cct agg tca aaa ttg cct tta gga ttt ggg gga     384
Leu Cys Ile Ser Lys Pro Arg Ser Lys Leu Pro Leu Gly Phe Gly Gly
        115                 120                 125 aaa gct tta gtt tgg ctt gat gca tta aaa gat agg caa gaa ggt tgc     432
Lys Ala Leu Val Trp Leu Asp Ala Leu Lys Asp Arg Gln Glu Gly Cys
130                 135                 140 ccg gat ttt ata ctt ata gat tgt cct gca ggt att gat gcc ggg ttc     480
Pro Asp Phe Ile Leu Ile Asp Cys Pro Ala Gly Ile Asp Ala Gly Phe
145                 150                 155                 160 ata acc gcc att aca ccg gct aac gaa gcc gta tta gtt aca aca cct     528
Ile Thr Ala Ile Thr Pro Ala Asn Glu Ala Val Leu Val Thr Thr Pro
                165                 170                 175 gat att act gca ttg aga gat gca gat aga gtt aca ggc ttg ctt gaa     576
Asp Ile Thr Ala Leu Arg Asp Ala Asp Arg Val Thr Gly Leu Leu Glu
            180                 185                 190
```

-continued

```
tgt gga att agg gat att aaa atg att gtg aac aga gtt aga act      624
Cys Asp Gly Ile Arg Asp Ile Lys Met Ile Val Asn Arg Val Arg Thr
        195                 200                 205 gat ttg ata agg ggt gaa gat atg atg tca gtt ctt gat gtt caa gag  672
Asp Leu Ile Arg Gly Glu Asp Met Met Ser Val Leu Asp Val Gln Glu
    210                 215                 220 atg ttg gga ttg tca ttg ttg agt gat acc cga gga ttc gaa gtg att  720
Met Leu Gly Leu Ser Leu Leu Ser Asp Thr Arg Gly Phe Glu Val Ile
225                 230                 235                 240 cgg agt acg aat aga ggg ttt ccg ctt gtg ttg aac aag cct ccg act  768
Arg Ser Thr Asn Arg Gly Phe Pro Leu Val Leu Asn Lys Pro Pro Thr
                245                 250                 255 tta gca gga ttg gca ttt gag cag gct gct tgg aga ttg gtt gag caa  816
Leu Ala Gly Leu Ala Phe Glu Gln Ala Ala Trp Arg Leu Val Glu Gln
            260                 265                 270 gat agc atg aag gct gtg atg gtg gag gaa gaa cct aaa aag agg gga  864
Asp Ser Met Lys Ala Val Met Val Glu Glu Glu Pro Lys Lys Arg Gly
        275                 280                 285 ttt ttc tcg ttt ttt gga ggt tag tga                              891
Phe Phe Ser Phe Phe Gly Gly
    290                 295

<210> SEQ ID NO 138
<211> LENGTH: 295
<212> TYPE: PRT
<213> ORGANISM: Tagetes erecta

<400> SEQUENCE: 138

Met Thr Ser Leu Arg Phe Leu Thr Glu Pro Ser Leu Val Cys Ser Ser
1               5                   10                  15

Thr Phe Pro Thr Phe Asn Pro Leu His Lys Thr Leu Thr Lys Pro Thr
            20                  25                  30

Pro Lys Pro Tyr Pro Lys Pro Pro Ile Arg Ser Val Leu Gln Tyr
        35                  40                  45

Asn Arg Lys Pro Glu Leu Ala Gly Asp Thr Pro Arg Val Val Ala Ile
    50                  55                  60

Asp Ala Asp Val Gly Leu Arg Asn Leu Asp Leu Leu Gly Leu Glu
65                  70                  75                  80

Asn Arg Val Asn Tyr Thr Val Val Glu Val Leu Asn Gly Asp Cys Arg
                85                  90                  95

Leu Asp Gln Ala Leu Val Arg Asp Lys Arg Trp Ser Asn Phe Glu Leu
            100                 105                 110

Leu Cys Ile Ser Lys Pro Arg Ser Lys Leu Pro Leu Gly Phe Gly Gly
        115                 120                 125

Lys Ala Leu Val Trp Leu Asp Ala Leu Lys Asp Arg Gln Glu Gly Cys
    130                 135                 140

Pro Asp Phe Ile Leu Ile Asp Cys Pro Ala Gly Ile Asp Ala Gly Phe
145                 150                 155                 160

Ile Thr Ala Ile Thr Pro Ala Asn Glu Ala Val Leu Val Thr Thr Pro
                165                 170                 175

Asp Ile Thr Ala Leu Arg Asp Ala Asp Arg Val Thr Gly Leu Leu Glu
            180                 185                 190

Cys Asp Gly Ile Arg Asp Ile Lys Met Ile Val Asn Arg Val Arg Thr
        195                 200                 205

Asp Leu Ile Arg Gly Glu Asp Met Met Ser Val Leu Asp Val Gln Glu
    210                 215                 220
```

Met Leu Gly Leu Ser Leu Leu Ser Asp Thr Arg Gly Phe Glu Val Ile
225                 230                 235                 240

Arg Ser Thr Asn Arg Gly Phe Pro Leu Val Leu Asn Lys Pro Pro Thr
            245                 250                 255

Leu Ala Gly Leu Ala Phe Glu Gln Ala Ala Trp Arg Leu Val Glu Gln
        260                 265                 270

Asp Ser Met Lys Ala Val Met Val Glu Glu Pro Lys Lys Arg Gly
    275                 280                 285

Phe Phe Ser Phe Phe Gly Gly
    290             295

<210> SEQ ID NO 139
<211> LENGTH: 332
<212> TYPE: DNA
<213> ORGANISM: Tagetes erecta
<220> FEATURE:
<221> NAME/KEY: CDS
<222> LOCATION: (1)..(330)

<400> SEQUENCE: 139 aag ctt gca cga gcc tct ctc tat ttt tac act tca atg gcg gca gca         48
Lys Leu Ala Arg Ala Ser Leu Tyr Phe Tyr Thr Ser Met Ala Ala Ala
1               5                   10                  15 att gct gtc cct tgt agc tca aga cca ttt ggc tta ggt cga atg cgg         96
Ile Ala Val Pro Cys Ser Ser Arg Pro Phe Gly Leu Gly Arg Met Arg
            20                  25                  30 tta ctt ggt cat aaa ccc aca acc ata act tgt cac ttc ccc ttt tct        144
Leu Leu Gly His Lys Pro Thr Thr Ile Thr Cys His Phe Pro Phe Ser
        35                  40                  45 ttt tct atc aaa tca ttt acc cca att gtt agg ggc aga aga tgt act        192
Phe Ser Ile Lys Ser Phe Thr Pro Ile Val Arg Gly Arg Arg Cys Thr
    50                  55                  60 gtt tgt ttt gtt gcc ggt ggc gac agt aat agt aac agt aat aat aat        240
Val Cys Phe Val Ala Gly Gly Asp Ser Asn Ser Asn Ser Asn Asn Asn
65                  70                  75                  80 agt gac agt aat agt aat aat ccg ggt ctg gat tta aac ccg gcg gtt        288
Ser Asp Ser Asn Ser Asn Asn Pro Gly Leu Asp Leu Asn Pro Ala Val
                85                  90                  95 atg aac cgt aac cgt ttg gtt gaa gaa aaa atg gag agg tcg ac            332
Met Asn Arg Asn Arg Leu Val Glu Glu Lys Met Glu Arg Ser
            100                 105                 110

<210> SEQ ID NO 140
<211> LENGTH: 110
<212> TYPE: PRT
<213> ORGANISM: Tagetes erecta

<400> SEQUENCE: 140

Lys Leu Ala Arg Ala Ser Leu Tyr Phe Tyr Thr Ser Met Ala Ala Ala
1               5                   10                  15

Ile Ala Val Pro Cys Ser Ser Arg Pro Phe Gly Leu Gly Arg Met Arg
            20                  25                  30

Leu Leu Gly His Lys Pro Thr Thr Ile Thr Cys His Phe Pro Phe Ser
        35                  40                  45

Phe Ser Ile Lys Ser Phe Thr Pro Ile Val Arg Gly Arg Arg Cys Thr
    50                  55                  60

Val Cys Phe Val Ala Gly Gly Asp Ser Asn Ser Asn Ser Asn Asn Asn
65                  70                  75                  80

```
Ser Asp Ser Asn Ser Asn Asn Pro Gly Leu Asp Leu Asn Pro Ala Val
            85                  90                  95

Met Asn Arg Asn Arg Leu Val Glu Glu Lys Met Glu Arg Ser
            100                 105                 110

<210> SEQ ID NO 141
<211> LENGTH: 332
<212> TYPE: DNA
<213> ORGANISM: Tagetes erceta
<220> FEATURE:
<221> NAME/KEY: misc_feature
<223> OTHER INFORMATION: beta-Hydroxylase Sense Fragment

<400> SEQUENCE: 141
aagcttgcac gagcctctct ctatttttac acttcaatgg cggcagcaat tgctgtccct      60
tgtagctcaa gaccatttgg cttaggtcga atgcggttac ttggtcataa acccacaacc     120
ataacttgtc acttcccctt ttcttttttct atcaaatcat ttaccccaat tgttaggggc    180
agaagatgta ctgtttgttt tgttgccggt ggcgacagta atagtaacag taataataat    240
agtgacagta atagtaataa tccgggtctg gatttaaacc cggcggttat gaaccgtaac    300
cgtttggttg aagaaaaaat ggagaggtcg ac                                   332

<210> SEQ ID NO 142
<211> LENGTH: 332
<212> TYPE: DNA
<213> ORGANISM: Tagetes erecta
<220> FEATURE:
<221> NAME/KEY: misc_feature
<223> OTHER INFORMATION: beta-Hydroxylase Antisense Fragment

<400> SEQUENCE: 142
gaattcggca cgagcctctc tctattttta cacttcaatg gcggcagcaa ttgctgtccc      60
ttgtagctca agaccatttg gcttaggtcg aatgcggtta cttggtcata aacccacaac    120
cataacttgt cacttcccct tttcttttc tatcaaatca tttaccccaa ttgttagggg      180
cagaagatgt actgtttgtt ttgttgccgg tggcgacagt aatagtaaca gtaataataa    240
tagtgacagt aatagtaata atccgggtct ggatttaaac ccggcggtta tgaaccgtaa    300
ccgtttggtt gaagaaaaaa tggagaggat cc                                   332
```

METHODS FOR PRODUCING ANIMAL FEED PREPARATIONS WITH ASTAXANTHIN-CONTAINING PLANTS OR PARTS OF PLANTS OF THE GENUS *TAGETES*

RELATED APPLICATIONS

This application is a national stage application (under 35 U.S.C. 371) of PCT/EP03/09109 filed Aug. 18, 2003, which claims benefit of German application 102 38 980.2 filed Aug. 20, 2002, German application 102 38 978.0 filed Aug. 20, 2002, German application 102 38 979.9 filed Aug. 20, 2002, German application 102 53 112.9 filed Nov. 13, 2002, and German application 102 58 971.2 filed Dec. 16, 2002.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence Listing -13173-00004-US, date recorded: Dec. 11, 2007, size: 364 KB.

BACKGROUND OF THE INVENTION

The present invention relates to the use of astaxanthin-containing plants or parts of plants of the genus *Tagetes* or astaxanthin-containing extracts of astaxanthin-containing plants or parts of plants of the genus *Tagetes* for oral administration to animals, methods for producing animal feed preparations, the animal feed preparations themselves, a method for pigmenting animals or animal products, and also a method for producing pigmented animals and animal products.

On account of its coloring properties astaxanthin is used as pigment in animal nutrition, in particular in trout, salmon and shrimp breeding.

Astaxanthin is currently chiefly produced by chemical synthesis methods. Natural astaxanthin is currently produced in biotechnological methods in small amounts by culturing algae, for example *Haematococcus pluvialis*, or by fermentation of genetically optimized microorganisms and subsequent isolation.

Synthetic astaxanthin or natural astaxanthin produced by isolation is chemically and/or physically stabilized by special formulation techniques for increasing storage life and is prepared for the respective use in accordance with the desired application sectors and bioavailabilities.

WO 9201754 describes an astaxanthin-containing wild type plant of the species *Adonis aestivalis*. In addition, the document discloses the use of the astaxanthin-containing petals of *Adonis aestivalis* and also extracts thereof as fish food, or as additive in fish food for pigmenting fish.

The use of *Adonis aestivalis* as a plant source of astaxanthin for pigmenting fish in the prior art, however, has the disadvantage that the yield of astaxanthin-containing biomass and thus of astaxanthin-containing plant material per unit of culture area is very low, and thus a satisfactory amount of astaxanthin-containing plant material can only be obtained by cost-intensive culture of large areas. This leads to high costs in the production of corresponding pigments.

BRIEF DESCRIPTION OF THE INVENTION

It was therefore an object of the invention to provide pigmenting-agents which no longer have the disadvantage of the prior art.

Accordingly it has been found that astaxanthin-containing plants or parts of plants of the genus *Tagetes* or astaxanthin-containing extracts of astaxanthin-containing plants or parts of plants of the genus *Tagetes* can be used for oral administration to animals.

BRIEF DESCRIPTION OF THE DRAWINGS

FIG. 1 shows the nucleotide sequence comparison between KETO2 (SEQ ID NO: 22) and X86782 (SEQ ID NO: 1).

FIG. 2 shows the protein sequence comparison between KETO2 (SEQ ID NO: 23) and X86782 (SEQ ID NO: 2).

FIG. 3 shows the construct for the overexpression of the ketolase (β-C-4-oxygenase) protein from *H. pluvialis* using rbcS transit peptide from pea under the control of the d35S promoter (*Tagetes* transformation construct).

FIG. 4 shows the construct pS5AP3PKETO2 for the overexpression of the ketolase (β-C-4-oxygenase) proteins from *H. pluvialis* using rbcS transit peptide from pea under the control of the AP3P promoter (*Tagetes* transformation construct).

FIG. 7 shows the cloning cassette for producing inverted-repeat expression cassettes for the flower-specific expression of epsilon-cyclase dsRNAs in *Tagetes erecta*.

FIG. 8 shows the expression vector for the flower-specific production of dsRNA transcripts comprising 5'-terminal fragments of the epsilon-cyclase cDNA (AF251016) under the control of the AP3P promoter.

FIG. 9 shows the expression vector for the flower-specific production of dsRNA transcripts comprising 5'-terminal fragments of the epsilon-cyclase cDNA (AF251016) under the control of the CHRC promoter.

FIG. 10 shows the expression vector for the flower-specific production of dsRNA transcripts comprising 3'-terminal fragments of the epsilon-cyclase cDNA (AF251016) under the control of the AP3P promoter.

FIG. 11 shows the inverse PCR amplicon which comprises the 312 bp fragment of the epsilon-cyclase promoter.

FIG. 12 shows the TAIL PCR amplicon which comprises the 199 bp fragment of the epsilon-cyclase promoter.

FIG. 13 shows the expression vector for the flower-specific production of dsRNA transcripts comprising the 312 bp promoter fragment of epsilon-cyclase under the control of the AP3P promoter.

FIG. 14 shows the expression vector for the flower-specific production of dsRNA transcripts comprising the 312 bp promoter fragment of epsilon-cyclase under the control of the CHRC promoter.

FIG. 15 shows the expression vector for the flower-specific production of dsRNA transcripts comprising the 312 bp promoter fragment of epsilon-cyclase under the control not only of the AP3P promoter, but also the CHRC promoter.

DETAILED DESCRIPTION OF THE INVENTION

Figure 5:
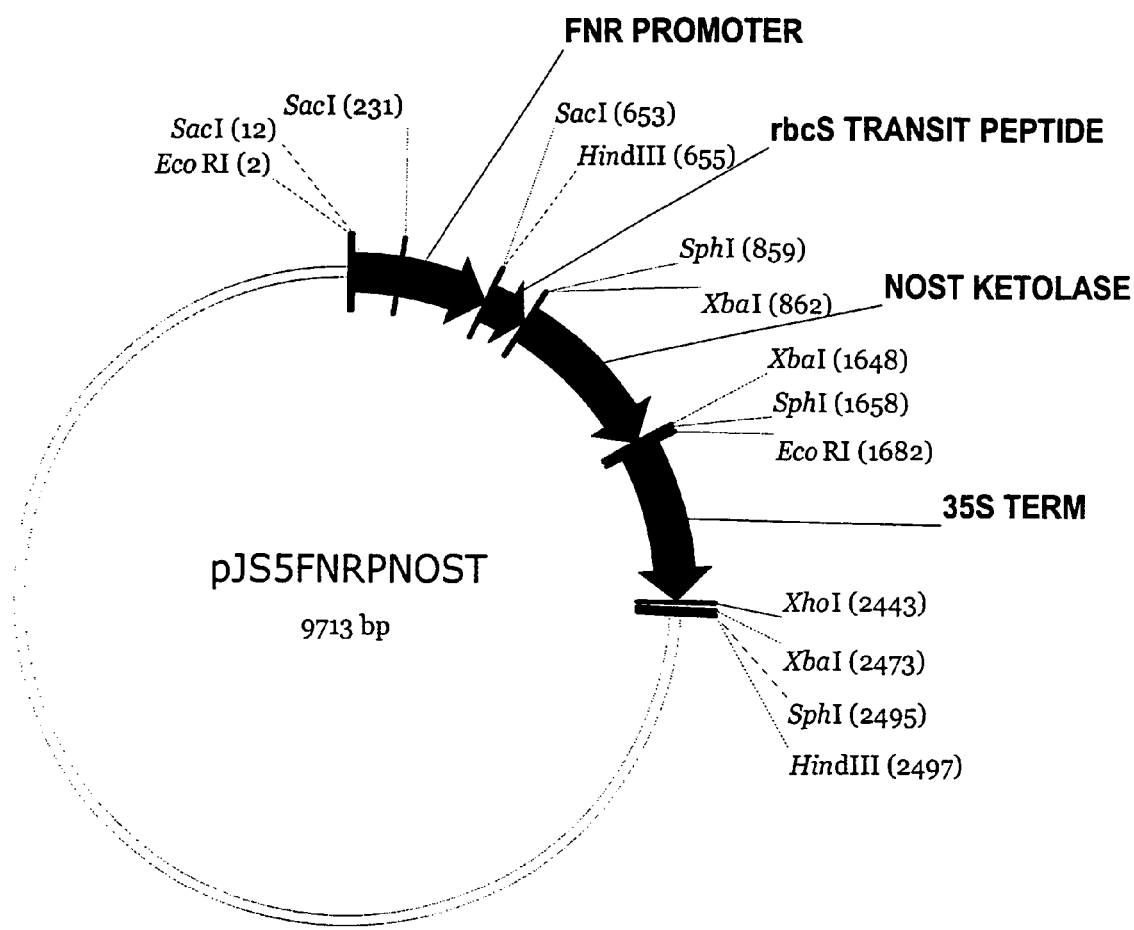
FIG. 5 shows the construct map of pJS5FNRPNOST.

In a preferred embodiment, the astaxanthin-containing plants or parts of plants of the genus *Tagetes* or the astaxanthin-containing extracts of astaxanthin-containing plants or parts of plants of the genus *Tagetes* are used for pigmenting animals and the corresponding animal products.

Astaxanthin-containing plants of the genus *Tagetes* are preferably taken to mean plants of the genus *Tagetes* which have a content of astaxanthin in at least one part of the plant.

The astaxanthin can be present in free form in the form of fatty acid diesters or monoesters. Preferred plants of the genus *Tagetes* are plants selected from the species *Tagetes erecta*, *Tagetes patula*, which are also termed Marigold, *Tagetes lucida*, *Tagetes pringlei*, *Tagetes palmeri*, *Tagetes minuta*, *Tagetes lemmonii*, *Tagetes tenuifolia*, or *Tagetes campanulata*, particularly preferably *Tagetes erecta* or *Tagetes patula*.

Astaxanthin-containing parts of plants of plants of the genus *Tagetes* are preferably taken to mean parts of plants which have a content of astaxanthin in at least one part of the plant part. Preferred plant parts are, for example, flowers, flower heads or, particularly preferably, flower leaves which are also called petals.

Wild type plants of the genus *Tagetes* do not have astaxanthin in flowers, but do have carotenoids such as lutein and zeaxanthin. However, it has been found according to the invention that the plants of the genus *Tagetes* can be given the capacity to produce astaxanthin, for example by genetic modification.

In a preferred embodiment, the plants of the genus *Tagetes* are given the capacity to produce astaxanthin, for example, by causing a ketolase activity in the plants of the genus *Tagetes* which have been genetically modified compared with the wild type.

Ketolase activity is taken to mean the enzyme activity of a ketolase.

A ketolase is taken to mean a protein which has the enzymatic activity to introduce a keto group at the optionally substituted β-ionone ring of carotenoids.

In particular, a ketolase is taken to mean a protein which has the enzymatic activity to convert β-carotene into canthaxanthin.

Accordingly, ketolase activity is taken to mean the amount of β-carotene converted or amount of canthaxanthin formed in a defined time by the protein ketolase.

The term "wild type" is taken to mean according to the invention the corresponding non-genetically modified starting plant of the genus *Tagetes*.

Depending on context, the term "plant" can be taken to mean the starting plant (wild type) of the genus *Tagetes* or an inventive genetically modified plant of the genus *Tagetes*, or both.

Preferably, "wild type" is taken to mean a reference plant in each case for the production of the ketolase activity, for the hereinafter described increase of the hydroxylase activity, for the hereinafter described increase of the β-cyclase activity, and for the hereinafter described reduction of the ε-cyclase activity and the increase of the astaxanthin content.

This reference plant of the genus *Tagetes* is *Tagetes erecta*, *Tagetes patula*, *Tagetes lucida*, *Tagetes pringlei*, *Tagetes palmeri*, *Tagetes minuta* or *Tagetes campanulata*, particularly preferably *Tagetes erecta*, very particularly preferably *Tagetes erecta* L., Accession number: TAG 72, cultivar Orangenprinz, available from the IPK Genebank, Corrensstr. 3, D-06466 Gatersleben.

The ketolase activity in inventive genetically modified plants of the genus *Tagetes* and in wild type or reference plants is preferably determined under the following conditions:

The ketolase activity in plant material is determined on the basis of the method of Frazer et al., (J. Biol. Chem. 272(10): 6128-6135, 1997). The ketolase activity in plant extracts is determined using the substrates beta-carotene and canthaxanthin in the presence of lipid (soylecithin) and detergent (sodium cholate). Substrate/product ratios from the ketolase assays are determined by means of HPLC.

The inventive genetically modified plant of the genus *Tagetes* has, in this preferred embodiment, compared to the nongenetically modified wild type, a ketolase activity, preferably in flower leaves, and is thus preferably able to express a ketolase transgenically.

In a further preferred embodiment, the ketolase activity in the plants of the genus *Tagetes* is brought about by bringing about the gene expression of a nucleic acid coding for a ketolase.

In this preferred embodiment, the gene expression of a nucleic acid coding for a ketolase is preferably brought about by introducing nucleic acids which code for ketolases in the starting plant of the genus *Tagetes*.

For this, in principle, any ketolase gene, that is to say any nucleic acids which code for a ketolase, can be used.

All nucleic acids mentioned in the description can be, for example, an RNA, DNA or cDNA sequence.

With genomic ketolase sequences from eukaryotic sources which comprise introns, in the event that the host plant of the genus *Tagetes* is not able to, or cannot be given the ability to, express the corresponding ketolase, preferably already-processed nucleic acid sequences such as the corresponding cDNAs are to be used.

Examples of nucleic acids coding for a ketolase and the corresponding ketolases which can be used in the inventive method are, for example, sequences from

*Haematoccus pluvialis*, in particular from *Haematoccus pluvialis* Flotow em. Wille (Accession NO: X86782; nucleic acid: SEQ ID NO: 1, protein SEQ ID NO: 2),

*Haematoccus pluvialis*, NIES-144 (Accession NO: D45881; nucleic acid: SEQ ID NO: 3, protein SEQ ID NO: 4),

*Agrobacterium aurantiacum* (Accession NO: D58420; nucleic acid: SEQ ID NO: 5, protein SEQ ID NO: 6),

*Alicaligenes* spec. (Accession NO: D58422; nucleic acid: SEQ ID NO: 7, protein SEQ ID NO: 8),

*Paracoccus marcusii* (Accession NO: Y15112; nucleic acid: SEQ ID NO: 9, protein SEQ ID NO: 10).

*Synechocystis* sp. Strain PC6803 (Accession NO: NP442491; nucleic acid: SEQ ID NO: 11, protein SEQ ID NO: 12).

*Bradyrhizobium* sp. (Accession NO: AF218415; nucleic acid: SEQ ID NO: 13, protein SEQ ID NO: 14).

*Nostoc* sp. Strain PCC7120 (Accession NO: AP003592, BAB74888; nucleic acid: SEQ ID NO: 15, protein SEQ ID NO: 16),

*Nostoc punctiforme* ATTC 29133, nucleic acid: Acc. No. NZ_AABC01000195, base pair 55,604 to 55,392 (SEQ ID NO: 81); protein: Acc. No. ZP_00111258 (SEQ ID NO: 82) (annotated as putative protein),

*Nostoc punctiforme* ATTC 29133, nucleic acid: Acc. No. NZ_AABC01000196, base pair 140,571 to 139,810 (SEQ ID NO: 83), protein: (SEQ ID NO: 84) (not annotated),

*Synechococcus* sp. WH 8102, nucleic acid: Acc. No. NZ_AABD01000001, base pair 1,354,725-1,355,528 (SEQ ID NO: 85), protein: Acc. No. ZP_00115639 (SEQ ID NO: 86) (annotated as putative protein),

*Haematococcus pluvialis* (Accession NO: AF534876, AAN03484; nucleic acid: SEQ ID NO: 97, protein: SEQ ID NO: 98),

*Paracoccus* sp. MBIC1143, (Accession NO: D58420, P54972; nucleic acid: SEQ ID NO: 99, protein: SEQ ID NO: 100),

*Brevundimonas aurantiaca* (Accession NO: AY166610, AAN86030; nucleic acid: SEQ ID NO: 101, protein: SEQ ID NO: 102),

*Nodularia spumigena* NSOR10 (Accession NO: AY210783, AA064399; nucleic acid: SEQ ID NO: 103, protein: SEQ ID NO: 104) and

*Deinococcus radiodurans* R1 (Accession NO: E75561, AE001872; nucleic acid: SEQ ID NO: 105, protein: SEQ ID NO: 106).

Further natural examples of ketolases and ketolase genes which can be used in the inventive method may be readily found, for example, from various organisms whose genomic sequence is known by comparing the identity of amino acid sequences or of the corresponding back-translated nucleic acid sequences from databases with the above-described sequences and, in particular, with the sequences SEQ ID NO: 2 and/or 16.

Further natural examples of ketolases and ketolase genes may in addition be readily found starting from the above-described nucleic acid sequences, in particular starting from the sequences SEQ ID NO: 2 and/or 16 from various organisms whose genomic sequence is not known by hybridization techniques in a manner known per se.

The hybridization can be performed under moderate (low stringency), or preferably under stringent (high stringency) conditions.

Such hybridization conditions are described, for example in Sambrook, J., Fritsch, E. F., Maniatis, T., in: Molecular Cloning (A Laboratory Manual), $2^{nd}$ edition, Cold Spring Harbor Laboratory Press, 1989, pages 9.31-9.57 or in Current Protocols in Molecular Biology, John Wiley & Sons, N.Y. (1989), 6.3.1-6.3.6.

For example, the conditions during the washing step can be selected from the range of conditions limited by those of low stringency (with 2×SSC at 50° C.) and those of high stringency (with 0.2×SSC at 50° C., preferably at 65° C.) (20×SSC: 0.3 M sodium citrate, 3 M sodium chloride, pH 7.0).

Furthermore, the temperature during the washing step can be elevated from moderate conditions at room temperature, 22° C., to stringent conditions at 65° C.

Both parameters, salt concentration and temperature, can be varied simultaneously, and also one of the two parameters can be kept constant and only the other varied. During the hybridization, denaturing agents, for example formamide or SDS, can also be used. In the presence of 50% formamide, the hybridization is preferably carried out at 42° C.

Some exemplary conditions for hybridization and washing step are given as follows:

(1) Hybridization Conditions having, for Example
(i) 4×SSC at 65° C., or
(ii) 6×SSC at 45° C., or
(iii) 6×SSC at 68° C., 100 mg/ml of denatured fish sperm DNA, or
(iv) 6×SSC, 0.5% SDS, 100 mg/ml of denatured fragmented salmon sperm DNA at 68° C., or
(v) 6×SSC, 0.5% SDS, 100 mg/ml of denatured fragmented salmon sperm DNA, 50% formamide at 42° C., or
(vi) 50% formamide, 4×SSC at 42° C., or
(vii) 50% (vol/vol) formamide, 0.1% bovine serum albumin, 0.1% Ficoll, 0.1% polyvinylpyrrolidone, 50 mM sodium phosphate buffer pH 6.5, 750 mM NaCl, 75 mM sodium citrate at 42° C., or
(viii) 2× or 4×SSC at 50° C. (moderate conditions), or
(ix) 30 to 40% formamide, 2× or 4×SSC at 420 (moderate conditions).

(2) Wash Steps for 10 Minutes in each Case, Using for Example
(i) 0.015 M NaCl/0.0015 M sodium citrate/0.1% SDS at 50° C., or
(ii) 0.1×SSC at 65° C., or
(iii) 0.1×SSC, 0.5% SDS at 68° C., or
(iv) 0.1×SSC, 0.5% SDS, 50% formamide at 42° C., or
(v) 0.2×SSC, 0.1% SDS at 42° C., or
(vi) 2×SSC at 65° C. (moderate conditions).

In a preferred embodiment of the inventive genetically modified plants of the genus *Tagetes*, nucleic acids are introduced, which nucleic acids code for a protein comprising the amino acid sequence SEQ ID NO: 2 or a sequence derived from this sequence by substitution, insertion or deletion of amino acids, which sequence has an identity of at least 20%, preferably at least 30%, more preferably at least 40%, more preferably at least 50%, more preferably at least 60%, more preferably at least 70%, more preferably at least 80%, particularly preferably at least 90%, at the amino acid level with the sequence SEQ ID NO: 2 and has the enzymatic property of a ketolase.

A natural ketolase sequence can be involved which, as described above, can be found by comparison of identity of the sequences from other organisms, or a synthetic ketolase sequence which has been modified, starting from the sequence SEQ ID NO: 2 by artificial variation, for example by substitution, insertion or deletion of amino acids.

In a further preferred embodiment of the inventive method, nucleic acids are introduced which code for a protein comprising the amino acid sequence SEQ ID NO: 16 or a sequence derived from this sequence by substitution, insertion or deletion of amino acids, which sequence has an identity of at least 20%, preferably at least 30%, more preferably at least 40%, more preferably at least 50%, more preferably at least 60%, more preferably at least 70%, more preferably at least 80%, particularly preferably at least 90%, at the amino acid level, with the sequence SEQ ID NO: 16 and the enzymatic property of a ketolase.

A natural ketolase sequence can be involved which, as described above, can be found by comparison of identity of the sequences from other organisms, or a synthetic ketolase sequence which has been modified starting from the sequence SEQ ID NO: 16 by artificial variation, for example by substitution, insertion or deletion of amino acids.

The term "substitution" is to be taken to mean in the description the exchange of one or more amino acids by one or more amino acids. Preferably, what are termed conservative exchanges are carried out, in which the amino acid replaced has a similar property to the original amino acid, for example exchange of Glu for Asp, Gln for Asn, Val for lie, Leu for lie, Ser for Thr.

Deletion is the replacement of an amino acid by a direct bond. Preferred positions for deletions are the termini of the polypeptide and the linkages between the individual protein domains.

Insertions are introductions of amino acids into the polypeptide chain, formally, a direct bond being replaced by one or more amino acids.

Identity between two proteins is taken to mean the identity of the amino acids over the whole protein length in each case, in particular the identity which is calculated by comparison using the Lasergene Software from DNASTAR, inc. Madison, Wis. (USA) using the Clustal method (Higgins DG, Sharp PM. Fast and sensitive multiple sequence alignments on a microcomputer. Comput Appl. Biosci. 1989 April, 5(2):151-1) with the following parameters being set:

Multiple Alignment Parameter:

| Gap penalty | 10 |
| Gap length penalty | 10 |

Pairwise Alignment Parameter:

| K-tuple | 1 |
| Gap penalty | 3 |
| Window | 5 |
| Diagonals saved | 5 |

A protein which has an identity of at least 20% at the amino acid level with the sequence SEQ ID NO: 2 or 16 is correspondingly taken to mean a protein which, in a comparison of its sequence with the sequence SEQ ID NO: 2 or 16, in particular according to the above program logarithm with the above parameter set, has an identity of at least 20%.

Suitable nucleic acid sequences are, for example, obtainable by back-translation of the polypeptide sequence according to the genetic code.

Preferably, for this, those codons are used which are used frequently in accordance with the *tagetes*-specific codon usage. The codon usage may be readily determined on the basis of computer evaluations of other known genes from plants of the genus *Tagetes*.

In a particularly preferred embodiment, a nucleic acid comprising the sequence SEQ ID NO: 1 is introduced into the plant of the genus.

In a further, particularly preferred embodiment, a nucleic acid comprising the sequence SEQ ID NO: 15 is introduced into the plant of the genus.

All of the abovementioned ketolase genes can be produced, furthermore, in a manner known per se by chemical synthesis from the nucleotide building blocks, for example by fragment condensation of individual overlapping complementary nucleic acid building blocks of the double helix. The chemical synthesis of oligonucleotides can be performed, for example, in a known manner by the phosphoamidite method (Voet, Voet, $2^{nd}$ edition, Wiley Press New York, pp. 896-897). The addition of synthetic oligonucleotides and filling-in of gaps using the Klenow fragment of DNA polymerase and ligation reactions and also general cloning methods are described in Sambrook et al. (1989), Molecular cloning: A laboratory manual, Cold Spring Harbor Laboratory Press.

In a particularly preferred embodiment of the inventive method, use is made of genetically modified plants of the genus *Tagetes* which, in flowers, have the highest expression rate of a ketolase.

Preferably, this is achieved by the ketolase gene being expressed under control of a flower-specific promoter. For example, for this, the above-described nucleic acids, as described extensively hereinafter, in a nucleic acid construct, functionally linked with a flower-specific promoter, are introduced into the plant of the genus *Tagetes*.

Particularly preferred plants of the genus *Tagetes* as starting plants, or inventive genetically modified plants, are plants selected from the species *Tagetes erecta*, *Tagetes patula*, which are also termed Marigold, *Tagetes lucida*, *Tagetes pringlei*, *Tagetes palmeri*, *Tagetes minuta*, *Tagetes lemmonii*, *Tagetes tenuifolia*, or *Tagetes campanulata*, particularly preferably *Tagetes erecta* or *Tagetes patula*.

In a preferred embodiment, use is made of genetically modified plants of the genus *Tagetes* which, compared with the wild type, additionally have an elevated hydroxylase activity and/or β-cyclase activity.

Hydroxylase activity is taken to mean the enzyme activity of a hydroxylase.

A hydroxylase is taken to mean a protein which has the enzymatic activity to introduce a hydroxyl group on the optionally substituted β-ionone ring of carotenoids.

In particular, a hydroxylase is taken to mean a protein which has the enzymatic activity to convert, β-carotene to zeaxanthin, or canthaxanthin to astaxanthin.

Accordingly, hydroxylase activity is taken to mean the amount of β-carotene or canthaxanthin converted, or amount of zeaxanthin or astaxanthin formed, in a defined time by the protein hydroxylase.

At an elevated hydroxylase activity compared with the wild type, thus, compared with the wild type, the amount of β-carotene or canthaxanthin converted, or the amount of zeaxanthin or astaxanthin formed by the protein hydroxylase in a defined time is increased.

Preferably, this increase of hydroxylase activity is at least 5%, further preferably at least 20%, further preferably at least 50%, further preferably at least 100%, more preferably at least 300%, still more preferably at least 500%, in particular at least 600%, of the hydroxylase activity of the wild type.

β-Cyclase activity is taken to mean the enzyme activity of a β-cyclase.

β-Cyclase is taken to mean a protein which has the enzymatic activity to convert a terminal linear residue of lycopene to a β-ionone ring.

In particular, β-cyclase is taken to mean a protein which has the enzymatic activity to convert carotene to β-carotene.

Accordingly, β-cyclase activity is taken to mean the amount of β-carotene converted or amount of β-carotene formed by the protein β-cyclase in a defined time.

At an elevated β-cyclase activity compared with the wild type, thus the amount of γ-carotene converted, or the amount of β-carotene formed, is increased by the protein β-cyclase in a defined time compared with the wild type.

Preferably, this increase of β-cyclase activity is at least 5%, further preferably at least 20%, further preferably at least 50%, further preferably at least 100%, more preferably at least 300%, still more preferably at least 500%, in particular at least 600%, of the β-cyclase activity of the wild type.

The hydroxylase activity in inventive genetically modified plants and in wild type or reference plants is preferably determined under the following conditions:

The activity of the hydroxylase is determined in vitro in accordance with Bouvier et al. (Biochim. Biophys. Acta 1391 (1998), 320-328). Ferredoxin, ferredoxin-NADP oxidoreductase, catalase, NADPH and beta-carotene together with mono- and digalactosyl glycerides are added to a defined amount of plant extract.

Particularly preferably, the hydroxylase activity is determined under the following conditions according to Bouvier, Keller, d'Harlingue and Camara (Xanthophyll biosynthesis: molecular and functional characterization of carotenoid hydroxylases from pepper fruits (*Capsicum annuum* L.; Biochim. Biophys. Acta 1391 (1998), 320-328):

The in vitro assay is carried out in a volume of 0.250 ml. The assay mix comprises 50 mM potassium phosphate (pH 7.6), 0.025 mg of spinach ferredoxin, 0.5 units of ferredoxin-$NADP^+$ spinach oxidoreductase, 0.25 mM NADPH, 0.010 mg of beta-carotene (emulsified in 0.1 mg of Tween 80), 0.05 mM of a mixture of mono- and digalactosyl glycerides (1:1), 1 unit of catalyse, 200 mono- and digalactosyl glycerides, (1:1), 0.2 mg of bovine serum albumin and plant extract in differing volumes. The reaction mixture is incubated at 30° C. for 2 hours. The reaction products are extracted with organic solvent such as acetone or chloroform/methanol (2:1) and determined by means of HPLC.

The β-cyclase activity in inventive genetically modified plants and in wild type or reference plants is preferably determined under the following conditions:

The β-cyclase activity is determined in vitro in accordance with Fraser and Sandmann (Biochem. Biophys. Res. Comm. 185(1) (1992) 9-15). To a defined amount of plant extract are added potassium phosphate buffer (pH 7.6), lycopene as substrate, paprika stroma protein, NADP+, NADPH and ATP.

Particularly preferably, the hydroxylase activity is determined under the following conditions according to Bouvier, d'Harlingue and Camara (Molecular Analysis of carotenoid cyclae inhibition; Arch. Biochem. Biophys. 346(1) (1997) 53-64):

The in vitro assay is carried out in a volume of 250 µl. The assay mix comprises 50 mM potassium phosphate (pH 7.6), differing amounts of plant extract, 20 nM lycopene, 250 g of paprika chromoplastid stroma protein, 0.2 mM NADP$^+$, 0.2 mM NADPH and 1 mM ATP. NADP/NADPH and ATP are dissolved in 10 ml of ethanol together with 1 mg of Tween 80 immediately before addition to incubation medium. After a reaction time of 60 minutes at 30° C., the reaction is ended by adding chloroform/methanol (2:1). The reaction products extracted in chloroform are analyzed by means of HPLC.

An alternative assay using radioactive substrate is described in Fraser and Sandmann (Biochem. Biophys. Res. Comm. 185(1) (1992) 9-15).

The hydroxylase activity and/or β-cyclase activity can be increased by various ways, for example by switching off inhibiting regulatory mechanisms at the expression and protein level, or by increasing the gene expression, compared with the wild type, of nucleic acids coding for a hydroxylase and/or nucleic acids coding for a β-cyclase.

The gene expression of the nucleic acids coding for a hydroxylase and/or the gene expression of the nucleic acid coding for a β-cyclase can likewise be increased compared with the wild type by various ways, for example by inducing the hydroxylase gene and/or β-cyclase gene by activators or by introducing one or more hydroxylase gene copies and/or β-cyclase gene copies, that is to say by introducing at least one nucleic acid coding for a hydroxylase and/or at least one nucleic acid coding for an ε-cyclase into the plant of the genus *Tagetes*.

Increasing the gene expression of a nucleic acid coding for a hydroxylase and/or β-cyclase is also taken to mean, according to the invention, the manipulation of the expression of the endogenous hydroxylase and/or β-cyclase of the plants of the genus *Tagetes*.

This can be achieved, for example, by modifying the genes coding for promoter DNA sequence for hydroxylases and/or β-cyclases. Such a modification which causes an increased expression rate of the gene, can be performed, for example, by deletion or insertion of DNA sequences.

It is possible, as described above, to change the expression of the endogenous hydroxylase and/or P-cyclase by applying exogenous stimuli. This can be performed by particular physiological conditions, that is to say by applying foreign substances.

Furthermore, an altered or increased expression of an endogenous hydroxylase and/or β-cyclase gene can be achieved by a regulator protein which does not occur in the non-transformed plant interacting with the promoter of this gene.

Such a regulator can be a chimeric protein which consists of a DNA-binding domain and a transcription activator domain, as described, for example, in WO 96/06166.

In a preferred embodiment, the gene expression of a nucleic acid coding for a hydroxylase and/or the gene expression of a nucleic acid coding for a β-cyclase is increased by introducing at least one nucleic acid coding for a hydroxylase and/or by introducing at least one nucleic acid coding for a β-cyclase into the plant of the genus *Tagetes*.

For this, in principle, use can be made of any hydroxylase gene or any β-cyclase gene, that is to say any nucleic acid which codes for a hydroxylase and any nucleic acid which codes for a β-cyclase.

With genomic hydroxylase or β-cyclase nucleic acid sequences from eukaryotic sources which comprise introns, in the event that the host plant does not have the capacity to, or cannot be given the capacity to, express the corresponding hydroxylase or β-cyclase, previously-processed nucleic acid sequences, such as the corresponding cDNAs are preferably to be used.

An example of a hydroxylase gene is a nucleic acid coding for a hydroxylase from *Haematococcus pluvialis* (Accession AX038729, WO 0061764); (nucleic acid: SEQ ID NO: 17, protein: SEQ ID NO: 18).

and also hydroxylases of the following accession numbers:
lembICAB55626.1, CAA70427.1, CM70888.1, CAB55625.1, AF499108__1, AF315289__1, AF296158__1, AAC49443.1, NP__194300.1, NP__200070.1, AAG10430.1, CAC06712.1, AAM88619.1, CAC95130.1, ML80006.1, AF162276__1, M053295.1, AAN85601.1, CRTZ_ERWHE, CRTZ_PANAN, BAB79605.1, CRTZ_ALCSP, CRTZ_AGRAU, CAB56060.1, ZP__00094836.1, MC44852.1, BAC77670.1, NP__745389.1, NP__344225.1, NP__849490.1, ZP__00087019.1, NP__503072.1, NP__852012.1, NP__115929.1, ZP__00013255.1

A particularly preferred hydroxylase is in addition the hydroxylase from tomato (Accession Y14809) (nucleic acid: SEQ ID NO: 107; protein: SEQ ID NO. 108).

Examples of α-cyclase genes are:
a nucleic acid coding for a β-cyclase from tomato (Accession X86452) (nucleic acid: SEQ ID NO: 19, protein: SEQ ID NO: 20).

And also β-cyclases of the following accession numbers:
S66350 lycopene beta-cyclase (EC 5.5.1.-)-tomato
CAA60119 lycopene synthase [*Capsicum annuum*]
S66349 lycopene beta-cyclase (EC 5.5.1.-)—common tobacco
CM57386 lycopene cyclase [*Nicotiana tabacum*]
MM21152 lycopene beta-cyclase [*Citrus sinensis*]
AAD38049 lycopene cyclase [Citrus×paradisi]
AAN86060 lycopene cyclase [*Citrus unshiu*]
MF44700 lycopene beta-cyclase [*Citrus sinensis*]
AAK07430 lycopene beta-cyclase [*Adonis palaestina*]
MG10429 beta-cyclase [*Tagetes erecta*]
AAA81880 lycopene cyclase
MB53337 lycopene beta-cyclase
ML92175 beta-lycopene cyclase [*Sandersonia aurantiaca*]
CM67331 lycopene cyclase [*Narcissus pseudonarcissus*]
MM45381 beta-cyclase [*Tagetes erecta*]
MO18661 lycopene beta-cyclase [*Zea mays*]
MG21133 chromoplast-specific lycopene beta-cyclase [*Lycopersicon esculentum*]

MF1 8989 lycopene beta-cyclase [*Daucus carota*]
ZP_001140 hypothetical protein [*Prochlorococcus marinus* str. MIT9313]
ZP_001050 hypothetical protein [*Prochlorococcus marinus* subsp. *pastoris* str. CCMP1378]
ZP_001046 hypothetical protein [*Prochlorococcus marinus* subsp. *pastoris* str. CCMP1378]
ZP_001134 hypothetical protein [*Prochlorococcus marinus* str. MIT9313]
ZP_001150 hypothetical protein [*Synechococcus* sp. WH 8102]
AAF1 0377 lycopene cyclase [*Deinococcus radiodurans*]
BAA29250 393aa long hypothetical protein [*Pyrococcus horikoshii*]
BAC77673 lycopene beta-monocyclase [marine bacterium P99-3]
AAL01999 lycopene cyclase [*Xanthobacter* sp. Py2]
ZP_000190 hypothetical protein [*Chloroflexus aurantiacus*]
ZP_000941 hypothetical protein [*Novosphingobium aromaticivorans*]
AAF78200 lycopene cyclase [*Bradyrhizobium* sp. ORS278]
BAB79602 crtY [*Pantoea agglomerans* pv. *milletiae*]
CAA64855 lycopene cyclase [*Streptomyces griseus*]
AAA21262 lycopene cyclase [*Pantoea agglomerans*]
C37802 crtY protein—*Erwinia uredovora*
BAB79602 crtY [*Pantoea agglomerans* pv. *milletiae*]
AAA64980 lycopene cyclase [*Pantoea agglomerans*]
AAC44851 lycopene cyclase
BAA09593 lycopene cyclase [*Paracoccus* sp. MBIC1143]
ZP_000941 hypothetical protein [*Novosphingobium aromaticivorans*]
CAB56061 lycopene beta-cyclase [*Paracoccus marcusii*]
BAA20275 lycopene cyclase [*Erythrobacter longus*]
ZP_000570 hypothetical protein [*Thermobifida fusca*]
ZP_000190 hypothetical protein [*Chloroflexus aurantiacus*]
AAK07430 lycopene beta-cyclase [*Adonis palaestina*]
CAA67331 lycopene cyclase [*Narcissus pseudonarcissus*]
AAB53337 lycopene beta-cyclase
BAC77673 lycopene beta-monocyclase [marine bacterium P99-3]

A particularly preferred β-cyclase is, in addition, the chromoplast-specific β-cyclase from tomato (AAG21133) (nucleic acid: SEQ ID No. 109; protein: SEQ ID No. 110).

In the inventive preferred transgenic plants of the genus *Tagetes*, there is therefore, in this preferred embodiment, compared with the wild type, at least one further hydroxylase gene and/or P-cyclase gene.

In this preferred embodiment the genetically modified plant has, for example, at least one exogenous nucleic acid coding for a hydroxylase, or at least two endogenous nucleic acids coding for a hydroxylase, and/or at least one exogenous nucleic acid coding for a β-cyclase, or at least two endogenous nucleic acids coding for a β-cyclase.

Preferably, in the above-described preferred embodiment, use is made of, as hydroxylase genes, nucleic acids which code for proteins comprising the amino acid sequence SEQ ID NO: 18 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 18, and which have the enzymatic property of a hydroxylase.

Further examples of hydroxylases and hydroxylase genes may be readily found, for example, from various organisms whose genomic sequence is known, as described above, by comparisons of homology of the amino acid sequences or the corresponding back-translated nucleic acid sequences from databases with the SEQ ID. NO: 18.

Further examples of hydroxylases and hydroxylase genes may further be readily found, for example, starting from the sequence SEQ ID NO: 17 from various organisms whose genomic sequence is not known, as described above, by hybridization and PCR techniques in a manner known per se.

In a further particularly preferred embodiment, to increase the hydroxylase activity, nucleic acids are introduced into organisms, which nucleic acids code for proteins comprising the amino acid sequence of the hydroxylase of the sequence SEQ ID NO: 18.

Suitable nucleic acid sequences are obtainable, for example, by back-translation of the polypeptide sequence according to the genetic code.

Preferably, for this, those codons are used which are frequently used in accordance with the plant-specific codon usage. The codon usage may be determined readily on the basis of computer evaluations of other known genes of the relevant organisms.

In a particularly preferred embodiment, a nucleic acid comprising the sequence SEQ ID NO: 17 is introduced into the organism.

Preferably, in the above-described preferred embodiment, as β-cyclase genes, use is made of nucleic acids which code for proteins comprising the amino acid sequence SEQ ID NO: 20 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level with the sequence SEQ ID NO: 20 and which have the enzymatic property of a β-cyclase.

Further examples of β-cyclases and β-cyclase genes may readily be found, for example, from various organisms whose genomic sequence is known, as described above, by comparisons of homology of the amino acid sequences or the corresponding back-translated nucleic acid sequences from databases with the SEQ ID NO: 20.

Further examples of β-cyclases and β-cyclase genes may further readily be found, for example, starting from the sequence SEQ ID NO: 19 from various organisms whose genomic sequence is not known, by hybridization and PCR techniques in a manner known per se.

In a further particularly preferred embodiment, to increase the β-cyclase activity, nucleic acids are introduced into organisms which code for proteins comprising the amino acid sequence of the β-cyclase of the sequence SEQ ID NO: 20.

Suitable nucleic acid sequences are obtainable, for example, by back-translation of the polypeptide sequence according to the genetic code.

Preferably, for this, those codons are used which are used frequently in accordance with the plant-specific codon usage. The codon usage may be determined readily on the basis of computer evaluations of other known genes of the relevant organisms.

In a particularly preferred embodiment, a nucleic acid comprising the sequence SEQ ID NO: 19 is introduced into the organism.

All abovementioned hydroxylase genes or β-cyclase genes can be produced, furthermore, in a manner known per se by chemical synthesis from the nucleotide building blocks, for example by fragment condensation of individual overlapping complementary nucleic acid building blocks of the double helix. The chemical synthesis of oligonucleotides can be performed, for example, in a known manner by the phosphoamidite method (Voet, Voet, $2^{nd}$ edition, Wiley Press New York, pages 896-897). The addition of synthetic oligonucleotides and filling-in of gaps using the Klenow fragment of DNA polymerase and ligation reactions and general cloning methods are described in Sambrook et al. (1989), Molecular cloning: A laboratory manual, Cold Spring Harbor Laboratory Press.

In a further preferred embodiment of the method, the plants of the genus *Tagetes* have, compared to the wild type, in addition, a reduced ε-cyclase activity.

ε-Cyclase activity is taken to mean the enzyme activity of an ε-cyclase.

An ε-cyclase is taken to mean a protein which has the enzymatic-activity to convert a terminal linear residue of lycopene into an ε-ionone ring.

An ε-cyclase is therefore taken to mean, in particular, a protein which has the enzymatic activity to convert lycopene to δcarotene.

Accordingly, ε-cyclase activity is taken to mean the amount of lycopene converted or amount of δ-carotene formed by the protein ε-cyclase in a defined time.

With an ε-cyclase activity which is reduced compared with the wild type, thus, compared with the wild type, the amount of lycopene converted, or the amount of δ-carotene formed, is reduced by the protein ε-cyclase in a defined time.

A reduced ε-cyclase activity is preferably taken to mean the partial or essentially complete suppression or blocking, based on differing mechanisms of cell biology, of the functionality of an ε-cyclase in a plant cell, plant or part derived therefrom, tissue, organ, cells or seed.

The ε-cyclase activity in plants can be reduced compared with the wild type, for example, by reducing the amount of ε-cyclase protein, or the amount of ε-cyclase mRNA in the plant. Accordingly, an ε-cyclase activity which is reduced compared with the wild type can be determined directly, or via the determination of the amount of δ-cyclase protein or the amount of ε-cyclase mRNA of the inventive plant, in comparison with the wild type.

A reduction of the ε-cyclase activity comprises a quantitative decrease of an ε-cyclase up to an essentially complete absence of the ε-cyclase (that is to say lack of detectability of ε-cyclase activity or lack of immunological detectability of the ε-cyclase). Preferably, the ε-cyclase activity (or the amount of ε-cyclase protein or the amount of ε-cyclase mRNA) in the plant, particularly preferably in flowers, is reduced, in comparison with the wild type, by at least 5%, further preferably by at least 20%, further preferably by at least 50%, further preferably by 100%. In particular, "reduction" also means the complete absence of ε-cyclase activity (or of the ε-cyclase protein or of ε-cyclase mRNA).

The ε-cyclase activity in inventive genetically modified plants and in wild type or reference plants is preferably determined under the following conditions:

The ε-cyclase activity can be determined in vitro in accordance with Fraser and Sandmann (Biochem. Biophys. Res. Comm. 185(1) (1992) 9-15), when, to a defined amount of plant extract, there are added potassium phosphate as buffer (pH 7.6), lycopene as substrate, paprika stroma protein, $NADP^+$, NADPH and ATP.

The ε-cyclase activity in inventive genetically modified plants and in wild type or reference plants is determined, particularly preferably, in accordance with Bouvier, d'Harlingue and Camara (Molecular Analysis of carotenoid cyclase inhibition; Arch. Biochem. Biophys. 346(1) (1997) 53-64):

The in vitro assay is carried out in a volume of 0.25 ml. The assay mix comprises 50 mM potassium phosphate (pH 7.6), differing amounts of plant extract, 20 nM lycopene, 0.25 mg of paprika chromoplastid stroma protein, 0.2 mM $NADP^+$, 0.2 mM NADPH and 1 mM ATP. NADP/NADPH and ATP are dissolved in 0.01 ml of ethanol together with 1 mg of Tween 80 immediately before addition to the incubation medium. After a reaction time of 60 minutes at 30° C., the reaction is terminated by addition of chloroform/methanol (2:1). The reaction products extracted in chloroform are analyzed by means of HPLC.

An alternative assay using radioactive substrate is described in Fraser and Sandmann (Biochem. Biophys. Res. Comm. 185(1) (1992) 9-15). A further analytical method is described in Beyer, Kröncke and Nievelstein (On the mechanism of the lycopene isomerase/cyclase reaction in *Narcissus pseudonarcissus* L. chromoplast; J. Biol. Chem. 266(26) (1991) 17072-17078).

Preferably the α-cyclase activity in plants is reduced by at least one of the following methods:

a) introduction of at least one double-stranded α-cyclase ribonucleic acid sequence, also termed hereinafter ε-cyclase-dsRNA, or an expression cassette ensuring expression thereof, or expression cassettes. Those methods in which the ε-cyclase-dsRNA is directed toward an ε-cyclase gene (that is to say genomic DNA sequences such as the promoter sequence) or an ε-cyclase transcript (that is to say mRNA sequences) are comprised b) introduction of at least one ε-cyclase antisense ribonucleic acid sequence, also termed hereinafter ε-cyclase-antisense RNA, or an expression cassette ensuring expression thereof. Those methods in which the ε-cyclase-antisense RNA is directed toward an ε-cyclase gene (that is to say genomic DNA sequences) or an ε-cyclase gene transcript (that is to say RNA sequences) are comprised. α-Anomeric nucleic acid sequences are also comprised c) introduction of at least one α-cyclase-antisense RNA combined with a ribozyme or an expression cassette ensuring expression thereof d) introduction of at least one ε-cyclase sense ribonucleic acid sequence, also termed hereinafter ε-cyclase-sense RNA, for induction of a cosuppression, or of an expression cassette ensuring expression thereof e) introduction of at least one DNA- or protein-binding factor against an ε-cyclase gene, RNA, or protein, or of an expression cassette ensuring expression thereof f) introduction of at least one viral nucleic acid sequence causing ε-cyclase RNA breakdown, or of an expression cassette ensuring expression thereof g) introduction of at least one construct for producing a loss of function, such as the generation of stop codons or a shift in the reading frame, on an ε-cyclase gene, for example, by producing an insertion, deletion, inversion or mutation in an ε-cyclase gene. Preferably, knockout mutants can be generated by means of targeted insertion into said ε-cyclase gene by homologous recombination or introduction of sequence-specific nucleases against ε-cyclase gene sequences.

It is known to those skilled in the art that other methods can also be used in the context of the present invention to reduce an ε-cyclase or its activity or function. For example, the introduction of a dominant-negative variant of an ε-cyclase or of an expression cassette ensuring expression thereof can also be advantageous. Each individual one of these methods can cause a reduction in the amount of protein, amount of mRNA and/or activity of an ε-cyclase. Combined employment is also conceivable. Further methods are known to those skilled in the art and can comprise the impairment or prevention of processing of the ε-cyclase, of transport of the ε-cyclase or mRNA thereof, inhibition of ribosome attachment, inhibition of RNA splicing, induction of an ε-cyclase RNA-degrading enzyme and/or inhibition of translation elongation or termination.

The individual preferred methods may be described hereinafter by exemplary embodiments:

a) Introduction of a Double-Stranded ε-cyclase Ribonucleic Acid Sequence (ε-cyclase-dsRNA)

The method of gene regulation by means of double-stranded RNA ("double-stranded RNA interference"; dsRNAi) is known and is described, for example, in Matzke M A et al. (2000) Plant Mol Biol 43:401-415; Fire A. et al. (1998) Nature 391:806-811; WO 99/32619; WO 99/53050; WO 00/68374; WO 00/44914; WO 00/44895; WO 00/49035 or WO 00/63364. The processes and methods described in the citations reported are hereby explicitly incorporated by reference into the present application.

"Double-stranded ribonucleic acid sequence" is taken to mean, according to the invention, one or more ribonucleic acid sequences which, owing to complementary sequences, theoretically, for example according to the base pair rules of Watson and Crick and/or in reality, for example on the basis of hybridization experiments, are able, in vitro and/or in vivo, to form double-stranded RNA structures.

It is known to those skilled in the art that the formation of double-stranded RNA structures is an equilibrium state. Preferably, the ratio of double-stranded molecules to corresponding dissociated forms is at least 1 to 10, preferably 1:1, particularly preferably 5:1, most preferably 10:1.

A double-stranded ε-cyclase ribonucleic acid sequence or ε-cyclase-dsRNA is preferably taken to mean an RNA molecule which has a region having double-stranded structure and, in this region, comprises a nucleic acid sequence which a) is identical to at least a part of the ε-cyclase transcript inherent to the plant and/or
b) is identical to at least a part of the ε-cyclase promoter sequence inherent to the plant.

In the inventive method, therefore to reduce the ε-cyclase activity, preferably an RNA is introduced into the plant, which RNA has a region having double-stranded structure and, in this region, comprises a nucleic acid sequence which a) is identical to at least a part of the ε-cyclase transcript inherent to the plant and/or
b) is identical to at least a part of the ε-cyclase promoter sequence inherent to the plant.

The term "α-cyclase transcript" is taken to mean the transcribed part of an ε-cyclase gene which, in addition to the sequence coding for ε-cyclase, also comprises, for example, non-coding sequences, for example also UTRs.

An RNA which "is identical to at least a part of the ε-cyclase promoter sequence inherent to the plant" is preferably taken to mean that the RNA sequence is identical to at least a part of the theoretical transcript of the ε-cyclase promoter sequence, that is to say to the corresponding RNA sequence.

"A part" of the ε-cyclase transcript inherent to the plant or of the ε-cyclase promoter sequence inherent to the plant is taken to mean partial sequences which can range from a few base pairs up to complete sequences of the transcript or of the promoter sequence. The optimum length of the partial sequences can readily be determined by those skilled in the art by routine experiments.

Generally, the length of the partial sequences is at least 10 bases and at most 2 kb, preferably at least 25 bases and at most 1.5 kb, particularly preferably at least 50 bases and at most 600 bases, very particularly preferably at least 100 bases and at most 500, most preferably at least 200 bases or at least 300 bases and at most 400 bases.

Preferably, the partial sequences are sought out in such a manner that a specificity as high as possible is achieved and activities of other enzymes, the reduction of which is not desired, are not reduced. It is therefore advantageous for the partial sequences of the ε-cyclase-dsRNA to select parts of the ε-cyclase transcript and/or partial sequences of the ε-cyclase promoter sequences which do not occur in other activities.

In a particularly preferred embodiment, therefore, the ε-cyclase-dsRNA comprises a sequence which is identical to a part of the plant-inherent α-cyclase transcript and comprises the 5' end or the 3' end of the plant-inherent nucleic acid coding for an ε-cyclase.

In particular, non-translated regions in the 5' or 3' of the transcript are suitable to produce selective double-stranded structures.

The invention further relates to double-stranded RNA molecules (dsRNA molecules) which, on introduction into a plant organism (or a cell, tissue, organ or propagating material derived therefrom), cause the reduction of an ε-cyclase.

A double-stranded RNA molecule for reducing the expression of an ε-cyclase (ε-cyclase-dsRNA) preferably comprises a) a "sense" RNA strand comprising at least one ribonucleotide sequence which is essentially identical to at least one part of a "sense" RNA-ε-cyclase transcript, and
b) an "antisense" RNA strand which is essentially, preferably completely, complementary to the RNA "sense" strand under a).

To transform the plant with an ε-cyclase-dsRNA, preferably a nucleic acid construct is used which is introduced into the plant and which is transcribed in the plant into the ε-cyclase-dsRNA.

Therefore, the present invention also relates to a nucleic acid construct which can be transcribed into a) a "sense" RNA strand comprising at least one ribonucleotide sequence which is essentially identical to at least a part of the "sense" RNA-ε-cyclase transcript, and
b) an "antisense" RNA strand which is essentially, preferably completely, complementary to the RNA sense strand under a).

These nucleic acid constructs are also termed hereinafter expression cassettes or expression vectors.

In relation to the dsRNA molecules, ε-cyclase nucleic acid sequence, or the corresponding transcript, is preferably taken to mean the sequence according to SEQ ID NO: 38 or a part of same.

"Essentially identical" means that the dsRNA sequence can also have insertions, deletions and individual point mutations compared with the ε-cyclase target sequence, and nevertheless causes an efficient reduction of expression. Preferably, the homology is at least 75%, preferably at least 80%, very particularly preferably at least 90%, most preferably 100%, between the "sense" strand of an inhibitory dsRNA and at least a part of the "sense" RNA transcript of an ε-cyclase gene, or between the "antisense" strand and the complementary strand of an ε-cyclase gene.

A 100% sequence identity between dsRNA and an α-cyclase gene transcript is not absolutely necessary in order to cause efficient reduction of the ε-cyclase expression. Accordingly, there is the advantage that the method is tolerant toward sequence deviations as can be present owing to genetic mutations, polymorphisms or evolutionary divergences. Thus, it is possible, for example, with the dsRNA, which was generated starting from the ε-cyclase sequence of the one organism, to suppress the ε-cyclase expression in another organism. For this purpose, the dsRNA preferably comprises sequence regions of ε-cyclase gene transcripts which correspond to conserved regions. Said conserved regions can be readily derived from sequence comparisons.

Alternatively, an "essentially identical" dsRNA can also be defined as a nucleic acid sequence which is capable of hybridizing with a part of an ε-cyclase gene transcript (e.g. in 400 mM NaCl, 40 mM PIPES pH 6.4, 1 mM EDTA at 50° C. or 70° C. for 12 to 16 h).

"Essentially complementary" means that the "antisense" RNA strand can also have insertions, deletions and also individual point mutations compared with the complement of the "sense" RNA strand. Preferably, the homology is at least 80%, preferably at least 90%, very particularly preferably at least 95%, most preferably 100%, between the "antisense" RNA strand and the complement of the "sense" RNA strand.

In a further embodiment, the ε-cyclase-dsRNA comprises
a) a "sense" RNA strand comprising at least one ribonucleotide sequence which is essentially identical to at least a part of the "sense" RNA transcript of the promoter region of an ε-cyclase gene, and
b) an "antisense" RNA strand which is essentially, preferably completely, complementary to the RNA "sense" strand under a).

The corresponding nucleic acid construct which is preferably to be used for transforming the plants comprises
a) a "sense" DNA strand which is essentially identical to at least a part of the promoter region of an ε-cyclase gene, and
b) an "antisense" DNA strand which is essentially, preferably completely, complementary to the DNA "sense" strand under a).

Preferably, the promoter region of an ε-cyclase is taken to mean a sequence according to SEQ ID NO: 47 or a part of same.

To produce the ε-cyclase-dsRNA sequences for reducing the ε-cyclase activity, use is particularly preferably made of the following partial sequences, in particular for *Tagetes erecta:*

SEQ ID NO: 40: sense fragment of the 5'-terminal region of the ε-cyclase
SEQ ID NO: 41: antisense fragment of the 5'-terminal region of the ε-yclase
SEQ ID NO: 42: sense fragment of the 3'-terminal region of the ε-cyclase
SEQ ID NO: 43: antisense fragment of the 3'-terminal region of the ε-cyclase
SEQ ID NO: 47: sense fragment of the ε-cyclase promoter
SEQ ID NO: 48: antisense fragment of the ε-cyclase promoter The dsRNA can consist of one or more strands of polyribonucleotides. Obviously, in order to achieve the same purpose, a plurality of individual dsRNA molecules, each of which comprises one of the above-defined ribonucleotide sequence sections, can also be introduced into the cell or the organism.

The double-stranded dsRNA structure can be formed starting from two complementary separate RNA strands or, preferably, starting from a single, self-complementary, RNA strand. In this case, "sense" RNA strand and "antisense" RNA strand are preferably covalently bound to one another in the form of an inverted "repeat".

As described, for example, in WO 99/53050, the dsRNA can also comprise a hairpin structure, by "sense" and "antisense" strand being connected by a linking sequence ("linker"; for example an intron). The self-complementary dsRNA structures are preferred, since they only require the expression of one RNA sequence and always comprise the complementary RNA strands in an equimolar ratio. Preferably, the linking sequence is an intron (for example an intron of the ST-LS1 gene from potato; Vancanneyt G F et al. (1990) Mol Gen Genet 220(2):245-250).

The nucleic acid sequence coding for a dsRNA can contain further elements, for example transcription termination signals or polyadenylation signals.

However, if the dsRNA is directed against the promoter sequence of an ε-cyclase, it preferably does not comprise transcription termination signals or polyadenylation signals. This enables retention of the dsRNA in the nucleus of the cell and prevents distribution of the dsRNA in the entire plant "spreading").

If the two strands of the dsRNA are to be brought together in a cell or plant, this can be achieved, for example, in the following manner:
a) transformation of the cell or plant by a vector which comprises both expression cassettes,
b) cotransformation of the cell or plant using two vectors, the one comprising the expression cassettes with the "sense" strand, the other comprising the expression cassettes with the "antisense" strand.
c) crossing of two individual plant lines, the one comprising the expression cassettes with the "sense" strand, the other comprising the expression cassettes with the "antisense" strand.

The formation of the RNA duplex can be initiated either outside the cell or inside same.

The dsRNA can be synthesized either in vivo or in vitro. For this, a DNA sequence coding for a dsRNA can be placed into an expression cassette under the control of at least one genetic control element (for example a promoter). Polyadenylation is not necessary, likewise, elements for initiating a translation need not be present. Preferably, the expression cassette for the MP-dsRNA is present on the transformation construct or the transformation vector.

In a particularly preferred embodiment, the dsRNA is expressed starting from an expression construct under functional control of a flower-specific promoter, particularly preferably under the control of the promoter described by SEQ ID NO: 28 or a functionally equivalent part of same.

The expression cassettes coding for the "antisense" and/or the "sense" strand of an ε-cyclase-dsRNA, or for the self-complementary strand of the dsRNA are, for this, preferably inserted into a transformation vector and introduced into the plant cell using the methods described below. For the inventive method, a stable insertion into the genome is advantageous.

The dsRNA can be introduced in an amount which makes possible at least one copy per cell. Higher amounts (for example at least 5, 10, 100, 500 or 1000 copies per cell) can if appropriate cause a more efficient reduction.

b) Introduction of an Antisense Ribonucleic Acid Sequence of an ε-cyclase (ε-cyclase-antisense RNA)

Methods for reducing a certain protein by "antisense" technology have been described repeatedly, also in plants (Sheehy et al. (1988) Proc Natl Acad Sci USA 85: 8805-8809; U.S. Pat. No. 4,801,340; Mol JN et al. (1990) FEBS Lett 268(2):427-430). The antisense nucleic acid molecule hybridizes with or binds to the cellular mRNA and/or genomic DNA coding for the ε-cyclase to be reduced. This suppresses the transcription and/or translation of the ε-cyclase. The hybridization can be performed in a conventional manner via the formation of a stable duplex or, in the case of genomic DNA, by binding the antisense nucleic acid molecule to the duplex of the genomic DNA by specific interaction in the deep groove of the DNA helix.

An ε-cyclase-antisense RNA can be derived according to the base pair rules of Watson and Crick using the nucleic acid sequence coding for this ε-cyclase, for example the nucleic acid sequence according to SEQ ID NO: 38. The ε-cyclase-antisense RNA can be complementary to the entire transcribed mRNA of the ε-cyclase, be restricted to the coding region, or consist only of an oligonucleotide which is in part complementary to the coding or non-coding sequence of the mRNA. For instance, the oligonucleotide can, for example, be complementary to the region which comprises the start of translation for the ε-cyclase. The ε-cyclase-antisense RNA can have a length of, for example, 5, 10, 15, 20, 25, 30, 35, 40, 45 or 50 nucleotides, but can also be longer and comprise at least 100, 200, 500, 1000, 2000 or 5000 nucleotides. ε-Cyclase-antisense RNAs, in the context of the inventive method, are preferably expressed in a recombinant manner in the target cell.

In a particularly preferred embodiment, the antisense RNA is expressed starting from an expression construct under functional control of a flower-specific promoter, particularly preferably under the control of the promoter described by SEQ ID NO: 28, or a functionally equivalent part of same.

Said expression cassettes can be part of a transformation construct or transformation vector, or else be introduced in the context of a cotransformation.

In a further, preferred embodiment, the expression of an ε-cyclase can be inhibited by nucleotide sequences which are complementary to the regulatory region of an ε-cyclase gene (for example an ε-cyclase promoter and/or enhancer) and form triple-helical structures with the DNA double helix there, so that the transcription of the ε-cyclase gene is reduced. Corresponding methods are described (Helene C (1991) Anticancer Drug Res 6(6):569-84; Helene C et al. (1992) Ann NY Acad Sci 660:27-36; Maher L J (1992) Bioassays 14(12):807-815).

In a further embodiment, the ε-cyclase-antisense RNA can be an α-anomeric nucleic acid. Such α-anomeric nucleic acid molecules form specific double-stranded hybrids with complementary RNA in which, in contrast to the conventional β-nucleic acids, the two strands run parallel to one another (Gautier C et al. (1987) Nucleic Acids Res 15:6625-6641).

c) Introduction of an ε-cyclase-antisense RNA Combined with a Ribozyme

Advantageously, the above-described antisense strategy can be coupled to a ribozyme method. Catalytic RNA molecules or ribozymes can be adapted to any desired target RNA and cleave the phosphodiester backbone at specific positions, which functionally deactivate the target RNA (Tanner NK (1999) FEMS Microbiol Rev 23(3):257-275). The ribozyme is not modified itself as a result, but is able to cleave further target RNA molecules in a similar manner, which gives it the properties of an enzyme. The incorporation of ribozyme sequences into "antisense" RNAs gives precisely these "antisense" RNAs this enzyme-like RNA-cleaving property, and thus increases their efficiency in the inactivation of the target RNA. The production and use of corresponding ribozyme "antisense" RNA molecules is described (inter alia in Haseloff et al. (1988) Nature 334: 585-591); Haselhoff and Gerlach (1988) Nature 334:585-591; Steinecke P et al. (1992) EMBO J. 11 (4):1525-1530; de Feyter R et al. (1996) Mol Gen Genet. 250(3):329-338).

In this manner, ribozymes (for example "Hammerhead" ribozymes; Haselhoff and Gerlach (1988) Nature 334:585-591) can be used to cleave catalytically the mRNA of an ε-cyclase to be reduced, and thus prevent translation. The ribozyme technology can increase the efficiency of an antisense strategy. Methods for the expression of ribozymes for reducing certain proteins are described in (EP 0 291 533, EP 0 321 201, EP 0 360 257). In plant cells, ribozyme expression is likewise described (Steinecke P et al. (1992) EMBO J. 11(4):1525-1530; de Feyter R et al. (1996) Mol Gen Genet. 250(3):329-338). Suitable target sequences and ribozymes can be determined, for example, as described in "Steinecke P, Ribozymes, Methods in Cell Biology 50, Galbraith et al. eds, Academic Press, Inc. (1995), pp. 449460", by secondary structural calculations of ribozyme and target RNA and also by interaction thereof (Bayley C C et al. (1992) Plant Mol. Biol. 18(2):353-361; Lloyd A M and Davis R W et al. (1994) Mol Gen Genet. 242(6):653-657). For example, derivatives of the Tetrahymena L-19 IVS RNA can be constructed which have regions complementary to the mRNA of the ε-cyclase to be suppressed (see also U.S. Pat. No. 4,987,071 and U.S. Pat. No. 5,116,742). Alternatively, such ribozymes can also be identified via a selection process from a library of diverse ribozymes (Bartel D and Szostak J W (1993) Science 261:1411-1418).

d) Introduction of a Sense Ribonucleic Acid Sequence of an ε-cyclase (ε-cyclase-Sense RNA) for Induction of a Cosuppression The expression of an ε-cyclase ribonucleic acid sequence (or a part of same) in the sense orientation can lead to cosuppression of the corresponding ε-cyclase gene. The expression of sense RNA having homology to an endogenous ε-cyclase gene can reduce or switch off the expression of same, in a similar manner to that which has been described for antisense approaches (Jorgensen et al. (1996) Plant Mol Biol 31(5):957-973; Goring et al. (1991) Proc Natl Acad Sci USA 88:1770-1774; Smith et al. (1990) Mol Gen Genet 224:447481; Napoli et al. (1990) Plant Cell 2:279-289; Van der Krol et al. (1990) Plant Cell 2:291-99). The construct introduced can represent the homologous gene to be reduced entirely or only in part. The possibility of translation is not required. The application of this technology to plants is described (for example Napoli et al. (1990) Plant Cell 2:279-289; in U.S. Pat. No. 5,034,323).

Preferably, the cosuppression is implemented using a sequence which is essentially identical to at least a part of the nucleic acid sequence coding for an ε-cyclase, for example the nucleic acid sequence according to SEQ ID NO: 38. Preferably, the ε-cyclase-sense RNA is selected so that translation of the ε-cyclase or a part of same cannot occur. For this, for example, the 5'-untranslated or 3'-untranslated region can be selected, or else the ATG start codon can be deleted or mutated.

e) Introduction of DNA- or Protein-Binding Factors Against ε-cyclase Genes, RNAs or Proteins A reduction of ε-cyclase expression is also possible using specific DNA-binding factors, for example using factors of the zinc finger transcription factor type. These factors attach themselves to the genomic sequence of the endogenous target gene, preferably in the regulatory regions, and cause a reduction of expression. Corresponding methods for producing corresponding factors are described (Dreier B et al. (2001) J Biol Chem 276(31):29466-78; Dreier B et al. (2000) J Mol Biol 303(4):489-502; Beerli R R et al. (2000) Proc Natl Acad Sci USA 97 (4):1495-1500; Beerli R R et al. (2000) J Biol Chem 275(42):32617-32627; Segal D J and Barbas C F 3rd. (2000) Curr Opin Chem Biol 4(1):34-39; Kang J S and Kim J S (2000) J Biol Chem 275(12):8742-8748; Beerli R R et al. (1998) Proc Natl Acad Sci USA 95(25):14628-14633; Kim J S et al. (1997) Proc Natl Acad Sci USA 94(8):3616-3620; Klug A (1999) J Mol Biol 293(2):215-218; Tsai S Y et al. (1998) Adv Drug Deliv Rev 30(1-3):23-31; Mapp A K et al. (2000) Proc Natl Acad Sci USA 97(8):3930-3935; Sharrocks A D et al. (1997) Int J Biochem Cell Biol 29(12):1371-1387; Zhang L et al. (2000) J Biol Chem 275(43):33850-33860).

These factors can be selected using any desired piece of an $\epsilon$-cyclase gene. Preferably, this section is in the promoter region. For gene suppression, however, it can also be in the region of the coding exons or introns.

In addition, factors can be introduced into a cell which inhibit the $\epsilon$-cyclase itself. These protein-binding factors can be, for example, aptamers (Famulok M and Mayer G (1999) Curr Top Microbiol Immunol 243:123-36) or antibodies or antibody fragments or single-chain antibodies. The isolation of these factors is described (Owen M et al. (1992) Biotechnology (N Y) 10(7):790-794; Franken E et al. (1997) Curr Opin Biotechnol 8(4):411-416; Whitelam (1996) Trend Plant Sci 1:268-272).

f) Introduction of the Viral Nucleic Acid Sequences Causing $\epsilon$-cyclase RNA Breakdown, and Expression Constructs The $\epsilon$-cyclase expression can also be effectively achieved by induction of the specific $\epsilon$-cyclase RNA breakdown by the plant using a viral expression system (Amplikon; Angell S M et al. (1999) Plant J 20(3):357-362). These systems, also termed "VIGS" (virus-induced gene silencing), introduce into the plant by means of viral vectors nucleic acid sequences having homology to the transcript of an $\epsilon$-cyclase to be reduced. The transcription is then switched off, presumably mediated by plant defense mechanisms against viruses. Corresponding techniques and methods are described (Ratcliff F et al. (2001) Plant J 25(2):23745; Fagard M and Vaucheret H (2000) Plant Mol Biol 43(2-3): 285-93; Anandalakshmi R et al. (1998) Proc Natl Acad Sci USA 95(22):13079-84; Ruiz M T (1998) Plant Cell 10(6): 937-46).

Preferably, the VIGS-mediated reduction is implemented using a sequence which is essentially identical to at least a part of the nucleic acid sequence coding for an $\epsilon$-cyclase, for example the nucleic acid sequence according to SEQ ID NO: 1.

g) Introduction of Constructs to Generate a Loss of Function, or a Reduction in Function of $\epsilon$-cyclase Genes Those skilled in the art know numerous methods as to how genomic sequences can be specifically modified. These include, in particular, methods such as generating knockout mutants by means of targeted homologous recombination, for example by generating stop codons, shifts in the reading frame etc. (Hohn B and Puchta H (1999) Proc Natl Acad Sci USA 96:8321-8323) or the targeted deletion or inversion of sequences by means of, for example, sequence-specific recombinases or nucleases (see below).

The reduction of $\epsilon$-cyclase amount, function and/or activity can also be achieved by a targeted insertion of nucleic acid sequences (for example the nucleic acid sequence to be inserted in the context of the inventive method) into the sequence coding for an $\epsilon$-cyclase (for example by means of intermolecular homologous recombination). In the context of this embodiment, use is preferably made of a DNA construct which comprises at least a part of the sequence of an $\epsilon$-cyclase gene or neighboring sequences and can thus be specifically recombined with these in the target cell, so that deletion, addition or substitution of at least one nucleotide changes the $\epsilon$-cyclase gene in such a manner that the functionality of the $\epsilon$-cyclase gene is reduced or completely eliminated. The change can also relate to the regulative elements (for example the promoter) of the $\epsilon$-cyclase gene, so that the coding sequence remains unchanged, however expression (transcription and/or translation) is stopped and reduced. In the conventional homologous recombination, the sequence to be inserted is flanked at its 5'- and/or 3'-end by further nucleic acid sequences (A' or B') which have sufficient length and homology to corresponding sequences of the $\epsilon$-cyclase gene (A and B) to enable homologous recombination. The length is generally in a range from several hundred bases up to several kilo bases (Thomas K R and Capecchi M R (1987) Cell 51:503; Strepp et al. (1998) Proc Natl Acad Sci USA 95(8):4368-4373). For homologous recombination, the plant cell having the recombination construct is transformed using the methods described below and successfully recombined clones are selected on the basis of the consequent inactivated $\epsilon$-cyclase.

In a further preferred embodiment, the efficiency of recombination is increased by combination with methods which promote homologous recombination. Such methods are described and comprise, for example, the expression of proteins such as RecA, or treatment with PARP inhibitors. It has been found that the intrachromosomal homologous recombination in tobacco plants can be increased by using PARP inhibitors (Puchta H et al. (1995) Plant J 7:203-210). By using these inhibitors, the rate of homologous recombination in the recombination constructs after induction of the sequence-specific DNA double strand break, thus the efficiency of deletion of the transgenic sequences, can be further increased. Various PARP inhibitors can be used for this. Those which are preferably comprised are inhibitors such as 3-aminobenzamide, 8-hydroxy-2-methylquinazolin-4-one (NU1025), 1,11 b-dihydro-[2H]benzopyrano-[4,3,2-de]isoquinolin-3-one (GPI 6150), 5-aminoisoquinolinone, 3,4-dihydro-5-[4-(1-piperidinyl)butoxy]-1-(2H)isoquinolinone, or the substances described in WO 00/26192, WO 00/29384, WO 00/32579, WO 00/64878, WO 00/68206, WO 00/67734, WO 01/23386 and WO 01/23390.

Other suitable methods are the introduction of nonsense mutations into endogenous marker protein genes, for example by means of introducing RNA/DNA oligonucleotides into the plant (Zhu et al. (2000) Nat Biotechnol 18(5):555-558), or generating knockout mutants using, for example, T-DNA mutagenesis (Koncz et al., Plant Mol. Biol. 1992, 20(5):963-976). Point mutations can also be generated by means of DNA-RNA hybrids, which are also known as "chimeraplasty" (Cole-Strauss et al. (1999) Nucl Acids Res 27(5):1323-1330; Kmiec (1999) Gene therapy American Scientist 87(3):240-247).

The methods of dsRNAi, cosuppression by means of sense RNA, and "VIGS" ("virus-induced gene silencing") are also termed "post-transcriptional gene silencing" (PTGS) or "transcriptional gene silencing" (TGS). PTGS/TGS methods are particularly advantageous because the requirements for homology between the marker protein gene to be decreased and the transgenically expressed sense or dsRNA nucleic acid sequence are less than, for example, in the case of a classic antisense approach. Thus, using the marker protein nucleic acid sequences from one species, the expression of homologous marker protein proteins in other species can also be effectively reduced without requiring the isolation and structural elucidation of the marker protein homologs occurring there. This considerably reduces the workload.

In a particularly preferred embodiment of the inventive method, the ε-cyclase activity is reduced compared with the wild type by:
a) introducing at least one double-stranded ε-cyclase ribonucleic acid sequence or an expression cassette ensuring expression thereof, or expression cassettes, in plants and/or
b) introducing at least one ε-cyclase antisense ribonucleic acid sequence, or an expression cassette ensuring expression thereof, into plants.

In a very particularly preferred embodiment, the ε-cyclase activity is reduced compared with the wild type by introducing into plants at least one double-stranded ε-cyclase ribonucleic acid sequence or an expression cassette ensuring expression thereof, or expression cassettes.

In a preferred embodiment, genetically modified plants are used which have in flowers the lowest expression rate of an ε-cyclase.

This is preferably achieved by reducing the ε-cyclase activity in a flower-specific manner, particularly preferably in a flower-leaf-specific manner.

In the above-described particularly preferred embodiment, this is achieved by the transcription of the ε-cyclase-dsRNA sequences being formed under control of a flower-specific promoter or, still more preferably, under the control of a flower-leaf-specific promoter.

In a further preferred embodiment, plants are cultivated which, in addition, compared with the wild type have an increased activity of at least one of the activities selected from the group consisting of HMG-CoA reductase activity, (E)-4-hydroxy-3-methylbut-2-enyl-diphosphate reductase activity, 1-deoxy-D-xylose-5-phosphate-synthase activity, 1-deoxy-D-xylose-5-phosphate reductoisomerase activity, isopentenyl-diphosphate Δ-isomerase activity, geranyl-diphosphate synthase activity, farnesyl-diphosphate synthase activity, geranylgeranyl diphosphate synthase activity, phytoene synthase activity, phytoene desaturase activity, zeta-carotene desaturase activity, crtISO activity, FtsZ activity and MinD activity.

HMG-CoA reductase activity is taken to mean the enzyme activity of an HMG-CoA reductase (3-hydroxy-3-methylglutaryl coenzyme-A reductase).

A HMG-CoA reductase is taken to mean a protein which has the enzymatic activity to convert 3-hydroxy-3-methylglutaryl coenzyme-A to mevalonate.

Accordingly, HMG-CoA reductase activity is taken to mean the amount of 3-hydroxy-3-methylglutaryl coenzyme-A converted, or amount of mevalonate formed, in a defined time by the protein HMG-CoA reductase.

With an elevated HMG-CoA reductase activity compared with the wild type, therefore, the amount of 3-hydroxy-3-methylglutaryl coenzyme-A converted, or the amount of mevalonate formed, is increased in a defined time by the protein HMG-CoA reductase compared with the wild type.

Preferably, this increase in HMG-CoA reductase activity is at least 5%, further preferably at least 20%, further preferably at least 50%, further preferably at least 100%, more preferably at least 300%, still more preferably at least 500%, in particular at least 600%, of the HMG-CoA reductase activity of the wild type. HMG-CoA reductase activity is taken to mean the enzyme activity of an HMG-CoA reductase.

The HMG-CoA reductase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM MgCl2, 10 mM KCl, 1 mM EDTA, 1 mM EGTA, 0.1% (v/v) Triton X-100, 2 mM ε-aminocaproic acid, 10% glycerol, 5 mM KHCO$_3$. Shortly before the extraction, 2 mM DTT and 0.5 mM PMSF are added.

The HMG-CoA reductase activity can be measured in accordance with published descriptions (e.g. Schaller, Grausem, Benveniste, Chye, Tan, Song and Chua, Plant Physiol. 109 (1995), 761-770; Chappell, Wolf, Proulx, Cuellar and Saunders, Plant Physiol. 109 (1995) 1337-1343). Plant tissue can be homogenized and extracted in cold buffer (100 mM potassium phosphate (pH 7.0), 4 mM MgCl$_2$, 5 mM DTT). The homogenate is centrifuged at 10 000 g for 15 minutes at 4° C. The supernatant is thereafter centrifuged again at 100 000 g for 45-60 minutes. The HMG-CoA reductase activity is determined in the supernatant and in the pellet of the microsomal fraction (after resuspension in 100 mM potassium phosphate (pH 7.0) and 50 mM DTT). Aliquots of the solution and the suspension (the protein content of the suspension is equivalent to about 1-10 μg) are incubated at 30° C. for 15-60 minutes in 100 mM potassium phosphate buffer (pH 7.0 comprising 3 mM NADPH and 20 M ($^{14}$C)HMG-CoA (58 μCi/μM), ideally in a volume of 26 μl. The reaction is terminated by adding 5 μl of mevalonate lactone (1 mg/ml) and 6 N HCl. After addition, the mixture is incubated at room temperature for 15 minutes. The ($^{14}$C) mevalonate formed in the reaction is quantified by adding 125 μl of a saturated potassium phosphate solution (pH 6.0) and 300 μl of ethyl acetate. The mixture is mixed well and centrifuged. The radioactivity can be determined by measuring scintillation.

(E)-4-Hydroxy-3-methylbut-2-enyl-diphosphate Reductase Activity, Also Termed lytB or IspH, is Taken to Mean the Enzyme Activity of an (E)-4-hydroxy-3-methylbut-2-enyl-diphosphate reductase.

An (E)-4-Hydroxy-3-methylbut-2-enyl-diphosphate reductase is taken to mean a protein which has the enzymatic activity to convert (E)-4-hydroxy-3-methylbut-2-enyl diphosphate to isopentenyl diphosphate and dimethylallyl diphosphates.

Accordingly, (E)-4-hydroxy-3-methylbut-2-enyl-diphosphate reductase activity is taken to mean the amount of (E)-4-hydroxy-3-methylbut-2-enyl diphosphate converted, or amount of isopentenyl diphosphate and/or dimethylallyl diphosphate formed, in a defined time by the protein (E)-4-hydroxy-3-methylbut-2-enyl-diphosphate reductase.

In the event of an elevated (E)-4-hydroxy-3-methylbut-2-enyl-diphosphate reductase activity compared with the wild type, thus, compared with the wild type, the amount of (E)-4-hydroxy-3-methylbut-2-enyl diphosphate converted or the amount of isopentenyl diphosphate and/or dimethylallyl diphosphate formed is elevated in a defined time by the protein (E)-4-hydroxy-3-methylbut-2-enyl-diphosphate reductase.

Preferably, this increase in (E)-4-hydroxy-3-methylbut-2-enyl-diphosphate reductase activity is at least 5%, further preferably at least 20%, further preferably at least 50%, further preferably at least 100%, more preferably at least 300%, still more preferably at least 500%, in particular at least 600%, of the (E)-4-hydroxy-3-methylbut-2-enyl-diphosphate reductase activity of the wild type.

The (E)-4-hydroxy-3-methylbut-2-enyl-diphosphate reductase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

The (E)-4-hydroxy-3-methylbut-2-enyl-diphosphate reductase activity can be determined via immunological detection. The production of specific antibodies has been described by Rohdich and colleagues (Rohdich, Hecht, Gartner, Adam, Krieger, Amslinger, Arigoni, Bacher and Eisenreich: Studies on the nonmevalonate terpene biosynthetic pathway: metabolic role of lspH (LytB) protein, Natl. Acad. Natl. Sci. USA 99 (2002), 1158-1163). For the determination of the catalytic activity, Altincicek and colleagues (Altincicek, Duin, Reichenberg, Hedderich, Kollas, Hintz, Wagner, Wiesner, Beck and Jomaa: LytB protein catalyzes the terminal step of the 2-C-methyl-D-erythritol-4-phosphate pathway of isoprenoid biosynthesis; FEBS Letters 532 (2002) 437-440) describe an in vitro system which follows the reduction of (E)-4-hydroxy-3-methylbut-2-enyl diphosphate to isopentenyl diphosphate and dimethylallyl diphosphate.

1-Deoxy-D-xylose-5-phosphate synthase activity is taken to mean the enzyme activity of a 1-deoxy-D-xylose-5-phosphate synthase.

A 1-deoxy-D-xylose-5-phosphate synthase is taken to mean a protein which has the enzymatic activity to convert hydroxyethyl-ThPP and glyceraldehyde-3-phosphate to 1-deoxy-D-xylose-5-phosphate.

Accordingly, 1-deoxy-D-xylose-5-phosphate synthase activity is taken to mean the amount of hydroxyethyl-ThPP and/or glyceraldehyde-3-phosphate converted, or amount of 1-deoxy-D-xylose-5-phosphate formed in a defined time by the protein 1-deoxy-D-xylose-5-phosphate synthase.

In the event of an elevated 1-deoxy-D-xylose-5-phosphate synthase activity compared with the wild type, thus, the amount of hydroxyethyl-ThPP and/or glyceraldehyde-3-phosphate converted, or the amount of 1-deoxy-D-xylose-5-phosphate formed is elevated in a defined time by the protein 1-deoxy-D-xylose-5-phosphate synthase compared with the wild type.

Preferably, this elevation in 1-deoxy-D-xylose-5-phosphate synthase activity is at least 5%, further preferably at least 20%, further preferably at least 50%, further preferably at least 100%, more preferably at least 300%, still more preferably at least 500%, in particular at least 600%, of the 1-deoxy-D-xylose-5-phosphate synthase activity of the wild type.

The 1-deoxy-D-xylose-5-phosphate synthase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

The reaction solution (50-200 µl) for determination of D-1-deoxyxylulose-5-phosphate synthase activity (DXS) consists of 100 mM Tris-HCl (pH 8.0), 3 mM $MgCl_2$, 3 mM $MnCl_2$, 3 mM ATP, 1 mM thiamine diphosphate, 0.1% Tween 60, 1 mM potassium fluoride, 30 µM ($2$-$^{14}$C) pyruvate (0.5 µCi), 0.6 mM DL-glyceraldehyde-3-phosphate. The plant extract is incubated in the reaction solution at 37° C. for 1 to 2 hours. Thereafter, the reaction is terminated by heating to 80° C. for 3 minutes. After centrifugation at 13 000 revolutions per minute for 5 minutes, the supernatant is evaporated, the remainder is resuspended in 50 µl of methanol, applied to a TLC plate for thin-layer chromatography (Silica-Gel 60, Merck, Darmstadt) and separated in n-propyl alcohol/ethyl acetate/water (6:1:3; v/v/v). Radioactively labeled D-1-deoxyxylulose-5-phosphate (or D-1-deoxyxylulose) separates from ($2$-$^{14}$C) pyruvate. The quantification is performed using a scintillation counter. The method has been described in Harker and Bramley (FEBS Letters 448 (1999) 115-119). Alternatively, a fluorometric assay for determining the DXS synthase activity has been described by Querol and colleagues (Analytical Biochemistry 296 (2001) 101-105).

1-Deoxy-D-xylose-5-phosphate reductoisomerase activity is taken to mean the enzyme activity of a 1-deoxy-D-xylose-5-phosphate reductoisomerase.

A 1-deoxy-D-xylose-5-phosphate reductoisomerase is taken to mean a protein which has the enzymatic activity to convert 1-deoxy-D-xylose-5-phosphate to β-carotene.

Accordingly, 1-deoxy-D-xylose-5-phosphate reductoisomerase activity is taken to mean the amount of 1-deoxy-D-xylose-5-phosphate converted or amount of isopentenyl diphosphate formed in a defined time by the protein 1-deoxy-D-xylose-5-phosphate reductoisomerase.

In the event of an elevated 1-deoxy-D-xylose-5-phosphate reductoisomerase activity compared with the wild type, thus, the amount of 1-deoxy-D-xylose-5-phosphate converted, or the amount of isopentenyl diphosphate formed, is elevated in a defined time by the protein 1-deoxy-D-xylose-5-phosphate reductoisomerase compared with the wild type.

Preferably, this elevation in 1-deoxy-D-xylose-5-phosphate reductoisomerase activity is at least 5%, further preferably at least 20%, further preferably at least 50%, further preferably at least 100%, more preferably at least 300%, still more preferably at least 500%, in particular at least 600%, of the 1-deoxy-D-xylose-5-phosphate reductoisomerase activity of the wild type.

The 1-deoxy-D-xylose-5-phosphate reductoisomerase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

The activity of D-1-deoxyxylulose-5-phosphate reductoisomerase (DXR) is measured in a buffer consisting of 100 mM Tris-HCl (pH 7.5), 1 mM $MnCl_2$, 0.3 mM NADPH and 0.3 mM 1-deoxy-D-xylulose-4-phosphate, which can be synthesized enzymatically, for example (Kuzuyama, Takahashi, Watanabe and Seto: Tetrahedon letters 39 (1998) 4509-4512). The reaction is started by addition of the plant extract. The reaction volume can typically be from 0.2 to 0.5 ml; the incubation is performed at 37° C. over 30-60 minutes. During this time, the oxidation of NADPH is followed photometrically at 340 nm.

Isopentenyl-diphosphate Δ-isomerase activity is taken to mean the enzyme activity of an isopentenyl-diphosphate Δ-isomerase.

An isopentenyl-diphosphate D-isomerase is taken to mean a protein which has the enzymatic activity to convert isopentenyl diphosphate to dimethylallyl phosphate.

Accordingly, isopentenyl-diphosphate D-isomerase activity is taken to mean the amount of isopentenyl diphosphate converted or amount of dimethylallyl phosphate formed in a defined time by the protein isopentenyl-diphosphate D-isomerase.

In the event of an elevated isopentenyl-diphosphate D-isomerase activity compared with the wild type, thus the amount of isopentenyl diphosphate converted or the amount of dimethylallyl phosphate formed is elevated in a defined time by the protein isopentenyl-diphosphate D-isomerase compared with the wild type.

Preferably, this elevation in isopentenyl-diphosphate Δ-isomerase activity is at least 5%, further preferably at least 20%, further preferably at least 50%, further preferably at least 100%, more preferably at least 300%, still more preferably at least 500%, in particular at least 600%, of the isopentenyl-diphosphate Δ-isomerase activity of the wild type.

The isopentenyl-diphosphate Δ-isomerase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

The isopentenyl-diphosphate isomerase (IPP isomerase) activity can be determined according to the method published by Fraser and colleagues (Fraser, Römer, Shipton, Mills, Kiano, Misawa, Drake, Schuch and Bramley: Evaluation of transgenic tomato plants expressing an additional phytoene synthase in a fruit-specific manner; Proc. Natl. Acad. Sci. USA 99 (2002), 1092-1097, based on Fraser, Pinto, Holloway and Bramley, Plant Journal 24 (2000), 551-558). For enzyme assays, incubations are carried out using 0.5 μCi (1-$^{14}$C) IPP (isopentenyl pyrophosphate) (56 mCi/mmol, Amersham plc) as substrate in 0.4 M Tris-HCl (pH 8.0) comprising 1 mM DTT, 4 mM $MgCl_2$, 6 mM $MnCl_2$, 3 mM ATP, 0.1% Tween 60, 1 mM potassium fluoride in a volume of about 150-500 μl. Extracts are mixed with buffer (for example in a ratio of 1:1) and incubated at 28° C. for at least 5 hours. Thereafter, about 200 μl of methanol are added and an acid hydrolysis is carried out at 37° C. for about 1 hour by adding concentrated hydrochloric acid (final concentration 25%). Then, a twice-repeated extraction (in each case 500 μl) with petroleum ether (admixed with 10% of diethyl ether) is carried out. The radioactivity is determined in an aliquot of the hyperphase using a scintillation counter. The specific enzyme activity can be determined with a short incubation of 5 minutes, since short reaction times suppress the formation of reaction by-products (see Lützow and Beyer: The isopentenyl-diphosphate Δ-isomerase and its relation to the phytoene synthase complex in daffodil chromoplasts; Biochim. Biophys. Acta 959 (1988), 118-126).

Geranyl-diphosphate synthase activity is taken to mean the enzyme activity of a geranyl-diphosphate synthase.

A geranyl-diphosphate synthase is taken to mean a protein which has the enzymatic activity to convert isopentenyl diphosphate and dimethylallyl phosphate to geranyl diphosphate.

Accordingly, geranyl-diphosphate synthase activity is taken to mean the amount of isopentenyl diphosphate and/or dimethylallyl phosphate converted, or amount of geranyl diphosphate formed by the protein geranyl-diphosphate synthase in a defined time.

In the case of an elevated geranyl-diphosphate synthase activity compared with the wild type, thus, the amount of isopentenyl diphosphate and/or dimethylallyl phosphate converted, or the amount of geranyl diphosphate formed, is elevated by the protein geranyl-diphosphate synthase in a defined time compared with the wild type.

Preferably, this elevation in geranyl-diphosphate synthase activity is at least 5%, further preferably at least 20%, further preferably at least 50%, further preferably at least 100%, more preferably at least 300%, still more preferably at least 500%, in particular at least 600%, of the geranyl-diphosphate synthase activity of the wild type.

The geranyl-diphosphate synthase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM KHCO$_3$. Shortly before the extraction, 2 mM DTT and 0.5 mM PMSF are added.

The geranyl-diphosphate synthase (GPP synthase) activity can be determined in 50 mM Tris-HCl (pH 7.6), 10 mM MgCl$_2$, 5 mM MnCl$_2$, 2 mM DTT, 1 mM ATP, 0.2% Tween-20, 5 μM ($^{14}$C) IPP and 50 μM DMAPP (dimethylallyl pyrophosphate) after addition of plant extract (according to Bouvier, Suire, d'Harlingue, Backhaus and Camara: Molecular cloning of geranyl diphosphate synthase and compartmentation of monoterpene synthesis in plant cells, Plant Journal 24 (2000) 241-252). After the incubation at 37° C. for, for example, 2 hours, the reaction products are dephosphorylated (according to Koyama, Fuji and Ogura: Enzymatic hydrolysis of polyprenyl pyrophosphate, Methods Enzymol. 110 (1985), 153-155) and analyzed by means of thin-layer chromatography and measurement of the radioactivity incorporated (Dogbo, Bardat, Quennemet and Camara: Metabolism of plastid terpenoids: In vitro inhibition of phytoene synthesis by phenethyl pyrophosphate derivates, FEBS Letters 219 (1987) 211-215).

Farnesyl-diphosphate synthase activity is taken to mean the enzyme activity of a farnesyl-diphosphate synthase.

A farnesyl-diphosphate synthase is taken to mean a protein which has the enzymatic activity to convert geranyl diphosphates and isopentenyl diphosphate into farnesyl diphosphate.

Accordingly, farnesyl-diphosphate synthase activity is the amount of geranyl diphosphates and/or isopentenyl diphosphate converted, or amount of farnesyl diphosphate formed, by the protein farnesyl-diphosphate synthase in a defined time.

In the event of an elevated farnesyl-diphosphate synthase activity compared with the wild type, thus the amount of geranyl diphosphate and/or isopentenyl diphosphate converted, or the amount of farnesyl diphosphate formed, is elevated by the protein farnesyl-diphosphate synthase in a defined time.

Preferably, this elevation in farnesyl-diphosphate synthase activity is at least 5%, further preferably at least 20%, further preferably at least 50%, further preferably at least 100%, more preferably at least 300%, still more preferably at least 500%, in particular at least 600%, of the farnesyl-diphosphate synthase activity of the wild type.

The farnesyl-diphosphate synthase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM MgCl$_2$, 10 mM KCl, 1 mM EDTA, 1 mM EGTA, 0.1% (v/v) Triton X-100, 2 mM ε-aminocaproic acid, 10% glycerol, 5 mM KHCO$_3$. Shortly before the extraction, 2 mM DTT and 0.5 mM PMSF are added.

The farnesyl-pyrophosphate synthase (FPP synthase) activity can be determined according to a procedure by Joly and Edwards (Journal of Biological Chemistry 268 (1993), 26983-26989). According to this, the enzyme activity is assayed in a buffer of 10 mM HEPES (pH 7.2), 1 mM MgCl$_2$, 1 mM dithiothreitol, 20 μM geranyl pyrophosphate and 40 μM (1-$^{14}$C) isopentenyl pyrophosphate (4 Ci/mmol).

The reaction mixture is incubated at 37° C.; the reaction is terminated by adding 2.5 N HCl (in 70% ethanol comprising 19 μg/ml of farnesol). The reaction products are thus hydrolyzed by acid hydrolysis at 37° C. within 30 minutes. By adding 10% NaOH, the mixture is neutralized, and is extracted by shaking with hexane. An aliquot of the hexane phase can be measured by means of a scintillation counter to determine the radioactivity incorporated.

Alternatively, after incubation of plant extract and radioactively labeled IPP, the reaction products can be separated by thin-layer chromatography (Silica-Gel SE60, Merck) in benzene/methanol (9:1). Radioactively labeled products are eluted and the radioactivity is determined (according to Gaffe, Bru, Causse, Vidal, Stamitti-Bert, Carde and Gallusci: LEFPS1, a tomato farnesyl pyrophosphate gene highly expressed during early fruit development; Plant Physiology 123 (2000) 1351-1362).

Geranylgeranyl-diphosphate synthase activity is taken to mean the enzyme activity of a geranylgeranyl-diphosphate synthase.

A geranylgeranyl-diphosphate synthase is taken to mean a protein which has the enzymatic activity to convert farnesyl diphosphate and isopentenyl diphosphate into geranylgeranyl diphosphate.

Accordingly, geranylgeranyl-diphosphate synthase activity is taken to mean the amount of farnesyl diphosphate and/or isopentenyl diphosphate converted, or amount of geranylgeranyl diphosphate formed, by the protein geranylgeranyl-diphosphate synthase in a defined time.

In the case of an elevated geranylgeranyl-diphosphate synthase activity compared with the wild type, thus the amount of farnesyl diphosphate and/or isopentenyl diphosphate converted, or the amount of geranylgeranyl diphosphate formed, is elevated by the protein geranylgeranyl-diphosphate synthase in a defined time compared with the wild type.

Preferably, this elevation in geranylgeranyl-diphosphate synthase activity is at least 5%, further preferably at least 20%, further preferably at least 50%, further preferably at least 100%, more preferably at least 300%, still more preferably at least 500%, in particular at least 600%, of the β-cyclase activity of the wild type.

The geranylgeranyl-diphosphate synthase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM MgCl$_2$, 10 mM KCl, 1 mM EDTA, 1 mM EGTA, 0.1% (v/v) Triton X-100, 2 mM ε-aminocaproic acid, 10% glycerol, 5 mM KHCO$_3$. Shortly before the extraction, 2 mM DTT and 0.5 mM PMSF are added.

Activity of the geranylgeranyl-pyrophosphate synthase (GGPP synthase) can be assayed according to the method described by Dogbo and Camara (in Biochim. Biophys. Acta 920 (1987), 140-148: Purification of isopentenyl pyrophosphate isomerase and geranylgeranyl pyrophosphate synthase from *Capsicum* chromoplasts by affinity chromatography). For this, plant extract is added to a buffer (50 mM Tris-HCl (pH 7.6), 2 mM MgCl$_2$, 1 mM MnCl$_2$, 2 mM dithiothreitol, (1-$^{14}$C) IPP (0.1 μCi, 10 μM), 15 μM DMAPP, GPP or FPP)

having a total volume of about 200 µl. The incubation can be carried out at 30° C. for 1-2 hours (or longer). The reaction is terminated by adding 0.5 ml of ethanol and 0.1 ml of 6N HCl. After incubation at 37° C. for 10 minutes, the reaction mixture is neutralized with 6N NaOH, mixed with 1 ml of water and extracted by shaking with 4 ml of diethyl ether. The radioactivity is determined in an aliquot (e.g. 0.2 ml) of the ether phase by means of scintillation counting. Alternatively, after acid hydrolysis, the radioactively labeled prenyl alcohols can be extracted by shaking in ether and separated by HPLC (25 cm column Spherisorb ODS-1, 5 µm; elution with methanol/water (90:10; v/v) at a flow rate of 1 ml/min) and quanitified by means of a radioactivity monitor (in accordance with Wiedemann, Misawa and Sandmann: Purification and enzymatic characterization of the geranylgeranyl pyrophosphate synthase from *Erwinia uredovora* after expression in *Escherichia coli*).

Phytoene synthase activity is taken to mean the enzyme activity of a phytoene synthase.

A phytoene synthase is taken to mean a protein which has the enzymatic activity of converting a terminal linear residue of lycopene into a β-ionone ring.

In particular, a phytoene synthase is taken to mean a protein which has the enzymatic activity to convert geranylgeranyl diphosphate into phytoene.

Accordingly, phytoene synthase activity is taken to mean the amount of geranylgeranyl diphosphate converted, or amount of phytoene formed, by the protein phytoene synthase in a defined time.

In the case of an elevated phytoene synthase activity compared with the wild type, thus, the amount of geranylgeranyl diphosphate converted, or the amount of phytoene formed, is elevated by the protein phytoene synthase in a defined time compared with the wild type.

Preferably, this elevation of phytoene synthase activity is at least 5%, further preferably at least 20%, further preferably at least 50%, further preferably at least 100%, more preferably at least 300%, still more preferably at least 500%, in particular at least 600%, of the phytoene synthase activity of the wild type.

The phytoene synthase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

Phytoene synthase (PSY) activity can be determined by the method published by Fraser and colleagues (Fraser, Romer, Shipton, Mills, Kiano, Misawa, Drake, Schuch and Bramley: Evaluation of transgenic tomato plants expressing an additional phytoene synthase in a fruit-specific manner; Proc. Natl. Acad. Sci. USA 99 (2002), 1092-1097, based on Fraser, Pinto, Holloway and Bramley, Plant Journal 24 (2000) 551-558). For enzyme assays, incubations with ($^3$H) geranylgeranyl pyrophosphate (15 mCi/mM, American Radiolabeled Chemicals, St. Louis) as substrate are carried out in 0.4 M Tris-HCl (pH 8.0) comprising 1 mM DTT, 4 mM $MgCl_2$, 6 mM $MnCl_2$, 3 mM ATP, 0.1% Tween 60, 1 mM potassium fluoride. Plant extracts are mixed with buffer, for example 295 µl of buffer with extract in a total volume of 500 µl. Incubation is performed for at least 5 hours at 28° C. Then, phytoene is extracted by shaking twice (each time 500 µl) with chloroform. The radioactively labeled phytoene formed during the reaction is separated by means of thin-layer chromatography on silica plates in methanol/water (95:5; v/v). Phytoene can be identified on the silica plates in an iodine-enriched atmosphere (by heating a few iodine crystals). A phytoene standard serves as reference. The amount of radioactively labeled product is determined by measurement in the scintillation counter. Alternatively, phytoene can also be quantified by means of HPLC which is provided with a radioactivity detector (Fraser, Albrecht and Sandmann: Development of high performance liquid chromatographic systems for the separation of radiolabeled carotenes and precursors formed in specific enzymatic reactions; J. Chromatogr. 645 (1993) 265-272).

Phytoene desaturase activity is taken to mean the enzyme activity of a phytoene desaturase.

A phytoene desaturase is taken to mean a protein which has the enzymatic activity to convert phytoene into phytofluene and/or phytofluene into ζ-carotene (zeta-carotene).

Accordingly, phytoene desaturase activity is taken to mean the amount of phytoene or phytofluene converted or the amount of phytofluene or ζ-carotene formed by the protein phytoene desaturase in a defined time.

In the case of an elevated phytoene desaturase activity compared with the wild type, thus the amount of phytoene or phytofluene converted or the amount of phytofluene or ζ-carotene is elevated formed by the protein phytoene desaturase in a defined time compared with the wild type.

Preferably, this elevation in phytoene desaturase activity is at least 5%, further preferably at least 20%, further preferably at least 50%, further preferably at least 100%, more preferably at least 300%, still more preferably at least 500%, in particular at least 600%, of the phytoene desaturase activity of the wild type.

The phytoene desaturase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

The activity of phytoene desaturase (PDS) can be assayed by the incorporation of radioactively labeled ($^{14}$C) phytoene into unsaturated carotenes (as reported by Römer, Fraser, Kiano, Shipton, Misawa, Schuch and Bramley: Elevation of the provitamin A content of transgenic tomato plants; Nature Biotechnology 18 (2000) 666-669). Radioactively labeled phytoenes can be synthesized as described by Fraser (Fraser, De la Rivas, Mackenzie, Bramley: *Phycomyces* blakesleanus CarB mutants: their use in assays of phytoene desaturase; Phytochemistry 30 (1991), 3971-3976). Membranes of plastids of the target tissue can be incubated with 100 mM MES buffer (pH 6.0) comprising 10 mM $MgCl_2$ and 1 mM dithiothreitol in a total volume of 1 ml. ($^{14}$C) Phytoene dissolved in acetone (about 100 000 disintegrations/minute for one incubation in each case) is added, in which case the acetone concentration should not exceed 5% (v/v). This mixture is incubated at 28° C. for about 6 to 7 hours in the dark with shaking. Thereafter, pigments are extracted three times with about 5 ml of petroleum ether (admixed with 10% diethyl ether) and separated by means of HPLC and quantified.

Alternatively, the activity of the phytoene desaturase can be assayed as reported by Fraser et al. (Fraser, Misawa, Linden, Yamano, Kobayashi and Sandmann: Expression in *Escherichia coli*, purification, and reactivation of the recombinant *Erwinia uredovora* phytoene desaturase, Journal of Biological Chemistry 267 (1992),19891-19895).

Zeta-carotene desaturase activity is taken to mean the enzyme activity of a zeta-carotene desaturase.

A zeta-carotene desaturase is taken to mean a protein which has the enzymatic activity to convert ζ-carotene into neurosporin and/or neurosporin into lycopene.

Accordingly, zeta-carotene desaturase activity is taken to mean the amount of ζ-carotene or neurosporin converted, or amount of neurosporin or lycopene formed, by the protein zeta-carotene desaturase in a defined time.

In the event of an elevated zeta-carotene desaturase activity compared with the wild type, thus the amount of ζ-carotene or neurosporin converted, or the amount of neurosporin or lycopene formed, is elevated by the protein zeta-carotene desaturase in a defined time compared with the wild type.

Preferably, this elevation in zeta-carotene desaturase activity is at least 5%, further preferably at least 20%, further preferably at least 50%, further preferably at least 100%, more preferably at least 300%, still more preferably at least 500%, in particular at least 600%, of the zeta-carotene desaturase activity of the wild type.

The zeta-carotene desaturase activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

Analyses for determining the ξ-carotene desaturase (ZDS desaturase) can be carried out in 0.2 M potassium phosphate (pH 7.8, buffer volume about 1 ml). The analytical method for this was published by Breitenbach and colleagues (Breitenbach, Kuntz, Takaichi and Sandmann: Catalytic properties of an expressed and purified higher plant type ξ-carotene desaturase from *Capsicum annuum*; European Journal of Biochemistry. 265(1):376-383, 1999 Oct.). Each analytical assay mix comprises 3 mg of phosphytidylcholine which is suspended in 0.4 M potassium phosphate buffer (pH 7.8), 5 μl of ξ-carotene or neurosporenes, 0.02% butyl-hydroxytoluene, 10 μl of decylplastoquinone (1 mM methanolic stock solution) and plant extract. The volume of the plant extract must be adapted to the amount of ZDS desaturase activity present in order to make quantifications in a linear range of measurement possible. Incubations are typically performed for about 17 hours with vigorous shaking (200 rpm) at about 28° C. in the dark. Carotenoids are extracted by addition of 4 ml of acetone at 50° C. for 10 minutes with shaking. From this mixture, the carotenoids are transferred to a petroleum ether phase (comprising 10% diethyl ether). The diethyl ether/petroleum ether phase is evaporated under nitrogen, the carotenoids are redissolved in 20 μl and separated and quantified by means of HPLC.

crtISO activity is taken to mean the enzyme activity of a crtISO protein.

A crtISO protein is taken to mean a protein which has the enzymatic activity to convert 7,9,7',9'-tetra-cis-lycopene into all-trans-lycopene.

Accordingly, crtISO activity is taken to mean the amount of 7,9,7',9'-tetra-cis-lycopene converted or amount of all-trans-lycopene formed by the protein b-cyclase in a defined time.

In the event of an elevated crtISO activity compared with the wild type, thus the amount of 7,9,7',9'-tetra-cis-lycopene converted, or the amount of all-trans-lycopene formed, is elevated by the crtISO protein in a defined time compared with the wild type.

Preferably, this elevation in crtISO activity is at least 5%, further preferably at least 20%, further preferably at least 50%, further preferably at least 100%, more preferably at least 300%, still more preferably at least 500%, in particular at least 600%, of the crtISO activity of the wild type.

The crtISO activity in inventive genetically modified plants and in wild type or reference plants is preferably determined under the following conditions:

Frozen plant material is homogenized by intensive grinding in a mortar in liquid nitrogen and extracted with extraction buffer in a ratio of from 1:1 to 1:20. The respective ratio depends on the enzyme activities in the plant material available, so that determination and quantification of the enzyme activities is possible within the linear range of measurement. Typically, the extraction buffer can consist of 50 mM HEPES-KOH (pH 7.4), 10 mM $MgCl_2$, 10 mM KCl, 1 mM EDTA, 1 mM EGTA, 0.1% (v/v) Triton X-100, 2 mM ε-aminocaproic acid, 10% glycerol, 5 mM $KHCO_3$. Shortly before the extraction, 2 mM DTT and 0.5 mM PMSF are added.

FtsZ activity is taken to mean the physiological activity of an FtsZ protein.

An FtsZ protein is taken to mean a protein which has activity promoting cell division and plastid division and has homologies to tubulin proteins.

MinD activity is taken to mean the physiological activity of a MinD protein.

A MinD protein is taken to mean a protein which has a multifunctional role in cell division. It is a membrane-associated ATPase and, within the cell, can show an oscillating motion from pole to pole.

Furthermore, the increase in activity of enzymes of the non-mevalonate pathway can lead to a further increase in the desired ketocarotenoid end product. Examples therefor are 4-diphosphocytidyl-2-C-methyl-D-erythritol synthase, 4-diphosphocytidyl-2-C-methyl-D-erythritol kinase and 2-C-methyl-D-erythritol-2,4-cyclodiphosphate synthase. By modifying the gene expression of the corresponding genes, the activity of said enzymes can be increased. The modified concentrations of the relevant proteins can be detected in a standard manner by means of antibodies and corresponding blotting techniques. The increase in HMG-CoA reductase activity and/or (E)-4-hydroxy-3-methylbut-2-enyl-diphosphate reductase activity and/or 1-deoxy-D-xylose-5-phosphate synthase activity and/or 1-deoxy-D-xylose-5-phosphate reductoisomerase activity and/or isopentenyl-diphosphate Δ-isomerase activity and/or geranyl-diphosphate synthase activity and/or farnesyl-diphosphate synthase activity and/or geranylgeranyl-diphosphate synthase activity and/or phytoene synthase activity and/or phytoene desaturase activity and/or zeta-carotene desaturase activity and/or crtISO activity and/or FtsZ activity and/or MinD activity can be achieved by various ways, for example by switching off restricting regulatory mechanisms at the expression and protein level, or by increasing gene expression of nucleic acids coding for an HMG-CoA reductase and/or nucleic acids coding for an (E)-4-hydroxy-3-methylbut-2-enyl-diphosphate reductase and/or nucleic acids coding for a 1-deoxy-D-xylose-5-phosphate synthase and/or nucleic acids coding for a 1-deoxy-D-xylose-5-phosphate reductoisomerase and/or nucleic acids coding for an isopentenyl-diphosphate Δ-isomerase and/or nucleic acids coding for a geranyl-diphosphate synthase and/or nucleic acids coding for a farnesyl-diphosphate synthase and/or nucleic acids coding for a geranylgeranyl-diphosphate synthase and/or nucleic acids coding for a phytoene synthase and/or nucleic acids coding for a phytoene desaturase and/or nucleic acids coding for a zeta-carotene desaturase and/or nucleic acids coding for a crtISO protein and/or nucleic acids coding for a FtsZ protein and/or nucleic acids coding for a MinD protein compared with the wild type.

The gene expression of the nucleic acids coding for an HMG-CoA reductase and/or nucleic acids coding for an (E)-4-hydroxy-3-methylbut-2-enyl-diphosphate reductase and/or nucleic acids coding for a 1-deoxy-D-xylose-5-phosphate synthase and/or nucleic acids coding for a 1-deoxy-D-xylose-5-phosphate reductoisomerase and/or nucleic acids coding for an isopentenyl-diphosphate Δ-isomerase and/or nucleic acids coding for a geranyl-diphosphate synthase and/or nucleic acids coding for a farnesyl-diphosphate synthase and/or nucleic acids coding for a geranylgeranyl-diphosphate synthase and/or nucleic acids coding for a phytoene synthase and/or nucleic acids coding for a phytoene desaturase and/or nucleic acids coding for a zeta-carotene desaturase and/or nucleic acids coding for a crtISO protein and/or nucleic acids coding for an FtsZ protein and/or nucleic acids coding for a MinD protein can likewise be increased compared with the wild type by various ways, for example by inducing the HMG-CoA reductase gene and/or (E)-4-hydroxy-3-methylbut-2-enyl-diphosphate reductase gene and/or 1-deoxy-D-xylose-5-phosphate synthase gene and/or 1-deoxy-D-xylose-5-phosphate reductoisomerase gene and/or isopentenyl-diphosphate Δ-isomerase gene and/or geranyl-diphosphate synthase gene and/or farnesyl-diphosphate synthase gene and/or geranylgeranyl-diphosphate synthase gene and/or phytoene synthase gene and/or phytoene desaturase gene and/or zeta-carotene desaturase gene and/or crtISO gene and/or FtsZ gene and/or MinD gene by activators or by introducing one or more copies of the HMG-CoA reductase gene and/or (E)-4-hydroxy-3-methylbut-2-enyl-diphosphate reductase gene and/or 1-deoxy-D-xylose-5-phosphate synthase gene and/or 1-deoxy-D-xylose-5-phosphate reductoisomerase gene and/or isopentenyl-diphosphate Δ-isomerase gene and/or geranyl-diphosphate synthase gene and/or farnesyl-diphosphate synthase gene and/or geranylgeranyl-diphosphate synthase gene and/or phytoene synthase gene and/or phytoene desaturase gene and/or zeta-carotene desaturase gene and/or crtISO gene and/or FtsZ gene and/or MinD gene, also by introducing at least one nucleic acid coding for an HMG-CoA reductase and/or at least one nucleic acid coding for a (E)-4-hydroxy-3-methylbut-2-enyl-diphosphate reductase and/or at least one nucleic acid coding for a 1-deoxy-D-xylose-5-phosphate synthase and/or at least one nucleic acid coding for a 1-deoxy-D-xylose-5-phosphate reductoisomerase and/or at least one nucleic acid coding for an isopentenyl-diphosphate Δ-isomerase and/or at least one nucleic acid coding for a geranyl-diphosphate synthase and/or at least one nucleic acid coding for a farnesyl-diphosphate synthase and/or at least one nucleic acid coding for a geranylgeranyl-diphosphate synthase and/or at least one nucleic acid coding for a phytoene synthase and/or at least one nucleic acid coding for a phytoene desaturase and/or at least one nucleic acid coding for a zeta-carotene desaturase and/or at least one nucleic acid coding for a crtISO protein and/or at least one nucleic acid coding for an FtsZ protein and/or at least one nucleic acid coding for a MinD protein into the plant.

Elevation of the gene expression of a nucleic acid coding for an HMG-CoA reductase and/or (E)-4-hydroxy-3-methylbut-2-enyl-diphosphate reductase and/or 1-deoxy-D-xylose-5-phosphate synthase and/or 1-deoxy-D-xylose-5-phosphate reductoisomerase and/or isopentenyl-diphosphate Δ-isomerase and/or geranyl-diphosphate synthase and/or farnesyl-diphosphate synthase and/or geranylgeranyl-diphosphate synthase and/or phytoene synthase and/or phytoene desaturase and/or zeta-carotene desaturase and/or a crtISO protein and/or FtsZ protein and/or MinD protein is according to the invention also taken to mean the manipulation of the expression of the plant-inherent, endogenous HMG-CoA reductase and/or (E)-4-hydroxy-3-methylbut-2-enyl-diphosphate reductase and/or 1-deoxy-D-xylose-5-phosphate synthase and/or 1-deoxy-D-xylose-5-phosphate reductoisomerase and/or isopentenyl-diphosphate Δ-isomerase and/or geranyl-diphosphate synthase and/or farnesyl-diphosphate synthase and/or geranylgeranyl-diphosphate synthase and/or phytoene synthase and/or phytoene desaturase and/or zeta-carotene desaturase and/or the plant-inherent crtISO protein and/or FtsZ protein and/or MinD protein.

This can be achieved, for example, by modifying the corresponding promoter DNA sequence. Such a modification which causes an elevated expression rate of the gene, can be achieved, for example, by deletion or insertion of DNA sequences.

In a preferred embodiment, the increase of the gene expression of a nucleic acid coding for an HMG-CoA reductase and/or the increase of the gene expression of a nucleic acid coding for an (E)-4-hydroxy-3-methylbut-2-enyl-diphosphate reductase and/or the increase of the gene expression of a nucleic acid coding for a 1-deoxy-D-xylose-5-phosphate synthase and/or the increase of the gene expression of a nucleic acid coding for a 1-deoxy-D-xylose-5-phosphate reductoisomerase and/or the increase of the gene expression of a nucleic acid coding for an isopentenyl-diphosphate Δ-isomerase and/or the increase of the gene expression of a nucleic acid coding for a geranyl-diphosphate synthase and/or the increase of the gene expression of a nucleic acid coding for a farnesyl-diphosphate synthase and/or the increase of the gene expression of a nucleic acid coding for a geranylgeranyl-diphosphate synthase and/or the increase of the gene expression of a nucleic acid coding for a phytoene synthase and/or the increase of the gene expression of a nucleic acid coding for a phytoene desaturase and/or the increase of the gene expression of a nucleic acid coding for a zeta-carotene desaturase and/or the increase of the gene expression of a nucleic acid coding for a crtISO protein and/or the increase of the gene expression of a nucleic acid coding for an FtsZ protein and/or the increase of the gene expression of a nucleic acid coding for a MinD protein is achieved by introducing at least one nucleic acid coding for an HMG-CoA reductase and/or by introducing at least one nucleic acid coding for an (E)-4-hydroxy-3-methylbut-2-enyl-diphosphate reductase and/or by introducing at least one nucleic acid coding for a 1-deoxy-D-xylose-5-phosphate synthase and/or by introducing at least one nucleic acid coding for a 1-deoxy-D-xylose-5-phosphate reductoisomerase and/or by introducing at least one nucleic acid coding for an isopentenyl-diphosphate Δ-isomerase and/or by introducing at least one nucleic acid coding for a geranyl-diphosphate synthase and/or by introducing at least one nucleic acid coding for a farnesyl-diphosphate synthase and/or by introducing at least one nucleic acid coding for a geranylgeranyl-diphosphate synthase and/or by introducing at least one nucleic acid coding for a phytoene synthase and/or by introducing at least one nucleic acid coding for a phytoene desaturase and/or by introducing at least one nucleic acid coding for a zeta-carotene desaturase and/or by introducing at least one nucleic acid coding for a crtISO protein and/or by introducing at least one nucleic acid coding for an FtsZ protein and/or by introducing at least one nucleic acid coding for a MinD protein into the plant.

For this, in principle, use can be made of any HMG-CoA reductase gene or (E)-4-hydroxy-3-methylbut-2-enyl-diphosphate reductase gene or 1-deoxy-D-xylose-5-phosphate synthase gene or 1-deoxy-D-xylose-5-phosphate reductoisomerase gene or isopentenyl-diphosphate Δ-isomerase gene or geranyl-diphosphate synthase gene or farnesyl-diphosphate synthase gene or geranylgeranyl-diphosphate synthase gene or phytoene synthase gene or phytoene desaturase gene or zeta-carotene desaturase gene or crtISO gene or FtsZ gene or MinD gene.

In genomic HMG-CoA reductase sequences or (E)-4-hydroxy-3-methylbut-2-enyl-diphosphate reductase sequences or 1-deoxy-D-xylose-5-phosphate synthase sequences or 1-deoxy-D-xylose-5-phosphate reductoisomerase sequences or isopentenyl-diphosphate Δ-isomerase sequences or geranyl-diphosphate synthase sequences or farnesyl-diphosphate synthase sequences or geranylgeranyl-diphosphate synthase sequences or phytoene synthase sequences or phytoene desaturase sequences or zeta-carotene desaturase sequences or crtISO sequences or FtsZ sequences or MinD sequences from eukaryotic sources which comprise introns, in the event that the host plant is not able to, or cannot be given the ability to, express the corresponding proteins, preferably previously-processed nucleic acid sequences, such as the corresponding cDNAs, are to be used.

In the inventive preferred transgenic plants, therefore, in this preferred embodiment there is, compared with the wild type, at least one further HMG-CoA reductase gene and/or (E)-4-hydroxy-3-methylbut-2-enyl-diphosphate reductase gene and/or 1-deoxy-D-xylose-5-phosphate synthase gene and/or 1-deoxy-D-xylose-5-phosphate reductoisomerase gene and/or isopentenyl-diphosphate Δ-isomerase gene and/or geranyl-diphosphate synthase gene and/or farnesyl-diphosphate synthase gene and/or geranylgeranyl-diphosphate synthase gene and/or phytoene synthase gene and/or phytoene desaturase gene and/or zeta-carotene desaturase gene and/or crtISO gene and/or FtsZ gene and/or MinD gene.

In this preferred embodiment, the genetically modified plant has, for example, at least one exogenous nucleic acid coding for an HMG-CoA reductase or at least two endogenous nucleic acids coding for an HMG-CoA reductase and/or at least one exogenous nucleic acid coding for an (E)-4-hydroxy-3-methylbut-2-enyl-diphosphate reductase or at least two endogenous nucleic acids coding for an (E)-4-hydroxy-3-methylbut-2-enyl-diphosphate reductase and/or at least one exogenous nucleic acid coding for a 1-deoxy-D-xylose-5-phosphate synthase or at least two endogenous nucleic acids coding for a 1-deoxy-D-xylose-5-phosphate synthase and/or at least one exogenous nucleic acid coding for a 1-deoxy-D-xylose-5-phosphate reductoisomerase or at least two endogenous nucleic acids coding for a 1-deoxy-D-xylose-5-phosphate reductoisomerase and/or at least one exogenous nucleic acid coding for an isopentenyl-diphosphate Δ-isomerase or at least two endogenous nucleic acids coding for an isopentenyl-diphosphate Δ-isomerase and/or at least one exogenous nucleic acid coding for a geranyl-diphosphate synthase or at least two endogenous nucleic acids coding for a geranyl-diphosphate synthase and/or at least one exogenous nucleic acid coding for a farnesyl-diphosphate synthase or at least two endogenous nucleic acids coding for a farnesyl-diphosphate synthase and/or at least one exogenous nucleic acid coding for a geranylgeranyl-diphosphate synthase or at least two endogenous nucleic acids coding for a geranylgeranyl-diphosphate synthase and/or at least one exogenous nucleic acid coding for a phytoene synthase or at least two endogenous nucleic acids coding for a phytoene synthase and/or at least one exogenous nucleic acid coding for a phytoene desaturase or at least two endogenous nucleic acids coding for a phytoene desaturase and/or at least one exogenous nucleic acid coding for a zeta-carotene desaturase or at least two endogenous nucleic acids coding for a zeta-carotene desaturase and/or at least one exogenous nucleic acid coding for a crtISO protein or at least two endogenous nucleic acids coding for a crtISO protein and/or at least one exogenous nucleic acid coding for an FtsZ protein or at least two endogenous nucleic acids coding for an FtsZ protein and/or at least one exogenous nucleic acid coding for a MinD protein or at least two-endogenous nucleic acids coding for a MinD protein.

Examples of HMG-CoA Reductase Genes are:

A nucleic acid coding for an HMG-CoA reductase from *Arabidopsis thaliana*, Accession NM_106299; (nucleic acid: SEQ ID NO: 111, protein: SEQ ID NO: 112), and also further HMG-CoA reductase genes from other organisms having the following accession numbers:
P54961, P54870, P54868, P54869, O02734, P22791, P54873, P54871, P23228, P13704, P54872, Q01581, P17425, P54874, P54839, P14891, P34135, O64966, P29057, P48019, P48020, P12683, P43256, Q9XEL8, P34136, O64967, P29058, P48022, Q41437, P12684, Q00583, Q9XHL5, Q41438, Q9YAS4, O76819, O28538, Q9Y7D2, P54960, O51628, P48021, Q03163, P00347, P14773, Q12577, Q59468, PO4035, O24594, P09610, Q58116, O26662, Q01237, Q01559, Q12649, O74164, O59469, P51639, Q10283, O08424, P20715, P13703, P13702, Q96UG4, Q8SQZ9, O15888, Q9TUM4, P93514, Q39628, P93081, P93080, Q944T9, Q40148, Q84MM0, Q84LS3, Q9Z9N4, Q9KLM0

Examples of (E)-4-hydroxy-3-methylbut-2-enyl-diphosphate reductase genes are:

A nucleic acid coding for an (E)-4-hydroxy-3-methylbut-2-enyl-diphosphate reductase from *Arabidopsis thaliana* (IytB/ISPH), ACCESSION AY168881, (nucleic acid: SEQ ID NO: 113, protein: SEQ ID NO: 114), and also further (E)-4-hydroxy-3-methylbut-2-enyl-diphosphate reductase genes from other organisms having the following accession numbers:

T04781, AF270978_1, NP_485028.1, NP_442089.1, NP_681832.1, ZP_00110421.1, ZP_00071594.1, ZP_00114706.1, ISPH_SYNY3, ZP_00114087.1, ZP_00104269.1, AF398145_1, AF398146_1, AAD55762.1, AF514843_1, NP_622970.1, NP_348471.1, NP_562001.1, NP_223698.1, NP_781941.1, ZP_00080042.1, NP_859669.1, NP_214191.1, ZP_00086191.1, ISPH_VIBCH, NP_230334.1, NP_742768.1, NP_302306.1, ISPH_MYCLE, NP_602581.1, ZP_00026966.1, NP_520563.1, NP_253247.1, NP_282047.1, ZP_00038210.1, ZP_00064913.1, —CAA61555.1, ZP_00125365.1, ISPH_ACICA, EAA24703.1, ZP_00013067.1, ZP_00029164.1, NP_790656.1, NP_217899.1, NP_641592.1, NP_636532.1, NP_719076.1, NP_660497.1, NP_422155.1, NP_715446.1, ZP_00090692.1, NP_759496.1, ISPH_BURPS, ZP_00129657.1, NP_215626.1, NP_335584.1, ZP_00135016.1, NP_789585.1, NP_787770.1, NP_769647.1, ZP_00043336.1, NP_242248.1, ZP_00008555.1, NP_246603.1, ZP_00030951.1, NP_670994.1, NP_404120.1, NP_540376.1, NP_733653.1, NP_697503.1, NP_840730.1, NP_274828.1, NP_796916.1, ZP_00123390.1, NP_824386.1, NP_737689.1, ZP_00021222.1, NP_757521.1, NP_390395.1, ZP_00133322.1, CAD76178.1, NP_600249.1, NP_454660.1, NP_712601.1, NP_385018.1, NP_751989.1

Examples of 1-deoxy-D-xylose-5-phosphate Synthase Genes are:

A nucleic acid coding for a 1-deoxy-D-xylose-5-phosphate synthase from *Lycopersicon esculentum*, ACCESSION #AF143812 (nucleic acid: SEQ ID NO: 115, protein: SEQ ID NO: 116), and also further 1-deoxy-D-xylose-5-phosphate synthase genes from other organisms having the following accession numbers:

AF143812_1, DXS_CAPAN, CAD22530.1, AF182286_1, NP_193291.1, T52289, AAC49368.1, AAP14353.1, D71420, DXS_ORYSA, AF443590_1, BAB02345.1, CAA09804.2, NP_850620.1, CAD22155.2, AAM65798.1, NP_566686.1, CAD22531.1, AAC33513.1, CAC08458.1, MG10432.1, T08140, AAP14354.1, AF428463_1, ZP_00010537.1, NP_769291.1, AAK59424.1, NP_107784.1, NP_697464.1, NP_540415.1, NP_196699.1, NP_384986.1, ZP_00096461.1, ZP_00013656.1, NP_353769.1, BAA83576.1, ZP_00005919.1, ZP_00006273.1, NP_420871.1, AAM48660.1, DXS_RHOCA, ZP_00045608.1, ZP_00031686.1, NP_841218.1, ZP_00022174.1, ZP_00086851.1, NP_742690.1, NP_520342.1, ZP_00082120.1, NP_790545.1, ZP_00125266.1, CAC17468.1, NP_252733.1, ZP_00092466.1, NP_439591.1, NP_414954.1, NP_752465.1, NP_622918.1, NP_286162.1, NP_836085.1, NP_706308.1, ZP_00081148.1, NP_797065.1, NP_213598.1, NP_245469.1, ZP_00075029.1, NP_455016.1, NP_230536.1, NP_459417.1, NP_274863.1, NP_283402.1, NP_759318.1, NP_406652.1, DXS_SYNLE, DXS_SYNP7, NP_440409.1, ZP_00067331.1, ZP_00122853.1, NP_717142.1, ZP_00104889.1, NP_243645.1, NP_681412.1, DXS_SYNEL, NP_637787.1, DXS_CHLTE, ZP_00129863.1, NP_661241.1, DXS_XANCP, NP_470738.1, NP_484643.1, ZP_00108360.1, NP_833890.1, NP_846629.1, NP_658213.1, NP_642879.1, ZP_00039479.1, ZP_00060584.1, ZP_00041364.1, ZP_00117779.1, NP_299528.1

Examples of 1-deoxy-D-xylose-5-phosphate Reductoisomerase Genes are:

A nucleic acid coding for a 1-deoxy-D-xylose-5-phosphate reductoisomerase from *Arabidopsis thaliana*, ACCESSION #AF148852, (nucleic acid: SEQ ID NO: 137, protein: SEQ ID NO: 138), and also further 1-deoxy-D-xylose-5-phosphate reductoisomerase genes from other organisms having the following accession numbers:

AF148852, AY084775, AY054682, AY050802, AY045634, AY081453, AY091405, AY098952, AJ242588, AB009053, AY202991, NP_201085.1, T52570, AF331705_1, BAB16915.1, AF367205_1, AF250235_1, CAC03581.1, CAD22156.1, AF182287_1, DXR_MENPI, ZP_00071219.1, NP_488391.1, ZP_00111307.1, DXR_SYNLE, AAP56260.1, NP_681831.1, NP_442113.1, ZP_00115071.1, ZP_00105106.1, ZP_00113484.1, NP_833540.1, NP_657789.1, NP_661031.1, DXR_BACHD, NP_833080.1, NP_845693.1, NP_562610.1, NP_623020.1, NP_810915.1, NP_243287.1, ZP_00118743.1, NP_464842.1, NP_470690.1, ZP_00082201.1, NP_781898.1, ZP_00123667.1, NP_348420.1, NP_604221.1, ZP_00053349.1, ZP_00064941.1, NP_246927.1, NP_389537.1, ZP_00102576.1, NP_519531.1, AF124757_19, DXR_ZYMMO, NP_713472.1, NP_459225.1, NP_454827.1, ZP_00045738.1, NP_743754.1, DXR_PSEPK, ZP_00130352.1, NP_702530.1, NP_841744.1, NP_438967.1, AF514841_1, NP_706118.1, ZP_00125845.1, NP_404661.1, NP_285867.1, NP_240064.1, NP_414715.1, ZP_00094058.1, NP_791365.1, ZP_00012448.1, ZP_00015132.1, ZP_00091545.1, NP_629822.1, NP_771495.1, NP_798691.1, NP_231885.1, NP_252340.1, ZP_00022353.1, NP_355549.1, NP_420724.1, ZP_00085169.1, EAA17616.1, NP_273242.1, NP_219574.1, NP_387094.1, NP_296721.1, ZP_00004209.1, NP_823739.1, NP_282934.1, BAA77848.1, NP_660577.1, NP_760741.1, NP_641750.1, NP_636741.1, NP_829309.1, NP_298338.1, NP_444964.1, NP_717246.1, NP 224545.1, ZP_00038451.1, DXR_KITGR, NP 778563.1.

Examples of isopentenyl-diphosphate Δ-isomerase Genes are:

A nucleic acid coding for an isopentenyl-diphosphate Δ-isomerase from *Adonis palaestina* clone AplPI28, (ipiAa1), ACCESSION #AF188060, published by Cunningham, F. X. Jr. and Gantt, E.: Identification of multi-gene families encoding isopentenyl diphosphate isomerase in plants by heterologous complementation in *Escherichia coli*, Plant Cell Physiol. 41 (1), 119-123 (2000) (nucleic acid: SEQ ID NO: 117, protein: SEQ ID NO: 118), and also further isopentenyl-diphosphate Δ-isomerase genes from other organisms having the following accession numbers:

Q38929, O48964, Q39472, Q13907, O35586, P58044, O42641, O35760, Q10132, P15496, Q9YB30, Q8YNH4, Q42553, O27997, P50740, O51627, O48965, Q8KFR5, Q39471, Q39664, Q9RVE2, Q01335, Q9HHE4,

Q9BXS1, Q9 KWF6, Q9CIF5, Q88WB6, Q92BX2, Q8Y7A5, Q8TT35 Q9KK75, Q8NN99, Q8XD58, Q8FE75, Q46822, Q9HP40, P72002, P26173, Q9Z5D3, Q8Z3X9, Q8ZM82, Q9X7Q6, O13504, Q9HFW8, Q8NJL9, Q9UUQ1, Q9NH02, Q9M6K9, Q9M6K5, Q9FXR6, O81691, Q9S7C4, Q8S3L8, Q9M592, Q9M6K3, Q9M6K7, Q9FV48, Q9LLB6, Q9AVJ1, Q9AVG8, Q9M6K6, Q9AVJ5, Q9M6K2, Q9AYS5, Q9M6K8, Q9AVG7, Q8S3L7, Q8W250, Q941E1, Q9AVI8, Q9AYS6, Q9SAY0, Q9M6K4, Q8GVZ0, Q84RZ8, Q8KZ12, Q8KZ66, Q8FND7, Q88QC9, Q8BFZ6, BAC26382, CAD94476.

Examples of geranyl-diphosphate synthase Genes are:

A nucleic acid coding for a geranyl-diphosphate synthase from *Arabidopsis thaliana*, ACCESSION #Y17376, Bouvier, F., Suire, C., d'Harlingue, A., Backhaus, R. A. and Camara, B.: Molecular cloning of geranyl diphosphate synthase and compartmentation of monoterpene synthesis in plant cells, Plant J. 24 (2), 241-252 (2000) (nucleic acid: SEQ ID NO: 119, protein: SEQ ID NO: 120), and also further geranyl-diphosphate synthase genes from other organisms having the following accession numbers:
Q9FT89, Q8LKJ2, Q9FSW8, Q8LKJ3, Q9SBR3, Q9SBR4, Q9FET8, Q8LKJ1, Q84LG1, Q9JK86

Examples of Farnesyl-diphosphate Synthase Genes are:

A nucleic acid coding for a farnesyl-diphosphate synthase from *Arabidopsis thaliana* (FPS1), ACCESSION #U80605, published by Cunillera, N., Arro, M., Delourme, D., Karst, F., Boronat, A. and Ferrer, A.: *Arabidopsis thaliana* comprises two differentially expressed farnesyl-diphosphate synthase genes, J. Biol. Chem. 271 (13), 7774-7780 (1996), (nucleic acid: SEQ ID NO: 121, protein: SEQ ID NO: 122), and also further farnesyl-diphosphate synthase genes from other organisms having the following accession numbers:
P53799, P37268, Q02769, Q09152, P49351, O24241, Q43315, P49352, O24242, P49350, P08836, P14324, P49349, P08524, O66952, Q08291, P54383, Q45220, P57537, Q8K9A0, P22939, P45204, O66126, P55539, Q9SWH9, Q9AVI7, Q9FRX2, Q9AYS7, Q941E8, Q9FXR9, Q9ZWF6, Q9FXR8, Q9AR37, O50009, Q941E9, Q8RVK7, Q8RVQ7, O04882, Q93RA8, Q93RB0, Q93RB4, Q93RB5, Q93RB3, Q93RB1, Q93RB2, Q920E5.

Examples of Geranylgeranyl-diphosphate Synthase Genes are:

A nucleic acid coding for a geranylgeranyl-diphosphate synthase from Sinapis alba, ACCESSION #X98795, published by Bonk, M., Hoffmann, B., Von Lintig, J., Schledz, M., Al-Babili, S., Hobeika, E., Kleinig, H. and Beyer, P.: Chloroplast import of four carotenoid biosynthetic enzymes in vitro reveals differential fates prior to membrane binding and oligomeric assembly, Eur. J. Biochem. 247 (3), 942-950 (1997), (nucleic acid: SEQ ID NO: 123, protein: SEQ ID NO: 124), and also further geranylgeranyl-diphosphate synthase genes from other organisms having the following accession numbers:
P22873, P34802, P56966, P80042, Q42698, Q92236, O95749, Q9WTN0, Q50727, P24322, P39464, Q9FXR3, Q9AYN2, Q9FXR2, Q9AVG6, Q9FRW4, Q9SXZ5, Q9AVJ7, Q9AYN1, Q9AVJ4, Q9FXR7, Q8LSC5, Q9AVJ6, Q8LSC4, Q9AVJ3, Q9SSU0, Q9SXZ6, Q9SST9, Q9AVJ0, Q9AVI9, Q9FRW3, Q9FXR5, Q941F0, Q9FRX1, Q9K567, Q93RA9, Q93QX8, CAD95619, EAA31459

Examples of Phytoene Synthase Genes are:

A nucleic acid coding for a phytoene synthase from *Erwinia* uredovora, ACCESSION # D90087, published by Misawa, N., Nakagawa, M., Kobayashi, K., Yamano, S., Izawa, Y., Nakamura, K. and Harashima, K.: Elucidation of the *Erwinia uredovora* carotenoid biosynthetic pathway by functional analysis of gene products expressed in *Escherichia coli*; J. Bacteriol. 172 (12), 6704-6712 (1990), (nucleic acid: SEQ ID NO: 125, protein: SEQ ID NO: 126), and also further phytoene synthase genes from other organisms having the following accession numbers:
CAB39693, BAC69364, MF10440, CAA45350, BAA20384, AAM72615, BAC09112, CM48922, P_001091, CAB84588, MF41518, CM48155, AAD38051, MF33237, AAG10427, AAA34187, BAB73532, CAC19567, AAM62787, CAA55391, AAB65697, AAM45379, CAC27383, AAA32836, AAK07735, BM84763, P_000205, AAB60314, P_001163, P_000718, AAB71428, AAA34153, AAK07734, CAA42969, CAD76176, CAA68575, P_000130, P_001142, CAA47625, CAA85775, BAC14416, CAA79957, BAC76563, P_000242, P_000551, AAL02001, AAK15621, CAB94795, AAA91951, P_000448

Examples of Phytoene Desaturase Genes are:

A nucleic acid coding for a phytoene desaturase from *Erwinia* uredovora, ACCESSION # D90087, published by Misawa, N., Nakagawa, M., Kobayashi, K., Yamano, S., Izawa, Y., Nakamura, K. and Harashima, K.: Elucidation of the *Erwinia uredovora* carotenoid biosynthetic pathway by functional analysis of gene products expressed in *Escherichia coli*; J. Bacteriol. 172 (12), 6704-6712 (1990), (nucleic acid: SEQ ID NO: 127, protein: SEQ ID NO: 128), and also further phytoene desaturase genes from other organisms having the following accession numbers:
AAL15300, A39597, CAA42573, AAK51545, BAB08179, CAA48195, BAB82461, AAK92625, CAA55392, AAG10426, AAD02489, AA024235, AAC12846, AAA99519, AAL38046, CAA60479, CAA75094, ZP_001041, ZP_001163, CAA39004, CAA44452, ZP_001142, ZP_000718, BAB82462, AAM45380, CAB56040, ZP_001091, BAC09113, AAP79175, ML80005, AAM72642, AAM72043, ZP_000745, ZP_001141, BAC07889, CAD55814, ZP_001041, CAD27442, CAE00192, ZP_001163, ZP_000197, BM18400, AAG10425, ZP_001119, MF13698, 2121278A, AAB35386, AAD02462, BAB68552, CAC85667, AAK51557, CM12062, AAG51402, AAM63349, AAF85796, BAB74081, AAA91161, CAB56041, AAC48983, AAG14399, CAB65434, BAB73487, ZP_001117, ZP_000448, CAB39695, CAD76175, BAC69363, BM17934, ZP_000171, AAF65586, ZP_000748, BAC07074, ZP_001133, CAA64853, BAB74484, ZP_001156, AAF23289, AAG28703, AAP09348, AAM71569, BAB69140, ZP_000130, AAF41516, AAG18866, CAD95940, NP_656310, AAG10645, ZP_000276, ZP_000192, ZP_000186, AAM94364, EM31371, ZP_000612, BAC75676, AAF65582

Examples of Zeta-carotene Desaturase Genes are:

A nucleic acid coding for a zeta-carotene desaturase from Narcissus pseudonarcissus, ACCESSION #AJ224683, published by Al-Babili, S., Oelschlegel, J. and Beyer, P.: A cDNA encoding for beta carotene desaturase (Accession No.AJ224683) from *Narcissus pseudonarcissus* L. (PGR98-103), Plant Physiol. 117, 719-719 (1998), (nucleic acid: SEQ ID NO: 129, protein: SEQ ID NO: 130), and also further zeta-carotene desaturase genes from other organisms having the following accession numbers:
Q9R6×4, Q38893, Q9SMJ3, Q9SE20, Q9ZTP4, O49901, P74306, Q9FV46, Q9RCT2, ZDS_NARPS, BAB68552.1, CAC85667.1, AF372617_1, ZDS_TARER, CAD55814.1, CAD27442.1, 2121278A, ZDS_CAPAN, ZDS_LYCES, NP_187138.1, AAM63349.1, ZDS_ARATH, AAA91161.1, ZDS_MAIZE, AAG14399.1, NP_441720.1, NP_486422.1, ZP_00111920.1, CAB56041.1, ZP_00074512.1, ZP_00116357.1, NP_681127.1, ZP_00114185.1, ZP_00104126.1, CAB65434.1, NP_662300.1

Examples of crtISO Genes are:

A nucleic acid coding for a crtISO from *Lycopersicon esculentum*; ACCESSION #AF416727, published by Isaacson, T., Ronen, G., Zamir, D. and Hirschberg, J.: Cloning of tangerine from tomato reveals a carotenoid isomerase essential for the production of beta-crotene and xanthophylls in plants; Plant Cell 14 (2), 333-342 (2002), (nucleic acid: SEQ ID NO: 131, protein: SEQ ID NO: 132), and also further crtISO genes from other organisms having the following accession numbers:
AAM53952

Examples of FtsZ Genes are:

A nucleic acid coding for an FtsZ from *Tagetes erecta*, ACCESSION #AF251346, published by Moehs, C. P., Tian, L., Osteryoung, K. W. and Dellapenna, D.: Analysis of carotenoid biosynthetic gene expression during marigold petal development; Plant Mol. Biol. 45 (3), 281-293 (2001), (nucleic acid: SEQ ID NO: 133, protein: SEQ ID NO: 134), and also further FtsZ genes from other organisms having the following accession numbers:
CAB89286.1, AF205858_1, NP_200339.1, CAB89287.1, CAB41987.1, AAA82068.1, T06774, AF383876_1, BAC57986.1, CAD22047.1, BAB91150.1, ZP_00072546.1, NP_440816.1, T51092, NP_683172.1, BAA85116.1, NP_487898.1, JC4289, BAA82871.1, NP_781763.1, BAC57987.1, ZP_00111461.1, T51088, NP_190843.1, ZP_00060035.1, NP_846285.1, AAL07180.1, NP_243424.1, NP_833626.1, AAN04561.1, AAN04557.1, CAD22048.1, T51089, NP_692394.1, NP_623237.1, NP_565839.1, T51090, CAA07676.1, NP_113397.1, T51087, CAC44257.1, E84778, ZP_00105267.1, BAA82091.1, ZP_00112790.1, BAA96782.1, NP_348319.1, NP_471472.1, ZP_00115870.1, NP_465556.1, NP_389412.1, BM82090.1, NP_562681.1, AAM22891.1, NP_371710.1, NP_764416.1, CAB95028.1, FTSZ_STRGR, AF120117_1, NP_827300.1, JE0282, NP_626341.1, AAC45639.1, NP_785689.1, NP_336679.1, NP_738660.1, ZP_00057764.1, AAC32265.1, NP_814733.1, FTSZ_MYCKA, NP_216666.1, CAA75616.1, NP_301700.1, NP_601357.1, ZP_00046269.1, CAA70158.1, ZP_00037834.1, NP_268026.1, FTSZ_ENTHR, NP_787643.1, NP_346105.1, AAC32264.1, JC5548, AAC95440.1, NP_710793.1, NP_687509.1, NP_269594.1, AAC32266.1, NP_720988.1, NP_657875.1, ZP_00094865.1, ZP_00080499.1, ZP_00043589.1, JC7087, NP_660559.1, AAC46069.1, AF179611_14, AAC44223.1, NP_404201.1.

Examples of MinD Genes are:

A nucleic acid coding for a MinD from *Tagetes erecta*, ACCESSION #AF251019, published by Moehs, C. P., Tian, L., Osteryoung, K. W. and Dellapenna, D.: Analysis of carotenoid biosynthetic gene expression during marigold petal development; Plant Mol. Biol. 45 (3), 281-293 (2001), (nucleic acid: SEQ ID NO: 135, protein: SEQ ID NO: 136), and also further MinD genes having the following accession numbers:
NP_197790.1, BAA90628.1, NP_038435.1, NP_045875.1, AAN33031.1, NP_050910.1, CAB53105.1, NP_050687.1, NP_682807.1, NP_487496.1, ZP_00111708.1, ZP_00071109.1, NP_442592.1, NP_603083.1, NP_782631.1, ZP_00097367.1, ZP_00104319.1, NP_294476.1, NP_622555.1, NP_563054.1, NP_347881.1, ZP_00113908.1, NP_834154.1, NP_658480.1, ZP_00059858.1, NP_470915.1, NP_243893.1, NP_465069.1, ZP_00116155.1, NP_390677.1, NP_692970.1, NP_298610.1, NP_207129.1, ZP_00038874.1, NP_778791.1, NP_223033.1, NP_641561.1, NP_636499.1, ZP_00088714.1, NP_213595.1, NP_743889.1, NP_231594.1, ZP_00085067.1, NP_797252.1, ZP_00136593.1, NP_251934.1, NP_405629.1, NP_759144.1, ZP_00102939.1, NP_793645.1, NP_699517.1, NP_460771.1, NP_860754.1, NP_456322.1, NP_718163.1, NP_229666.1, NP_357356.1, NP_541904.1, NP_287414.1, NP_660660.1, ZP_00128273.1, NP_103411.1, NP_785789.1, NP_715361.1, AF149810_1, NP_841854.1, NP_437893.1, ZP_00022726.1, EAA24844.1, ZP_00029547.1, NP_521484.1, NP_240148.1, NP_770852.1, AF345908_2, NP_777923.1, ZP_00048879.1, NP_579340.1, NP_143455.1, NP_126254.1, NP_142573.1, NP_613505.1, NP_127112.1, NP_712786.1, NP_578214.1, NP_069530.1, NP_247526.1, AAA85593.1, NP_212403.1, NP_782258.1, ZP_00058694.1, NP_247137.1, NP_219149.1, NP_276946.1, NP_614522.1, ZP_00019288.1, CAD78330.1

Preferably, in the above-described preferred embodiment, as HMG-CoA reductase genes, use is made of nucleic acids which code for proteins comprising the amino acid sequence SEQ ID NO: 112 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 112, and which have the enzymatic property of an HMG-CoA reductase.

Further examples of HMG-CoA reductases and HMG-CoA reductase genes may readily be found, for example, from various organisms, the genomic sequence of which is known, as described above, by comparisons of homology of the amino acid sequences or of the corresponding back-translated nucleic acid sequences from databases with the SEQ ID NO: 112.

Further examples of HMG-CoA reductases and HMG-CoA reductase genes may furthermore readily be found, for example, starting from the sequence SEQ ID NO: 111 from various organisms, the genomic sequence of which is not known, as described above, by hybridization and PCR techniques in a manner known per se.

In a further particularly preferred embodiment, to increase the HMG-CoA reductase activity, nucleic acids which code for proteins comprising the amino acid sequence of the HMG-CoA reductase of the sequence SEQ ID NO: 112 are introduced into organisms.

Suitable nucleic acid sequences are, for example, obtainable by back-translation of the polypeptide sequence according to the genetic code.

Preferably, for this, those codons are used which are used frequently in accordance with the plant-specific codon usage. The codon usage may be readily determined on the basis of computer evaluations of other known genes of the relevant organisms.

In a particularly preferred embodiment, a nucleic acid comprising the sequence SEQ ID NO: 111 is introduced into the organism.

Preferably, in the above-described preferred embodiment, as (E)-4-hydroxy-3-methylbut-2-enyl-diphosphate reductase genes, use is made of nucleic acids which code for proteins comprising the amino acid sequence SEQ ID NO: 114 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 114 and which have the enzymatic property of an (E)-4-hydroxy-3-methylbut-2-enyl-diphosphate reductase.

Further examples of (E)-4-hydroxy-3-methylbut-2-enyl-diphosphate reductases and (E)-4-hydroxy-3-methylbut-2-enyl-diphosphate reductase genes may be readily found, for example, from various organisms whose genomic sequence is known, as described above, by comparisons of homology of the amino acid sequences or of the corresponding back-translated nucleic acid sequences from databases with the SEQ ID NO: 114.

Further examples of (E)-4-hydroxy-3-methylbut-2-enyl-diphosphate reductases and (E)-4-hydroxy-3-methylbut-2-enyl-diphosphate reductase genes may furthermore readily be found, for example, starting from the sequence SEQ ID NO: 113 from various organisms, the genomic sequence of which is not known, as described above, by hybridization and PCR techniques in a manner known per se.

In a further particularly preferred embodiment, to increase the (E)-4-hydroxy-3-methylbut-2-enyl-diphosphate reductase activity, nucleic acids are introduced into organisms which code for proteins comprising the amino acid sequence of the (E)-4-hydroxy-3-methylbut-2-enyl-diphosphate reductase of the sequence SEQ ID NO: 114.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 113 is introduced into the organism.

Preferably, in the above-described preferred embodiment, as 1-deoxy-D-xylose-5-phosphate synthase genes, use is made of nucleic acids which code for proteins comprising the amino acid sequence SEQ ID NO: 116 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 116 and which have the enzymatic property of a 1-deoxy-D-xylose-5-phosphate synthase.

Further examples of 1-deoxy-D-xylose-5-phosphate synthases and 1-deoxy-D-xylose-5-phosphate synthase genes may readily be found, for example, from various organisms, the genomic sequence of which is known, as described above, by comparisons of homology of the amino acid sequences or of the corresponding back-translated nucleic acid sequences from databases with the SEQ ID NO: 116.

Further examples of 1-deoxy-D-xylose-5-phosphate synthases and 1-deoxy-D-xylose-5-phosphate synthase genes may in addition readily be found, for example, starting from the sequence SEQ ID NO: 115 from various organisms, the genomic sequence of which is not known, as described above, by hybridization and PCR techniques in a manner known per se.

In a further particularly preferred embodiment, to increase the 1-deoxy-D-xylose-5-phosphate synthase activity, nucleic acids which code for proteins comprising the amino acid sequence of the 1-deoxy-D-xylose-5-phosphate synthase of the sequence SEQ ID NO: 116 are introduced into organisms.

Suitable nucleic acid sequences are obtainable, for example, by back-translation of the polypeptide sequence in accordance with the genetic code.

Preferably, for this, those codons are used which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 115 is introduced into the organism.

Preferably, in the above-described preferred embodiment, as 1-deoxy-D-xylose-5-phosphate reductoisomerase genes, use is made of nucleic acids which code for proteins comprising the amino acid sequence SEQ ID NO: 138 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 138 and which have the enzymatic property of a 1-deoxy-D-xylose-5-phosphate reductoisomerase.

Further examples of 1-deoxy-D-xylose-5-phosphate reductoisomerases and 1-deoxy-D-xylose-5-phosphate reductoisomerase genes may readily be found, for example, from various organisms, the genomic sequence of which is known, as described above, by comparisons of homology of the amino acid sequences or of the corresponding back-translated nucleic acid sequences from databases with the SEQ ID NO: 138.

Further examples of 1-deoxy-D-xylose-5-phosphate reductoisomerases and 1-deoxy-D-xylose-5-phosphate reductoisomerase genes may in addition readily be found, for example, starting from the sequence SEQ ID NO: 137 from various organisms, the genomic sequence of which is not known, as described above, by hybridization and PCR techniques in a manner known per se.

In a further particularly preferred embodiment, to increase the 1-deoxy-D-xylose-5-phosphate reductoisomerase activity, nucleic acids are introduced into organisms, which nucleic acids code for proteins comprising the amino acid sequence of the 1-deoxy-D-xylose-5-phosphate reductoisomerase of the sequence SEQ ID NO: 138.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 137 is introduced into the organism.

Preferably, in the above-described preferred embodiment, as isopentenyl D-isomerase genes, use is made of nucleic acids which code for proteins comprising the amino acid sequence SEQ ID NO: 118, or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 118 and which have the enzymatic property of an isopentenyl D-isomerase.

Further examples of isopentenyl D-isomerases and isopentenyl D-isomerase genes may readily be found, for example, from various organisms, the genomic sequence of which is known, as described above, by comparisons of homology of the amino acid sequences or of the corresponding back-translated nucleic acid sequences from databases with the SEQ ID NO: 118.

Further examples of isopentenyl D-isomerases and isopentenyl D-isomerase genes may in addition readily be found, for example, starting from the sequence SEQ ID NO: 117 from various organisms, the genomic sequence of which is not known, as described above, by hybridization and PCR techniques in a manner known per se.

In a further particularly preferred embodiment, to increase the isopentenyl D-isomerase activity, nucleic acids are introduced into organisms, which nucleic acids code for proteins comprising the amino acid sequence of the isopentenyl D-isomerase of the sequence SEQ ID NO: 118.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 117 is introduced into the organism.

Preferably, in the above-described preferred embodiment, as geranyl-diphosphate synthase genes, use is made of nucleic acids which code for proteins comprising the amino acid sequence SEQ ID NO: 120 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 120 and which have the enzymatic property of a geranyl-diphosphate synthase.

Further examples of geranyl-diphosphate synthases and geranyl-diphosphate synthase genes may readily be found, for example, from various organisms, the genomic sequence of which is known, as described above, by comparisons of homology of the amino acid sequences or of the corresponding back-translated nucleic acid sequences from databases with the SEQ ID NO: 120.

Further examples of geranyl-diphosphate synthases and geranyl-diphosphate synthase genes may in addition readily be found, for example, starting from the sequence SEQ ID NO: 119 from various organisms, the genomic sequence of which is not known, as described above, by hybridization and PCR techniques in a manner known per se.

In a further particularly preferred embodiment, to increase the geranyl-diphosphate synthase activity, nucleic acids are introduced into organisms, which nucleic acids code for proteins comprising the amino acid sequence of the geranyl-diphosphate synthase of the sequence SEQ ID NO: 120.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 119 is introduced into the organism.

Preferably, in the above-described preferred embodiment, as farnesyl-diphosphate synthase genes, use is made of nucleic acids which code for proteins comprising the amino acid sequence SEQ ID NO: 122 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 122 and which have the enzymatic property of a farnesyl-diphosphate synthase.

Further examples of farnesyl-diphosphate synthases and farnesyl-diphosphate synthase genes may readily be found, for example, from various organisms, the genomic sequence of which is known, as described above, by comparisons of homology of the amino acid sequences or of the corresponding back-translated nucleic acid sequences from databases with the SEQ ID NO: 122.

Further examples of farnesyl-diphosphate synthases and farnesyl-diphosphate synthase genes may, in addition, readily be found, for example, starting from the sequence SEQ ID NO: 121 from various organisms, the genomic sequence of which is not known, as described above, by hybridization and PCR techniques in a manner known per se.

In a further particularly preferred embodiment, to increase the farnesyl-diphosphate synthase activity, nucleic acids are introduced into organisms, which nucleic acids code for proteins comprising the amino acid sequence of the farnesyl-diphosphate synthase of the sequence SEQ ID NO: 122.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 121 is introduced into the organism.

Preferably, in the above-described preferred embodiment, as geranylgeranyl-diphosphate synthase genes, use is made of nucleic acids which code for proteins comprising the amino acid sequence SEQ ID NO: 124 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 124 and which have the enzymatic property of a geranylgeranyl-diphosphate synthase.

Further examples of geranylgeranyl-diphosphate synthases and geranylgeranyl-diphosphate synthase genes may readily be found, for example, from various organisms, the genomic sequence of which is known, as described above, by comparisons of homology of the amino acid sequences or of the corresponding back-translated nucleic acid sequences from databases with the SEQ ID NO: 124.

Further examples of geranylgeranyl-diphosphate synthases and geranylgeranyl-diphosphate synthase genes may in addition readily be found, for example, starting from the sequence SEQ ID NO: 123 from various organisms, the genomic sequence of which is not known, as described above, by hybridization and PCR techniques in a manner known per se.

In a further particularly preferred embodiment, to increase the geranylgeranyl-diphosphate synthase activity, nucleic acids are introduced into organisms, which nucleic acids code for proteins comprising the amino acid sequence of the geranylgeranyl-diphosphate synthase of the sequence SEQ ID NO: 124.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 123 is introduced into the organism.

Preferably, in the above-described preferred embodiment, as phytoene synthase genes, use is made of nucleic acids which code for proteins comprising the amino acid sequence SEQ ID NO: 126 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 126 and which have the enzymatic property of a phytoene synthase.

Further examples of phytoene synthases and phytoene synthase genes may readily be found, for example, from various organisms, the genomic sequence of which is known, as described above, by comparisons of homology of the amino acid sequences or of the corresponding back-translated nucleic acid sequences from databases with the SEQ ID NO: 126.

Further examples of phytoene synthases and phytoene synthase genes may in addition readily be found, for example, starting from the sequence SEQ ID NO: 125 from various organisms, the genomic sequence of which is not known, as described above, by hybridization and PCR techniques in a manner known per se.

In a further particularly preferred embodiment, to increase the phytoene synthase activity, nucleic acids are introduced into organisms, which nucleic acids code for proteins comprising the amino acid sequence of the phytoene synthase of the sequence SEQ ID NO: 126.

Suitable nucleic acid sequences are, for example, obtainable by back-translation of the polypeptide sequence in accordance with the genetic code.

Preferably, for this, use is made of those codons which are frequently used in accordance with the plant-specific codon usage. The codon usage may readily be determined on the basis of computer evaluations of other known genes of the relevant organisms.

In a particularly preferred embodiment; a nucleic acid comprising the sequence SEQ ID NO: 125 is introduced into the organism.

Preferably, in the above-described preferred embodiment, as phytoene desaturase genes, use is made of nucleic acids which code for proteins comprising the amino acid sequence SEQ ID NO: 128 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 128, and which have the enzymatic property of a phytoene desaturase.

Further examples of phytoene desaturases and phytoene desaturase genes may readily be found, for example, from various organisms, the genomic sequence of which is known, as described above, by comparisons of homology of the amino acid sequences or of the corresponding back-translated nucleic acid sequences from databases with the SEQ ID NO: 128.

Further examples of phytoene desaturases and phytoene desaturase genes may in addition readily be found, for example, starting from the sequence SEQ ID NO: 127 from various organisms, the genomic sequence of which is not known, as described above, by hybridization and PCR techniques in a manner known per se.

In a further particularly preferred embodiment, to increase the phytoene desaturase activity, nucleic acids are introduced into organisms, which nucleic acids code for proteins comprising the amino acid sequence of the phytoene desaturase of the sequence SEQ ID NO: 128.

Suitable nucleic acid sequences are obtainable, for example, by back-translation of the polypeptide sequence in accordance with the genetic code.

Preferably, for this, use is made of those codons which are frequently used in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 127 is introduced into the organism.

Preferably, in the above-described preferred embodiment, as zeta-carotene desaturase genes, use is made of nucleic acids which code for proteins comprising the amino acid sequence SEQ ID NO: 130 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 130, and which have the enzymatic property of a zeta-carotene desaturase.

Further examples of zeta-carotene desaturases and zeta-carotene desaturase genes may readily be found, for example, from various organisms, the genomic sequence of which is known, as described above, by comparisons of homology of the amino acid sequences or of the corresponding back-translated nucleic acid sequences from databases with the SEQ ID NO: 130.

Further examples of zeta-carotene desaturases and zeta-carotene desaturase genes may in addition readily be found, for example, starting from the sequence SEQ ID NO: 129 from various organisms, the genomic sequence of which is not known, as described above, by hybridization and PCR techniques in a manner known per se.

In a further particularly preferred embodiment, to increase the zeta-carotene desaturase activity, nucleic acids are introduced into organisms, which nucleic acids code for proteins comprising the amino acid sequence of the zeta-carotene desaturase of the sequence SEQ ID NO: 130.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 129 is introduced into the organism.

Preferably, in the above-described preferred embodiment, as CrtIso genes, use is made of nucleic acids which code for proteins comprising the amino acid sequence SEQ ID NO: 132 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 132, and which have the enzymatic property of a CrtIso.

Further examples of CrtIsos and CrtIso genes may readily be found, for example, from various organisms, the genomic sequence of which is known, as described above, by comparisons of homology of the amino acid sequences or of the corresponding back-translated nucleic acid sequences from databases with the SEQ ID NO: 132.

Further examples of CrtIsos and CrtIso genes may, in addition, readily be found, for example, starting from the sequence SEQ ID NO: 131 from various organisms, the genomic sequence of which is not known, as described above, by hybridization and PCR techniques in a manner known per se.

In a further particularly preferred embodiment, to increase the CrtIso activity, nucleic acids are introduced into organisms, which nucleic acids code for proteins comprising the amino acid sequence of the CrtIso of the sequence SEQ ID NO: 132.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 131 is introduced into the organism.

Preferably, in the above-described preferred embodiment, as FtsZ genes, use is made of nucleic acids which code for proteins comprising the amino acid sequence SEQ ID NO: 134 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 134, and which have the enzymatic property of an FtsZ.

Further examples of FtsZs and FtsZ genes may readily be found, for example, from various organisms, the genomic sequence of which is known, as described above, by comparisons of homology of the amino acid sequences or of the corresponding back-translated nucleic acid sequences from databases with the SEQ ID NO: 134.

Further examples of FtsZs and FtsZ genes may, in addition, readily be found, for example, starting from the sequence SEQ ID NO: 133 from various organisms, the genomic sequence of which is not known, as described above, by hybridization and PCR techniques in a manner known per se.

In a further particularly preferred embodiment, to increase the FtsZ activity, nucleic acids are introduced into organisms, which nucleic acids code for proteins comprising the amino acid sequence of the FtsZ of the sequence SEQ ID NO: 134.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 133 is introduced into the organism.

Preferably, in the above-described preferred embodiment, as MinD genes, use is made of nucleic acids which code for proteins comprising the amino acid sequence SEQ ID NO: 136 or a sequence derived from this sequence by substitution, insertion or deletion of amino acids, which proteins have an identity of at least 30%, preferably at least 50%, more preferably at least 70%, still more preferably at least 90%, most preferably at least 95%, at the amino acid level, with the sequence SEQ ID NO: 136 and which have the enzymatic property of a MinD.

Further examples of MinDs and MinD genes may readily be found, for example, from various organisms, the genomic sequence of which is known, as described above, by comparisons of homology of the amino acid sequences or of the corresponding back-translated nucleic acid sequences from databases with the SEQ ID NO: 136.

Further examples of MinDs and MinD genes may, in addition, readily be found, for example, starting from the sequence SEQ ID NO: 135 from various organisms, the genomic sequence of which is not known, as described above, by hybridization and PCR techniques in a manner known per se.

In a further particularly preferred embodiment, to increase the MinD activity, nucleic acids are introduced into organisms, which nucleic acids code for proteins comprising the amino acid sequence of the MinD of the sequence SEQ ID NO: 136.

Suitable nucleic acid sequences are obtainable, for example, by back-translation of the polypeptide sequence in accordance with the genetic code.

Preferably, for this, use is made of those codons which are used frequently in accordance with the plant-specific codon usage. The codon usage may readily be determined on the basis of computer evaluations of other known genes of the relevant organisms.

In a particularly preferred embodiment, a nucleic acid comprising the sequence SEQ ID NO: 135 is introduced into the organism.

All of the abovementioned HMG-CoA reductase genes, (E)-4-hydroxy-3-methylbut-2-enyl-diphosphate reductase genes, 1-deoxy-D-xylose-5-phosphate synthase genes, 1-deoxy-D-xylose-5-phosphate reductoisomerase genes, isopentenyl-diphosphate Δ-isomerase genes, geranyl-diphosphate synthase genes, farnesyl-diphosphate synthase genes, geranylgeranyl-diphosphate synthase genes, phytoene synthase genes, phytoene desaturase genes, zeta-carotene desaturase genes, crtISO genes, FtsZ genes or MinD genes, furthermore, can be prepared in a manner known per se by chemical synthesis from the nucleotide building blocks, for example by fragment condensation of individual overlapping complementary nucleic acid building blocks of the double helix. The chemical synthesis of oligonucleotides can be performed, for example, in a known manner by the phosphoamidite method (Voet, Voet, $2^{nd}$ edition, Wiley Press New York, pages 896-897). The attachment of synthetic oligonucleotides and filling-in of gaps using the Klenow fragment of the DNA polymerase and ligation reactions and also general cloning methods are described in Sambrook et al. (1989), Molecular cloning: A laboratory manual, Cold Spring Harbor Laboratory Press.

In a further preferred embodiment of the method, the plants additionally have a reduced endogenous β-hydroxylase activity compared with the wild type.

A reduced activity is, as mentioned above, preferably taken to mean the partial or essentially complete suppression or blocking, based on differing mechanisms of cell biology, of the functionality of an enzyme in a plant cell, plant or part derived therefrom, tissue, organ, cells or seeds.

The reduction of an activity in plants compared with the wild type can be achieved, for example, by reducing the amount of protein, or the amount of mRNA in the plant. Accordingly, an activity reduced compared with the wild type can be determined directly, or via the determination of the amount of protein or amount of mRNA of the inventive plant compared with the wild type.

A reduction of an activity comprises a quantitative decrease of a protein up to an essentially complete absence of the protein (that is to say absence of detectability of the corresponding activity or absence of immunological detectability of the corresponding protein).

Endogenous β-hydroxylase activity is taken to mean the enzyme activity of the endogenous plant-inherent β-hydroxylase.

An endogenous β-hydroxylase is taken to mean an endogenous plant-inherent hydroxylase as described above. If, for example, *Tagetes erecta* is the target plant to be genetically modified, the endogenous β-hydroxylase is taken to mean the β-hydroxylase of *Tagetes erecta*.

An endogenous β-hydroxylase is therefore taken to mean, in particular, a plant-inherent protein which has the enzymatic activity to convert β-carotene to zeaxanthin.

Accordingly, endogenous β-hydroxylase activity is taken to mean the amount of β-carotene converted or amount of zeaxanthin formed by the protein endogenous β-hydroxylase in a defined time.

In the case of a reduced endogenous β-hydroxylase activity compared with the wild type, the amount of β-carotene converted or the amount of zeaxanthin formed by the protein endogenous β-hydroxylase is reduced in a defined time compared with the wild type.

Preferably, this reduction of the endogenous p-hydroxylase activity is at least 5%, further preferably at least 20%, further preferably at least 50%, further preferably 100%. Particularly preferably, the endogenous β-hydroxylase activity is completely switched off.

It has surprisingly been found that in plants which by a majority produce carotenoids of the α-carotene pathway, for example lutein, for example plants of the genus *Tagetes*, it is advantageous to reduce the activity of the endogenous β-hydroxylase and if appropriate to increase the activity of a heterologous hydroxylase. Particularly preferably, use is made of hydroxylases or functional equivalents thereof which originate from plants which produce by a majority carotenoids of the β-carotene pathway, for example the above-described β-hydroxylase from tomato (nucleic acid: SEQ ID No. 107, protein: SEQ ID No. 108).

The endogenous β-hydroxylase activity is determined as described above in a similar manner to determination of hydroxylase activity.

Preferably, the endogenous β-hydroxylase activity in plants is reduced by at least one of the following methods:

a) introducing at least one double-stranded endogenous β-hydroxylase ribonucleic acid sequence, hereinafter also termed endogenous β-hydroxylase-dsRNA, or an expression cassette ensuring expression thereof, or expression cassettes.

Those methods are comprised in which the endogenous β-hydroxylase-dsRNA is directed against an endogenous β-hydroxylase gene (that is to say genomic DNA sequences such as the promoter sequence) or an endogenous β-hydroxylase transcript (that is to say mRNA sequences), b) introducing at least one endogenous β-hydroxylase antisense ribonucleic acid sequence, hereinafter also termed endogenous β-hydroxylase-antisense RNA, or an expression cassette ensuring expression thereof. Those methods are comprised in which the endogenous β-hydroxylase-antisense RNA is directed against an endogenous β-hydroxylase gene (that is to say genomic DNA sequences) or an endogenous β-hydroxylase gene transcript (that is to say RNA sequences). α-Anomeric nucleic acid sequences are also comprised c) introducing at least one endogenous β-hydroxylase-antisense RNA combined with a ribozyme or an expression cassette ensuring expression thereof d) introducing at least one endogenous β-hydroxylase sense ribonucleic acid sequence, hereinafter also termed endogenous β-hydroxylase-sense RNA, for inducing a cosuppression or an expression cassette ensuring expression thereof e) introducing at least one DNA- or protein-binding factor against an endogenous β-hydroxylase gene, β-hydroxylase RNA or β-hydroxylase protein or an expression cassette ensuring expression thereof f) introducing at least one viral nucleic acid sequence, or an expression cassette ensuring expression thereof, causing breakdown of the endogenous β-hydroxylase RNA g) introducing at least one construct for generating a loss of function, for example the generation of stop codons or a shift in the reading frame, in an endogenous β-hydroxylase gene, for example by generating an insertion, deletion, inversion or mutation in an endogenous β-hydroxylase gene. Preferably, knockout mutants can be generated by means of targeted insertion into said endogenous β-hydroxylase gene by homologous recombination or introduction of sequence-specific nucleases against endogenous p-hydroxylase gene sequences.

Those skilled in the art know that other methods can also be used in the context of the present invention for reducing an endogenous β-hydroxylase or activity thereof, or function. For example, introducing a dominant-negative variant of an endogenous β-hydroxylase or an expression cassette ensuring expression thereof can also be advantageous. Each individual one of these methods can cause a reduction of the amount of protein, amount of mRNA and/or activity of an endogenous β-hydroxylase. Combined use is also conceivable. Further methods are known to those skilled in the art and can comprise the inhibition or suppression of processing of the endogenous β-hydroxylase, of the transport of the zeaxanthin epoxidase and/or endogenous β-hydroxylase or mRNA thereof, inhibition of ribosome attachment, inhibition of RNA splicing, induction of an endogenous β-hydroxylase-RNA-degrading enzyme and/or inhibition of the elongation or termination of translation.

The individual preferred methods may be described hereinafter by exemplary embodiments:

a) Introducing a Double-stranded Endogenous β-hydroxylase Ribonucleic Acid Sequence (endogenous β-hydroxylase-dsRNA)

The method of gene regulation by means of double-stranded RNA has been described extensively above for reducing the ε-cyclase activity. In a similar manner, this method may be carried out for reducing the endogenous β-hydroxylase activity.

A double-stranded endogenous β-hydroxylase ribonucleic acid sequence or else endogenous β-hydroxylase-dsRNA is preferably taken to mean an RNA molecule which has a region having double-stranded structure and, in this region, comprises a nucleic acid sequence which
a) is identical to at least a part of the plant-inherent endogenous β-hydroxylase transcript and/or
b) is identical to at least a part of the plant-inherent endogenous β-hydroxylase promoter sequence.

In the inventive method, for the reduction of the endogenous p-hydroxylase activity, preferably an RNA is introduced into the plant, which RNA has a region having double-stranded structure and, in this region, comprises a nucleic acid sequence which
a) is identical to at least a part of the plant-inherent endogenous β-hydroxylase transcript and/or
b) is identical to at least a part of the plant-inherent endogenous β-hydroxylase promoter sequence.

The term "endogenous β-hydroxylase transcript" is taken to mean the transcribed part of an endogenous β-hydroxylase gene which, in addition to the sequence coding for the endogenous β-hydroxylase, also comprises, for example, non-coding sequences, for example also UTRs.

An RNA which "is identical to at least a part of the plant-inherent endogenous β-hydroxylase promoter sequence" is preferably taken to mean the fact that the RNA sequence is identical to at least a part of the theoretical transcript of the endogenous β-hydroxylase promoter sequence, that is to say the corresponding RNA sequence.

"A part" of the plant-inherent endogenous β-hydroxylase transcript or of the plant-inherent endogenous β-hydroxylase promoter sequence is taken to mean partial sequences which can range from a few base pairs up to complete sequences of the transcript or of the promoter sequence. The optimum length of the partial sequences can readily be determined by those skilled in the art by routine experiments.

Generally, the length of the partial sequences is at least 10 bases and at most 2 kb, preferably at least 25 bases and at most 1.5 kb, particularly preferably at least 50 bases and at most 600 bases, very particularly preferably at least 100 bases and at most 500, most preferably at least 200 bases or at least 300 bases and at most 400 bases.

Preferably, the partial sequences are sought out in such a manner that a specificity as high as possible is achieved and activities of other enzymes, the reduction of which is not desired, are not reduced. It is therefore advantageous for the partial sequences of the endogenous β-hydroxylase-dsRNA to select parts of the endogenous β-hydroxylase transcript and/or partial sequences of the endogenous β-hydroxylase promoter sequences which do not occur in other activities.

In a particularly preferred embodiment, therefore, the endogenous β-hydroxylase-dsRNA comprises a sequence which is identical to a part of the plant-inherent endogenous β-hydroxylase transcript and comprises the 5' end or the 3' end of the plant-inherent nucleic acid coding for an endogenous β-hydroxylase. In particular, non-translated regions in the 5' or 3' of the transcript are suitable for producing selective double-stranded structures.

The invention further relates to double-stranded RNA molecules (dsRNA molecules) which, on introduction into a plant organism (or a cell, tissue, organ or propagated material derived therefrom), cause the reduction of an endogenous β-hydroxylase.

The invention further relates to a double-stranded RNA molecule for reducing the expression of an endogenous β-hydroxylase (endogenous β-hydroxylase-dsRNA), preferably comprising
a) a "sense" RNA strand comprising at least one ribonucleotide sequence which is essentially identical to at least a part of a "sense" RNA-endogenous β-hydroxylase transcript, and
b) an "antisense" RNA strand which is essentially, preferably completely, complementary to the RNA "sense" strand under a).

For the transformation of the plant with an endogenous β-hydroxylase-dsRNA, preferably a nucleic acid construct is used which is introduced into the plant and which is transcribed in the plant into the endogenous β-hydroxylase-dsRNA.

The present invention also further relates to a nucleic acid construct which can be transcribed into
a) a "sense" RNA strand comprising at least one ribonucleotide sequence which is essentially identical to at least a part of the "sense" RNA endogenous β-hydroxylase transcript, and
b) an "antisense" RNA strand which is essentially, preferably completely, complementary to the RNA sense strand under a).

These nucleic acid constructs are also termed hereinafter expression cassettes or expression vectors.

With respect to the dsRNA molecules, the endogenous β-hydroxylase nucleic acid sequence, or the corresponding transcript, is preferably taken to mean the sequence according to SEQ ID NO: 139 or a part of same.

"Essentially identical" means that the dsRNA sequence can also have insertions, deletions and individual point mutations compared with the endogenous β-hydroxylase target sequence and nevertheless causes an efficient reduction of expression. Preferably, the homology is at least 75%, preferably at least 80%, very particularly preferably at least 90%, most preferably 100%, between the "sense" strand of an inhibitory dsRNA and at least a part of the "sense" RNA transcript of an endogenous β-hydroxylase gene, or between the "antisense" strand to the complementary strand of an endogenous β-hydroxylase gene.

A 100% sequence identity between dsRNA and an endogenous β-hydroxylase gene transcript is not absolutely required to cause efficient reduction of the endogenous β-hydroxylase expression. Accordingly, there is the advantage that the method is tolerant toward sequence deviations as can occur as a result of genetic mutations, polymorphisms or evolutionary divergences. For instance it is possible, for example, using the dsRNA which was generated starting from the endogenous β-hydroxylase sequence of the one organism to suppress the endogenous β-hydroxylase expression in another organism. For this purpose, the dsRNA preferably comprises sequence regions of endogenous β-hydroxylase gene transcripts which correspond to conserved regions. Said conserved regions can readily be derived from sequence comparisons.

Alternatively, an "essentially identical" dsRNA can also be defined as a nucleic acid sequence which is capable of hybridizing with a part of an endogenous β-hydroxylase gene transcript (for example in 400 mM NaCl, 40 mM PIPES pH 6.4, 1 mM EDTA at 50° C. or 70° C. for 12 to 16 h).

"Essentially complementary" means that the "antisense" RNA strand can also have insertions, deletions and also individual point mutations compared with the complement of the "sense" RNA strand. Preferably, the homology is at least 80%, preferably at least 90%, very particularly preferably at least 95%, most preferably 100%, between the "antisense" RNA strand and the complement of the "sense" RNA strand.

In a further embodiment, the endogenous p-hydroxylase-dsRNA comprises
a) a "sense" RNA strand comprising at least one ribonucleotide sequence which is essentially identical to at least a part of the "sense" RNA transcript of the promoter region of an endogenous β-hydroxylase gene, and
b) an "antisense" RNA strand which is essentially, preferably completely, complementary to the RNA "sense" strand under a).

The corresponding nucleic acid construct which is preferably to be used for transforming of the plants comprises
a) a "sense" DNA strand which is essentially identical to at least a part of the promoter region of an endogenous β-hydroxylase gene, and
b) an "antisense" DNA strand which is essentially, preferably completely, complementary to the DNA "sense" strand under a).

To produce the endogenous β-hydroxylase sequences for reducing the endogenous β-hydroxylase activity, particularly preferably, in particular for *Tagetes erecta*, the following partial sequences are used:
SEQ ID NO: 141: sense fragment of the 5' terminal region of the endogenous β-hydroxylase
SEQ ID NO: 142: antisense fragment of the 5' terminal region of the endogenous β-hydroxylase The dsRNA can consist of one or more strands of polyribonucleotides. Of course, to achieve the same purpose, a plurality of individual dsRNA molecules each of which comprises one of the above-defined ribonucleotide sequence sections, can also be introduced into the cell or the organism.

The double-stranded dsRNA structure can be formed starting from two complementary separate RNA strands or, preferably, starting from a single, self-complementary RNA strand. In this case, "sense" RNA strand and "antisense" RNA strand are preferably covalently bound to one another in the form of an inverted "repeat".

As described, for example, in WO 99/53050, the dsRNA can also comprise a hairpin structure, by "sense" and "antisense" strand being connected by a linking sequence ("linker"; for example an intron). The self-complementary dsRNA structures are preferred, since they only require the expression of one RNA sequence and always comprise the complementary RNA strands in an equimolar ratio. Preferably, the linking sequence is an intron (for example an intron of the ST-LS1 gene from potato; Vancanneyt G F et al. (1990) Mol Gen Genet 220(2):245-250).

The nucleic acid sequence coding for a dsRNA can contain further elements, for example transcription termination signals or polyadenylation signals.

Further preferred embodiments for reducing the endogenous β-hydroxylase activity result similarly to the above-described preferred embodiments of the reduction of the ε-cyclase activity with exchange of the ε-cyclase by endogenous β-hydroxylase.

Particularly preferably in the inventive method, use is made of genetically modified plants having the following combinations of genetic modifications:
genetically modified plants which, compared with the wild type, have an elevated or induced ketolase activity in flower leaves and an elevated hydroxylase activity,
genetically modified plants which, compared with the wild type, have an elevated or induced ketolase activity in flower leaves and an elevated β-cyclase activity,
genetically modified plants which, compared with the wild type, have an elevated or induced ketolase activity in flower leaves and a reduced ε-cyclase activity,
genetically modified plants which, compared with the wild type, have an elevated or induced ketolase activity in flower leaves and an elevated hydroxylase activity and an elevated β-cyclase activity,
genetically modified plants which, compared with the wild type, have an elevated or induced ketolase activity in flower leaves and an elevated hydroxylase activity and a reduced ε-cyclase activity,
genetically modified plants which, compared with the wild type, have an elevated or induced ketolase activity in flower leaves and an elevated β-cyclase activity and a reduced ε-cyclase activity, and also
genetically modified plants which, compared with the wild type, have an elevated or induced ketolase activity in flower leaves and an elevated hydroxylase activity and an elevated β-cyclase activity and a reduced ε-cyclase activity,
genetically modified plants which, compared with the wild type, have an elevated or induced ketolase activity in flower leaves, a reduced ε-cyclase activity and an elevated β-cyclase activity,
genetically modified plants which, compared with the wild type, have an elevated or induced ketolase activity in flower leaves, a reduced ε-cyclase activity and a reduced endogenous β-hydroxylase activity, genetically modified plants which, compared with the wild type, have an elevated or induced ketolase activity in flower leaves, a reduced ε-cyclase activity and an elevated hydroxylase activity, genetically modified plants which, compared with the wild type, have an elevated or induced ketolase activity in flower leaves, an elevated β-cyclase activity and an elevated hydroxylase activity, genetically modified plants which, compared with the wild type, have an elevated or induced ketolase activity in flower leaves, an elevated β-cyclase activity and a reduced endogenous β-hydroxylase activity, genetically modified plants which, compared with the wild type, have an elevated or induced ketolase activity in flower leaves and an elevated β-cyclase activity, genetically modified plants which, compared with the wild type, have an elevated or induced ketolase activity in flower leaves, a reduced ε-cyclase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, in comparison with the wild type, have an elevated or induced ketolase activity in flower leaves, a reduced ε-cyclase activity, an elevated β-cyclase activity and an elevated hydroxylase activity, genetically modified plants which, compared with the wild type, have an elevated or induced ketolase activity in flower leaves, a reduced ε-cyclase activity, an elevated β-cyclase activity and a reduced endogenous β-hydroxylase activity, genetically modified plants which, compared with the wild type, have an elevated or induced ketolase activity in flower leaves, a reduced ε-cyclase activity and an elevated β-cyclase activity, genetically modified plants which, compared with the wild type, have an elevated or induced ketolase activity in flower leaves, a reduced ε-cyclase activity and an elevated hydroxylase activity, genetically modified plants which, compared with the wild type, have an elevated or induced ketolase activity in flower leaves, a reduced ε-cyclase activity and a reduced endogenous β-hydroxylase activity, genetically modified plants which, compared with the wild type, have an elevated or induced ketolase activity in flower leaves, a reduced ε-cyclase activity, an elevated hydroxylase activity and a reduced endogenous β-hydroxylase activity, genetically modified plants which, compared with the wild type, have an elevated or induced ketolase activity in flower leaves, an elevated β-cyclase activity, an elevated hydroxylase activity and a reduced endogenous β-hydroxylase activity, genetically modified plants which, compared with the wild type, have an elevated or induced ketolase activity in flower leaves, a reduced ε-cyclase activity, an elevated β-cyclase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, compared with the wild type, have an elevated or induced ketolase activity in flower leaves, a reduced ε-cyclase activity, an elevated β-cyclase activity, an elevated hydroxylase activity and a reduced endogenous β-hydroxylase activity, genetically modified plants which, compared with the wild type, have an elevated or induced ketolase activity in flower leaves, a reduced ε-cyclase activity, an elevated β-cyclase activity and an elevated hydroxylase activity, genetically modified plants which, compared with the wild type, have an elevated or induced ketolase activity in flower leaves, a reduced ε-cyclase activity, an elevated β-cyclase activity and a reduced endogenous β-hydroxylase activity, genetically modified plants which, compared with the wild type, have an elevated or induced ketolase activity in flower leaves, a reduced ε-cyclase activity, an elevated hydroxylase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, compared with the wild type, have an elevated or induced ketolase activity in flower leaves, a reduced ε-cyclase activity, a reduced endogenous p-hydroxylase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, compared with the wild type, have an elevated or induced ketolase activity in flower leaves, an elevated β-cyclase activity, an elevated hydroxylase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate Δ-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, compared with the wild type, have an elevated or induced ketolase activity in flower leaves, an elevated β-cyclase activity, a reduced endogenous β-hydroxylase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, compared with the wild type, have an elevated or induced ketolase activity in flower leaves, a reduced ε-cyclase activity, an elevated β-cyclase activity and an elevated hydroxylase activity and a reduced β-hydroxylase activity, genetically modified plants which, compared with the wild type, have an elevated or induced ketolase activity in flower leaves, a reduced ε-cyclase activity, an elevated β-cyclase activity, an elevated hydroxylase activity and at least one further elevated activity selected from the group consisting of HMG-CoA reductase activity, (E)$_4$-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity, genetically modified plants which, compared with the wild type, have an elevated or induced ketolase activity in flower leaves, a reduced ε-cyclase activity, an elevated β-cyclase activity, a reduced endogenous β-hydroxylase activity and at least one further elevated activity selected from the group consisting of HMG-CoA reductase activity, (E)-4-hydroxy-3-methylbut-2-enyl-diphosphate reductase activity, 1-deoxy-D-xylose-5-phosphate synthase activity, 1-deoxy-D-xylose-5-phosphate reductoisomerase activity, isopentenyl-diphosphate D-isomerase activity, geranyl-diphosphate synthase activity, farnesyl-diphosphate synthase activity, geranylgeranyl-diphosphate synthase activity, phytoene synthase activity, phytoene desaturase activity, zeta-carotene desaturase activity, crtISO activity, FtsZ activity and MinD activity.

Particularly preferred genetically modified plants, compared with the wild type, have an elevated or induced ketolase activity in flower leaves, an elevated β-cyclase activity and an elevated hydroxylase activity, the elevated ketolase activity being induced by introducing nucleic acids which code for a protein comprising the amino acid sequence SEQ ID NO: 2 or a sequence derived from this sequence by substitution, insertion or deletion of amino acids, which sequence has an identity of at least 20% at the amino acid level with the sequence SEQ ID NO: 2 and has the enzymatic property of a ketolase, the elevated β-cyclase activity being induced by introducing nucleic acid coding for a β-cyclase comprising the amino acid sequence SEQ ID NO: 110 or a sequence derived from this sequence by substitution, insertion or deletion of amino acids, which sequence has an identity of at least 20% at the amino acid level with the sequence SEQ ID NO: 110, and the elevated hydroxylase activity being induced by introducing nucleic acids coding for a hydroxylase comprising the amino acid sequence SEQ ID NO: 108 or a sequence derived from this sequence by substitution, insertion or deletion of amino acids, which sequence has an identity of at least 20% at the amino acid level with the sequence SEQ ID NO: 108.

Particularly preferred genetically modified plants have, compared with the wild type, an elevated or induced ketolase activity in flower leaves, a reduced ε-cyclase activity, an elevated β-cyclase activity, an elevated hydroxylase activity and a reduced endogenous β-hydroxylase activity, the elevated ketolase activity being induced by introducing nucleic acids which code for a protein comprising the amino acid sequence SEQ ID NO: 2 or a sequence derived from this sequence by substitution, insertion or deletion of amino acids, which sequence has an identity of at least 20% at the amino acid level with the sequence SEQ ID NO: 2 and which has the enzymatic property of a ketolase, the elevated β-cyclase activity being induced by introducing nucleic acid coding for a β-cyclase comprising the amino acid sequence SEQ ID NO: 110 or a sequence derived from this sequence by substitution, insertion or deletion of amino acids, which sequence has an identity of at least 20% at the amino acid level with the sequence SEQ ID NO: 100, the elevated hydroxylase activity being induced by introducing nucleic acids coding for a hydroxylase comprising the amino acid sequence SEQ ID NO: 108 or a sequence derived from this sequence by substitution, insertion or deletion of amino acids, which sequence has an identity of at least 20% at the amino acid level with the sequence SEQ ID NO: 108, and the reduced ε-cyclase activity and a reduced endogenous β-hydroxylase activity being induced in accordance with the above-described preferred embodiments.

These genetically modified plants of the genus *Tagetes* can, as described hereinafter, be produced, for example by introducing individual nucleic acid constructs (expression cassettes) or by introducing multiple constructs which comprise up to two, three or four of the described activities.

Hereinafter, the production of genetically modified plants having elevated or induced ketolase activity in flower leaves is described by way of example. The elevation of further activities, for example the hydroxylase activity and/or the β-cyclase activity and/or the HMG-CoA reductase activity and/or the (E)-4-hydroxy-3-methylbut-2-enyl-diphosphate reductase activity and/or the 1-deoxy-D-xylose-5-phosphate synthase activity and/or the 1-deoxy-D-xylose-5-phosphate reductoisomerase activity and/or the isopentenyl-diphosphate D-isomerase activity and/or the geranyl-diphosphate synthase activity and/or the farnesyl-diphosphate synthase activity and/or the geranylgeranyl-diphosphate synthase activity and/or the phytoene synthase activity and/or the phytoene desaturase activity and/or the zeta-carotene desaturase activity and/or the crtISO activity and/or the FtsZ activity and/or the MinD activity, can be achieved in a similar manner using nucleic acid sequences coding for a hydroxylase or β-cyclase or nucleic acids coding for an HMG-CoA reductase and/or nucleic acids coding for an (E)-4-hydroxy-3-methylbut-2-enyl-diphosphate reductase and/or nucleic acids coding for a 1-deoxy-D-xylose-5-phosphate synthase and/or nucleic acids coding for a 1-deoxy-D-xylose-5-phosphate reductoisomerase and/or nucleic acids coding for an isopentenyl-diphosphate D-isomerase and/or nucleic acids coding for a geranyl-diphosphate synthase and/or nucleic acids coding for a farnesyl-diphosphate synthase and/or nucleic acids coding for a geranylgeranyl-diphosphate synthase and/or nucleic acids coding for a phytoene synthase and/or nucleic acids coding for a phytoene desaturase and/or nucleic acids coding for a zeta-carotene desaturase and/or nucleic acids coding for a crtIso protein and/or nucleic acids coding for an FtsZ protein and/or nucleic acids coding for a MinD protein instead of nucleic acid sequences coding for a ketolase. The reduction of further activities, for example the reduction of the ε-cyclase activity, or of the endogenous β-hydroxylase activity can be performed in a similar manner using anti-ε-cyclase nucleic acid sequences or ε-cyclase inverted-repeat nucleic acid sequence or using anti-endogenous β-hydroxylase nucleic acid sequences or endogenous β-hydroxylase inverted-repeat nucleic acid sequences instead of nucleic acid sequences coding for a ketolase. The transformation can take place in the combinations of genetic changes, individually or by multiple constructs.

The transgenic plants of the genus *Tagetes* are produced, preferably, by transforming the starting plants using a nucleic acid construct which comprises the above-described nucleic acids coding for a ketolase which are functionally linked to one or more regulatory signals which ensure transcription and translation in plants.

These nucleic acid constructs in which the coding nucleic acid sequences are functionally linked to one or more regulatory signals which ensure the transcription and translation in plants are also termed hereinafter expression cassettes.

Preferably, the regulatory signals comprise one or more promoters which ensure transcription and translation in plants.

The expression cassettes contain regulatory signals, that is to say regulatory nucleic acid sequences which control the expression of the coding sequence in the host cell. According to a preferred embodiment, an expression cassette comprises upstream, that is to say at the 5' end of the coding sequence, a promoter, and downstream, that is to say at the 3' end, a polyadenylation signal and if appropriate further regulatory elements which are operationally linked to the coding sequence in-between from at least one of the above-described genes. An operational link is taken to mean the sequential arrangement of promoter, coding sequence, terminator and if appropriate further regulatory elements in such a manner that each of the regulatory elements can fulfill its function in the proper manner in the expression of the coding sequence.

Hereinafter, by way of example, the preferred nucleic acid constructs, expression cassettes and vectors for plants of the genus *Tagetes* and methods for producing transgenic plants of the genus *Tagetes*, and also the transgenic plants of the genus *Tagetes* themselves, are described.

The sequences which are preferred for the operational link, that are not restricted thereto, are targeting sequences for ensuring subcellular localization in the apoplast, in the vacuole, in plastids, in the mitochondrion, in the endoplasmatic reticulum (ER), in the cell nucleus, in oil bodies or other compartments and translation enhancers such as the 5' lead sequence from tobacco mosaic virus (Gailie et al., Nucl. Acids Res. 15 (1987), 8693-8711).

As promoters of the expression cassette, in principle, any promoter is suitable which can control the expression of foreign genes in plants.

"Constitutive" promoter means those promoters which ensure expression in numerous, preferably all, tissues over a very great period of plant development, preferably at all time points of plant development.

Preferably, use is made of in particular a plant promoter or a promoter which originates from a plant virus. In particular, preference is given to the promoter of the 35S transcript of the CaMV cauliflower mosaic virus (Franck et al. (1980) Cell 21:285-294; Odell et al. (1985) Nature 313:810-812; Shewmaker et al. (1985) Virology 140:281-288; Gardner et al. (1986) Plant Mol Biol 6:221-228) or the 19S CaMV promoter (U.S. Pat. No. 5,352,605; WO 84/02913; Benfey et al. (1989) EMBO J. 8:2195-2202).

A further suitable constitutive promoter is the pds promoter (Pecker et al. (1992) Proc. Natl. Acad. Sci USA 89:49624966) or the "Rubisco small subunit (SSU)" promoter (U.S. Pat. No. 4,962,028), the LeguminB promoter (GenBank Acc. No. X03677), the promoter of the nopalin synthase from *Agrobacterium*, the TR double promoter, the OCS (octopin synthase) promoter from *Agrobacterium*, the ubiquitin promoter (Holtorf S et al. (1995) Plant Mol Biol 29:637-649), the ubiquitin 1 promoter (Christensen et al. (1992) Plant Mol Biol 18:675-689; Bruce et al. (1989) Proc Natl Acad Sci USA 86:9692-9696), the Smas promoter, the cinnamyl alcohol dehydrogenase promoter (U.S. Pat. No. 5,683,439), the promoters of the vacuolar ATPase subunits or the promoter of a proline-rich protein from wheat (WO 91/13991), the Pnit promoter (Y07648.L, Hillebrand et al. (1998), Plant. Mol. Biol. 36, 89-99, Hillebrand et al. (1996), Gene, 170, 197-200) and also further promoters of genes, the constitutive expression of which in plants is known to those skilled in the art.

The expression cassettes can also comprise a chemically inducible promoter (review article: Gatz et al. (1997) Annu Rev Plant Physiol Plant Mol Biol 48:89-108), by which the expression of the ketolase gene in the plant can be controlled at a defined time point. Such promoters, for example the PRP1 promoter (Ward et al. (1993) Plant Mol Biol 22:361-366), salicylic acid-inducible promoter (WO 95/19443), a benzenesulfonamide-inducible promoter (EP 0 388 186), a tetracycline-inducible promoter (Gatz et al. (1992) Plant J 2:397-404), an abscisic acid-inducible promoter (EP 0 335 528) and an ethanol- or cyclohexanone-inducible promoter (WO 93/21334) can likewise be used.

Furthermore, promoters are preferred which are induced by biotic or abiotic stress, for example the pathogen-inducible promoter of the PRP1 gene (Ward et al. (1993) Plant Mol Biol 22:361-366), the heat-inducible hsp70 or hsp80 promoter from tomato (U.S. Pat. No. 5,187,267), the cold-inducible alpha-amylase promoter from potato (WO 96/12814), the light-inducible PPDK promoter or the wound-induced pinII promoter (EP 375091).

Pathogen-inducible promoters comprise those of genes which are induced as a result of pathogen attack, for example genes of PR proteins, SAR proteins, β-1,3-glucanase, chitinase etc. (for example Redolfi et al. (1983) Neth J Plant Pathol 89:245-254; Uknes, et al. (1992) The Plant Cell 4:645-656; Van Loon (1985) Plant Mol Viral 4:111-116; Marineau et al. (1987) Plant Mol Biol 9:335-342; Matton et al. (1987) Molecular Plant-Microbe Interactions 2:325-342; Somssich et al. (1986) Proc Natl Acad Sci USA 83:2427-2430; Somssich et al. (1988) Mol Gen Genetics 2:93-98; Chen et al. (1996) Plant J 10:955-966; Zhang and Sing (1994) Proc Natl Acad Sci USA 91:2507-2511; Warner, et al. (1993) Plant J 3:191-201; Siebertz et al. (1989) Plant Cell 1:961-968(1989).

Those which are also comprised are wound-inducible promoters such as that of the pinII gene (Ryan (1990) Ann Rev Phytopath 28:425-449; Duan et al. (1996) Nat Biotech 14:494-498), of the wun1 and wun2 gene (U.S. Pat. No. 5,428,148), of the win1 and win2 gene (Stanford et al. (1989) Mol Gen Genet 215:200-208), of the systemin (McGurl et al. (1992) Science 225:1570-1573), of the WIP1 gene (Rohmeier et al. (1993) Plant Mol Biol 22:783-792; Ekelkamp et al. (1993) FEBS Letters 323:73-76), of the MPI gene (Corderok et al. (1994) The Plant J 6(2):141-150) and the like.

Further suitable promoters are, for example, fruit-ripening-specific promoters, for example the fruit-ripening-specific promoter from tomato (WO 94/21794, EP 409 625). Development-dependent promoters include in part the tissue-specific promoters, since individual tissues, of course, form in a development-dependent manner.

Furthermore, in particular those promoters are preferred which ensure the expression in tissues or plant parts in which, for example, the biosynthesis of ketocarotenoids, or precursors thereof takes place. Preference is given to, for example, promoters having specificities for anthers, ovaries, petals, sepals, flowers, leaves, stems and roots and combinations thereof.

Tuber-, storage root- or root-specific promoters are, for example, the patatin promoter class I (B33) or the promoter of the cathepsin D inhibitor from potatoes.

Leaf-specific promoters are, for example, the promoter of the cytosol FBPase from potatoes (WO 97/05900), the SSU promoter (small subunit) of rubisco (ribulose-1,5-bisphosphate carboxylase) or the ST-LSI promoter from potatoes (Stockhaus et al. (1989) EMBO J. 8:2445-2451).

Flower-specific promoters are, for example, the phytoene synthase promoter (WO 92/16635) or the promoter of the P-rr gene (WO 98/22593) or the AP3 promoter from *Arabidopsis thaliana* (see Example 1).

Anther-specific promoters are, for example, the 5126 promoter (U.S. Pat. No. 5,689,049, U.S. Pat. No. 5,689,051), the glob-1 promoter or the g-zein promoter.

Further promoters suitable for expression in plants are described in Rogers et al. (1987) Meth in Enzymol 153:253-277; Schardl et al. (1987) Gene 61:1-11 and Berger et al. (1989) Proc Natl Acad Sci USA 86:8402-8406).

All of the promoters described in the present application generally make possible the expression of the ketolase in flower leaves of the inventive plants.

Particular preference in the inventive method is given to constitutive flower-specific, and in particular flower leaf-specific, promoters.

An expression cassette is preferably produced by fusion of a suitable promoter with an above-described nucleic acid coding for a ketolase and preferably a nucleic acid which is inserted between promoter and nucleic acid sequence and codes for a plastid-specific transit peptide and also with a polyadenylation signal according to customary recombination and cloning techniques, as described, for example, in T. Maniatis, E. F. Fritsch and J. Sambrook, Molecular Cloning: A Laboratory Manual, Cold Spring Harbor Laboratory, Cold Spring Harbor, N.Y. (1989) and also in T. J. Silhavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley-Interscience (1987).

The nucleic acids which are preferably inserted and code for a plastid transit peptide ensure localization in plastids, and in particular in chromoplasts.

Expression cassettes can also be used, the nucleic acid sequence of which codes for a ketolase fusion protein, a part of the fusion protein being a transit peptide which controls the translocation of the polypeptide. Preference is given, for the chromoplasts, to specific transit peptides which, after translocation of the ketolase into the chromoplasts, are enzymatically cleaved from the ketolase part.

In particular, preference is given to the transit peptide which is derived from the plastid *Nicotiana tabacum* transketolase or from another transit peptide (for example the transit peptide of the small subunit of rubisco (rbcS) or the ferredoxin NADP oxidoreductase, but also the isopentenyl-pyrophosphate isomerase-2 or its functional equivalent.

Particular preference is given to nucleic acid sequences of three cassettes of the plastid transit peptide of the plastid transketolase from tobacco in three reading frames as KpnI/BamHI fragments having an ATG codon in the NcoI cut site:

```
pTP09
KpnI_GGTACCATGGCGTCTTCTTCTTCTCTCACTCTCTCTCAAGCTATCCTCTCTC    (SEQ ID NO:143)

GTTCTGTCCCTCGCCATGGCTCTGCCTCTTCTTCTCAACTTTCCCCTTCTTCTCTC

ACTTTTTCCGGCCTTAAATCCAATCCCAATATCACCACCTCCCGCCGCCGTACTCC

TTCCTCCGCCGCCGCCGCCGCCGTCGTAAGGTCACCGGCGATTCGTGCCTCAGC

TGCAACCGAAACCATAGAGAAAACTGAGACTGCGGGATCC_BamHI pTP10
KpnI_GGTACCATGGCGTCTTCTTCTTCTCTCACTCTCTCTCAAGCTATCCTCTCTC    (SEQ ID NO:144)

GTTCTGTCCCTCGCCATGGCTCTGCCTCTTCTTCTCAACTTTCCCCTTCTTCTCTC

ACTTTTTCCGGCCTTAAATCCAATCCCAATATCACCACCTCCCGCCGCCGTACTCC

TTCCTCCGCCGCCGCCGCCGCCGTCGTAAGGTCACCGGCGATTCGTGCCTCAGC

TGCAACCGAAACCATAGAGAAAACTGAGACTGCGCTGGATCC_BamHI pTP11
KpnI_GGTACCATGGCGTCTTCTTCTTCTCTCACTCTCTCTCAAGCTATCCTCTCTC    (SEQ ID NO:145)

GTTCTGTCCCTCGCCATGGCTCTGCCTCTTCTTCTCAACTTTCCCCTTCTTCTCTC

ACTTTTTCCGGCCTTAAATCCAATCCCAATATCACCACCTCCCGCCGCCGTACTCC

TTCCTCCGCCGCCGCCGCCGCCGTCGTAAGGTCACCGGCGATTCGTGCCTCAGC

TGCAACCGAAACCATAGAGAAAACTGAGACTGCGGGGATCC_BamHI
```

Further examples of a plastid transit peptide are the transit peptide of the plastid isopentenyl-pyrophosphate isomerase-2 (IPP-2) from *Arabidopsis thaliana* and the transit peptide of the small subunit of ribulose-bisphosphate carboxylase (rbcS) from peas (Guerineau, F, Woolston, S, Brooks, L, Mullineaux, P (1988) An expression cassette for targeting foreign proteins into the chloroplasts. Nucl. Acids Res. 16: 11380).

The inventive nucleic acids can be prepared synthetically or produced naturally or comprise a mixture of synthetic and natural nucleic acid constituents, and can also consist of various heterologous gene sections of various organisms.

Preference is given to, as described above, synthetic nucleotide sequences having codons which are preferred by plants of the genus *Tagetes*. These codons preferred by plants can be determined from codons having the highest protein frequency which are expressed in the most plant species of interest.

In the preparation of an expression cassette, various DNA fragments can be manipulated to obtain a nucleotide sequence which expediently reads in the correct direction and which is equipped with a correct reading frame. For connecting the DNA fragments to one another, adapters or linkers can be attached to the fragments.

Expediently, the promoter and terminator regions can be provided in the transcription direction with a linker or polylinker which comprises one or more restriction sites for the insertion of this sequence. Generally, the linker has from 1 to 10, usually from 1 to 8, preferably from 2 to 6, restriction sites. Generally, the linker, within the regulatory regions, has a size of less than 100 bp, frequently less than 60 bp, but at least 5 bp. The promoter can either be native or homologous but also foreign or heterologous to the host plant. The expression cassette preferably comprises in the 5'-3' transcription direction the promoter, a coding nucleic acid sequence or a nucleic acid construct and a region for the transcriptional termination. Various termination regions are exchangeable for one another as desired.

Examples of a terminator are the 35S terminator (Guerineau et al. (1988) Nucl Acids Res. 16: 11380), the nos terminator (Depicker A, Stachel S, Dhaese P, Zambryski P, Goodman H M. Nopaline synthase: transcript mapping and DNA sequence. J Mol Appl Genet. 1982;1(6):561-73) or the ocs terminator (Gielen, J, de Beuckeleer, M, Seurinck, J, Debroek, H, de Greve, H, Lemmers, M, van Montagu, M, Schell, J (1984) The complete sequence of the TL-DNA of the *Agrobacterium tumefaciens* plasmid pTiAch5. EMBO J. 3: 835-846).

Furthermore, use can be made of manipulations which provide matching restriction cut sites or which remove the excess DNA or restriction cut sites. Where insertions, deletions or substitutions, for example transitions and transversions, come into question, in vitro mutagenesis, "primer repair", restriction or ligation can be used.

With suitable manipulations, for example restriction, "chewing-back" or filling-in of overhangs for "blunt ends", complementary ends of the fragments for ligation can be made available.

Preferred polyadenylation signals are plant polyadenylation signals, preferably those which essentially correspond to T-DNA polyadenylation signals from *Agrobacterium tumefaciens*, in particular gene 3 of the T-DNA (octopine synthase) of the Ti plasmid pTiACH5 (Gielen et al., EMBO J. 3 (1984), 835 ff) or functional equivalents.

The transfer of foreign genes to the genome of a plant is termed transformation.

For this, methods known per se can be utilized for the transformation and regeneration of plants from plant tissues or plant cells for transient or stable transformation.

Suitable methods for the transformation of plants are protoplast transformation by polyethylene glycol-induced DNA uptake, the biolistic method using the gene gun, what is termed the particle bombardment method, electroporation, the incubation of dry embryos in DNA-containing solution, microinjection and the above-described gene transfer mediated by *Agrobacterium*. Said methods are described, for example, in B. Jenes et al., Techniques for Gene Transfer, in: Transgenic Plants, Vol. 1, Engineering and Utilization, published by S. D. Kung and R. Wu, Academic Press (1993), 128-143 and also in Potrykus, Annu. Rev. Plant Physiol. Plant Molec. Biol. 42 (1991), 205-225).

Preferably, the construct to be expressed is cloned into a vector which is suitable for transforming *Agrobacterium tumefaciens*, for example pBin19 (Bevan et al., Nucl. Acids Res. 12 (1984), 8711) or particularly preferably pSUN2, pSUN3, pSUN4 or pSUN5 (WO 02/00900).

Agrobacteria transformed by an expression plasmid can be used in a known manner for the transformation of plants, for example by bathing wounded leaves or leaf pieces in an Agrobacteria solution and then culturing them in suitable media.

For the preferred production of genetically modified plants, hereinafter also termed transgenic plants, the fused expression cassette which expresses a ketolase is cloned into a vector, for example pBin19, or in particular pSUN2, which is suitable for being transformed in *Agrobacteirum tumefaciens*. Agrobacteria transformed using such a vector can then be used in a known manner for transforming plants, in particular cultivated plants by, for example, bathing wounded leaves or leaf pieces in an Agrobacteria solution and then culturing them in suitable media.

The transformation of plants by Agrobacteria is disclosed, inter alia, by F. F. White, Vectors for Gene Transfer in Higher Plants; in Transgenic Plants, Vol. 1, Engineering and Utilization, published by S. D. Kung and R. Wu, Academic Press, 1993, pp. 15-38. From the transformed cells of the wounded leaves or leaf pieces, in a known manner, transgenic plants can be regenerated which comprise a gene which is integrated into the expression cassette and is for the expression of a nucleic acid coding for a ketolase.

For the transformation of a host plant of the genus *Tagetes* having a nucleic acid coding for a ketolase, an expression cassette is incorporated as insertion into a recombinant vector, the vector DNA of which comprises additional functional regulatory signals, for example sequences for replication or integration. Suitable vectors are described, inter alia, in "Methods in Plant Molecular Biology and Biotechnology" (CRC Press), Chapters 617, pp. 71-119 (1993).

Using the above-cited recombination and cloning techniques, the expression cassettes can be cloned into suitable vectors which allow their multiplication, for example in *E. coli*. Suitable cloning vectors are, inter alia, pJIT117 (Guerineau et al. (1988) Nucl. Acids Res.16:11380), pBR332, pUC series, M13 mp series and pACYC184. Particularly suitable vectors are binary vectors which can replicate not only in *E. coli* but also in Agrobacteria.

Depending on the choice of promoter, the expression can be performed in the flower leaves constitutively or preferably specifically.

The inventive genetically modified plants of the genus *Tagetes*, compared with the wild type, have a content of astaxanthin, in particular in petals.

As mentioned above, the invention relates to the use of astaxanthin-containing plants or parts of plants of the genus *Tagetes* or astaxanthin-containing extracts of astaxanthin-containing plants or parts of plants of the genus *Tagetes* for oral administration to animals.

In a preferred embodiment, the astaxanthin-containing plants or parts of plants of the genus *Tagetes* or the astaxanthin-containing extracts of astaxanthin-containing plants or parts of plants of the genus *Tagetes* are used for pigmenting animals and the corresponding animal products.

Astaxanthin-containing extracts of astaxanthin-containing plants or plant parts are preferably taken to mean solutions comprising astaxanthin which have been produced by extraction from astaxanthin-containing plants or plant parts with at least one suitable solvent. Depending on solvent used and further chemical and physical purification methods used, the astaxanthin can be present in the extract in any desired degrees of purity. It is advantageous to prepare the astaxanthin-containing plants or plant parts appropriately before extraction, for example to dry the plants or plant parts and comminute them, the sequence being optional.

Astaxanthin can be extracted from the astaxanthin-containing plants or plant parts, which if appropriate have been previously dried and/or comminuted, by organic solvents, for example acetone, hexane, methylene chloride, methyl tertiary-butyl ether, or by solvent mixtures such as ethanol/hexane or acetone/hexane. By means of differing mixing ratios of the solvents, owing to the differing polarity, the extraction effect can be varied. By means of such an extraction, astaxanthin may be enriched at high concentration.

The purity of astaxanthin can be further increased by then extracting astaxanthin by shaking and chromatographic separation of the mixture. Astaxanthin is generally present as a mixture of mono- and diesters, usually as esters of palmitic acid.

"Pigmenting" according to the invention is preferably taken to mean the intensifying or initiating of a color, at least of a part of an animal or animal product of the pigmented animal, compared with the non-pigmented animal. Astaxanthin-containing pigments generally pigment and initiate or intensify a pink to pink-red color note.

Preferred animals which can be pigmented by the inventive oral administration are animals selected from the group fish, crustaceae or birds, in particular Galliformes and Anatridae.

Preferred fish are Salmonids, in particular salmon or trout.
Preferred Crustaceae are shrimps or crabs.
Preferred Galliformes are chickens, ducks or geese.
Preferred Anatridae is flamingo.

Depending on the pigmented animal, preferably, pigmented animal products are taken to mean, in particular meat for salmon or trout, skin for chickens, ducks or geese, feathers for chickens, ducks, geese or flamingo, and egg or egg yolk for chickens, ducks or geese.

The oral administration of the astaxanthin-containing plants or parts of plants of the genus *Tagetes* or the astaxanthin-containing extracts of astaxanthin-containing plants or parts of plants of the genus *Tagetes* to animals can be performed directly or via oral administration of animal feed preparations to which the astaxanthin-containing plants or parts of plants of the genus *Tagetes* or the astaxanthin-containing extracts of astaxanthin-containing plants or parts of plants of the genus *Tagetes* have been admixed in advance.

In a preferred embodiment, the astaxanthin-containing plants or parts of plants of the genus *Tagetes* or the astaxanthin-containing extracts of astaxanthin-containing plants or parts of plants of the genus *Tagetes* are admixed to animal feed preparations and the animal feed preparation is orally administered to animals.

It is advantageous to process the astaxanthin-containing plants or parts of plants of the genus *Tagetes* or the astaxanthin-containing extracts of astaxanthin-containing plants or parts of plants of the genus *Tagetes*, before the admixture to animal feed preparations, into a form which makes possible admixture to corresponding animal feed preparations and preferably leads to high stability and bioavailability of astaxanthin in the respective field of use.

Depending on the animal to which the oral administration is to take place and thus depending on animal feed preparation, various processing steps can be advantageous for this.

For astaxanthin-containing plants or parts of plants of the genus *Tagetes* it is advantageous in this embodiment to dry and/or comminute the astaxanthin-containing plants or parts of plants, in particular flower heads and petals. Particularly preferably, the astaxanthin-containing plants or parts of plants of the genus *Tagetes* are present in pulverulent form.

Every embodiment however arranged of the astaxanthin-containing plants or parts of plants of the genus *Tagetes*, whether processed or unprocessed, can be admixed in a manner known per se to animal feed preparations.

For astaxanthin-containing extracts of astaxanthin-containing plants or parts of plants of the genus *Tagetes*, in this embodiment, various processing steps are advantageous.

The astaxanthin-containing extracts can, provided that the solvents still present are physiologically harmless for the corresponding animals, be admixed directly to the animal feed preparation.

The extracts, after evaporating off the solvents still present, can be used in the form of astaxanthin-containing powders or oils.

The resultant astaxanthin-containing powders or oils can, for example, be incorporated into fish oil, applied to pulverulent carrier materials, for example wheat flour or grated *Tagetes* petals, or included in alginates, gelatin or lipids.

The astaxanthin-containing extracts or processed extracts are thus preferably in liquid or pulverulent form.

Every embodiment however arranged of the astaxanthin-containing extracts of astaxanthin-containing plants or parts of plants of the genus *Tagetes*, whether processed or unprocessed, can be admixed in a manner known per se to animal feed preparations.

The invention therefore also relates to animal feed preparations comprising astaxanthin-containing plants or parts of plants of the genus *Tagetes* or the astaxanthin-containing extracts of astaxanthin-containing plants or parts of plants of the genus *Tagetes*.

The invention further relates to a method for producing animal feed preparations by combining astaxanthin-containing plants or parts of plants of the genus *Tagetes* or astaxanthin-containing extracts of astaxanthin-containing plants or parts of plants of the genus *Tagetes* and customary animal feedstuffs.

A preferred embodiment of the method comprises processing the astaxanthin-containing plants or parts of plants of the genus *Tagetes* or the astaxanthin-containing extracts of astaxanthin-containing plants or parts of plants of the genus *Tagetes*, before the combination with animal feedstuffs, into a form which makes possible combination with animal feedstuffs.

For example, for fish, the fish feed preparations can comprise further customary fish feed components, for example fish meal and/or other proteins, oils, for example fish oils, cereals, vitamins, minerals, preservatives and if appropriate medicaments in customary amounts.

A typical fish feed formula for trout is composed, for example, from the following components:

| Components | % by weight | Weight for 500 kg kg |
|---|---|---|
| Fish meal | 30.00 | 150.00 |
| Full fat soybeans | 20.00 | 100.00 |
| Pregelatinized wheat starch | 18.00 | 90.00 |
| Vitamin premix | 0.80 | 4.00 |
| Choline chloride (50%) | 0.20 | 1.00 |
| Wheat gluten | 20.00 | 100.00 |
| Sipernat 50S | 3.00 | 15.00 |
| Fish oil | 8.00 | 40.00 |

A typical fish feed formula for salmon is composed, for example, of the following components:

| Components | % by weight |
|---|---|
| Fish meal | 75.00 |
| Plant protein | 5.00 |
| Cereal | 7.80 |
| Vitamins/minerals | 1.00 |
| Antioxidants/preservatives | 0.20 |
| Fish oil | 11.00 |

In one embodiment, the astaxanthin-containing plants or parts of plants of the genus *Tagetes* or the astaxanthin-containing extracts are admixed to the animal feed preparations preferably in dried and comminuted pulverulent form.

The resultant animal feed preparations comprising astaxanthin-containing plants or parts of plants of the genus *Tagetes* or astaxanthin-containing extracts of astaxanthin-containing plants or parts of plants of the genus *Tagetes* can, in the case of fish feed, be, for example in a manner known per se, pelleted, or particularly advantageously extruded.

In a preferred embodiment, the astaxanthin-containing extracts are admixed to the animal feed preparations, preferably in liquid form. This is advantageous, in particular, in the production of extruded fish feed preparations. The extrusion process leads to extrusion stress on the sensitive substances, for example astaxanthin, which can lead to an astaxanthin loss. Extrusion stress is primarily the action of mechanical forces (kneading, shearing, pressure, etc.), but also hydrothermal stress, caused by additions of water and steam, and also oxidative stress may be observed.

To avoid the astaxanthin losses occurring as a result of the above-described extrusion process, liquid astaxanthin-containing extracts may be applied under vacuum after the extrusion and drying process by the PPA technique (post-pelleting application).

In a further, preferred embodiment, the astaxanthin-containing plants or parts of plants of the genus *Tagetes* or the astaxanthin-containing extracts of astaxanthin-containing plants or parts of plants of the genus *Tagetes* are orally administered directly to animals.

It is advantageous to process the astaxanthin-containing plants or parts of plants of the genus *Tagetes* or the astaxanthin-containing extracts of astaxanthin-containing plants or parts of plants of the genus *Tagetes*, before the administration, into a form which makes possible direct oral administration to animals and preferably leads to a high stability and bioavailability of astaxanthin in the respective field of use.

Depending on the animal to which the oral administration is to take place, and thus depending on animal feed preparation, various processing steps can be advantageous for this.

For astaxanthin-containing plants or parts of plants of the genus *Tagetes*, it is advantageous in this embodiment to dry and/or comminute the astaxanthin-containing plants or parts of plants, in particular flower heads and petals. Particularly preferably, the astaxanthin-containing plants or parts of plants of the genus *Tagetes* are present in pulverulent form.

Every embodiment, however arranged, of the astaxanthin-containing plants or parts of plants of the genus *Tagetes*, whether processed or unprocessed, can be orally administered to animals in a manner known per se.

For astaxanthin-containing extracts of astaxanthin-containing plants or parts of plants of the genus *Tagetes*, various processing steps are advantageous in this embodiment.

The astaxanthin-containing extracts, provided that the solvents still present are physiologically harmless for the respective animals, can be administered orally directly to animals.

The extracts can be administered, after evaporation of the solvents which are still present, in the form of astaxanthin-containing powders or oils.

The resultant astaxanthin-containing powders or oils can be incorporated, for example, into fish oil, can be applied to pulverulent support materials, for example wheat flour or grated *Tagetes* petals, or included in alginates, gelatin or lipids.

The astaxanthin-containing extracts or processed extracts are thus preferably in liquid or pulverulent form.

Every embodiment however arranged of the astaxanthin-containing extracts of astaxanthin-containing plants or parts of plants of the genus *Tagetes*, whether processed or unprocessed, can be administered orally to animals in a manner known perse.

The invention therefore also relates to pigmenting agents comprising astaxanthin-containing plants or parts of plants of the genus *Tagetes* or the astaxanthin-containing extracts of astaxanthin-containing plants or parts of plants of the genus *Tagetes*, in which case the astaxanthin-containing plants or parts of plants of the genus *Tagetes* or the astaxanthin-containing extracts of astaxanthin-containing plants or parts of plants of the genus *Tagetes* can if appropriate be processed as described above.

In a preferred embodiment, the pigmenting agents consist of astaxanthin-containing plants or parts of plants of the genus *Tagetes* or astaxanthin-containing extracts of astaxanthin-containing plants or parts of plants of the genus *Tagetes*, in which case the astaxanthin-containing plants or parts of plants of the genus *Tagetes* or the astaxanthin-containing extracts of astaxanthin-containing plants or parts of plants of the genus *Tagetes* can if appropriate be processed as described above.

In particularly preferred pigmenting agents, the plant parts used are flower heads or petals.

The invention further relates to a method for pigmenting animals or animal products by oral administration of astaxanthin-containing plants or parts of plants of the genus *Tagetes* or astaxanthin-containing extracts of astaxanthin-containing plants or parts of plants of the genus *Tagetes* to animals.

The invention further relates to a method for producing pigmented animals or animal products by oral administration of astaxanthin-containing plants or parts of plants of the genus *Tagetes* or astaxanthin-containing extracts of astaxanthin-containing plants or parts of plants of the genus *Tagetes* to animals.

The invention further relates to the use of astaxanthin-containing plants or parts of plants of the genus *Tagetes* or astaxanthin-containing extracts of astaxanthin-containing plants or parts of plants of the genus *Tagetes* as animal feed or animal feed additive.

The pigmenting agents comprising astaxanthin-containing plants or parts of plants of the genus *Tagetes* or astaxanthin-containing extracts of astaxanthin-containing plants or parts of plants of the genus *Tagetes*, or animal feedstuffs comprising these pigmenting agents further have the advantage of a high storage stability and bioavailability of the pigment astaxanthin.

The invention will now be described by the following examples, but is not restricted thereto:

EXAMPLE I

Production of Astaxanthin-Containing Genetically Modified Plants of the Genus *Tagetes*

General Experimental Conditions:

Sequence Analysis of Recombinant DNA

Recombinant DNA molecules are sequenced using a laser fluorescence DNA-sequencer from Licor (distributed by MWG Biotech, Ebersbach) by the method of Sanger (Sanger et al., Proc. Natl. Acad. Sci. USA 74 (1977), 5463-5467).

Example I.1

Amplification of a cDNA which codes for the entire primary sequence of the ketolase from *Haematococcus pluvialis* Flotow em. Wille The cDNA which codes for the ketolase from *Haematococcus pluvialis* was amplified by means of PCR from *Haematococcus pluvialis* (strain 192.80 of the Collection of Algal Cultures of the University of Göttingen) suspension culture.

For the preparation of total RNA from a suspension culture of *Haematococcus pluvialis* (strain 192.80) which had been grown for 2 weeks in indirect daylight at room temperature in *Haematococcus* medium (1.2 g/l of sodium acetate, 2 g/l of yeast extract, 0.2 g/l of $MgCl_2.6H_2O$, 0.02 $CaCl_2.2H_2O$; pH 6.8; after autoclaving, addition of 400 mg/l of L-asparagine, 10 mg/l of $FeSO_4.H_2O$), the cells were harvested, frozen in liquid nitrogen and ground in the mortar. 100 mg of the frozen pulverized algae cells were then transferred to a reaction vessel and taken up in 0.8 ml of Trizol buffer (Life Technologies). The suspension was extracted with 0.2 ml of chloroform. After centrifugation for 15 minutes at 12 000 g, the aqueous supernatant was taken off and transferred to a new reaction vessel and extracted with one volume of ethanol. The RNA was precipitated with one volume of isopropanol, washed with 75% ethanol and the pellet was dissolved in DEPC water (overnight incubation of water with 1/1000 volume of diethyl pyrocarbonate at room temperature, then autoclaved). The RNA concentration was determined photometrically.

For the cDNA synthesis, 2.5 μg of total RNA were denatured for 10 min at 60° C., cooled on ice for 2 min and transcribed to cDNA by means of a cDNA kit (Ready-to-go-you-prime-beads, Pharmacia Biotech) according to the manufacturer's instructions, using an antisense-specific primer (PR1 SEQ ID NO: 29).

The nucleic acid coding for a ketolase from *Haematococcus pluvialis* (strain 192.80) was amplified by means of the polymerase chain reaction (PCR) from *Haematococcus pluvialis* using a sense-specific primer (PR2 SEQ ID NO: 30) and an antisense-specific primer (PR1 SEQ ID NO: 29).

The PCR conditions were as follows:

The PCR for amplification of the cDNA which codes for a ketolase protein consisting of the entire primary sequence was carried out in a 50 ml reaction mix in which the following were present:

- 4 ml of a *Haematococcus pluvialis* cDNA (prepared as described above)
- 0.25 mM dNTPs
- 0.2 mM PR1 (SEQ ID NO: 29)
- 0.2 mM PR2 (SEQ ID NO: 30)
- 5 ml of 10×PCR buffer (TAKARA)
- 0.25 ml of R Taq polymerase (TAKARA)
- 25.8 ml of distilled water.

The PCR was carried out under the following cycle conditions:

| | | |
|---|---|---|
| 1x | 94° C. | 2 minutes |
| 35x | 94° C. | 1 minute |
| | 53° C. | 2 minutes |
| | 72° C. | 3 minutes |
| 1x | 72° C. | 10 minutes |

The PCR amplification using SEQ ID NO: 29 and SEQ ID NO: 30 resulted in a 1155 bp fragment which codes for a protein consisting of the entire primary sequence (SEQ ID NO: 22). Using standard methods, the amplicon was cloned into the PCR cloning vector pGEM-Teasy (Promega) and the clone pGKETO2 was obtained.

Sequencing the clone pGKETO2 having the T7 and the SP6 primer confirmed a sequence which only differs from the published sequence X86782 in the three codons 73, 114 and 119, each in one base. These nucleotide replacements were reproduced in an independent amplification experiment and thus represent the nucleotide sequence in the *Haematococcus pluvialis* strain 192.80 used (FIGS. 1 and 2, sequence comparisons).

This clone was therefore used for the cloning into the expression vector pJIT 17 (Guerineau et al. 1988, Nucl. Acids Res. 16: 11380). The cloning was performed by isolating the 1027 bp SpHI fragment from pGEM-Teasy and ligation into the SpHI-cut vector pJIT117. The clone which comprises the *Haematococcus pluvialis* ketolase in the correct orientation as N-terminal translational fusion with the rbcs transit peptide is called pJKETO2.

Example I.2

Amplification of a cDNA which codes for the ketolase from *Haematococcus pluvialis* Flotow em. Wille having an N terminus shortened by 14 amino acids The cDNA which codes for the ketolase from *Haematococcus pluvialis* (strain 192.80) having an N terminus shortened by 14 amino acids was amplified by means of PCR from *Haematococcus pluvialis* suspension culture (strain 192.80 of the Collection of Algal Cultures of the University of Göttingen).

Total RNA was prepared from a suspension culture of *Haematococcus pluvialis* (strain 192.80) as described in Example 1.

The cDNA synthesis was performed as described under Example 1.

The nucleic acid coding for a ketolase from *Haematococcus pluvialis* (strain 192.80) having an N terminus shortened by 14 amino acids was amplified by means of the polymerase chain reaction (PCR) from *Haematococcus pluvialis* using a sense-specific primer (PR3 SEQ ID NO: 31) and an antisense-specific primer (PR1 SEQ ID NO: 29).

The PCR conditions were as follows:

The PCR for amplification of the cDNA which codes for a ketolase protein having an N terminus shortened by 14 amino acids was performed in a 50 ml reaction mix in which the following were present:

- 4 ml of a *Haematococcus pluvialis* cDNA (prepared as described above)
- 0.25 mM dNTPs
- 0.2 mM PR1 (SEQ ID NO: 29)
- 0.2 mM PR3 (SEQ ID NO: 31)
- 5 ml of 10×PCR buffer (TAKARA)
- 0.25 ml of R Taq polymerase (TAKARA)
- 25.8 ml of distilled water.

The PCR was carried out under the following cycle conditions:

| 1x | 94° C. | 2 minutes |
|---|---|---|
| 35x | 94° C. | 1 minute |
|  | 53° C. | 2 minutes |
|  | 72° C. | 3 minutes |
| 1x | 72° C. | 10 minutes |

The PCR amplification using SEQ ID NO: 29 and SEQ ID NO: 31 resulted in a 1111 bp fragment which codes for a ketolase protein in which N-terminal amino acids (positions 2-16) are replaced by a single amino acid (leucine).

The amplicon was cloned using standard methods into the PCR cloning vector pGEM-Teasy (Promega). Sequencing with the primers T7 and SP6 confirmed a sequence identical to sequence SEQ ID NO: 22, in which the 5' region (positions 1-53) of SEQ ID NO: 22 was replaced in the amplicon SEQ ID NO: 24 by a nonamer sequence deviating in the sequence. This clone was therefore used for cloning into the expression vector pJIT117 (Guerineau et al. 1988, Nucl. Acids Res. 16: 11380).

The cloning was performed by isolating the 985 bp SpHI fragment from pGEM-Teasy and ligation with the SpHI-cut vector pJIT117. The clone which comprises the *Haematococcus pluvialis* ketolase having an N terminus shortened by 14 amino acids in the correct orientation as N-terminal translational fusion with the rbcs transit peptide is called pJKETO3.

Example I.3

Amplification of a cDNA which codes for the ketolase from *Haematococcus pluvialis* Flotow em. Wille (strain 192.80 of the Collection of Algal Cultures of the University of Göttingen) consisting of the entire primary sequence and fused C-terminal myc-Tag The cDNA which codes for the ketolase from *Haematococcus pluvialis* (strain 192.80) consisting of the entire primary sequence and fused C-terminal myc-Tag was prepared by means of PCR using the plasmid pGKETO2 (described in Example 1) and the primer PR15 (SEQ ID NO: 32). The primer PR15 is composed of an antisense specific 3' region (nucleotides 40 to 59) and an myc-Tag coding 5' region (nucleotides 1 to 39).

The denaturation (5 min at 95° C.) and annealing (slow cooling at room temperature to 40° C.) of pGKETO2 and PR15 was performed in a 11.5 ml reaction mix in which the following were present:

- 1 mg of pGKETO2 plasmid DNA
- 0.1 mg of PR15 (SEQ ID NO: 32)

The 3' ends were filled in (30 min at 30° C.) in a 20 ml reaction mix in which the following were present:

- 11.5 ml of pGKETO2/PR15 annealing reaction (produced as described above)
- 50 mM dNTPs
- 2 ml of 1× Klenow buffer
- 2 U of Klenow enzyme The nucleic acid coding for a ketolase from *Haematococcus pluvialis* (strain 192.80) consisting of the entire primary sequence and fused C terminal myc-Tag was amplified by means of the polymerase chain reaction (PCR) from *Haematococcus pluvialis* using a sense-specific primer (PR2 SEQ ID NO: 30) and an antisense-specific primer (PR15 SEQ ID NO: 32).

The PCR conditions were as follows:

The PCR for amplification of the cDNA which codes for a ketolase protein having a fused C-terminal myc-Tag was performed in a 50 ml reaction mix in which the following were present:

- 1 ml of an annealing reaction (produced as described above)
- 0.25 mM dNTPs
- 0.2 mM PR15 (SEQ ID NO: 32)
- 0.2 mM PR2 (SEQ ID NO: 30)
- 5 ml of 10×PCR buffer (TAKARA)
- 0.25 ml of R Taq polymerase (TAKARA)
- 28.8 ml of distilled water.

The PCR was carried out under the following cycle conditions:

| 1x | 94° C. | 2 minutes |
|---|---|---|
| 35x | 94° C. | 1 minute |
|  | 53° C. | 1 minute |
|  | 72° C. | 1 minute |
| 1x | 72° C. | 10 minutes |

The PCR amplification with SEQ ID NO: 32 and SEQ ID NO: 30 resulted in a 1032 bp fragment which codes for a protein consisting of the entire primary sequence of the ketolase from *Haematococcus pluvialis* as two-fold translational fusion with the rbcS transit peptide at the N terminus and the myc-Tag at the C terminus.

The amplicon was cloned using standard methods into the PCR cloning vector pGEM-Teasy (Promega). Sequencing with the primers T7 and SP6 confirmed a sequence identical to the sequence SEQ ID NO: 22, where the 3' region (positions 993 to 1155) of SEQ ID NO: 22 was replaced in the amplicon SEQ ID NO: 26 by a deviating sequence of 39 bp. This clone was therefore used for cloning into the expression vector pJIT117 (Guerineau et al. 1988, Nucl. Acids Res. 16: 11380).

The cloning was performed by isolating the 1038 bp EcoRI-SpHI fragment from pGEM-Teasy and ligation with the EcoRI-SpHI-cut vector pJIT117. The ligation produces a translational fusion between the C terminus of the rbcS transit peptide sequence and the N terminus of the ketolase sequence. The clone which comprises the *Haematococcus pluvialis* ketolase having the fused C terminus myc-Tag in the correct orientation as translational N-terminal fusion with the rbcs peptide is called pJKETO4.

Example I.4

Amplification of a DNA which codes for the entire primary sequence of the ketolase from *Nostoc* sp. PCC 7120

The DNA which codes for the ketolase from Nostoc PCC 7120 was amplified by means of PCR from Nostoc PCC 7120 (strain of the "Pasteur Culture Collection of Cyanobacterium").

For the preparation of genomic DNA from a suspension culture of Nostoc PCC 7120 which had grown for 1 week under constant light with constant shaking (150 rpm) at 25° C. in BG 11 medium (1.5 g/l of $NaNO_3$, 0.04 g/l of $K_2PO_4 \cdot 3H_2O$, 0.075 g/l of $MgSO_4 \cdot H_2O$, 0.036 g/l of $CaCl_2 \cdot 2H_2O$, 0.006 g/l of citric acid, 0.006 g/l of ferric ammonium citrate, 0.001 g/l of EDTA disodium magnesium, 0.04 g/l of $Na_2CO_3$, 1 ml of trace metal mix A5+Co (2.86 g/l of $H_3BO_3$, 1.81 g/l of $MnCl_2 \cdot 4H_2O$, 0.222 g/l of $ZnSO_4 \cdot 7H_2O$, 0.39 g/l of $NaMoO_4 \cdot 2H_2O$, 0.079 g/l of $CuSO_4 \cdot 5H_2O$, 0.0494 g/l of $Co(NO_3)_2 \cdot 6H_2O$), the cells were harvested by centrifugation, frozen in liquid nitrogen and pulverized in the mortar.

Protocol for DNA isolation from Nostoc PCC7120:

The bacterial cells were pelleted from a 10 ml liquid culture by centrifugation for 10 minutes at 8000 rpm. The bacterial cells were then crushed and ground in liquid nitrogen using a mortar. The cell material was resuspended in 1 ml of 10 mM Tris HCl (pH 7.5) and transferred to an Eppendorf reaction vessel (2 ml volume). After addition of 100 µl of proteinase K (concentration: 20 mg/ml), the cell suspension was incubated at 37° C. for 3 hours. The suspension was then extracted with 500 µl of phenol. After centrifugation for 5 minutes at 13 000 rpm, the upper, aqueous phase was transferred to a new 2 ml Eppendorf reaction vessel. The extraction with phenol was repeated 3 times. The DNA was precipitated by addition of 1/10 volume of 3 M sodium acetate (pH 5.2) and 0.6 volume of isopropanol, and then washed with 70% ethanol. The DNA pellet was dried at room temperature, taken up in 25 µl of water and dissolved with heating at 65° C.

The nucleic acid coding for a ketolase from Nostoc PCC 7120 was amplified by means of the polymerase chain reaction (PCR) from Nostoc PCC 7120 using a sense-specific primer (NOSTF, SEQ ID No. 87) and an antisense-specific primer (NOSTG, SEQ ID NO. 88).

The PCR conditions were as follows:

The PCR for amplification of the DNA which codes for a ketolase protein consisting of the entire primary sequence was performed in a 50 µl reaction mix in which the following were present:

1 µl of a Nostoc PCC 7120 DNA (prepared as described above)
0.25 mM dNTPs
0.2 mM NOSTF (SEQ ID No. 87)
0.2 mM NOSTG (SEQ ID No. 88)
5 µl of 10×PCR buffer (TAKARA)
0.25 µl of R Taq polymerase (TAKARA)
25.8 µl of distilled water.

The PCR was carried out under the following cycle conditions:

| 1x  | 94° C. | 2 minutes  |
|-----|--------|------------|
| 35x | 94° C. | 1 minute   |
|     | 55° C. | 1 minute   |
|     | 72° C. | 3 minutes  |
| 1x  | 72° C. | 10 minutes |

The PCR amplification with SEQ ID No. 87 and SEQ ID No. 88 resulted in an 805 bp fragment which codes for a protein consisting of the entire primary sequence (SEQ ID No. 89). Using standard methods, the amplicon was cloned into the PCR cloning vector pGEM-T (Promega) and the clone pNOSTF-G was obtained.

Sequencing the clone pNOSTF-G with the M13F and the M13R primer confirmed a sequence which is identical to the DNA sequence of the database entry AP003592. This nucleotide sequence was reproduced in an independent amplification experiment and thus represents the nucleotide sequence in the Nostoc PCC 7120 used.

This clone pNOSTF-G was therefore used for cloning into the expression vector pJIT117 (Guerineau et al. 1988, Nucl. Acids Res. 16: 11380). The cloning was performed by isolating the 1027 bp SphI fragment from pGEM-T and ligation into the SphI-cut vector pJIT117. The clone which comprises the ketolase of Nostoc in the correct orientation as N-terminal translational fusion with the rbcS transit peptide is called pJNOST.

Example I.5

Production of expression vectors for the constitutive expression of *Haematococcus pluvialis* ketolase in *Tagetes erecta*.

The ketolase from *Haematococcus pluvialis* was expressed in *Tagetes erecta* under the control of the constitutive promoter d35S from CaMV (Franck et al. 1980, Cell 21: 285-294). The expression was performed using the transit peptide rbcS from pea (Anderson et al. 1986, Biochem J. 240:709-715).

An expression cassette for the *Agrobacterium*-mediated transformation of the ketolase from *Haematococcus pluvialis* in *Tagetes erecta* was produced using the binary vector pSUN5 (WO 02/00900).

For production of the *Tagetes* expression vector pS5KETO2, the 2.8 Kb SacI-XhoI fragment from pJKETO2 was ligated with the SacI-XhoI-cut vector pSUN5 (FIG. 3, construct map). In FIG. 3, fragment d35S comprises the duplicated 35S promoter (747 bp), fragment rbcS, the rbcS transit peptide from pea (204 bp), fragment KET02 (1027 bp) the entire primary sequence coding for the Haematococcus pluvialis ketolase, fragment term (761 bp) the polyadenylation signal of CaMV.

Example I.5A

Production of expression vectors for the flower-specific expression of the *Haematococcus pluvialis* ketolase in *Tagetes erecta*

The ketolase from *Haematococcus pluvialis* was expressed in *Tagetes erecta* using the transit peptide rbcS from pea (Anderson et al. 1986, Biochem J. 240:709-715). The expression was performed under the control of a modified version AP3P of the flower-specific promoter AP3 from *Arabidopsis thaliana* (AL132971: nucleotide region 9298 to 10 200; Hill et al. (1998) Development 125: 1711-1721).

The DNA fragment which comprises the AP3 promoter region −902 to +15 from *Arabidopsis thaliana* was produced by means of PCR using genomic DNA (isolated by standard methods from *Arabidopsis thaliana*) and also the primer PR7 (SEQ ID NO: 33) and PR10 (SEQ ID NO: 36).

The PCR conditions were as follows:

The PCR for amplification of the DNA which comprises the AP3 promoter fragment (−902 to +15) was carried out in a 50 ml reaction mix in which the following were present:
100 ng of genomic DNA from *A.thaliana*
0.25 mM dNTPs
0.2 mM PR7 (SEQ ID NO: 33)
0.2 mM PR10 (SEQ ID NO: 36)
5 ml of 10×PCR buffer (Stratagene)
0.25 ml of Pfu polymerase (Stratagene)
28.8 ml of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The 922 bp amplicon was cloned into the PCR cloning vector pCR 2.1 (Invitrogen) using standard methods, and the plasmid pTAP3 was obtained.

Sequencing the clone pTAP3 confirmed a sequence which differs from the published AP3 sequence (AL132971, nucleotide region 9298 to 10 200) only in an insertion (a G in position 9765 of the sequence AL132971) and a base exchange (a G instead of an A in position 9726 of the sequence AL132971). These nucleotide differences were reproduced in an independent amplification experiment and thus represent the actual nucleotide sequence in the *Arabidopsis thaliana* plants used.

The modified version AP3P was produced by means of recombinant PCR using the plasmid pTAP3. The region 10 200 to 9771 was amplified with the primers PR7 (SEQ ID NO: 33) and PR9 (SEQ ID NO: 35) (amplicon A719), the region 9526 to 9285 was amplified with PR8 (SEQ ID NO: 34) and PR10 (SEQ ID NO: 36) (amplicon A8/10).

The PCR conditions were as follows:

The PCR reactions for amplification of the DNA fragments which comprise the regions region 10 200-9771 and region 9526 to 9285 of the AP3 promoter were carried out in 50 ml reaction mixes, in which the following were present:
100 ng of AP3 amplicon (described above)
0.25 mM dNTPs
0.2 mM sense primer (PR7 SEQ ID NO: 33 or PR8 SEQ ID NO: 34)
0.2 mM antisense primer (PR9 SEQ ID NO: 35 or PR10 SEQ ID NO: 36)
5 ml of 10×PCR buffer (Stratagene)
0.25 ml of Pfu Taq polymerase (Stratagene)
28.8 ml of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The recombinant PCR comprises annealing of the amplicons A7/9 and A8/10 overlapping over a sequence of 25 nucleotides, completion to give a double strand and subsequent amplification. This produces a modified version of the AP3 promoter, AP3P, in which positions 9670 to 9526 are deleted. The denaturation (5 min at 95° C.) and annealing (slow cooling at room temperature to 40° C.) of both amplicons A7/9 and A8/10 was carried out in a 17.6 ml reaction mix in which the following were present:
0.5 mg of A7/9 amplicon
0.25 mg of A8/10 amplicon The 3' ends were filled in (30 min at 30° C.) in a 20 ml reaction mix in which the following were present:
17.6 ml of gA7/9 and A8/10 annealing reaction (produced as described above)
50 mM dNTPs
2 ml of 1× Klenow buffer
2 U of Klenow enzyme The nucleic acid coding for the modified promoter version AP3P was amplified by means of PCR using a sense-specific primer (PR7 SEQ ID NO: 33) and an antisense-specific primer (PR10 SEQ ID NO: 36).

The PCR conditions were as follows:

The PCR for amplification of the AP3P fragment was carried out in a 50 ml reaction mix in which the following were present:
1 ml of annealing reaction (produced as described above)
0.25 mM dNTPs
0.2 mM PR7 (SEQ ID NO: 33)
0.2 mM PR10 (SEQ ID NO: 36)
5 ml of 10×PCR buffer (Stratagene)
0.25 ml of Pfu Taq polymerase (Stratagene)
28.8 ml of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The PCR amplification with SEQ ID NO: 33 and SEQ ID NO: 36 resulted in a 778 bp fragment which codes for the modified promoter version AP3P. The amplicon was cloned into the cloning vector pCR2.1 (Invitrogen). Sequencing with the primers T7 and M13 confirmed a sequence identical to the sequence AL132971, region 10 200 to 9298, with the internal region 9285 to 9526 having been deleted. This clone was therefore used for cloning into the expression vector pJIT117 (Guerineau et al. 1988, Nucl. Acids Res. 16:11380).

The cloning was performed by isolating the 771 bp SacI-HindIII fragment from pTAP3P and ligation into the SacI-HindIII-cut vector pJIT117. The clone which comprises the promoter AP3P instead of the original promoter d35S is called pJAP3P.

For the production of an expression cassette pJAP3PKETO2, the 1027 bp SphI fragment KETO2 was cloned into the SphI-cut vector pJAP3P. The clone which comprises the fragment KETO2 in the correct orientation as N-terminal fusion with the rbcS transit peptide is called pJAP3PKETO2.

For the production of an expression cassette pJAP3PKETO4, the 1032 bp SphI-EcoRI fragment KETO4 (described in Example 3) was cloned into the SphI-EcoRIcut vector pJAP3P. The clone which comprises the fragment KETO4 in the correct orientation as N-terminal fusion with the rbcS transit peptide is called pJAP3PKETO4.

The preparation of an expression vector for the *Agrobacterium*-mediated transformation of the AP3P-controlled ketolase from *Haematococcus pluvialis* in *Tagetes erecta* was carried out using the binary vector pSUN5 (WO 02100900).

For production of the expression vector pS5AP3PKETO2, the 2.8 KB bp SacI-XhoI fragment from pJAP3PKETO2 was ligated to the SacI-XhoI-cut vector pSUN5 (FIG. 4, construct map). In FIG. 4, fragment AP3P comprises the modified AP3P promoter (771 bp), fragment rbcS the rbcs transit peptide from pea (204 bp), fragment KETO2 (1027 bp) the entire primary sequence coding for the *Haematococcus pluvialis* ketolase, fragment term (761 bp) the polyadenylation signal of CaMV.

Example I.5.B

Production of expression vectors for the constitutive expression of *Nostoc* sp. PCC 7120 ketolase in *Tagetes erecta*

The ketolase from Nostoc in *Tagetes erecta* was expressed under the control of the constitutive promoter FNR (ferredoxin-NADPH oxidoreductase) from *Arabidopsis thaliana*. The expression was carried out using the transit peptide rbcS from pea (Anderson et al. 1986, Biochem J. 240:709-715).

The DNA fragment which comprises the FNR promoter region −635 to −1 from *Arabidopsis thaliana* was produced by means of PCR using genomic DNA (isolated from *Arabidopsis thaliana* using standard methods) and also the primer FNR-1 (SEQ ID No.90) and FNR-2 (SEQ ID No. 91).

The PCR conditions were as follows:

The PCR for amplification of the DNA which comprises the FNR promoter fragment FNR1-2 (−635 to −1) was carried out in a 50 μl reaction mix in which the following were present:

100 ng of genomic DNA from *A. thaliana*-
0.25 mM dNTPs
0.2 mM FNR-1 (SEQ ID No. 90)
0.2 mM FNR-2 (SEQ ID No. 91)
5 μl of 10×PCR buffer (Stratagene)
0.25 μl of Pfu polymerase (Stratagene)
28.8 μl of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The 653 bp amplicon was cloned into the PCR cloning vector pCR 2.1 (Invitrogen) using standard methods and the plasmid pFNR was obtained.

Sequencing the clone pFNR confirmed a sequence which agreed with a sequence section of chromosome 5 of *Arabidopsis thaliana* (database entry ABO11474) from position 70 127 to 69 493. The gene starts at base pair 69 492 and is annotated "ferredoxin-NADP+reductase".

This clone is called pFNR and was therefore used for cloning into the expression vector pJIT117 (Guerineau et al. 1988, Nucl. Acids Res. 16: 11380).

The cloning was performed by isolating the 635 bp SacI-HindIII fragment from pFNR and ligation into the SacI-HindIII-cut vector pJIT117. The clone which comprises the promoter FNR instead of the original promoter d35S is called pJITFNR.

For the production of an expression cassette pJFN-RNOST, the 805 bp SpHI fragment NOSTF-G (described in Example 1) was cloned into the SpHI-cut vector pJITFNR. The clone which comprises the fragment NOSTF-G in the correct orientation as N-terminal fusion with the rbcS transit peptide is called pJFNRNOST.

An expression cassette for the *Agrobacterium*-mediated transformation of the expression vector with the ketolase from Nostoc in *Tagetes erecta* was produced using the binary vector pSUN5 (WO 02/00900).

For the production of the *Tagetes* expression vector pS5FNRNOST, the 2.4 Kb SacI-XhoI fragment (partial SacI hydrolysis) from pJFNRNOST was ligated with the SacI-XhoI-cut vector pSUN5 (FIG. 5, construct map). In FIG. 5, fragment FNR promoter comprises the duplicated FNR promoter (655 bp), fragment rbcS Transit Peptide the rbcS transit peptide from pea (204 bp), fragment *Nost* Ketolase (799 bp) the entire primary sequence coding for the *Nostoc* ketolase, fragment 35S Terminator (761 bp) comprises the polyadenylation signal of CaMV.

Example I.5C

Production of expression vectors for the flower-specific expression of the *Nostoc* sp. PCC 7120 ketolase in *Tagetes erecta*

The ketolase from *Nostoc* was expressed in *Tagetes erecta* using the transit peptide rbcS from pea (Anderson et al. 1986, Biochem J. 240:709-715). The expression was carried out under the control of a modified version AP3P of the flower-specific promoter AP3 from *Arabidopsis thaliana* (AL132971: nucleotide region 9298-10 200; Hill et al. (1998) Development 125:1711-1721).

The DNA fragment which comprises the AP3 promoter region −902 to +15 from *Arabidopsis thaliana* was produced by means of PCR using genomic DNA (isolated from *Arabidopsis thaliana* using standard methods) and also the primer AP3-1 (SEQ ID No. 93) and AP3-2 (SEQ ID No. 94).

The PCR conditions were as follows:

The PCR for the amplification of the DNA which comprises the AP3 promoter fragment (−902 to +15) was carried out in a 50 μl reaction mix in which the following were present:

100 ng of genomic DNA from *A.thaliana*
0.25 mM dNTPs
0.2 mM AP3-1 (SEQ ID No. 93)
0.2 mM AP3-2 (SEQ ID No. 94)
5 μl of 10×PCR buffer (Stratagene)
0.25 μl of Pfu polymerase (Stratagene)
28.8 μl of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The 929 bp amplicon was cloned into the PCR cloning vector pCR 2.1 (Invitrogen) using standard methods and the plasmid pAP3 was obtained.

Sequencing of the clone pAP3 confirmed a sequence which differs from the published AP3 sequence (AL132971, nucleotide region 9298-10 200) only in an insertion (a G in position 9765 of sequence AL132971) and a base exchange (a G instead of an A in position 9726 of sequence AL132971). These nucleotide differences were reproduced in an independent amplification experiment and thus represent the actual nucleotide sequence in the *Arabidopsis thaliana* plants used.

The modified version AP3P was produced by means of recombinant PCR using the plasmid pAP3. The region 10 200-9771 was amplified (amplicon A1/4) with the primers AP3-1 (SEQ ID No. 93) and AP3-4 (SEQ ID No. 96), the region 9526-9285 was amplified (amplicon A2/3) with the AP3-3 (SEQ ID No. 95) and AP3-2 (SEQ ID No. 94).

The PCR conditions were as follows:

The PCR reactions for amplification of the DNA fragments which comprise the regions region 10 200-9771 and region 9526-9285 of the AP3 promoter were carried out in 50 µl reaction mixes in which the following were present:

100 ng of AP3 amplicon (described above)
0.25 mM dNTPs
0.2 mM sense primer (AP3-1 SEQ ID No. 93 or AP3-3 SEQ ID No. 95)
0.2 mM antisense primer (AP3-4 SEQ ID No. 96 or AP3-2 SEQ ID No. 94)
5 µl of 10×PCR buffer (Stratagene)
0.25 µl of Pfu Taq polymerase (Stratagene)
28.8 µl of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The recombinant PCR comprises annealing the amplicons A1/4 and A2/3 overlapping over a sequence of 25 nucleotides, completion to give a double strand and subsequent amplification. This produces a modified version of the AP3 promoter, AP3P, in which positions 9670-9526 are deleted. The denaturation (5 min at 95° C.) and annealing (slow cooling at room temperature to 40° C.) of both amplicons A1/4 and A2/3 was carried out in a 17.6 µl reaction mix in which the following were present:

0.5 µg of A1/4 amplicon
0.25 µg of A2/3 amplicon

The 3' ends were filled in (30 min at 30° C.) in a 20 µl reaction mix in which the following were present:

17.6 µl of A1/4 and A2/3 annealing reaction (produced as described above)
50 µM dNTPs
2 µl of 1× Klenow buffer
2 U of Klenow enzyme The nucleic acid coding for the modified promoter version AP3P was amplified by means of PCR using a sense-specific primer (AP3-1 SEQ ID No. 93) and an antisense-specific primer (AP3-2 SEQ ID No. 94).

The PCR conditions were as follows:

The PCR for amplification of the AP3P fragment was carried out in a 50 µl reaction mix in which the following were present:

1 µl of annealing reaction (produced as described above)
0.25 mM dNTPs
0.2 mM AP3-1 (SEQ ID No. 93)
0.2 mM AP3-2 (SEQ ID No. 94)
5 µl of 10×PCR buffer (Stratagene)
0.25 µl of Pfu Taq polymerase (Stratagene)
28.8 µl of distilled water.

The PCR was carried out under the following cycle conditions:

| 1x  | 94° C. | 2 minutes  |
|-----|--------|------------|
| 35x | 94° C. | 1 minute   |
|     | 50° C. | 1 minute   |
|     | 72° C. | 1 minute   |
| 1x  | 72° C. | 10 minutes |

The PCR amplification with SEQ ID No. 93 (AP3-1) and SEQ ID No. 94 (AP3-2) resulted in a 783 bp fragment which codes for the modified promoter version AP3P. The amplicon was cloned into the cloning vector pCR2.1 (Invitrogen) and the plasmid pAP3P was obtained. Sequencing with the primers T7 and M13 confirmed a sequence identical to the sequence AL132971, region 10 200-9298, the internal region 9285-9526 having been deleted. This clone was therefore used for cloning into the expression vector pJIT117 (Guerineau et al. 1988, Nucl. Acids Res. 16: 11380).

The cloning was performed by isolating the 783 bp SacI-HindIII fragment from pAP3P and ligation into the SacI-HindIII-cut vector pJIT117. The clone which comprises the promoter AP3P instead of the original promoter d35S is called pJITAP3P. For the production of an expression cassette pJAP3NOST, the 805 bp SpHI fragment NOSTF-G (described in Example 1) was cloned into the SpHI-cut vector pJITAP3P. The clone which comprises the fragment NOSTF-G in the correct orientation as N-terminal fusion with the rbcS transit peptide is called pJAP3PNOST.

An expression vector for the *Agrobacterium*-mediated transformation of the AP3P-controlled ketolase from Nostoc in *Tagetes erecta* was produced using the binary vector pSUN5 (WO02/00900).

Figure 6:
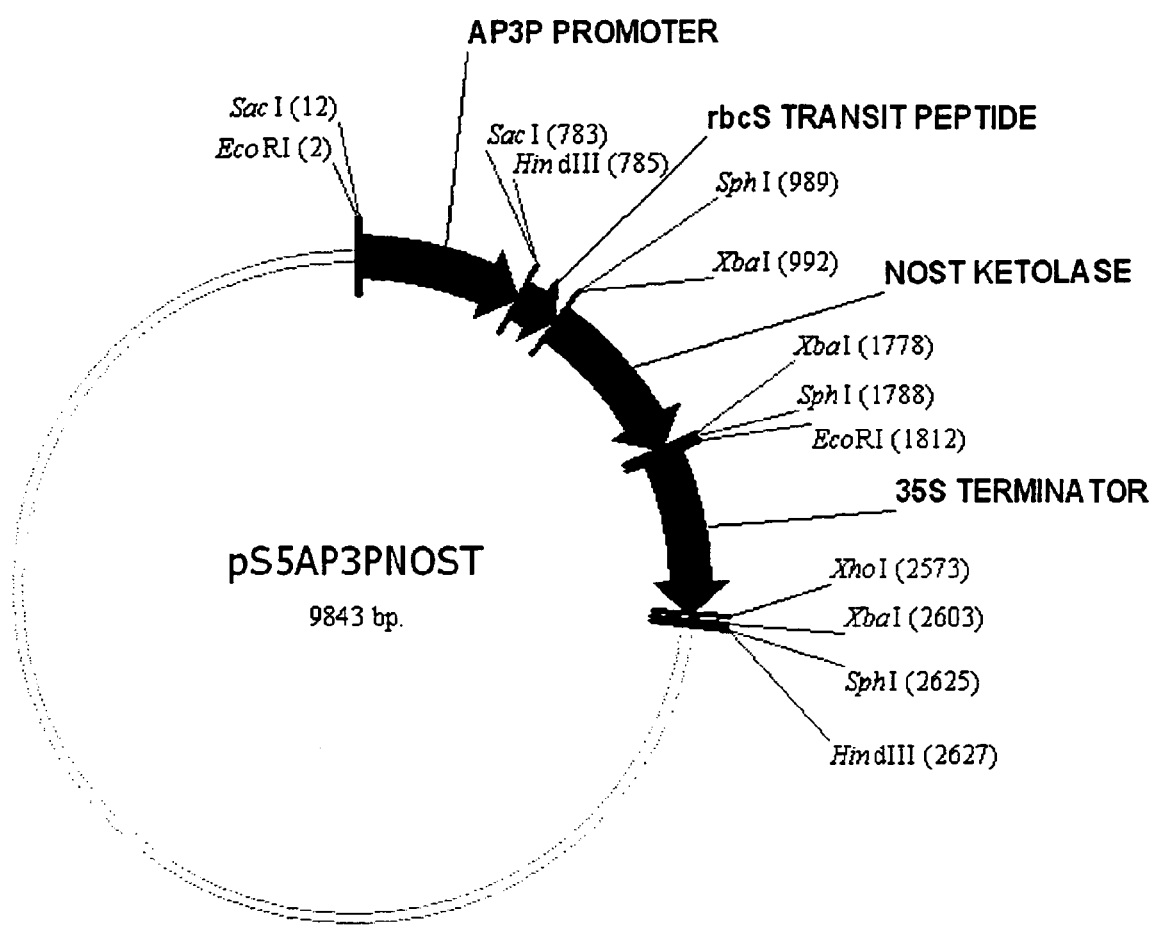
FIG. 6 shows the construct map of pS5AP3PNOST.

For the production of the expression vector pS5AP3PNOST, the 2.6. KB bp SacI-XhoI (partial SacI hydrolysis) fragment from pS5AP3PNOST was ligated with the SacI-XhoI-cut vector pSUN5 (FIG. 6, construct map). In FIG. 6, fragment AP3P comprises the modified AP3P promoter (783 bp), fragment rbcs the rbcS transit peptide from pea (207 bp), fragment NOSTF-G (792 bp) the entire primary sequence coding for the Nostoc ketolase, fragment term (795 bp) the polyadenylation signal of CaMV.

Example I.6

Production of Transgenic *Tagetes* Plants

*Tagetes* seeds are sterilized and placed on germination medium (MS medium; Murashige and Skoog, Physiol. Plant. 15 (1962), 473-497) pH 5.8, 2% sucrose). The germination takes place in a temperature/ligh/time interval of 18 to 28° C./20-200 mE/3 to 16 weeks, but preferably at 21° C., 20 to 70 mE, for 4 to 8 weeks.

All leaves of the plants which have developed in vitro by then are harvested and cut transversely to the middle rib. The leaf explants produced as a result having a size of from 10 to 60 mm² are kept in the course of the preparation in liquid MS medium at room temperature for a maximum of 2 h.

An optional *Agrobacterium tumefaciens* strain, but preferably a supervirulent strain, for example EHA105 having a corresponding binary plasmid which can bear a selection marker gene (preferably bar or pat) and also one or more trait or reporter genes (for example pS5KETO2 and pS5AP3PKETO2), is grown overnight and used for co-culturing with the leaf material. The growth of the bacterial strain can be performed as follows: a single colony of the corresponding strain is inoculated in YEB (0.1% yeast extract, 0.5% beef extract, 0.5% peptone, 0.5% sucrose, 0.5% magnesium sulfate.7H$_2$O) comprising 25 mg/l of kanamycin and cultured at 28° C. for 16 to 20 h. The bacterial suspension is then harvested by centrifugation at 6000 g for 10 min and resuspended in liquid MS medium in such a manner that an OD$_{600}$ of approximately 0.1 to 0.8 resulted. This suspension is used for the co-culture with the leaf material.

Immediately before the co-culture, the MS medium in which the leaves have been kept is replaced by the bacterial suspension. The leaves were incubated in the *Agrobacteria* suspension for 30 min with gentle shaking at room temperature. The infected explants are then placed on an agar-solidified (e.g. 0.8% plant agar (Duchefa, NL)) MS medium comprising growth regulators, for example 3 mg/l of benzylaminopurine (BAP) and also 1 mg/l of indolylacetic acid (IM). The orientation of the leaves on the medium is of no importance. The explants are cultured for from 1 to 8 days, but preferably for 6 days, with the following conditions being able to be used: light intensity: from 30 to 80 mmol/m$^2$×sec, temperature: from 22 to 24° C., light/dark change of 16/8 hours. Then, the co-cultured explants are transferred to fresh MS medium, preferably comprising the same growth regulators, this second medium additionally comprising an antibiotic for suppressing bacterial growth. Timentin at a concentration of from 200 to 500 mg/l is very suitable for this purpose. As second selective component, one is used for selecting the success of transformation. Phosphinothricin at a concentration of from 1 to 5 mg/l selects very efficiently, but other selective components according to the method to be used are also conceivable.

After in each case from one to three weeks, the explants are transferred to fresh medium until plumules and small buds develop which are then transferred to the same basal medium including Timentin and PPT or alternative components with growth regulators, that is to say, for example, 0.5 mg/l indolylbutyric acid (IBA) and 0.5 mg/l of gibberillic acid GA$_3$, for rooting. Rooted buds can be transferred to the glasshouse.

In addition to the described method, the following advantageous modifications are possible:

Before the explants are infected with the bacteria, they can be preincubated for from 1 to 12 days, preferably from 3 to 4, on the above-described medium for the co-culture. The infection, co-culture and selective regeneration are then carried out as described above.

The pH for the regeneration (usually 5.8) can be lowered to pH 5.2. This improves the control of the Agrobacterial growth.

The addition of AgNO$_3$ (3-10 mg/l) to the regeneration medium improves the state of the culture, including regeneration itself.

Components which reduce the phenol formation and are known to those skilled in the art, for example citric acid, ascorbic acid, PVP and many more, have a beneficial effect on the culture.

For the entire method, liquid culture medium can also be used. The culture can also be incubated on commercially conventional supports which are positioned on the liquid medium.

According to the above-described transformation method, using the following expression constructs, the following lines were obtained:

With pS5KETO2, for example, the following were obtained: cs18-1 and cs18-2, with pS5AP3PKETO2, for example, the following were obtained: cs19-1, cs19-2 and cs19-3.

With pS5FNRNOST, for example, the following were obtained: ms 103-1, ms103-2, ms103-3, with pS5AP3NOST, for example, the following were obtained: ms 104-1, ms104-2, ms104-3.

Example I.8

Characterization of the Transgenic Plant Flowers

Example I.8.1

Separation of Carotenoid Esters in Flower Leaves of Transgenic Plants

General Working Instructions:

The flower leaves of the transgenic plants are ground in a mortar in liquid nitrogen and the petal powder (about 40 mg) is extracted with 100% acetone (three times, each time 500 ml). The solvent is evaporated and the carotenoids are resuspended in from 100 to 200 ml of petroleum ether/acetone (5:1, v/v).

The carotenoids are separated according to their phobicity in concentrated form by means of thin-layer chromatography (TLC) on Silica60 F254 plates (Merck) in an organic mobile phase (petroleum ether/acetone; 5:1). Yellow (xanthophyll esters), red (ketocarotenoid esters) and orange bands (mixture of xanthophyll and ketocarotenoid esters) are scraped off on the TLC.

The silica-bound carotenoids are eluted three times with 500 ml of acetone, the solvent is evaporated and the carotenoids are separated by means of HPLC and identified.

By means of a C30 reversed-phase column, mono- and diesters of carotenoids can be differentiated. HPLC running conditions were virtually identical to a published method (Frazer et al. (2000), Plant Journal 24(4): 551-558). It is possible to identify the carotenoids on the basis of the UV-VIS spectra.

Example I.9

Enzymatic Hydrolysis of Carotenoid Esters and Identification of the Carotenoids

General Working Instructions

Petal material (50 to 100 mg fresh weight) ground in a mortar is extracted with 100% acetone (three times with 500 ml; shake each time for about 15 minutes). The solvent is evaporated. Carotenoids are then taken up in 400 ml of acetone (absorption at 475 nm between 0.75 and 1.25) and treated in the ultrasonic bath for 5 min. The carotenoid extract is mixed with 300 ml of 50 mM Tris-HCl buffer (pH 7.0) and incubated at 37° C. for 5 to 10 minutes. Thereafter, from 100 to 200 ml of cholesterol esterase are added (stock solution: 6.8 units/ml of a cholesterol esterase of *Pseudomonas* spec.). After from 8 to 12 hours, from 100 to 200 ml of enzyme are again added; the esters are hydrolyzed within 24 hours on incubation at 37° C. After adding 0.35 g of Na$_2$SO$_4$.10H$_2$O and 500 ml of petroleum ether, the mixture is mixed well and centrifuged (3 minutes; 4500 g). The petroleum ether phase is taken off and once more mixed with 0.35 g of Na$_2$SO$_4$.10H$_2$O (anhydrous). Centrifugation for 1 minute at 10 000 g. Petroleum ether is evaporated and free carotenoids are taken up in from 100 to 120 ml of acetone. By means of HPLC and C30 reversed-phase column, free carotenoids can be identified on the basis of retention time and UV-VIS spectra.

Example I.10

Production of a Cloning Vector for Producing Inverted-Repeat Expression Cassettes for the Flower-Specific Expression of Epsilon-Cyclase dsRNAs in *Tagetes Erecta*

Inverted-repeat transcripts consisting of fragments of the epsilon-cyclase in *Tagetes erecta* were expressed under the control of a modified version AP3P of the flower-specific promoter AP3 from *Arabidopsis thaliana* (AL132971: nucleotide region 9298 to 10 200; Hill et al. (1998) Development 125: 1711 to 1721).

The inverted-repeat transcript comprises in each case one fragment in correct orientation (sense fragment) and one sequence-identical fragment in the opposite orientation (antisense fragment) which are connected to one another by a functional intron, the PIV2 intron of the ST-LH1 gene from potatoes (Vancanneyt G. et al. (1990) Mol Gen Genet 220: 245-50).

The cDNA which codes for the AP3 promoter (−902 to +15) from *Arabidopsis thaliana* was produced by means of PCR using genomic DNA (isolated from *Arabidopsis thaliana* by standard method) and the primers PR7 (SEQ ID NO: 49) and PR10 (SEQ ID NO: 52).

The PCR conditions were as follows:
The PCR for amplification of the DNA which codes for the AP3 promoter fragment (−902 to +15) was carried out in a 50 ml reaction mix in which the following were present:
1 ml of genomic DNA from *A. thaliana* (1:100 dilution produced as described above)
0.25 mM dNTPs
0.2 mM PR7 (SEQ ID NO: 49)
0.2 mM PR10 (SEQ ID NO: 52)
5 ml of 10×PCR buffer (Stratagene)
0.25 ml of Pfu polymerase (Stratagene)
28.8 ml of distilled water.
The PCR was carried out under the following cycle conditions:

| 1x | 94° C. | 2 minutes |
|---|---|---|
| 35x | 94° C. | 1 minute |
| | 50° C. | 1 minute |
| | 72° C. | 1 minute |
| 1x | 72° C. | 10 minutes |

The 922 bp amplicon was cloned into the PCR cloning vector pCR 2.1 (Invitrogen) using standard methods and the plasmid pTAP3 was obtained. Sequencing the clone pTAP3 confirmed a sequence which differs from the published AP3 sequence (AL132971, nucleotide region 9298 to 10 200) only by an insertion (a G in position 9765 of the sequence AL132971) and a base exchange (a G instead of an A in position 9726 of sequence AL132971) (position 33: T instead of G, position 55: T instead of G). These nucleotide differences were reproduced in an independent amplification experiment and thus represent the nucleotide sequence in the *Arabidopsis thaliana* plant used.

The modified version AP3P was produced by means of recombinant PCR using the plasmid pTAP3. The region 10 200 to 9771 was amplified with the primers PR7 (SEQ ID NO: 49) and primers PR9 (SEQ ID NO: 51) (amplicon A7/9), the region 9526 to 9285 was amplified with PR8 (SEQ ID NO: 50) and PR10 (SEQ ID NO: 52) (amplicon A8/10).

The PCR conditions were as follows:
The PCR reactions for amplification of the DNA fragments which code for the regions region 10 200 to 9771 and 9526 to 9285 of the AP3 promoter were carried out in 50 ml reaction mixes in which the following were present:
100 ng of AP3 amplicon (described above)
0.25 mM dNTPs
0.2 mM PR7 (SEQ ID NO: 49) or PR8 (SEQ ID NO: 50)
0.2 mM PR9 (SEQ ID NO: 51) or PR10 (SEQ ID NO: 52)
5 ml of 10×PCR buffer (Stratagene)
0.25 ml of Pfu Taq polymerase (Stratagene)
28.8 ml of distilled water.
The PCR was carried out under the following cycle conditions:

| 1x | 94° C. | 2 minutes |
|---|---|---|
| 35x | 94° C. | 1 minute |
| | 50° C. | 2 minutes |
| | 72° C. | 3 minutes |
| 1x | 72° C. | 10 minutes |

The recombinant PCR comprises annealing of the amplicons A7/9 and A8/10 which are overlapping over a sequence of 25 nucleotides, completion to form a double strand and subsequent amplification. This produces a modified version of the AP3 promoter, AP3P, in which the positions 9670 to 9526 are deleted. The denaturation (5 min at 95° C.) and annealing (slow cooling at room temperature to 40° C.) of both amplicons A7/9 and A8/10 was carried out in a 17.6 ml reaction mix in which the following were present:
0.5 mg of A7/9
0.25 mg of A8/10
The 3' ends were filled in (30 min at 30° C.) in a 20 ml reaction mix in which the following were present:
17.6 ml of A7/9 and A8/10 annealing reaction (produced as described above)
50 mM dNTPs
2 ml of 1× Klenow buffer
2 U of Klenow enzyme
The nucleic acid coding for the modified promoter version AP3P was amplified by means of PCR using a sense-specific primer (PR7 SEQ ID NO: 49) and an antisense-specific primer (PR10 SEQ ID NO: 52).
The PCR conditions were as follows:
The PCR for the amplification of the AP3P fragment was carried out in a 50 ml reaction mix in which the following were present:
1 ml of annealing reaction (produced as described above)
0.25 mM dNTPs
0.2 mM PR7 (SEQ ID NO: 49)
0.2 mM PR10 (SEQ ID NO: 52)
5 ml of 10×PCR buffer (Stratagene)
0.25 ml of Pfu Taq polymerase (Stratagene)
28.8 ml of distilled water.

The PCR was carried out under the following cycle conditions:

| | | |
|---|---|---|
| 1x | 94° C. | 2 minutes |
| 35x | 94° C. | 1 minute |
| | 50° C. | 1 minute |
| | 72° C. | 1 minute |
| 1x | 72° C. | 10 minutes |

The PCR amplification with PR7, SEQ ID NO: 49 and PR10 SEQ ID NO: 52 resulted in a 778 bp fragment which codes for the modified promoter version AP3P. The amplicon was cloned into the cloning vector pCR2.1 (Invitrogen). Sequencing with the primers T7 and M13 confirmed a sequence identical to the sequence AL132971, region 10 200 to 9298, with the internal region 9285 to 9526 having been deleted. This clone was therefore used for cloning into the expression vector pJIT117 (Guerineau et al. 1988, Nucl. Acids Res. 16: 11380).

The cloning was carried out by isolating the 771 bp SacI-HindIII fragment from pTAP3P and ligation into the SacI-HindIII-cut vector pJIT117. The clone which comprises the promoter AP3P instead of the original promoter d35S is called pJAP3P.

A DNA fragment which comprises the PIV2 intron of the gene ST-LS1 was amplified by means of PCR using plasmid DNA p35SGUS INT (Vancanneyt G. et al. (1990) Mol Gen Genet 220: 245-50) and also the primers PR40 (Seq ID NO: 54) and PR41 (Seq ID NO: 55).

The PCR conditions were as follows:

The PCR for amplification of the sequence of the intron PIV2 of the gene ST-LS1 was carried out in a 50 ml reaction mix in which the following were present:

1 ml of p35SGUS INT
0.25 mM dNTPs
0.2 mM PR40 (SEQ ID NO: 54)
0.2 mM PR41 (SEQ ID NO: 55)
5 ml of 10×PCR buffer (TAKARA)
0.25 ml of R Taq polymerase (TAKARA)
28.8 ml of distilled water.

The PCR was carried out under the following cycle conditions:

| | | |
|---|---|---|
| 1x | 94° C. | 2 minutes |
| 35x | 94° C. | 1 minute |
| | 53° C. | 1 minute |
| | 72° C. | 1 minute |
| 1x | 72° C. | 10 minutes |

The PCR amplification using PR40 and PR41 resulted in a 206 bp fragment. Using standard methods, the amplicon was cloned into the PCR cloning vector pBluntII (Invitrogen) and the clone pBluntII-40-41 was obtained. Sequencing this clone with the primer SP6 confirmed a sequence which is identical to the corresponding sequence from the vector p35SGUS INT.

This clone was therefore used for cloning into the vector pJAP3P (described above).

The cloning was performed by isolating the 206 bp SalI-BamHI fragment from pBluntII-40-41 and ligation to the SalI-BamHI-cut vector pJAP3P. The clone which comprises the intron PIV2 of the gene ST-LS1 in the correct orientation then to the 3' end of the rbcs transit peptide is called pJAI1 and is suitable for producing expression cassettes for the flower-specific expression of inverted-repeat transcripts.

In FIG. 7, fragment AP3P comprises the modified AP3P promoter (771 bp), fragment rbcs the rbcS transit peptide from pea (204 bp), fragment intron the intron PIV2 of the potato gene ST-LS1, and fragment term (761 bp) the polyadenylation signal of CaMV.

Example I.11

Production of Inverted-Repeat Expression Cassettes for the Flower-Specific Expression of Epsilon-Cyclase dsRNAs in *Tagetes Erecta*(Directed Against the 5' Region of the Epsilon-Cyclase cDNA)

The nucleic acid which comprises the 5'-terminal 435 bp region of the epsilon-cyclase cDNA (Genbank accession NO: AF251016) was amplified by means of the polymerase chain reaction (PCR) from *Tagetes erecta* cDNA using a sense-specific primer (PR42 SEQ ID NO: 56) and an antisense-specific primer (PR43 SEQ ID NO: 57). The 5'-terminal 435 bp region of the epsilon-cyclase cDNA from *Tagetes erecta* is composed of 138 bp 5'-non-translated sequence (5'UTR) and 297 bp of the coding region corresponding to the N terminus.

For the preparation of total RNA from flowers of *Tagetes*, 100 mg of the frozen pulverized flowers were transferred to a reaction vessel and taken up in 0.8 ml of Trizol buffer (LifeTechnologies). The suspension was extracted with 0.2 ml of chloroform. After centrifugation at 12 000 g for 15 minutes, the aqueous supernatant was taken off and transferred to a new reaction vessel and extracted with one volume of ethanol. The RNA was precipitated with one volume of isopropanol, washed with 75% ethanol and the pellet was dissolved in DEPC water (overnight incubation of water with 1/1000 volume of diethyl pyrocarbonate at room temperature, then autoclaved). The RNA concentration was determined photometrically. For the cDNA synthesis, 2.5 μg of total RNA were denatured at 60° C. for 10 min, cooled on ice for 2 min and transcribed into cDNA by means of a cDNA kit (Ready-to-go-you-prime-beads, Pharmacia Biotech) according to manufacturer's instructions, using an antisense-specific primer (PR17 SEQ ID NO: 53).

The conditions of the subsequent PCR reactions were as follows:

The PCR for the amplification of the PR42-PR43 DNA fragment which comprises the 5'-terminal 435 bp region of the epsilon-cyclase was performed in a 50 ml reaction mix in which the following were present:

1 ml of cDNA (produced as described above)
0.25 mM dNTPs
0.2 mM PR42 (SEQ ID NO: 56)
0.2 mM PR43 (SEQ ID NO: 57)
5 ml of 10×PCR buffer (TAKARA)
0.25 ml of R Taq polymerase (TAKARA)
28.8 ml of distilled water.

The PCR for the amplification of the PR44-PR45 DNA fragment which comprises the 5'-terminal 435 bp region of the epsilon-cyclase was performed in a 50 ml reaction mix in which the following were present:

1 ml of cDNA (produced as described above)
0.25 mM dNTPs
0.2 mM PR44 (SEQ ID NO: 58)
0.2 mM PR45 (SEQ ID NO: 59)
5 ml of 10×PCR buffer (TAKARA)
0.25 ml of R Taq polymerase (TAKARA)
28.8 ml of distilled water.

The PCR reactions were carried out under the following cycle conditions:

| 1x  | 94° C. | 2 minutes  |
|-----|--------|------------|
| 35x | 94° C. | 1 minute   |
|     | 58° C. | 1 minute   |
|     | 72° C. | 1 minute   |
| 1x  | 72° C. | 10 minutes |

The PCR amplification using primer PR42 and PR43 resulted in a 443 bp fragment, and the PCR amplification using primer PR44 and PR45 resulted in a 444 bp fragment.

The two amplicons, the PR42-PR43 (HindIII-SalI sense) fragment and the PR44-PR45 (EcoRI-BamHI antisense) fragment, were cloned using standard methods into the PCR cloning vector pCR-BluntII (Invitrogen). Sequencing with the primer SP6 confirmed in each case a sequence identical to the published sequence AF251016 (SEQ ID NO: 38), apart from the introduced restriction sites. This clone was therefore used for the production of an inverted-repeat construct in the cloning vector pJAI1 (see Example I.10).

The first cloning step was performed by isolating the 444 bp PR44—PR45 BamHI-EcoRI fragment from the cloning vector pCR-BluntII (Invitrogen) and ligation to the BamHI-EcoRI-cut vector pJAI1. The clone which comprises the 5'-terminal region of the epsilon-cyclase in the antisense orientation is called pJAI2. The ligation produces a transcriptional fusion between the antisense fragment of the 5'-terminal region of the epsilon-cyclase and the polyadenylation signal from CaMV.

The second cloning step was performed by isolating the 443 bp PR42-PR43 HindIII-SalI fragment from the cloning vector pCR-BluntII (Invitrogen) and ligation to the HindIII-SalI-cut vector pJAI2. The clone which comprises the 435 bp 5'-terminal region of the epsilon-cyclase cDNA in the sense orientation is called pJAI3. The ligation produces a transcriptional fusion between the AP3P and the sense fragment of the 5' terminal region of the epsilon-cyclase.

For the production of an inverted-repeat expression cassette under the control of the CHRC promoter, a CHRC promoter fragment was amplified using genomic DNA from petunia (produced according to standard methods) and also the primers PRCHRC5 (SEQ ID NO: 76) and PRCHRC3 (SEQ ID NO: 77). The amplicon was cloned into the cloning vector pCR2.1 (Invitrogen). Sequencing the resulting clone pCR2.1-CHRC using the primers M13 and T7 confirmed a sequence identical to the sequence AF099501. This clone was therefore used for cloning into the expression vector pJAI3.

The cloning was carried out by isolating the 1537 bp SacI-HindIII fragment from pCR2.1-CHRC and ligation into the SacI-HindIII-cut vector pJAI3. The clone which comprises the promoter CHRC instead of the original promoter AP3P is called pJCI3.

The expression vectors for the *Agrobacterium*-mediated transformation of the AP3P- or CHRC-controlled inverted-repeat transcript in *Tagetes erecta* were produced using the binary vector pSUN5 (WO02/00900).

For production of the expression vector pS5AI3, the 2622 bp SacI-XhoI fragment from pJAI3 was ligated to the SacI-XhoI-cut vector pSUN5 (FIG. 8, construct map).

In FIG. 8, fragment AP3P comprises the modified AP3P promoter (771 bp), fragment 5sense the 5' region of the epsilon-cyclase from *Tagetes erecta* (435 bp) in the sense orientation, fragment intron the intron PIV2 of the potato gene ST-LS1, fragment 5anti the 5' region of the epsilon-cyclase from *Tagetes erecta* (435 bp) in the antisense orientation, and fragment term (761 bp) the polyadenylation signal of CaMV.

For the production of the expression vector pS5CI3, the 3394 bp-SacI-XhoI fragment from pJCI3 was ligated to the SacI-XhoI-cut vector pSUN5 (FIG. 9, construct map).

In FIG. 9, fragment CHRC comprises the promoter (1537 bp), fragment 5sense the 5' region of the epsilon-cyclase from *Tagetes erecta* (435 bp) in the sense orientation, fragment intron the intron PIV2 of the potato gene ST-LS1, fragment 5anti the 5' region of the epsilon-cyclase from *Tagetes erecta* (435 bp) in the antisense orientation, and fragment term (761 bp) the polyadenylation signal of CaMV.

Example I.12

Production of an Inverted-Repeat Expression Cassette for the Flower-Specific Expression of Epsilon-Cyclase dsRNAs in *Tagetes erecta* (Directed Against the 3' Region of the Epsilon-Cyclase cDNA)

The nucleic acid which comprises the 3'-terminal region (384 bp) of the epsilon-cyclase cDNA (Genbank accession NO: AF251016) was amplified by means of the polymerase chain reaction (PCR) from *Tagetes erecta* cDNA using a sense-specific primer (PR46 SEQ ID NO: 60) and an antisense-specific primer (PR47 SEQ ID NO: 61). The 3'-terminal region (384 bp) of the epsilon-cyclase cDNA from *Tagetes erecta* is composed of a 140 bp 3'-non-translated sequence (3'UTR) and 244 bp of the coding region corresponding to the C terminus.

Total RNA was prepared from flowers of *Tagetes* as described under Example I.11.

The cDNA was synthesized as described under Example I.11, using the antisense-specific primer PR17 (SEQ ID NO: 53).

The conditions for the subsequent PCR reactions were as follows:

The PCR for amplification of the PR46-PR47 DNA fragment which comprises the 3'-terminal 384 bp region of the epsilon-cyclase was performed in a 50 ml reaction mix in which the following were present:
1 ml of cDNA (produced as described above)
0.25 mM dNTPs
0.2 mM PR46 (SEQ ID NO: 60)
0.2 mM PR47 (SEQ ID NO: 61)
5 ml of 10×PCR buffer (TAKARA)
0.25 ml of R Taq polymerase (TAKARA)
28.8 ml of distilled water.

The PCR for amplification of the PR48-PR49 DNA fragment which comprises the 5'-terminal 384 bp region of the epsilon-cyclase was performed in a 50 ml reaction mix in which the following were present:
1 ml of cDNA (produced as described above)
0.25 mM dNTPs
0.2 mM PR48 (SEQ ID NO: 62)
0.2 mM PR49 (SEQ ID NO: 63)
5 ml of 10×PCR buffer (TAKARA)
0.25 ml of R Taq polymerase (TAKARA)
28.8 ml of distilled water.

The PCR reactions were carried out under the following cycle conditions:

| 1x  | 94° C. | 2 minutes  |
|-----|--------|------------|
| 35x | 94° C. | 1 minute   |
|     | 58° C. | 1 minute   |
|     | 72° C. | 1 minute   |
| 1x  | 72° C. | 10 minutes |

The PCR amplification using SEQ ID NO: 60 and SEQ ID NO: 61 resulted in a 392 bp fragment, and the PCR amplification using SEQ ID NO: 62 and SEQ ID NO: 63 resulted in a 396 bp fragment.

The two amplicons, the PR46-PR47 fragment and the PR48—PR49 fragment, were cloned using standard methods into the PCR cloning vector pCR-BluntII (Invitrogen). Sequencing using the primer SP6 confirmed in each case a sequence identical to the published sequence AF251016 (SEQ ID NO: 38) apart from the restriction sites introduced. This clone was therefore used for production of an inverted-repeat construct in the cloning vector pJAI1 (see Example I.10).

The first cloning step was performed by isolating the 396 bp PR48-PR49 BamHI-EcoRI fragment from the cloning vector pCR-BluntII (Invitrogen) and ligation to the BamHI-EcoRI-cut vector pJAI1. The clone which comprises the 3'-terminal region of the epsilon-cyclase in the antisense orientation is called pJAI4. The ligation produces a transcriptional fusion between the antisense fragment of the 3'-terminal region of the epsilon-cyclase and the polyadenylation signal from CaMV.

The second cloning step was performed by isolating the 392 bp PR46-PR47 HindIII-SalI fragment from the cloning vector pCR-BluntII (Invitrogen) and ligation to the HindIII-SalI-cut vector pJAI4. The clone which comprises the 392 bp 3'-terminal region of the epsilon-cyclase cDNA in the sense orientation is called pJAI5. The ligation produces a transcriptional fusion between the AP3P and the sense fragment 3'-terminal region of the epsilon-cyclase.

An expression vector for the *Agrobacterium*-mediated transformation of the AP3P-controlled inverted-repeat transcript in *Tagetes erecta* was produced using the binary vector pSUN5 (WO02/00900). For production of the expression vector pS5AI5, the 2523 bp SacI-XhoI fragment from pJAI5 was ligated to the SacI-XhoI-cut vector pSUN5 (FIG. 10, construct map).

In FIG. 10, fragment AP3P comprises the modified AP3P promoter (771 bp), fragment 3sense the 3' region of the epsilon-cyclase from *Tagetes erecta* (435 bp) in the sense orientation, fragment intron the intron IV2 of the potato gene ST-LS1, fragment 3anti the 3' region of the epsilon-cyclase from *Tagetes erecta* (435 bp) in the antisense orientation, and fragment term (761 bp) the polyadenylation signal of CaMV.

Example I.13

Cloning the Epsilon-Cyclase Promoter

A 199 bp fragment and the 312 bp fragment of the epsilon-cyclase promoter were isolated by two independent cloning strategies, inverse PCR (adapted from Long et al. Proc. Natl. Acad. Sci USA 90: 10370) and TAIL-PCR (Liu Y-G. et al. (1995) Plant J. 8: 457-463) using genomic DNA (isolated by standard method from *Tagetes erecta*, Orangenprinz line).

For the inverse PCR approach, 2 µg of genomic DNA were digested in a 25 µl reaction mix with EcoRV and RsaI, then diluted to 300 ml and religated overnight at 16° C. using 3 U of ligase. Using the primers PR50 (SEQ ID NO: 64) and PR51 (SEQ ID NO: 65), by PCR amplification, a fragment was produced which, in each case in the sense orientation, comprises 354 bp of the epsilon-cyclase cDNA (Genbank Accession AF251016), ligated to 300 bp of the epsilon-cyclase promoter and also 70 bp of the 5'-terminal region of the cDNA epsilon-cyclase (see FIG. 11).

The conditions of the PCR reactions were as follows:

The PCR for amplification of the PR50-PR51 DNA fragment which, inter alia, comprises the 312 bp promoter fragment of the epsilon-cyclase was performed in a 50 ml reaction mix in which the following were present:
1 ml of ligation mix (produced as described above)
0.25 mM dNTPs
0.2 mM PR50 (SEQ ID NO: 64)
0.2 mM PR51 (SEQ ID NO: 65)
5 ml of 10×PCR buffer (TAKARA)
0.25 ml of R Taq polymerase (TAKARA)
28.8 ml of distilled water.

The PCR reactions were carried out under the following cycle conditions:

| | | |
|---|---|---|
| 1x | 94° C. | 2 minutes |
| 35x | 94° C. | 1 minute |
| | 53° C. | 1 minute |
| | 72° C. | 1 minute |
| 1x | 72° C. | 10 minutes |

The PCR amplification using primer PR50 and PR51 resulted in a 734 bp fragment which, inter alia, comprises the 312 bp promoter fragment of epsilon-cyclase (FIG. 11).

The amplicon was cloned using standard methods into the PCR cloning vector pCR2.1 (Invitrogen). Sequencing using the primers M13 and T7 gave the sequence SEQ ID NO: 45. This sequence was reproduced in an independent amplification experiment and thus represents the nucleotide sequence in the *Tagetes erecta* line Orangenprinz used.

For the TAIL-PCR approach, three successive PCR reactions were carried out using in each case different gene-specific primers (nested primers).

The TAIL1-PCR was performed in a 20 ml reaction mix in which the following were present:
1 ng of genomic DNA (produced as described above)
0.2 mM each dNTP
0.2 mM PR60 (SEQ ID NO: 66)
0.2 mM AD1 (SEQ ID NO: 69)
2 ml of 10×PCR buffer (TAKARA)
0.5 U of R Taq polymerase (TAKARA)
made up to 20 ml with distilled water.
AD1 was first a mixture of primers of the sequences (a/c/g/t)tcga(g/c)t(alt)t(g/c)g(a/t)gtt.

The PCR reaction TAIL1 was carried out under the following cycle conditions:

| | |
|---|---|
| 1x | 93° C.: 1 minute, 95° C.: 1 minute |
| 5x | 94° C.: 30 seconds, 62° C.: 1 minute, 72° C.: 2.5 minutes |
| 1x | 94° C.: 30 seconds, 25° C.: 3 minutes, ramp to 72° C. in 3 minutes, 72° C.: 2.5 minutes |
| 15x | 94° C.: 10 seconds, 68° C.: 1 minute, 72° C.: 2.5 minutes; 94° C.: 10 seconds, 68° C.: 1 minute, 72° C.: 2.5 minutes; 94° C.: 10 seconds, 29° C.: 1 minute, 72° C.: 2.5 minutes |
| 1x | 72° C.: 5 minutes |

The TAIL2-PCR was performed in a 21 ml reaction mix in which the following were present:
1 ml of a 1:50 dilution of the TAIL1 reaction mix (produced as described above)
0.8 mM dNTP
0.2 mM PR61 (SEQ ID NO: 67)
0.2 mM AD1 (SEQ ID NO: 69)
2 ml of 10×PCR buffer (TAKARA)
0.5 U of R Taq polymerase (TAKARA)
made up to 21 ml with distilled water.

The PCR reaction TAIL2 was carried out under the following cycle conditions:

| | |
|---|---|
| 12x | 94° C.: 10 seconds, 64° C.: 1 minute, 72° C.: 2.5 minutes; |
| | 94° C.: 10 seconds, 64° C.: 1 minute, 72° C.: 2.5 minutes; |
| | 94° C.: 10 seconds, 29° C.: 1 minute, 72° C.: 2.5 minutes |
| 1x | 72° C.: 5 minutes |

The TAIL3-PCR was performed in a 100 ml reaction mix in which the following were present:
 1 ml of a 1:10 dilution of the TAIL2 reaction mix (produced as described above)
 0.8 mM dNTP
 0.2 mM PR63 (SEQ ID NO: 68)
 0.2 mM AD1 (SEQ ID NO: 69)
 10 ml of 10×PCR buffer (TAKARA)
 0.5 U of R Taq polymerase (TAKARA)
 made up to 100 ml with distilled water.

The PCR reaction TAIL3 was carried out under the following cycle conditions:

| | |
|---|---|
| 20x | 94° C.: 15 seconds, 29° C.: 30 seconds, 72° C.: 2 minutes |
| 1x | 72° C.: 5 minutes |

The PCR amplification using primer PR63 and AD1 resulted in a 280 bp fragment which, inter alia, comprises the 199 bp promoter fragment of epsilon-cyclase (FIG. 12).

The amplicon was cloned using standard methods into the PCR cloning vector pCR2.1 (Invitrogen). Sequencing using the primers M13 and T7 gave the sequence SEQ ID NO: 46. This sequence is identical to the sequence SEQ ID NO: 45 which was isolated by the IPCR strategy and thus represents the nucleotide sequence in the *Tagetes* erecta line Orangenprinz used.

The pCR2.1 clone which comprises the 312 bp fragment (SEQ ID NO: 45) of the epsilon-cyclase promoter which was isolated by the IPCR strategy is called pTA-ecycP and was used for producing the IR constructs.

Example I.14

Production of an inverted-repeat expression cassette for the flower-specific expression of epsilon-cyclase dsRNAs in *Tagetes erecta* (directed against the promoter region of the epsilon-cyclase cDNA)

The expression of inverted-repeat transcripts consisting of promoter fragments of the epsilon-cyclase in *Tagetes erecta* was performed under the control of a modified version AP3P of the flower-specific promoter AP3 from *Arabidopsis* (see Example I.10) or of the flower-specific promoter CHRC (Genbank accession NO: AF099501). The inverted-repeat transcript comprises in each case one epsilon-cyclase promoter fragment in correct orientation (sense fragment) and a sequence-identical epsilon-cyclase promoter fragment in the opposite orientation (antisense fragment) which are joined together by a functional intron (see Example I.10).

The promoter fragments were produced by means of PCR using plasmid DNA (clone pTA-ecycP, see Example 1.13) and the primers PR124 (SEQ ID NO: 70) and PR126 (SEQ ID NO: 72) and the primers PR125 (SEQ ID NO: 71) and PR127 (SEQ ID NO: 73).

The conditions of the PCR reactions were as follows:

The PCR for amplification of the PR124-PR126 DNA fragment which comprises the promoter fragment of the epsilon-cyclase was performed in a 50 ml reaction mix in which the following were present:
 1 ml of cDNA (produced as described above)
 0.25 mM dNTPs
 0.2 mM PR124 (SEQ ID NO: 70)
 0.2 mM PR126 (SEQ ID NO: 72)
 5 ml of 10×PCR buffer (TAKARA)
 0.25 ml of R Taq polymerase (TAKARA)
 28.8 ml of distilled water.

The PCR for amplification of the PR125-PR127 DNA fragment which comprises the 312 bp promoter fragment of the epsilon-cyclase was performed in a 50 ml reaction mix in which the following were present:
 1 ml of cDNA (produced as described above)
 0.25 mM dNTPs
 0.2 mM PR125 (SEQ ID NO: 71)
 0.2 mM PR127 (SEQ ID NO: 73)
 5 ml of 10×PCR buffer (TAKARA)
 0.25 ml of R Taq polymerase (TAKARA)
 28.8 ml of distilled water.

The PCR reactions were carried out under the following cycle conditions:

| | | |
|---|---|---|
| 1x | 94° C. | 2 minutes |
| 35x | 94° C. | 1 minute |
| | 53° C. | 1 minute |
| | 72° C. | 1 minute |
| 1x | 72° C. | 10 minutes |

The PCR amplification using primer PR124 and PR126 resulted in a 358 bp fragment, and the PCR amplification using primer PR125 and PR127 resulted in a 361 bp fragment.

The two amplicons, the PR124-PR126 (HindIII-SalI sense) fragment and the PR 25-PR127 (EcoRI-BamHI antisense) fragment, were cloned using standard methods into the PCR cloning vector pCR-BluntII (Invitrogen). Sequencing using the primer SP6 confirmed in each case a sequence which, apart from the restriction sites introduced, is identical to SEQ ID NO: 45. This clone was therefore used for the production of an inverted-repeat construct in the cloning vector pJAI1 (see Example I.10).

The first cloning step was performed by isolating the 358 bp PR124-PR126 HindIII-SalI fragment from the cloning vector pCR-BluntII (Invitrogen) and ligation to the BamHI-EcoRI-cut vector pJAI1. The clone which comprises the epsilon-cyclase promoter fragment in the sense orientation is called cs43. The ligation introduces the sense fragment of the epsilon-cyclase promoter between the AP3P promoter and the intron.

The second cloning step was performed by isolating the 361 bp PR125-PR127 BamHI-EcoRI fragment from the cloning vector pCR-BluntII (Invitrogen) and ligation to the BamHI-EcoRI-cut vector cs43. The clone which comprises the epsilon-cyclase promoter fragment in the antisense orientation is called cs44. The ligation forms a transcriptional fusion between the intron and the antisense fragment of the epsilon-cyclase promoter.

For the production of an inverted-repeat expression cassette under the control of the CHRC promoter, a CHRC promoter fragment was amplified using genomic DNA from petunia (produced according to standard methods) and also the primer PRCHRC3' (SEQ ID NO: 77) and PRCHRC5' (SEQ ID NO: 76). The amplicon was cloned into the cloning vector pCR2.1 (Invitrogen). Sequencing of the resultant clone pCR2.1-CHRC using the primers M13 and T7 confirmed a sequence identical to the sequence AF099501. This clone was therefore used for cloning into the expression vector cs44.

The cloning was performed by isolating the 1537 bp SacI-HindIII fragment from pCR2.1-CHRC and ligation into the SacI-HindIII-cut vector cs44. The clone which comprises the promoter CHRC instead of the original promoter AP3P is called cs45.

For the production of an inverted-repeat expression cassette under the control of two promoters, the CHRC promoter and the AP3P promoter, the AP3P promoter was cloned into cs45 in antisense orientation to the 3' terminus of the epsilon-cyclase antisense fragment. The AP3P promoter fragment from pJAI 1 was amplified using the primers PR128 and PR129. The amplicon was cloned into the cloning vector pCR2.1 (Invitrogen). Sequencing using the primers M13 and T7 confirmed a sequence identical to the sequence SEQ ID NO: 28 (AL132971). This clone pCR2.1-AP3PSX was used for the production of an inverted-repeat expression cassette under the control of two promoters.

The cloning was performed by isolating the 771 bp SalI-XhoI fragment from pCR2.1-AP3PSX and ligation into the XhoI-cut vector cs45. The clone which comprises on the 3' side of the inverted repeat the promoter AP3P in antisense orientation is called cs46.

The expression vectors for the *Agrobacterium*-mediated transformation of the AP3P-controlled inverted-repeat transcript in *Tagetes erecta* were produced using the binary vector pSUN5 (WO 02/00900).

For the production of the expression vector pS5AI7, the 1685 bp SacI-XhoI fragment from cs44 was ligated to the SacI-XhoI-cut vector pSUN5 (FIG. 13, construct map). In FIG. 13, fragment AP3P comprises the modified AP3P promoter (771 bp), fragment P-sense the 312 bp promoter fragment of the epsilon-cyclase in sense orientation, fragment intron the intron IV2 of the potato gene ST-LS1), and fragment P-anti the 312 bp promoter fragment of the epsilon-cyclase in antisense orientation.

For the production of the expression vector pS5CI7, the 2445 bp SacI-XhoI fragment from cs45 was ligated to the SacI-XhoI-cut vector pSUN5 (FIG. 14, construct map).

In FIG. 14, fragment CHRC comprises the CHRC promoter (1537 bp), fragment P-sense the 312 bp promoter fragment of the epsilon-cyclase in sense orientation, fragment intron the intron IV2 of the potato gene ST-LS1), and fragment P-anti the 312 bp promoter fragment of the epsilon-cyclase in antisense orientation.

For the production of the expression vector pS5CAI7, the 3219 bp SacI-XhoI fragment from cs46 was ligated to the SacI-XhoI-cut vector pSUN5 (FIG. 15, construct map).

In FIG. 15, fragment CHRC comprises the CHRC promoter (1537.bp), fragment P-sense the 312 bp promoter fragment of the epsilon-cyclase in sense orientation, fragment intron the intron IV2 of the potato gene ST-LS1), fragment P-anti the 312 bp promoter fragment of the epsilon-cyclase in antisense orientation and the fragment AP3P the 771 bp AP3P promoter fragment in antisense orientation.

Example I.15

Production of Transgenic *Tagetes* Plants Having Reduced ε-Cyclase Activity

*Tagetes* seeds are sterilized and placed on germination medium (MS medium; Murashige and Skoog, Physiol. Plant. 15 (1962), 473-497) pH 5.8, 2% sucrose). The germination takes place in a temperature/light/time interval of from 18 to 28° C./from 20 to 200 mE/from 3 to 16 weeks, but preferably at 21° C., from 20 to 70 mE, for from 4 to 8 weeks.

All leaves of the plants which have developed in vitro by then are harvested and cut transversely to the middle rib. The resulting leaf explants having a size of from 10 to 60 mm$^2$ are stored in liquid MS medium at room temperature for a maximum of 2 h in the course of the preparation.

The *Agrobacterium tumefaciens* strain EHA105 was transformed using the binary plasmid pS5AI3. The transformed *A. tumefaciens* strain EHA 05 was grown overnight under the following conditions: an individual colony was inoculated into YEB (0.1% yeast extract, 0.5% beef extract, 0.5% peptone, 0.5% sucrose, 0.5% magnesium sulfate.7H$_2$O) comprising 25 mg/l of kanamycin and grown at 28° C. for from 16 to 20 h. The bacterial suspension was then harvested by centrifugation at 6000 g for 10 min and resuspended in liquid MS medium in such a manner that an OD$_{600}$ of approximately from 0.1 to 0.8 resulted. This suspension was used for the co-culture with the leaf material.

Immediately before the co-culture, the MS medium in which the leaves had been kept is replaced by the bacterial suspension. The leaves were incubated in the *Agrobacteria* suspension for 30 min with gentle shaking at room temperature. The infected explants are then placed on an agar-solidified (for example 0.8% plant agar (Duchefa, NL)) MS medium comprising growth regulators, for example 3 mg/l of benzylaminopurine (BAP) and also 1 mg/l of indolylacetic acid (IAA). The orientation of the leaves on the medium is of no importance. The explants are cultured for from 1 to 8 days, but preferably for 6 days, the following conditions being able to be used: light intensity: from 30 to 80 mmol/m$^2$×sec, temperature: from 22 to 24° C., light/dark change of 16/8 hours. The co-cultured explants are then transferred to fresh MS medium, preferably comprising the same growth regulators, this second medium additionally comprising an antibiotic for suppressing bacterial growth. Timentin at a concentration of from 200 to 500 mg/l is very suitable for this purpose. As second selective component, use is made of a component for selecting the transformation success. Phosphinothricin at a concentration of from 1 to 5 mg/l selects very efficiently, but other selective components are also conceivable, according to the method to be used.

After in each case from one to three weeks, the explants are transferred to fresh medium until plumules and small buds develop which are then transferred to the same basal medium including Timentin and PPT or alternative components comprising growth regulators, that is to say, for example, 0.5 mg/l of indolylbutyric acid (IBA) and 0.5 mg/l of gibberillic acid GA$_3$, for rooting. Rooted buds can be transferred to the glasshouse.

In addition to the described method, the following advantageous modifications are possible:

Before the explants are infected with the bacteria, they can be preincubated for from 1 to 12 days, preferably from 3 to 4, on the above-described medium for the co-culture. Then the infection, co-culture and selective regeneration are performed as described above.

The pH for the regeneration (usually 5.8) can be lowered to pH 5.2. This improves the control of the Agrobacterial growth.

The addition of AgNO$_3$ (3-10 mg/l) to the regeneration medium improves the state of the culture, including regeneration itself.

Components which reduce the phenol formation and are known to those skilled in the art, for example citric acid, ascorbic acid, PVP, and many others, have a beneficial effect on the culture.

For the entire method, liquid culture medium can also be used. The culture can also be incubated on commercially conventional supports which are positioned on the liquid medium.

According to the above-described transformation method, using the expression construct pS5AI3, the following lines were obtained:
CS30-1, CS30-3 and CS304

Example I.16

Characterization of the Transgenic *Tagetes* Plants Having Reduced ε-cyclase Activity The flower material of the transgenic *Tagetes erecta* plants from Example I.15 was ground in a mortar in liquid nitrogen and the powder (from about 250 to 500 mg) was extracted with 100% acetone (three times, each 500 ml). The solvent was evaporated and the carotenoids were resuspended in 100 ml of acetone.

By means of a C30 reversed-phase column, the individual carotenoids were quantified. The HPLC running conditions were virtually identical to a published method (Frazer et al. (2000), Plant Journal 24(4): 551-558). It was possible to identify the carotenoids on the basis of the UV-VIS spectra.

Table 2 shows the carotenoid profile in *Tagetes* petals of the transgenic *Tagetes* plants and control *Tagetes* plants produced in accordance with the above-described examples. All carotenoid quantities are given in [μg/g] fresh weight, percentage changes compared with the control plant are given in brackets.

Compared with the non-genetically modified control plant, the genetically modified plants having reduced epsilon-cyclase activity have a significantly increased content of carotenoids of the "β-carotenepath", for example β-carotene and zeaxanthin and a markedly reduced content of carotenoids of the "α-carotene path", for example lutein.

TABLE 2

| Plant | Lutein | β-Carotene | Zeaxanthin | Violaxanthin | Total carotenoids |
|---|---|---|---|---|---|
| Control | 260 | 4.8 | 2.7 | 36 | 304 |
| CS 30-1 | 35 (−86%) | 13 (+170%) | 4.4 (+62%) | 59 (+63%) | 111 (−63%) |
| Control | 456 | 6.4 | 6.9 | 58 | 527 |
| CS 30-3 | 62 (−86%) | 13 (+103%) | 8.9 (+29%) | 75 (+29%) | 159 (−70%) |
| CS 30-4 | 68 (−85%) | 9.1 (+42%) | 5.7 (−17%) | 61 (+5%) | 144 (−73%) |

EXAMPLE II

Production of Astaxanthin-Containing Parts of Plants of the Genus *Tagetes*

The flower heads or the petals of the astaxanthin-containing plants of the genus *Tagetes* produced according to Example I.6 are separated off and dried. The dried flower heads or petals are then converted to powder form by comminution.

EXAMPLE III

Production of Astaxanthin-Containing Extracts and Further Purification

Dried flower leaves or dried flower heads of *Tagetes erecta*, produced in accordance with Example I.6 are homogenized in a homogenizer with an excess (about 10 parts of solvent with one part of plant material) of solvent (for example acetone, hexane, methylene chloride, methyl tertiary-butyl ether, tetrahydrofuran, ethanol, heptane, cycloheptane or petroleum ether, but not restricted exclusively to these) or with a solvent mixture (for example acetone/hexane, ethanol/hexane (50:50, v/v) or acetone/methanol (7:3, v/v) and extracted with shaking in the dark and in the cold. The residue can be re-extracted up to three times with the solvent/solvent mixture used. The collected organic solvent or solvent mixture is evaporated using an evaporator until a reduced concentrate is obtained. In addition, the material can further be extracted with hexane. The hexane used is (again in the dark and in the cold) evaporated.

The concentrate produced in this way is dissolved in hexane and chromatographed by means of column chromatography using silica material. One part of silica material for this is mixed with 1-2 parts of carotenoid solution and packed into a column. The column is extensively washed with hexane in the dark and in the cold. The eluate is discarded. Ketocarotenoids, particularly astaxanthin, are eluted by a mixture of hexane and ethanol (2-5% ethanol in hexane) until an orange-reddish fraction elutes. This orange-reddish eluate is collected until the color changes. The orange-reddish eluate comprises astaxanthin as a mixture of mono- and diesters.

EXAMPLE IV

Production of Extruded Trout Feed, Comprising Astaxanthin-Containing Plants or Parts of Plants of the Genus *Tagetes* or Astaxanthin-Containing Extracts of Astaxanthin-Containing Plants or Parts of Plants of the Genus *Tagetes*

The following components are extruded in a double-screw extruder.

| Components | (%) | Weight for 500 kg kg |
|---|---|---|
| Fish meal | 30.00 | 150.00 |
| Full fat soybeans | 20.00 | 100.00 |
| Pregelatinized wheat starch | 18.00 | 90.00 |
| Vitamin premix | 0.80 | 4.00 |
| Choline chloride (50%) | 0.20 | 1.00 |
| Wheat gluten | 20.00 | 100.00 |
| Sipernat 50S | 3.00 | 15.00 |
| Fish oil | 8.00 | 40.00 |

The pulverulent processed astaxanthin-containing plants or parts of plants of the genus *Tagetes* or astaxanthin-containing extracts of astaxanthin-containing plants or parts of plants of the genus *Tagetes*, produced for example according to Example II are added as component before the extrusion.

The astaxanthin-containing extracts or processed extracts of astaxanthin-containing plants or parts of plants of the genus *Tagetes* are sprayed in liquid form, for example produced according to Example III, onto the extrudate after the extrusion (application by PPA method).

The dosage rate of astaxanthin active compound is 10, 20 and 40 mg of astaxanthin per kg of diet.

After completion of the extrusion process, the extrudate is dried and cooled.

EXAMPLE V

Oral administration of Astaxanthin-Containing Plants or Parts of Plants of the Genus *Tagetes* or Astaxanthin-Containing Extracts of Astaxanthin-Containing Plants or Parts of Plants of the Genus *Tagetes* to Trout in a Standard Trout Feed—Examination of Bioavailability The trout feed comprising the inventive astaxanthin pigments is produced in accordance with Example IV and administered orally to trout (mean live mass 180 g). 3 concentrations are tested: 10, 20 and 40 mg of astaxanthin from the inventive astaxanthin pigmenting per kg of diet.

The trout are raised as described hereinafter:

The trout are given as standard an adaptation phase of 14 days.

During the feeding experiment, 10 trout are kept per pool in constant-flow plastic tanks of volume 80 l of water. The water temperature is 15° C. The water is biologically purified and at least 10% of the total amount of water is replaced by fresh water per day.

The illumination period is 12 hours per day to avoid premature sexual maturation of the animals.

The number of pools per treatment is 3. This is equivalent to 30 trout per dose level.

The diets are stored at −20° C. to avoid astaxanthin losses. The feed is thawed by portions (weekly) and administered.

The experimental period is 8 weeks.

Trout feeding is performed as described hereinafter

The experimental diets administered are extruded trout feed produced in accordance with Example IV which is additionally oil coated.

During the adaptation phase, extruded oil-coated astaxanthin-free standard trout feed in accordance with Example IV without astaxanthin is administered.

As negative control, extruded oil-coated astaxanthin-free standard trout feed according to Example IV without astaxanthin is administered for the entire experimental period.

Feeding is performed 2× per day by hand until the animals are replete.

The influence of the inventive astaxanthin pigmenting not only on performance parameters of the fish, such as feed intake, feed utilization and live mass gain, but also on the bioefficiency of pigmenting is studied.

The average feed consumption per fish, feed conversion and live mass gain are statistically evaluated.

The pigmenting of the fish is measured by reflectance spectrophotometric measurements (Minolta a value =red value at the fillet incision) and by determining the astaxanthin content (mg/kg) in the fillet in each case compared with the negative control.

The Minolta a values which represent the red portion of the color tone, increase with decreasing gradient of the function in a dose-dependent manner. The Minolta b values which reflect the yellow portion are in the negative range or range around zero. This means that the red tone of the trout fillets depends on the amount of astaxanthin consumed.

During the experiment, for the performance parameters observed, no statistically secured differences are observed either between, or else within, treatments (astaxanthin-containing powder, astaxanthin-containing extract in liquid form, synthetic astaxanthin, negative control).

It is found that astaxanthin-containing plants or parts of plants of the genus *Tagetes* or astaxanthin-containing extracts of astaxanthin-containing plants or parts of plants of the genus *Tagetes* are bioavailable in the pigmenting of trout as representatives of Salmonids and in addition do not lead to adverse effects on the biological performance of the trout.

---

The invention claimed is:

1. A method for producing animal feed preparations comprising combining astaxanthin-containing plants or parts of plants of the genus Tagetes or astaxanthin-containing extracts of astaxanthin-containing plants or parts of plants of the genus Tagetes and customary animal feed components.

2. The method according to claim 1, wherein the astaxanthin-containing plants or parts of plants of the genus Tagetes or the astaxanthin-containing extracts of astaxanthin-containing plants or parts of plants of the genus Tagetes are, before combining with animal feed components, processed into a form which makes the combining with animal feed components possible.

3. The method according to claim 1, wherein the astaxanthin-containing plants of the genus Tagetes have, by genetic manipulation, been made capable of producing astaxanthin.

4. The method according to claim 1, wherein the plant parts used are flower heads or petals.

* * * * *